(12) United States Patent
Michaelides et al.

(10) Patent No.: US 9,957,274 B2
(45) Date of Patent: May 1, 2018

(54) INDANE INHIBITORS OF EED AND METHODS OF THEIR USE

(71) Applicant: AbbVie Inc., North Chicago, IL (US)

(72) Inventors: Michael R. Michaelides, Libertyville, IL (US); Michael L. Curtin, Pleasant Prairie, WI (US); Huan-Qiu Li, Wilmette, IL (US); Marina A Pliushchev, Vernon Hills, IL (US); Ying Wang, Libertyville, IL (US); Hongyu H. Zhao, Libertyville, IL (US); Richard F. Clark, Gurnee, IL (US); Alan S. Florjancic, Kenosha, WI (US); Zhiqin Ji, Libertyville, IL (US); Mariazel Torrent, Lake Bluff, IL (US); Ramzi F. Sweis, Lake Bluff, IL (US); Anil Vasudevan, Union Grove, WI (US); Justin D. Dietrich, Lidenhurst, IL (US)

(73) Assignee: AbbVie Inc., North Chicago, IL (US)

( * ) Notice: Subject to any disclaimer, the term of this patent is extended or adjusted under 35 U.S.C. 154(b) by 0 days. days.

(21) Appl. No.: 15/588,398

(22) Filed: May 5, 2017

(65) Prior Publication Data

US 2017/0320880 A1    Nov. 9, 2017

Related U.S. Application Data

(60) Provisional application No. 62/332,749, filed on May 6, 2016.

(51) Int. Cl.
| | | |
|---|---|---|
| C07D 207/14 | (2006.01) |
| A61K 31/40 | (2006.01) |
| C07D 487/04 | (2006.01) |
| C07D 403/10 | (2006.01) |
| C07D 405/04 | (2006.01) |
| C07D 413/10 | (2006.01) |
| C07D 403/12 | (2006.01) |
| C07D 401/12 | (2006.01) |
| C07D 403/04 | (2006.01) |
| C07D 403/14 | (2006.01) |
| C07D 417/14 | (2006.01) |
| C07D 471/04 | (2006.01) |
| C07D 401/04 | (2006.01) |
| C07D 401/14 | (2006.01) |

(52) U.S. Cl.
CPC ............ *C07D 487/04* (2013.01); *A61K 31/40* (2013.01); *C07D 207/14* (2013.01); *C07D 401/04* (2013.01); *C07D 401/12* (2013.01); *C07D 401/14* (2013.01); *C07D 403/04* (2013.01); *C07D 403/10* (2013.01); *C07D 403/12* (2013.01); *C07D 403/14* (2013.01); *C07D 405/04* (2013.01); *C07D 413/10* (2013.01); *C07D 417/14* (2013.01); *C07D 471/04* (2013.01)

(58) Field of Classification Search
CPC .............................. C07D 207/14; A61K 31/40
See application file for complete search history.

(56) References Cited

U.S. PATENT DOCUMENTS 6,620,823 B2 *   9/2003   Maduskuie .......... C07D 207/27
                                                              514/314

\* cited by examiner

*Primary Examiner* — Rebecca L Anderson
*Assistant Examiner* — Karen Cheng
(74) *Attorney, Agent, or Firm* — Changxia Sun

(57) ABSTRACT

Compounds having a structure of Formula (I):

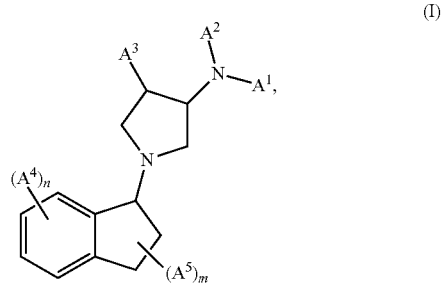

or a stereoisomer, tautomer or pharmaceutically acceptable salt thereof, wherein $A^1$, $A^2$, $A^3$, $A^4$, $A^5$, n, and m are as defined herein and are provided. Pharmaceutical compositions comprising such compounds and methods for treating various EED-related conditions or diseases, including cancer, by administration of such compounds are also provided.

9 Claims, No Drawings

INDANE INHIBITORS OF EED AND METHODS OF THEIR USE

CROSS-REFERENCE TO RELATED APPLICATIONS

This application claims priority to U.S. Provisional Application Ser. No. 62/332,749 filed May 6, 2016, which is incorporated by reference in its entirety.

FIELD OF THE INVENTION

This invention pertains to compounds which inhibit the activity of embryonic ectoderm development (EED), compositions containing the compounds, and methods of treating diseases in which EED is expressed.

BACKGROUND OF THE INVENTION

DNA is wrapped around histone complexes termed nucleosomes and gene accessibility is determined largely by the local chromatin configuration (Chase, A. et. al. *Clin. Cancer Res.* 17, 2613-2618, 2011). Local chromatin structure is influenced, in part, by covalent modifications to histone tails including histone methylation. Histone methyltransferases (HMTs), a class of enzymatic "writers" of epigenetic marks, have recently emerged as targets of potential therapeutic value. They catalyze the methylation of histone lysines and arginines utilizing S-adenosyl-methionine (SAM) as the cofactor/methyl-source. This process can result in either the activation or repression of transcription. Dysregulation of methylation at specific histone sites (alterations in the "histone code") has been implicated in many cancers (Chi P. et al. *Nat. Rev. Cancer* 10, 457-469, 2010). Hence, targeting HMT activity has been the subject of much investigation in the field of oncology.

More specifically, trimethylation of histone H3 lysine 27 (H3K27me3), catalyzed by the PcG (polycomb group) enhancer of zeste homolog 2 (EZH2), is associated with transcriptional repression. H3K27 methylation is catalyzed by the SET domain of EZH2 and requires the presence of additional proteins including embryonic ectoderm development (EED) as part of a larger protein complex known as polycomb repressive complex 2 (PRC2) (Bracken, A. et. al. *Curr. Opin. Cell Biol.* 37, 42-48, 2015).

EED functions to localize the PRC2 complex to trimethylated histone marks which propagates the repressive trimethyl mark to neighboring nucleosomes (Chinnaiyan, A. et. al. *Nat. Commun.* 5, 3127, 2014). Overexpression of EZH2, and in turn EED, is a marker of advanced and metastatic disease in many solid tumors including prostate (Varambally, S. et. al. *Nature* 419, 624-629, 2002), breast (Kleer, C. G. et. al. *Proc. Natl. Acad. Sci. USA* 100, 11606-11611, 2003) and esophageal cancer (He, L. et. al. *Int. J. Cancer* 127, 138-147, 2010). An EZH2 mutation that is linked to subsets of human B-cell lymphoma has been shown to enhance the catalytic efficiency of histone H3K27 trimethylation (Sneeringer, C. J. et. al. *Proc. Natl. Acad. Sci.* 107, 20980-20985, 2010). Increasing evidence suggests that repression of histone trimethylation through inhibition of the PRC2 complex has potential to treat human cancer (Orkin, S. H. *Nat. Chem. Biol.* 9, 643-650, 2013; Yin, J. et. al. *Proc. Natl. Acad. Sci. USA* 2015; Jin, P. *Anticancer Agents Med. Chem.* 2015; Curry, E. et. al. *Clin. Epigenetics* 7, 84, 2015; Xu, B. et. al. *Exp. Hematol.* 43, 698-712, 2015; Campbell, J. E. et. al. *ACS Med. Chem. Lett.* 6, 1031-1043, 2015; Verma, S. K. *Curr. Top. Med. Chem.* 15, 714-719, 2015; Katona, B. W. et. al. *Cancer Biol. Ther.* 15, 1677-1687, 2014; Mayr, C. et. al. *Expert Opin. Ther. Targets* 19, 363-375, 2015; Zhang, L. *Oncotarget.* 5, 10665-10677, 2014; Liu, T. P et. al. *Anticancer Drugs* 26, 139-147, 2015; Kondo, Y. *J. Biochem.* 156, 249-257, 2014; McCabe, M. T. *Epigenomics* 6, 341-351, 2014; Campbell, R. M. *J. Clin. Invest.* 124, 64-69, 2014).

Inhibitors of EED have the potential to suppress PRC2-dependent cancer cell growth. Thus, small molecule inhibitors of EED could be beneficial for therapeutic intervention in cancer and other PRC2-dependent disorders.

SUMMARY OF THE INVENTION

One aspect of this invention, therefore, pertains to compounds or pharmaceutically acceptable salts thereof, which are useful as inhibitors of EED, the compounds having Formula (I)

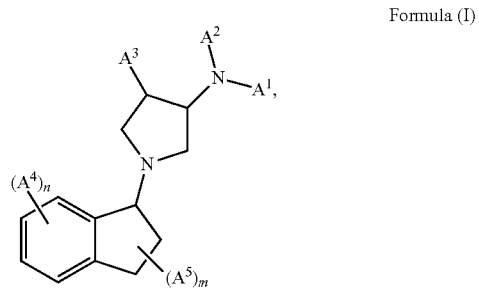

Formula (I)

wherein $A^1$ and $A^2$ are each independently $C_1$-$C_2$ alkyl;

$A^3$ is selected from the group consisting of aryl, heterocyclyl, and heteroaryl, wherein the $A^3$ aryl, heterocyclyl, and heteroaryl are optionally substituted with one or more substituents independently selected from the group consisting of $R^1$, $OR^1$, $SR^1$, $S(O)R^1$, $SO_2R^1$, $C(O)R^1$, $CO(O)R^1$, $OC(O)R^1$, $OC(O)OR^1$, $NH_2$, $NHR^1$, $N(R^1)_2$, $NHC(O)R^1$, $NR^1C(O)R^1$, $NHS(O)_2R^1$, $NR^1S(O)_2R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $C(O)NH_2$, $C(O)NHR^1$, $C(O)N(R^1)_2$, $C(O)NHOH$, $C(O)NHOR^1$, $C(O)NHSO_2R^1$, $C(O)NR^1SO_2R^1$, $SO_2NH_2$, $SO_2NHR^1$, $SO_2N(R^1)_2$, $C(O)H$, $C(O)OH$, $C(N)NH_2$, $C(N)NHR^1$, $C(N)N(R^1)_2$, $CNOH$, $CNOCH_3$, $OH$, (O), $CN$, $NO_2$, $CF_3$, $CF_2CF_3$, $OCF_3$, $OCF_2CF_3$, F, Cl, Br and I;

$A^4$, at each occurrence, is a substituent on a substitutable position of the benzene ring of the indane independently selected from the group consisting of $C_1$-$C_6$ alkyl, OH, F, Cl, Br and I;

$A^5$ is a substituent on a substitutable position of the cyclopentane ring of the indane independently selected from the group consisting of $C_1$-$C_6$ alkyl, OH, F, Cl, Br and I;

$R^1$, at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^1$ $C_1$-$C_6$ alkyl, $C_2$-$C_6$ alkenyl, and $C_2$-$C_6$ alkynyl is optionally substituted with one or more substituents independently selected from the group consisting of $R^2$, $OR^2$, $SR^2$, $S(O)R^2$, $SO_2R^2$, $C(O)R^2$, $CO(O)R^2$, $OC(O)R^2$, $OC(O)OR^2$, $NH_2$, $NHR^2$, $N(R^2)_2$, $NHC(O)R^2$, $NR^2C(O)R^2$, $NHS(O)_2R^2$, $NR^2S(O)_2R^2$, $NHC(O)OR^2$, $NR^2C(O)OR^2$, $NHC(O)NH_2$, $NHC(O)NHR^2$, $NHC(O)N(R^2)_2$, $NR^2C(O)NHR^2$, $NR^2C(O)N(R^2)_2$, $C(O)NH_2$, $C(O)NHR^2$, $C(O)$ N(R$^2$)$_2$, C(O)NHOH, C(O)NHOR$^2$, C(O)NHSO$_2$R$^2$, C(O)NR$^2$SO$_2$R$^2$, SO$_2$NH$_2$, SO$_2$NHR$^2$, SO$_2$N(R$^2$)$_2$, C(O)H, C(O)OH, OH, (O), CN, NO$_2$, CF$_3$, CF$_2$CF$_3$, OCF$_3$, OCF$_2$CF$_3$, F, Cl, Br and I; wherein each R$^1$ aryl, heteroaryl, heterocyclyl, cycloalkyl, and cycloalkenyl is optionally substituted with one or more substituents independently selected from the group consisting of R$^3$, OR$^3$, SR$^3$, S(O)R$^3$, SO$_2$R$^3$, C(O)R$^3$, CO(O)R$^3$, OC(O)R$^3$, OC(O)OR$^3$, NH$_2$, NHR$^3$, N(R$^3$)$_2$, NHC(O)R$^3$, NR$^3$C(O)R$^3$, NHS(O)$_2$R$^3$, NR$^3$S(O)$_2$R$^3$, NHC(O)OR$^3$, NR$^3$C(O)OR$^3$, NHC(O)NH$_2$, NHC(O)NHR$^3$, NHC(O)N(R$^3$)$_2$, NR$^3$C(O)NHR$^3$, NR$^3$C(O)N(R$^3$)$_2$, C(O)NH$_2$, C(O)NHR$^3$, C(O)N(R$^3$)$_2$, C(O)NHOH, C(O)NHOR$^3$, C(O)NHSO$_2$R$^3$, C(O)NR$^3$SO$_2$R$^3$, SO$_2$NH$_2$, SO$_2$NHR$^3$, SO$_2$N(R$^3$)$_2$, C(O)H, C(O)OH, C(O)C(O)NH$_2$, C(O)C(O)NHR$^3$, C(O)C(O)N(R$^3$)$_2$, C(N)NH$_2$, C(N)NHR$^3$, C(N)N(R$^3$)$_2$, CNOH, CNOCH$_3$, OH, (O), CN, NO$_2$, CF$_3$, CF$_2$CF$_3$, OCF$_3$, OCF$_2$CF$_3$, F, Cl, Br and I;

R$^2$, at each occurrence, is independently selected from the group consisting of C$_1$-C$_6$ alkyl, C$_2$-C$_6$ alkenyl, C$_2$-C$_6$ alkynyl, aryl, heteroaryl, heterocyclyl, cycloalkyl, and cycloalkenyl; wherein each R$^2$ C$_1$-C$_6$ alkyl, C$_2$-C$_6$ alkenyl, and C$_2$-C$_6$ alkynyl is optionally substituted with one or more substituents independently selected from the group consisting of NH$_2$, C(O)NH$_2$, SO$_2$NH$_2$, C(O)H, C(O)OH, OH, (O), CN, NO$_2$, CF$_3$, CF$_2$CF$_3$, OCF$_3$, OCF$_2$CF$_3$, F, Cl, Br and I; wherein each R$^2$ aryl, heteroaryl, heterocyclyl, cycloalkyl, and cycloalkenyl is optionally substituted with one or more substituents independently selected from the group consisting of NH$_2$, C(O)NH$_2$, SO$_2$NH$_2$, C(O)H, C(O)OH, OH, (O), CN, NO$_2$, CF$_3$, CF$_2$CF$_3$, OCF$_3$, OCF$_2$CF$_3$, F, Cl, Br and I;

R$^3$, at each occurrence, is independently selected from the group consisting of C$_1$-C$_6$ alkyl, C$_2$-C$_6$ alkenyl, C$_2$-C$_6$ alkynyl, aryl, heteroaryl, heterocyclyl, cycloalkyl, and cycloalkenyl; wherein each R$^3$ C$_1$-C$_6$ alkyl, C$_2$-C$_6$ alkenyl, and C$_2$-C$_6$ alkynyl is optionally substituted with one or more substituents independently selected from the group consisting of R$^4$, OR$^4$, SR$^4$, S(O)R$^4$, SO$_2$R$^4$, C(O)R$^4$, CO(O)R$^4$, OC(O)R$^4$, OC(O)OR$^4$, NH$_2$, NHR$^4$, N(R$^4$)$_2$, NHC(O)R$^4$, NR$^4$C(O)R$^4$, NHS(O)$_2$R$^4$, NR$^4$S(O)$_2$R$^4$, NHC(O)OR$^4$, NR$^4$C(O)OR$^4$, NHC(O)NH$_2$, NHC(O)NHR$^4$, NHC(O)N(R$^4$)$_2$, NR$^4$C(O)NHR$^4$, NR$^4$C(O)N(R$^4$)$_2$, C(O)NH$_2$, C(O)NHR$^4$, C(O)jN(R$^4$)$_2$, C(O)NHOH, C(O)NHOR$^4$, C(O)NHSO$_2$R$^4$, C(O)NR$^4$SO$_2$R$^4$, SO$_2$NH$_2$, SO$_2$NHR$^4$, SO$_2$N(R$^4$)$_2$, C(O)H, C(O)OH, OH, (O), CN, NO$_2$, CF$_3$, CF$_2$CF$_3$, OCF$_3$, OCF$_2$CF$_3$, F, Cl, Br and I; wherein each R$^3$ aryl, heteroaryl, heterocyclyl, cycloalkyl, and cycloalkenyl is optionally substituted with one or more substituents independently selected from the group consisting of R$^5$, OR$^5$, SR$^5$, S(O)R$^5$, SO$_2$R$^5$, C(O)R$^5$, CO(O)R$^5$, OC(O)R$^5$, OC(O)OR$^5$, NH$_2$, NHR$^5$, N(R$^5$)$_2$, NHC(O)R$^5$, NR$^5$C(O)R$^5$, NHS(O)$_2$R$^5$, NR$^5$S(O)$_2$R$^5$, NHC(O)OR$^5$, NR$^5$C(O)OR$^5$, NHC(O)NH$_2$, NHC(O)NHR$^5$, NHC(O)N(R$^5$)$_2$, NR$^5$C(O)NHR$^5$, NR$^5$C(O)N(R$^5$)$_2$, C(O)NH$_2$, C(O)NHR$^5$, C(O)N(R$^5$)$_2$, C(O)NHOH, C(O)NHOR$^5$, C(O)NHSO$_2$R$^5$, C(O)NR$^5$SO$_2$R$^5$, SO$_2$NH$_2$, SO$_2$NHR$^5$, SO$_2$N(R$^5$)$_2$, C(O)H, C(O)OH, C(N)NH$_2$, C(N)NHR$^5$, C(N)N(R$^5$)$_2$, CNOH, CNOCH$_3$, OH, (O), CN, NO$_2$, CF$_3$, CF$_2$CF$_3$, OCF$_3$, OCF$_2$CF$_3$, F, Cl, Br and I;

R$^4$ is at each occurrence, is independently selected from the group consisting of C$_1$-C$_6$ alkyl, C$_2$-C$_6$ alkenyl, C$_2$-C$_6$ alkynyl, aryl, heteroaryl, heterocyclyl, cycloalkyl, and cycloalkenyl; wherein each R$^4$ C$_1$-C$_6$ alkyl, C$_2$-C$_6$ alkenyl, and C$_2$-C$_6$ alkynyl is optionally substituted with one or more substituents independently selected from the group consisting of NH$_2$, C(O)NH$_2$, SO$_2$NH$_2$, C(O)H, C(O)OH, OH, (O), CN, NO$_2$, CF$_3$, CF$_2$CF$_3$, OCF$_3$, OCF$_2$CF$_3$, F, Cl, Br and I; wherein each R$^4$ aryl, heteroaryl, heterocyclyl, cycloalkyl, and cycloalkenyl is optionally substituted with one or more substituents independently selected from the group consisting of NH$_2$, C(O)NH$_2$, SO$_2$NH$_2$, C(O)H, C(O)OH, OH, (O), CN, NO$_2$, CF$_3$, CF$_2$CF$_3$, OCF$_3$, OCF$_2$CF$_3$, F, Cl, Br and I;

R$^5$ is at each occurrence, is independently selected from the group consisting of C$_1$-C$_6$ alkyl, C$_2$-C$_6$ alkenyl, C$_2$-C$_6$ alkynyl, aryl, heteroaryl, heterocyclyl, cycloalkyl, and cycloalkenyl; wherein each R$^5$ C$_1$-C$_6$ alkyl, C$_2$-C$_6$ alkenyl, and C$_2$-C$_6$ alkynyl is optionally substituted with one or more substituents independently selected from the group consisting of NH$_2$, C(O)NH$_2$, SO$_2$NH$_2$, C(O)H, C(O)OH, OH, (O), CN, NO$_2$, CF$_3$, CF$_2$CF$_3$, OCF$_3$, OCF$_2$CF$_3$, F, Cl, Br and I; wherein each R$^5$ aryl, heteroaryl, heterocyclyl, cycloalkyl, and cycloalkenyl is optionally substituted with one or more substituents independently selected from the group consisting of NH$_2$, C(O)NH$_2$, SO$_2$NH$_2$, C(O)H, C(O)OH, OH, (O), CN, NO$_2$, CF$_3$, CF$_2$CF$_3$, OCF$_3$, OCF$_2$CF$_3$, F, Cl, Br and I;

n is 0, 1, or 2; and m is 0 or 1.

Another aspect pertains to compounds of Formula (IIIa) or Formula (IIIb), or a pharmaceutically acceptable salt thereof,

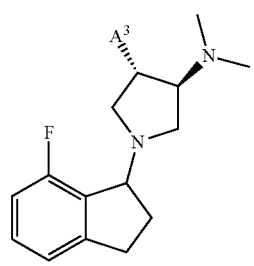

Formula (IIIa)

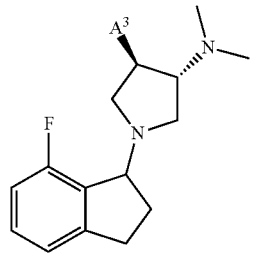

Formula (IIIb)

wherein

A$^3$ is selected from the group consisting of aryl, heterocyclyl, and heteroaryl, wherein the A$^3$ aryl, heterocyclyl, and heteroaryl are optionally substituted with one or more substituents independently selected from the group consisting of R$^1$, OR$^1$, SR$^1$, S(O)R$^1$, SO$_2$R$^1$, C(O)R$^1$, CO(O)R$^1$, OC(O)R$^1$, OC(O)OR$^1$, NH$_2$, NHR$^1$, N(R$^1$)$_2$, NHC(O)R$^1$, NR$^1$C(O)R$^1$, NHS(O)$_2$R$^1$, NR$^1$S(O)$_2$R$^1$, NHC(O)OR$^1$, NR$^1$C(O)OR$^1$, NHC(O)NH$_2$, NHC(O)NHR$^1$, NHC(O)N(R$^1$)$_2$, NR$^1$C(O)NHR$^1$, NR$^1$C(O)N(R$^1$)$_2$, C(O)NH$_2$, C(O)NHR$^1$, C(O)N(R$^1$)$_2$, C(O)NHOH, C(O)NHOR$^1$, C(O)NHSO$_2$R$^1$, C(O)NR$^1$SO$_2$R$^1$, SO$_2$NH$_2$, SO$_2$NHR$^1$, SO$_2$N(R$^1$)$_2$, C(O)H, C(O)OH, C(N)NH$_2$, C(N)NHR$^1$, C(N)N(R$^1$)$_2$, CNOH, CNOCH$_3$, OH, (O), CN, NO$_2$, CF$_3$, CF$_2$CF$_3$, OCF$_3$, OCF$_2$CF$_3$, F, Cl, Br and I;

R$^1$, at each occurrence, is independently selected from the group consisting of C$_1$-C$_6$ alkyl, C$_2$-C$_6$ alkenyl, C$_2$-C$_6$ alkynyl, aryl, heteroaryl, heterocyclyl, cycloalkyl, and cycloalkenyl; wherein each R$^1$ C$_1$-C$_6$ alkyl, C$_2$-C$_6$ alkenyl, and C$_2$-C$_6$ alkynyl is optionally substituted with one or more substituents independently selected from the group consisting of R$^2$, $OR^2$, $SR^2$, $S(O)R^2$, $SO_2R^2$, $C(O)R^2$, $CO(O)R^2$, $OC(O)R^2$, $OC(O)OR^2$, $NH_2$, $NHR^2$, $N(R^2)_2$, $NHC(O)R^2$, $NR^2C(O)R^2$, $NHS(O)_2R^2$, $NR^2S(O)_2R^2$, $NHC(O)OR^2$, $NR^2C(O)OR^2$, $NHC(O)NH_2$, $NHC(O)NHR^2$, $NHC(O)N(R^2)_2$, $NR^2C(O)NHR^2$, $NR^2C(O)N(R^2)_2$, $C(O)NH_2$, $C(O)NHR^2$, $C(O)N(R^2)_2$, $C(O)NHOH$, $C(O)NHOR^2$, $C(O)NHSO_2R^2$, $C(O)NR^2SO_2R^2$, $SO_2NH_2$, $SO_2NHR^2$, $SO_2N(R^2)_2$, $C(O)H$, $C(O)OH$, $OH$, $(O)$, $CN$, $NO_2$, $CF_3$, $CF_2CF_3$, $OCF_3$, $OCF_2CF_3$, F, Cl, Br and I; wherein each $R^1$ aryl, heteroaryl, heterocyclyl, cycloalkyl, and cycloalkenyl is optionally substituted with one or more substituents independently selected from the group consisting of $R^3$, $OR^3$, $SR^3$, $S(O)R^3$, $SO_2R^3$, $C(O)R^3$, $CO(O)R^3$, $OC(O)R^3$, $OC(O)OR^3$, $NH_2$, $NHR^3$, $N(R^3)_2$, $NHC(O)R^3$, $NR^3C(O)R^3$, $NHS(O)_2R^3$, $NR^3S(O)_2R^3$, $NHC(O)OR^3$, $NR^3C(O)OR^3$, $NHC(O)NH_2$, $NHC(O)NHR^3$, $NHC(O)N(R^3)_2$, $NR^3C(O)NHR^3$, $NR^3C(O)N(R^3)_2$, $C(O)NH_2$, $C(O)NHR^3$, $C(O)N(R^3)_2$, $C(O)NHOH$, $C(O)NHOR^3$, $C(O)NHSO_2R^3$, $C(O)NR^3SO_2R^3$, $SO_2NH_2$, $SO_2NHR^3$, $SO_2N(R^3)_2$, $C(O)H$, $C(O)OH$, $C(O)C(O)NH_2$, $C(O)C(O)NHR^3$, $C(O)C(O)N(R^3)_2$, $C(N)NH_2$, $C(N)NHR^3$, $C(N)N(R^3)_2$, $CNOH$, $CNOCH_3$, $OH$, $(O)$, $CN$, $NO_2$, $CF_3$, $CF_2CF_3$, $OCF_3$, $OCF_2CF_3$, F, Cl, Br and I;

$R^2$, at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^2$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)NH_2$, $SO_2NH_2$, $C(O)H$, $C(O)OH$, $OH$, $(O)$, $CN$, $NO_2$, $CF_3$, $CF_2CF_3$, $OCF_3$, $OCF_2CF_3$, F, Cl, Br and I; wherein each $R^2$ aryl, heteroaryl, heterocyclyl, cycloalkyl, and cycloalkenyl is optionally substituted with one or more substituents independently selected from the group consisting of $NH_2$, $C(O)NH_2$, $SO_2NH_2$, $C(O)H$, $C(O)OH$, $OH$, $(O)$, $CN$, $NO_2$, $CF_3$, $CF_2CF_3$, $OCF_3$, $OCF_2CF_3$, F, Cl, Br and I;

$R^3$, at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^3$ $C_1$-$C_6$ alkyl, $C_2$-$C_6$ alkenyl, and $C_2$-$C_6$ alkynyl is optionally substituted with one or more substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $OH$, $(O)$, $CN$, $NO_2$, $CF_3$, $CF_2CF_3$, $OCF_3$, $OCF_2CF_3$, F, Cl, Br and I; wherein each $R^3$ aryl, heteroaryl, heterocyclyl, cycloalkyl, and cycloalkenyl is optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, $C(N)NH_2$, $C(N)NHR^5$, $C(N)N(R^5)_2$, $CNOH$, $CNOCH_3$, $OH$, $(O)$, $CN$, $NO_2$, $CF_3$, $CF_2CF_3$, $OCF_3$, $OCF_2CF_3$, F, Cl, Br and I;

$R^4$ is at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^4$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)NH_2$, $SO_2NH_2$, $C(O)H$, $C(O)OH$, $OH$, $(O)$, $CN$, $NO_2$, $CF_3$, $CF_2CF_3$, $OCF_3$, $OCF_2CF_3$, F, Cl, Br and I; wherein each $R^4$ aryl, heteroaryl, heterocyclyl, cycloalkyl, and cycloalkenyl is optionally substituted with one or more substituents independently selected from the group consisting of $NH_2$, $C(O)NH_2$, $SO_2NH_2$, $C(O)H$, $C(O)OH$, $OH$, $(O)$, $CN$, $NO_2$, $CF_3$, $CF_2CF_3$, $OCF_3$, $OCF_2CF_3$, F, Cl, Br and I; and $R^5$ is at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^5$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)NH_2$, $SO_2NH_2$, $C(O)H$, $C(O)OH$, $OH$, $(O)$, $CN$, $NO_2$, $CF_3$, $CF_2CF_3$, $OCF_3$, $OCF_2CF_3$, F, Cl, Br and I; wherein each $R^5$ aryl, heteroaryl, heterocyclyl, cycloalkyl, and cycloalkenyl is optionally substituted with one or more substituents independently selected from the group consisting of $NH_2$, $C(O)NH_2$, $SO_2NH_2$, $C(O)H$, $C(O)OH$, $OH$, $(O)$, $CN$, $NO_2$, $CF_3$, $CF_2CF_3$, $OCF_3$, $OCF_2CF_3$, F, Cl, Br and I.

Another aspect pertains to compounds of Formula (I), or a pharmaceutically acceptable salt thereof, wherein $A^1$ and $A^2$ are each $CH_3$;

$A^3$ is selected from the group consisting of aryl, heterocyclyl, and heteroaryl, wherein the $A^3$ aryl, heterocyclyl, and heteroaryl are optionally substituted with one or more substituents independently selected from the group consisting of $R^1$, $OR^1$, $SR^1$, $S(O)R^1$, $SO_2R^1$, $C(O)R^1$, $CO(O)R^1$, $OC(O)R^1$, $OC(O)OR^1$, $NH_2$, $NHR^1$, $N(R^1)_2$, $NHC(O)R^1$, $NR^1C(O)R^1$, $NHS(O)_2R^1$, $NR^1S(O)_2R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $C(O)NH_2$, $C(O)NHR^1$, $C(O)N(R^1)_2$, $C(O)NHOH$, $C(O)NHOR^1$, $C(O)NHSO_2R^1$, $C(O)NR^1SO_2R^1$, $SO_2NH_2$, $SO_2NHR^1$, $SO_2N(R^1)_2$, $C(O)H$, $C(O)OH$, $C(N)NH_2$, $C(N)NHR^1$, $C(N)N(R^1)_2$, $CNOH$, $CNOCH_3$, $OH$, $(O)$, $CN$, $NO_2$, $CF_3$, $CF_2CF_3$, $OCF_3$, $OCF_2CF_3$, F, Cl, Br and I;

$A^4$, at each occurrence, is a substituent on a substitutable position of the benzene ring of the indane independently selected from the group consisting of $C_1$-$C_6$ alkyl, OH, F, Cl, Br and I;

$A^5$ is a substituent on a substitutable position of the cyclopentane ring of the indane independently selected from the group consisting of $C_1$-$C_6$ alkyl, OH, F, Cl, Br and I; $R^1$, at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^1$ $C_1$-$C_6$ alkyl, $C_2$-$C_6$ alkenyl, and $C_2$-$C_6$ alkynyl is optionally substituted with one or more substituents independently selected from the group consisting of $R^2$, $OR^2$, $SR^2$, $S(O)R^2$, $SO_2R^2$, $C(O)R^2$, $CO(O)R^2$, $OC(O)R^2$, $OC(O)OR^2$, $NH_2$, $NHR^2$, $N(R^2)_2$, $NHC(O)R^2$, $NR^2C(O)R^2$, $NHS(O)_2R^2$, $NR^2S(O)_2R^2$, $NHC(O)OR^2$, $NR^2C(O)OR^2$, $NHC(O)NH_2$, $NHC(O)NHR^2$, $NHC(O)N(R^2)_2$, $NR^2C(O)NHR^2$, $NR^2C(O)N(R^2)_2$, $C(O)NH_2$, $C(O)NHR^2$, $C(O)N(R^2)_2$, $C(O)NHOH$, $C(O)NHOR^2$, $C(O)NHSO_2R^2$, $C(O)NR^2SO_2R^2$, $SO_2NH_2$, $SO_2NHR^2$, $SO_2N(R^2)_2$, $C(O)H$, $C(O)OH$, $OH$, $(O)$, $CN$, $NO_2$, $CF_3$, $CF_2CF_3$, $OCF_3$, $OCF_2CF_3$, F, Cl, Br and I; wherein each $R^1$ aryl, heteroaryl, heterocyclyl, cycloalkyl, and cycloalkenyl is optionally substituted with one or more substituents independently selected from the group consisting of $R^3$, $OR^3$, $SR^3$, $S(O)R^3$, $SO_2R^3$, $C(O)R^3$, $CO(O)R^3$, $OC(O)R^3$, $OC(O)OR^3$, $NH_2$, $NHR^3$, $N(R^3)_2$, $NHC(O)R^3$, $NR^3C(O)R^3$, $NHS(O)_2R^3$, $NR^3S(O)_2R^3$, NHC (O)OR³, NR³C(O)OR³, NHC(O)NH₂, NHC(O)NHR³, NHC(O)N(R³)₂, NR³C(O)NHR³, NR³C(O)N(R³)₂, C(O) NH₂, C(O)NHR³, C(O)N(R³)₂, C(O)NHOH, C(O)NHOR³, C(O)NHSO₂R³, C(O)NR³SO₂R³, SO₂NH₂, SO₂NHR³, SO₂N(R³)₂, C(O)H, C(O)OH, C(O)C(O)NH₂, C(O)C(O) NHR³, C(O)C(O)N(R³)₂, C(N)NH₂, C(N)NHR³, C(N)N (R³)₂, CNOH, CNOCH₃, OH, (O), CN, NO₂, CF₃, CF₂CF₃, OCF₃, OCF₂CF₃, F, Cl, Br and I;

R², at each occurrence, is independently selected from the group consisting of C₁-C₆ alkyl, C₂-C₆ alkenyl, C₂-C₆ alkynyl, aryl, heteroaryl, heterocyclyl, cycloalkyl, and cycloalkenyl; wherein each R² C₁-C₆ alkyl, C₂-C₆ alkenyl, and C₂-C₆ alkynyl is optionally substituted with one or more substituents independently selected from the group consisting of NH₂, C(O)NH₂, SO₂NH₂, C(O)H, C(O)OH, OH, (O), CN, NO₂, CF₃, CF₂CF₃, OCF₃, OCF₂CF₃, F, Cl, Br and I; wherein each R² aryl, heteroaryl, heterocyclyl, cycloalkyl, and cycloalkenyl is optionally substituted with one or more substituents independently selected from the group consisting of NH₂, C(O)NH₂, SO₂NH₂, C(O)H, C(O)OH, OH, (O), CN, NO₂, CF₃, CF₂CF₃, OCF₃, OCF₂CF₃, F, Cl, Br and I;

R³, at each occurrence, is independently selected from the group consisting of C₁-C₆ alkyl, C₂-C₆ alkenyl, C₂-C₆ alkynyl, aryl, heteroaryl, heterocyclyl, cycloalkyl, and cycloalkenyl; wherein each R³ C₁-C₆ alkyl, C₂-C₆ alkenyl, and C₂-C₆ alkynyl is optionally substituted with one or more substituents independently selected from the group consisting of R⁴, OR⁴, SR⁴, S(O)R⁴, SO₂R⁴, C(O)R⁴, CO(O)R⁴, OC(O)R⁴, OC(O)OR⁴, NH₂, NHR⁴, N(R⁴)₂, NHC(O)R⁴, NR⁴C(O)R⁴, NHS(O)₂R⁴, NR⁴S(O)₂R⁴, NHC(O)OR⁴, NR⁴C(O)OR⁴, NHC(O)NH₂, NHC(O)NHR⁴, NHC(O)N(R⁴)₂, NR⁴C(O) NHR⁴, NR⁴C(O)N(R⁴)₂, C(O)NH₂, C(O)NHR⁴, C(O) N(R⁴)₂, C(O)NHOH, C(O)NHOR⁴, C(O)NHSO₂R⁴, C(O) NR⁴SO₂R⁴, SO₂NH₂, SO₂NHR⁴, SO₂N(R⁴)₂, C(O)H, C(O) OH, OH, (O), CN, NO₂, CF₃, CF₂CF₃, OCF₃, OCF₂CF₃, F, Cl, Br and I; wherein each R³ aryl, heteroaryl, heterocyclyl, cycloalkyl, and cycloalkenyl is optionally substituted with one or more substituents independently selected from the group consisting of R⁵, OR⁵, SR⁵, S(O)R⁵, SO₂R⁵, C(O)R⁵, CO(O)R⁵, OC(O)R⁵, OC(O)OR⁵, NH₂, NHR⁵, N(R⁵)₂, NHC(O)R⁵, NR⁵C(O)R⁵, NHS(O)₂R⁵, NR⁵S(O)₂R⁵, NHC (O)OR⁵, NR⁵C(O)OR⁵, NHC(O)NH₂, NHC(O)NHR⁵, NHC(O)N(R⁵)₂, NR⁵C(O)NHR⁵, NR⁵C(O)N(R⁵)₂, C(O) NH₂, C(O)NHR⁵, C(O)N(R⁵)₂, C(O)NHOH, C(O)NHOR⁵, C(O)NHSO₂R⁵, C(O)NR⁵SO₂R⁵, SO₂NH₂, SO₂NHR⁵, SO₂N(R⁵)₂, C(O)H, C(O)OH, C(N)NH₂, C(N)NHR⁵, C(N) N(R⁵)₂, CNOH, CNOCH₃, OH, (O), CN, NO₂, CF₃, CF₂CF₃, OCF₃, OCF₂CF₃, F, Cl, Br and I;

R⁴ is at each occurrence, is independently selected from the group consisting of C₁-C₆ alkyl, C₂-C₆ alkenyl, C₂-C₆ alkynyl, aryl, heteroaryl, heterocyclyl, cycloalkyl, and cycloalkenyl; wherein each R⁴ C₁-C₆ alkyl, C₂-C₆ alkenyl, and C₂-C₆ alkynyl is optionally substituted with one or more substituents independently selected from the group consisting of NH₂, C(O)NH₂, SO₂NH₂, C(O)H, C(O)OH, OH, (O), CN, NO₂, CF₃, CF₂CF₃, OCF₃, OCF₂CF₃, F, Cl, Br and I; wherein each R⁴ aryl, heteroaryl, heterocyclyl, cycloalkyl, and cycloalkenyl is optionally substituted with one or more substituents independently selected from the group consisting of NH₂, C(O)NH₂, SO₂NH₂, C(O)H, C(O)OH, OH, (O), CN, NO₂, CF₃, CF₂CF₃, OCF₃, OCF₂CF₃, F, Cl, Br and I;

R⁵ is at each occurrence, is independently selected from the group consisting of C₁-C₆ alkyl, C₂-C₆ alkenyl, C₂-C₆ alkynyl, aryl, heteroaryl, heterocyclyl, cycloalkyl, and cycloalkenyl; wherein each R⁵ C₁-C₆ alkyl, C₂-C₆ alkenyl, and C₂-C₆ alkynyl is optionally substituted with one or more substituents independently selected from the group consisting of NH₂, C(O)NH₂, SO₂NH₂, C(O)H, C(O)OH, OH, (O), CN, NO₂, CF₃, CF₂CF₃, OCF₃, OCF₂CF₃, F, Cl, Br and I; wherein each R⁵ aryl, heteroaryl, heterocyclyl, cycloalkyl, and cycloalkenyl is optionally substituted with one or more substituents independently selected from the group consisting of NH₂, C(O)NH₂, SO₂NH₂, C(O)H, C(O)OH, OH, (O), CN, NO₂, CF₃, CF₂CF₃, OCF₃, OCF₂CF₃, F, Cl, Br and I;

n is 0, 1, or 2; and m is 0 or 1.

Another aspect pertains to compounds of Formula (I), or a pharmaceutically acceptable salt thereof, wherein $A^1$ and $A^2$ are each independently $C_1$-$C_2$ alkyl;

$A^3$ is aryl, wherein the $A^3$ aryl is optionally substituted with one or more substituents independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, $C(O)OH$, CN, F, Cl, Br and I;

$A^4$, at each occurrence, is a substituent on a substitutable position of the benzene ring of the indane independently selected from the group consisting of $C_1$-$C_6$ alkyl, OH, F, Cl, Br and I;

$A^5$ is a substituent on a substitutable position of the cyclopentane ring of the indane independently selected from the group consisting of $C_1$-$C_6$ alkyl, OH, F, Cl, Br and I;

R¹, at each occurrence, is independently selected from the group consisting of C₁-C₆ alkyl, C₂-C₆ alkenyl, C₂-C₆ alkynyl, aryl, heteroaryl, heterocyclyl, cycloalkyl, and cycloalkenyl; wherein each R¹ C₁-C₆ alkyl, C₂-C₆ alkenyl, and C₂-C₆ alkynyl is optionally substituted with one or more substituents independently selected from the group consisting of R², OR², SR², S(O)R², SO₂R², C(O)R², CO(O)R², OC(O)R², OC(O)OR², NH₂, NHR², N(R²)₂, NHC(O)R², NR²C(O)R², NHS(O)₂R², NR²S(O)₂R², NHC(O)OR², NR²C(O)OR², NHC(O)NH₂, NHC(O)NHR², NHC(O)N(R²)₂, NR²C(O) NHR², NR²C(O)N(R²)₂, C(O)NH₂, C(O)NHR², C(O) N(R²)₂, C(O)NHOH, C(O)NHOR², C(O)NHSO₂R², C(O) NR²SO₂R², SO₂NH₂, SO₂NHR², SO₂N(R²)₂, C(O)H, C(O) OH, OH, (O), CN, NO₂, CF₃, CF₂CF₃, OCF₃, OCF₂CF₃, F, Cl, Br and I; wherein each R¹ aryl, heteroaryl, heterocyclyl, cycloalkyl, and cycloalkenyl is optionally substituted with one or more substituents independently selected from the group consisting of R³, OR³, SR³, S(O)R³, SO₂R³, C(O)R³, CO(O)R³, OC(O)R³, OC(O)OR³, NH₂, NHR³, N(R³)₂, NHC(O)R³, NR³C(O)R³, NHS(O)₂R³, NR³S(O)₂R³, NHC (O)OR³, NR³C(O)OR³, NHC(O)NH₂, NHC(O)NHR³, NHC(O)N(R³)₂, NR³C(O)NHR³, NR³C(O)N(R³)₂, C(O) NH₂, C(O)NHR³, C(O)N(R³)₂, C(O)NHOH, C(O)NHOR³, C(O)NHSO₂R³, C(O)NR³SO₂R³, SO₂NH₂, SO₂NHR³, SO₂N(R³)₂, C(O)H, C(O)OH, C(O)C(O)NH₂, C(O)C(O) NHR³, C(O)C(O)N(R³)₂, C(N)NH₂, C(N)NHR³, C(N)N (R³)₂, CNOH, CNOCH₃, OH, (O), CN, NO₂, CF₃, CF₂CF₃, OCF₃, OCF₂CF₃, F, Cl, Br and I;

R², at each occurrence, is independently selected from the group consisting of C₁-C₆ alkyl, C₂-C₆ alkenyl, C₂-C₆ alkynyl, aryl, heteroaryl, heterocyclyl, cycloalkyl, and cycloalkenyl; wherein each R² C₁-C₆ alkyl, C₂-C₆ alkenyl, and C₂-C₆ alkynyl is optionally substituted with one or more substituents independently selected from the group consisting of NH₂, C(O)NH₂, SO₂NH₂, C(O)H, C(O)OH, OH, (O), CN, NO₂, CF₃, CF₂CF₃, OCF₃, OCF₂CF₃, F, Cl, Br and I; wherein each R² aryl, heteroaryl, heterocyclyl, cycloalkyl, and cycloalkenyl is optionally substituted with one or more substituents independently selected from the group consisting of NH₂, C(O)NH₂, SO₂NH₂, C(O)H, C(O)OH, OH, (O), CN, NO₂, CF₃, CF₂CF₃, OCF₃, OCF₂CF₃, F, Cl, Br and I;

$R^3$, at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^3$ $C_1$-$C_6$ alkyl, $C_2$-$C_6$ alkenyl, and $C_2$-$C_6$ alkynyl is optionally substituted with one or more substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $OH$, $(O)$, $CN$, $NO_2$, $CF_3$, $CF_2CF_3$, $OCF_3$, $OCF_2CF_3$, $F$, $Cl$, $Br$ and $I$; wherein each $R^3$ aryl, heteroaryl, heterocyclyl, cycloalkyl, and cycloalkenyl is optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, $C(N)NH_2$, $C(N)NHR^5$, $C(N)N(R^5)_2$, $CNOH$, $CNOCH_3$, $OH$, $(O)$, $CN$, $NO_2$, $CF_3$, $CF_2CF_3$, $OCF_3$, $OCF_2CF_3$, $F$, $Cl$, $Br$ and $I$;

$R^4$ is at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^4$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)NH_2$, $SO_2NH_2$, $C(O)H$, $C(O)OH$, $OH$, $(O)$, $CN$, $NO_2$, $CF_3$, $CF_2CF_3$, $OCF_3$, $OCF_2CF_3$, $F$, $Cl$, $Br$ and $I$; wherein each $R^4$ aryl, heteroaryl, heterocyclyl, cycloalkyl, and cycloalkenyl is optionally substituted with one or more substituents independently selected from the group consisting of $NH_2$, $C(O)NH_2$, $SO_2NH_2$, $C(O)H$, $C(O)OH$, $OH$, $(O)$, $CN$, $NO_2$, $CF_3$, $CF_2CF_3$, $OCF_3$, $OCF_2CF_3$, $F$, $Cl$, $Br$ and $I$;

$R^5$ is at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^5$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)NH_2$, $SO_2NH_2$, $C(O)H$, $C(O)OH$, $OH$, $(O)$, $CN$, $NO_2$, $CF_3$, $CF_2CF_3$, $OCF_3$, $OCF_2CF_3$, $F$, $Cl$, $Br$ and $I$; wherein each $R^5$ aryl, heteroaryl, heterocyclyl, cycloalkyl, and cycloalkenyl is optionally substituted with one or more substituents independently selected from the group consisting of $NH_2$, $C(O)NH_2$, $SO_2NH_2$, $C(O)H$, $C(O)OH$, $OH$, $(O)$, $CN$, $NO_2$, $CF_3$, $CF_2CF_3$, $OCF_3$, $OCF_2CF_3$, $F$, $Cl$, $Br$ and $I$;

n is 0, 1, or 2; and m is 0 or 1.

Another aspect pertains to compounds of Formula (IIIa) or Formula (IIIb), or a pharmaceutically acceptable salt thereof, wherein $A^3$ is aryl, wherein the $A^3$ aryl is optionally substituted with one or more substituents independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, $C(O)OH$, $CN$, $F$, $Cl$, $Br$ and $I$;

$R^1$, at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^1$ $C_1$-$C_6$ alkyl, $C_2$-$C_6$ alkenyl, and $C_2$-$C_6$ alkynyl is optionally substituted with one or more substituents independently selected from the group consisting of $R^2$, $OR^2$, $SR^2$, $S(O)R^2$, $SO_2R^2$, $C(O)R^2$, $CO(O)R^2$, $OC(O)R^2$, $OC(O)OR^2$, $NH_2$, $NHR^2$, $N(R^2)_2$, $NHC(O)R^2$, $NR^2C(O)R^2$, $NHS(O)_2R^2$, $NR^2S(O)_2R^2$, $NHC(O)OR^2$, $NR^2C(O)OR^2$, $NHC(O)NH_2$, $NHC(O)NHR^2$, $NHC(O)N(R^2)_2$, $NR^2C(O)NHR^2$, $NR^2C(O)N(R^2)_2$, $C(O)NH_2$, $C(O)NHR^2$, $C(O)N(R^2)_2$, $C(O)NHOH$, $C(O)NHOR^2$, $C(O)NHSO_2R^2$, $C(O)NR^2SO_2R^2$, $SO_2NH_2$, $SO_2NHR^2$, $SO_2N(R^2)_2$, $C(O)H$, $C(O)OH$, $OH$, $(O)$, $CN$, $NO_2$, $CF_3$, $CF_2CF_3$, $OCF_3$, $OCF_2CF_3$, $F$, $Cl$, $Br$ and $I$; wherein each $R^1$ aryl, heteroaryl, heterocyclyl, cycloalkyl, and cycloalkenyl is optionally substituted with one or more substituents independently selected from the group consisting of $R^3$, $OR^3$, $SR^3$, $S(O)R^3$, $SO_2R^3$, $C(O)R^3$, $CO(O)R^3$, $OC(O)R^3$, $OC(O)OR^3$, $NH_2$, $NHR^3$, $N(R^3)_2$, $NHC(O)R^3$, $NR^3C(O)R^3$, $NHS(O)_2R^3$, $NR^3S(O)_2R^3$, $NHC(O)OR^3$, $NR^3C(O)OR^3$, $NHC(O)NH_2$, $NHC(O)NHR^3$, $NHC(O)N(R^3)_2$, $NR^3C(O)NHR^3$, $NR^3C(O)N(R^3)_2$, $C(O)NH_2$, $C(O)NHR^3$, $C(O)N(R^3)_2$, $C(O)NHOH$, $C(O)NHOR^3$, $C(O)NHSO_2R^3$, $C(O)NR^3SO_2R^3$, $SO_2NH_2$, $SO_2NHR^3$, $SO_2N(R^3)_2$, $C(O)H$, $C(O)OH$, $C(O)C(O)NH_2$, $C(O)C(O)NHR^3$, $C(O)C(O)N(R^3)_2$, $C(N)NH_2$, $C(N)NHR^3$, $C(N)N(R^3)_2$, $CNOH$, $CNOCH_3$, $OH$, $(O)$, $CN$, $NO_2$, $CF_3$, $CF_2CF_3$, $OCF_3$, $OCF_2CF_3$, $F$, $Cl$, $Br$ and $I$;

$R^2$, at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^2$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)NH_2$, $SO_2NH_2$, $C(O)H$, $C(O)OH$, $OH$, $(O)$, $CN$, $NO_2$, $CF_3$, $CF_2CF_3$, $OCF_3$, $OCF_2CF_3$, $F$, $Cl$, $Br$ and $I$; wherein each $R^2$ aryl, heteroaryl, heterocyclyl, cycloalkyl, and cycloalkenyl is optionally substituted with one or more substituents independently selected from the group consisting of $NH_2$, $C(O)NH_2$, $SO_2NH_2$, $C(O)H$, $C(O)OH$, $OH$, $(O)$, $CN$, $NO_2$, $CF_3$, $CF_2CF_3$, $OCF_3$, $OCF_2CF_3$, $F$, $Cl$, $Br$ and $I$;

$R^3$, at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^3$ $C_1$-$C_6$ alkyl, $C_2$-$C_6$ alkenyl, and $C_2$-$C_6$ alkynyl is optionally substituted with one or more substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $OH$, $(O)$, $CN$, $NO_2$, $CF_3$, $CF_2CF_3$, $OCF_3$, $OCF_2CF_3$, $F$, $Cl$, $Br$ and $I$; wherein each $R^3$ aryl, heteroaryl, heterocyclyl, cycloalkyl, and cycloalkenyl is optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, $C(N)NH_2$, $C(N)NHR^5$, $C(N)N(R^5)_2$, $CNOH$, $CNOCH_3$, $OH$, $(O)$, $CN$, $NO_2$, $CF_3$, $CF_2CF_3$, $OCF_3$, $OCF_2CF_3$, $F$, $Cl$, $Br$ and $I$;

$R^4$ is at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^4$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I; wherein each $R^4$ aryl, heteroaryl, heterocyclyl, cycloalkyl, and cycloalkenyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I; and $R^5$ is at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^5$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I; wherein each $R^5$ aryl, heteroaryl, heterocyclyl, cycloalkyl, and cycloalkenyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I.

Another aspect pertains to compounds of Formula (I), or a pharmaceutically acceptable salt thereof, wherein $A^1$ and $A^2$ are each $CH_3$;

$A^3$ is aryl, wherein the $A^3$ aryl is optionally substituted with one or more substituents independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, $C(O)OH$, CN, F, Cl, Br and I;

$A^4$, at each occurrence, is a substituent on a substitutable position of the benzene ring of the indane independently selected from the group consisting of $C_1$-$C_6$ alkyl, OH, F, Cl, Br and I;

$A^5$ is a substituent on a substitutable position of the cyclopentane ring of the indane independently selected from the group consisting of $C_1$-$C_6$ alkyl, OH, F, Cl, Br and I;

$R^1$, at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^1$ $C_1$-$C_6$ alkyl, $C_2$-$C_6$ alkenyl, and $C_2$-$C_6$ alkynyl is optionally substituted with one or more substituents independently selected from the group consisting of $R^2$, $OR^2$, $SR^2$, $S(O)R^2$, $SO_2R^2$, $C(O)R^2$, $CO(O)R^2$, $OC(O)R^2$, $OC(O)OR^2$, $NH_2$, $NHR^2$, $N(R^2)_2$, $NHC(O)R^2$, $NR^2C(O)R^2$, $NHS(O)_2R^2$, $NR^2S(O)_2R^2$, $NHC(O)OR^2$, $NR^2C(O)OR^2$, $NHC(O)NH_2$, $NHC(O)NHR^2$, $NHC(O)N(R^2)_2$, $NR^2C(O)NHR^2$, $NR^2C(O)N(R^2)_2$, $C(O)NH_2$, $C(O)NHR^2$, $C(O)N(R^2)_2$, $C(O)NHOH$, $C(O)NHOR^2$, $C(O)NHSO_2R^2$, $C(O)NR^2SO_2R^2$, $SO_2NH_2$, $SO_2NHR^2$, $SO_2N(R^2)_2$, $C(O)H$, $C(O)OH$, OH, (O), CN, $NO_2$, $CF_3$, $CF_2CF_3$, $OCF_3$, $OCF_2CF_3$, F, Cl, Br and I; wherein each $R^1$ aryl, heteroaryl, heterocyclyl, cycloalkyl, and cycloalkenyl is optionally substituted with one or more substituents independently selected from the group consisting of $R^3$, $OR^3$, $SR^3$, $S(O)R^3$, $SO_2R^3$, $C(O)R^3$, $CO(O)R^3$, $OC(O)R^3$, $OC(O)OR^3$, $NH_2$, $NHR^3$, $N(R^3)_2$, $NHC(O)R^3$, $NR^3C(O)R^3$, $NHS(O)_2R^3$, $NR^3S(O)_2R^3$, $NHC(O)OR^3$, $NR^3C(O)OR^3$, $NHC(O)NH_2$, $NHC(O)NHR^3$, $NHC(O)N(R^3)_2$, $NR^3C(O)NHR^3$, $NR^3C(O)N(R^3)_2$, $C(O)NH_2$, $C(O)NHR^3$, $C(O)N(R^3)_2$, $C(O)NHOH$, $C(O)NHOR^3$, $C(O)NHSO_2R^3$, $C(O)NR^3SO_2R^3$, $SO_2NH_2$, $SO_2NHR^3$, $SO_2N(R^3)_2$, $C(O)H$, $C(O)OH$, $C(O)C(O)NH_2$, $C(O)C(O)NHR^3$, $C(O)C(O)N(R^3)_2$, $C(N)NH_2$, $C(N)NHR^3$, $C(N)N(R^3)_2$, CNOH, $CNOCH_3$, OH, (O), CN, $NO_2$, $CF_3$, $CF_2CF_3$, $OCF_3$, $OCF_2CF_3$, F, Cl, Br and I;

$R^2$, at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^2$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I; wherein each $R^2$ aryl, heteroaryl, heterocyclyl, cycloalkyl, and cycloalkenyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I;

$R^3$, at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^3$ $C_1$-$C_6$ alkyl, $C_2$-$C_6$ alkenyl, and $C_2$-$C_6$ alkynyl is optionally substituted with one or more substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, OH, (O), CN, $NO_2$, $CF_3$, $CF_2CF_3$, $OCF_3$, $OCF_2CF_3$, F, Cl, Br and I; wherein each $R^3$ aryl, heteroaryl, heterocyclyl, cycloalkyl, and cycloalkenyl is optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, $C(N)NH_2$, $C(N)NHR^5$, $C(N)N(R^5)_2$, CNOH, $CNOCH_3$, OH, (O), CN, $NO_2$, $CF_3$, $CF_2CF_3$, $OCF_3$, $OCF_2CF_3$, F, Cl, Br and I;

$R^4$ is at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^4$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I; wherein each $R^4$ aryl, heteroaryl, heterocyclyl, cycloalkyl, and cycloalkenyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I;

$R^5$ is at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^5$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I; wherein each $R^5$ aryl, heteroaryl, heterocyclyl, cycloalkyl, and cycloalkenyl is optionally substituted with one or more substituents independently selected from the group consisting of $NH_2$, $C(O)NH_2$, $SO_2NH_2$, $C(O)H$, $C(O)OH$, $OH$, $(O)$, $CN$, $NO_2$, $CF_3$, $CF_2CF_3$, $OCF_3$, $OCF_2CF_3$, F, Cl, Br and I;

n is 0, 1, or 2; and m is 0 or 1.

Another aspect pertains to compounds of Formula (I), or a pharmaceutically acceptable salt thereof, wherein $A^1$ and $A^2$ are each independently $C_1$-$C_2$ alkyl;

$A^3$ is heterocyclyl, wherein the $A^3$ heterocyclyl is optionally substituted with one or more substituents independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, $C(O)OH$, CN, F, Cl, Br and I;

$A^4$, at each occurrence, is a substituent on a substitutable position of the benzene ring of the indane independently selected from the group consisting of $C_1$-$C_6$ alkyl, OH, F, Cl, Br and I;

$A^5$ is a substituent on a substitutable position of the cyclopentane ring of the indane independently selected from the group consisting of $C_1$-$C_6$ alkyl, OH, F, Cl, Br and I;

$R^1$, at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^1$ $C_1$-$C_6$ alkyl, $C_2$-$C_6$ alkenyl, and $C_2$-$C_6$ alkynyl is optionally substituted with one or more substituents independently selected from the group consisting of $R^2$, $OR^2$, $SR^2$, $S(O)R^2$, $SO_2R^2$, $C(O)R^2$, $CO(O)R^2$, $OC(O)R^2$, $OC(O)OR^2$, $NH_2$, $NHR^2$, $N(R^2)_2$, $NHC(O)R^2$, $NR^2C(O)R^2$, $NHS(O)_2R^2$, $NR^2S(O)_2R^2$, $NHC(O)OR^2$, $NR^2C(O)OR^2$, $NHC(O)NH_2$, $NHC(O)NHR^2$, $NHC(O)N(R^2)_2$, $NR^2C(O)NHR^2$, $NR^2C(O)N(R^2)_2$, $C(O)NH_2$, $C(O)NHR^2$, $C(O)N(R^2)_2$, $C(O)NHOH$, $C(O)NHOR^2$, $C(O)NHSO_2R^2$, $C(O)NR^2SO_2R^2$, $SO_2NH_2$, $SO_2NHR^2$, $SO_2N(R^2)_2$, $C(O)H$, $C(O)OH$, OH, (O), CN, $NO_2$, $CF_3$, $CF_2CF_3$, $OCF_3$, $OCF_2CF_3$, F, Cl, Br and I; wherein each $R^1$ aryl, heteroaryl, heterocyclyl, cycloalkyl, and cycloalkenyl is optionally substituted with one or more substituents independently selected from the group consisting of $R^3$, $OR^3$, $SR^3$, $S(O)R^3$, $SO_2R^3$, $C(O)R^3$, $CO(O)R^3$, $OC(O)R^3$, $OC(O)OR^3$, $NH_2$, $NHR^3$, $N(R^3)_2$, $NHC(O)R^3$, $NR^3C(O)R^3$, $NHS(O)_2R^3$, $NR^3S(O)_2R^3$, $NHC(O)OR^3$, $NR^3C(O)OR^3$, $NHC(O)NH_2$, $NHC(O)NHR^3$, $NHC(O)N(R^3)_2$, $NR^3C(O)NHR^3$, $NR^3C(O)N(R^3)_2$, $C(O)NH_2$, $C(O)NHR^3$, $C(O)N(R^3)_2$, $C(O)NHOH$, $C(O)NHOR^3$, $C(O)NHSO_2R^3$, $C(O)NR^3SO_2R^3$, $SO_2NH_2$, $SO_2NHR^3$, $SO_2N(R^3)_2$, $C(O)H$, $C(O)OH$, $C(O)C(O)NH_2$, $C(O)C(O)NHR^3$, $C(O)C(O)N(R^3)_2$, $C(N)NH_2$, $C(N)NHR^3$, $C(N)N(R^3)_2$, CNOH, $CNOCH_3$, OH, (O), CN, $NO_2$, $CF_3$, $CF_2CF_3$, $OCF_3$, $OCF_2CF_3$, F, Cl, Br and I;

$R^2$, at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^2$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I; wherein each $R^2$ aryl, heteroaryl, heterocyclyl, cycloalkyl, and cycloalkenyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I;

$R^3$, at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^3$ $C_1$-$C_6$ alkyl, $C_2$-$C_6$ alkenyl, and $C_2$-$C_6$ alkynyl is optionally substituted with one or more substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, OH, (O), CN, $NO_2$, $CF_3$, $CF_2CF_3$, $OCF_3$, $OCF_2CF_3$, F, Cl, Br and I; wherein each $R^3$ aryl, heteroaryl, heterocyclyl, cycloalkyl, and cycloalkenyl is optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, $C(N)NH_2$, $C(N)NHR^5$, $C(N)N(R^5)_2$, CNOH, $CNOCH_3$, OH, (O), CN, $NO_2$, $CF_3$, $CF_2CF_3$, $OCF_3$, $OCF_2CF_3$, F, Cl, Br and I;

$R^4$ is at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^4$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I; wherein each $R^4$ aryl, heteroaryl, heterocyclyl, cycloalkyl, and cycloalkenyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I;

$R^5$ is at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^5$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I; wherein each $R^5$ aryl, heteroaryl, heterocyclyl, cycloalkyl, and cycloalkenyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I;

n is 0, 1, or 2; and m is 0 or 1.

Another aspect pertains to compounds of Formula (IIIa) or Formula (IIIb), or a pharmaceutically acceptable salt thereof, wherein $A^3$ is heterocyclyl, wherein the $A^3$ heterocyclyl is optionally substituted with one or more substituents independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, $C(O)OH$, CN, F, Cl, Br and I;

$R^1$, at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^1$ $C_1$-$C_6$ alkyl, $C_2$-$C_6$ alkenyl, and $C_2$-$C_6$ alkynyl is optionally substituted with one or more substituents independently selected from the group consisting of $R^2$, $OR^2$, $SR^2$, $S(O)R^2$, $SO_2R^2$, $C(O)R^2$, $CO(O)R^2$, $OC(O)R^2$, $OC(O)OR^2$, $NH_2$, $NHR^2$, $N(R^2)_2$, $NHC(O)R^2$, $NR^2C(O)R^2$, $NHS(O)_2R^2$, $NR^2S(O)_2R^2$, $NHC(O)OR^2$, $NR^2C(O)OR^2$, NHC(O)NH$_2$, NHC(O)NHR$^2$, NHC(O)N(R$^2$)$_2$, NR$^2$C(O)NHR$^2$, NR$^2$C(O)N(R$^2$)$_2$, C(O)NH$_2$, C(O)NHR$^2$, C(O)N(R$^2$)$_2$, C(O)NHOH, C(O)NHOR$^2$, C(O)NHSO$_2$R$^2$, C(O)NR$^2$SO$_2$R$^2$, SO$_2$NH$_2$, SO$_2$NHR$^2$, SO$_2$N(R$^2$)$_2$, C(O)H, C(O)OH, OH, (O), CN, NO$_2$, CF$_3$, CF$_2$CF$_3$, OCF$_3$, OCF$_2$CF$_3$, F, Cl, Br and I; wherein each R$^1$ aryl, heteroaryl, heterocyclyl, cycloalkyl, and cycloalkenyl is optionally substituted with one or more substituents independently selected from the group consisting of R$^3$, OR$^3$, SR$^3$, S(O)R$^3$, SO$_2$R$^3$, C(O)R$^3$, CO(O)R$^3$, OC(O)R$^3$, OC(O)OR$^3$, NH$_2$, NHR$^3$, N(R$^3$)$_2$, NHC(O)R$^3$, NR$^3$C(O)R$^3$, NHS(O)$_2$R$^3$, NR$^3$S(O)$_2$R$^3$, NHC(O)OR$^3$, NR$^3$C(O)OR$^3$, NHC(O)NH$_2$, NHC(O)NHR$^3$, NHC(O)N(R$^3$)$_2$, NR$^3$C(O)NHR$^3$, NR$^3$C(O)N(R$^3$)$_2$, C(O)NH$_2$, C(O)NHR$^3$, C(O)N(R$^3$)$_2$, C(O)NHOH, C(O)NHOR$^3$, C(O)NHSO$_2$R$^3$, C(O)NR$^3$SO$_2$R$^3$, SO$_2$NH$_2$, SO$_2$NHR$^3$, SO$_2$N(R$^3$)$_2$, C(O)H, C(O)OH, C(O)C(O)NH$_2$, C(O)C(O)NHR$^3$, C(O)C(O)N(R$^3$)$_2$, C(N)NH$_2$, C(N)NHR$^3$, C(N)N(R$^3$)$_2$, CNOH, CNOCH$_3$, OH, (O), CN, NO$_2$, CF$_3$, CF$_2$CF$_3$, OCF$_3$, OCF$_2$CF$_3$, F, Cl, Br and I;

R$^2$, at each occurrence, is independently selected from the group consisting of C$_1$-C$_6$ alkyl, C$_2$-C$_6$ alkenyl, C$_2$-C$_6$ alkynyl, aryl, heteroaryl, heterocyclyl, cycloalkyl, and cycloalkenyl; wherein each R$^2$ C$_1$-C$_6$ alkyl, C$_2$-C$_6$ alkenyl, and C$_2$-C$_6$ alkynyl is optionally substituted with one or more substituents independently selected from the group consisting of NH$_2$, C(O)NH$_2$, SO$_2$NH$_2$, C(O)H, C(O)OH, OH, (O), CN, NO$_2$, CF$_3$, CF$_2$CF$_3$, OCF$_3$, OCF$_2$CF$_3$, F, Cl, Br and I; wherein each R$^2$ aryl, heteroaryl, heterocyclyl, cycloalkyl, and cycloalkenyl is optionally substituted with one or more substituents independently selected from the group consisting of NH$_2$, C(O)NH$_2$, SO$_2$NH$_2$, C(O)H, C(O)OH, OH, (O), CN, NO$_2$, CF$_3$, CF$_2$CF$_3$, OCF$_3$, OCF$_2$CF$_3$, F, Cl, Br and I;

R$^3$, at each occurrence, is independently selected from the group consisting of C$_1$-C$_6$ alkyl, C$_2$-C$_6$ alkenyl, C$_2$-C$_6$ alkynyl, aryl, heteroaryl, heterocyclyl, cycloalkyl, and cycloalkenyl; wherein each R$^3$ C$_1$-C$_6$ alkyl, C$_2$-C$_6$ alkenyl, and C$_2$-C$_6$ alkynyl is optionally substituted with one or more substituents independently selected from the group consisting of R$^4$, OR$^4$, SR$^4$, S(O)R$^4$, SO$_2$R$^4$, C(O)R$^4$, CO(O)R$^4$, OC(O)R$^4$, OC(O)OR$^4$, NH$_2$, NHR$^4$, N(R$^4$)$_2$, NHC(O)R$^4$, NR$^4$C(O)R$^4$, NHS(O)$_2$R$^4$, NR$^4$S(O)$_2$R$^4$, NHC(O)OR$^4$, NR$^4$C(O)OR$^4$, NHC(O)NH$_2$, NHC(O)NHR$^4$, NHC(O)N(R$^4$)$_2$, NR$^4$C(O)NHR$^4$, NR$^4$C(O)N(R$^4$)$_2$, C(O)NH$_2$, C(O)NHR$^4$, C(O)N(R$^4$)$_2$, C(O)NHOH, C(O)NHOR$^4$, C(O)NHSO$_2$R$^4$, C(O)NR$^4$SO$_2$R$^4$, SO$_2$NH$_2$, SO$_2$NHR$^4$, SO$_2$N(R$^4$)$_2$, C(O)H, C(O)OH, OH, (O), CN, NO$_2$, CF$_3$, CF$_2$CF$_3$, OCF$_3$, OCF$_2$CF$_3$, F, Cl, Br and I; wherein each R$^3$ aryl, heteroaryl, heterocyclyl, cycloalkyl, and cycloalkenyl is optionally substituted with one or more substituents independently selected from the group consisting of R$^5$, OR$^5$, SR$^5$, S(O)R$^5$, SO$_2$R$^5$, C(O)R$^5$, CO(O)R$^5$, OC(O)R$^5$, OC(O)OR$^5$, NH$_2$, NHR$^5$, N(R$^5$)$_2$, NHC(O)R$^5$, NR$^5$C(O)R$^5$, NHS(O)$_2$R$^5$, NR$^5$S(O)$_2$R$^5$, NHC(O)OR$^5$, NR$^5$C(O)OR$^5$, NHC(O)NH$_2$, NHC(O)NHR$^5$, NHC(O)N(R$^5$)$_2$, NR$^5$C(O)NHR$^5$, NR$^5$C(O)N(R$^5$)$_2$, C(O)NH$_2$, C(O)NHR$^5$, C(O)N(R$^5$)$_2$, C(O)NHOH, C(O)NHOR$^5$, C(O)NHSO$_2$R$^5$, C(O)NR$^5$SO$_2$R$^5$, SO$_2$NH$_2$, SO$_2$NHR$^5$, SO$_2$N(R$^5$)$_2$, C(O)H, C(O)OH, C(N)NH$_2$, C(N)NHR$^5$, C(N)N(R$^5$)$_2$, CNOH, CNOCH$_3$, OH, (O), CN, NO$_2$, CF$_3$, CF$_2$CF$_3$, OCF$_3$, OCF$_2$CF$_3$, F, Cl, Br and I;

R$^4$ is at each occurrence, is independently selected from the group consisting of C$_1$-C$_6$ alkyl, C$_2$-C$_6$ alkenyl, C$_2$-C$_6$ alkynyl, aryl, heteroaryl, heterocyclyl, cycloalkyl, and cycloalkenyl; wherein each R$^4$ C$_1$-C$_6$ alkyl, C$_2$-C$_6$ alkenyl, and C$_2$-C$_6$ alkynyl is optionally substituted with one or more substituents independently selected from the group consisting of NH$_2$, C(O)NH$_2$, SO$_2$NH$_2$, C(O)H, C(O)OH, OH, (O), CN, NO$_2$, CF$_3$, CF$_2$CF$_3$, OCF$_3$, OCF$_2$CF$_3$, F, Cl, Br and I; wherein each R$^4$ aryl, heteroaryl, heterocyclyl, cycloalkyl, and cycloalkenyl is optionally substituted with one or more substituents independently selected from the group consisting of NH$_2$, C(O)NH$_2$, SO$_2$NH$_2$, C(O)H, C(O)OH, OH, (O), CN, NO$_2$, CF$_3$, CF$_2$CF$_3$, OCF$_3$, OCF$_2$CF$_3$, F, Cl, Br and I; and R$^5$ is at each occurrence, is independently selected from the group consisting of C$_1$-C$_6$ alkyl, C$_2$-C$_6$ alkenyl, C$_2$-C$_6$ alkynyl, aryl, heteroaryl, heterocyclyl, cycloalkyl, and cycloalkenyl; wherein each R$^5$ C$_1$-C$_6$ alkyl, C$_2$-C$_6$ alkenyl, and C$_2$-C$_6$ alkynyl is optionally substituted with one or more substituents independently selected from the group consisting of NH$_2$, C(O)NH$_2$, SO$_2$NH$_2$, C(O)H, C(O)OH, OH, (O), CN, NO$_2$, CF$_3$, CF$_2$CF$_3$, OCF$_3$, OCF$_2$CF$_3$, F, Cl, Br and I; wherein each R$^5$ aryl, heteroaryl, heterocyclyl, cycloalkyl, and cycloalkenyl is optionally substituted with one or more substituents independently selected from the group consisting of NH$_2$, C(O)NH$_2$, SO$_2$NH$_2$, C(O)H, C(O)OH, OH, (O), CN, NO$_2$, CF$_3$, CF$_2$CF$_3$, OCF$_3$, OCF$_2$CF$_3$, F, Cl, Br and I.

Another aspect pertains to compounds of Formula (I), or a pharmaceutically acceptable salt thereof,
wherein
A$^1$ and A$^2$ are each CH$_3$;
A$^3$ is heterocyclyl, wherein the A$^3$ heterocyclyl is optionally substituted with one or more substituents independently selected from the group consisting of R$^1$, OR$^1$, SO$_2$R$^1$, C(O)R$^1$, CO(O)R$^1$, C(O)NH$_2$, C(O)NHR$^1$, C(O)N(R$^1$)$_2$, SO$_2$NH$_2$, C(O)OH, CN, F, Cl, Br and I;
A$^4$, at each occurrence, is a substituent on a substitutable position of the benzene ring of the indane independently selected from the group consisting of C$_1$-C$_6$ alkyl, OH, F, Cl, Br and I;
A$^5$ is a substituent on a substitutable position of the cyclopentane ring of the indane independently selected from the group consisting of C$_1$-C$_6$ alkyl, OH, F, Cl, Br and I;
R$^1$, at each occurrence, is independently selected from the group consisting of C$_1$-C$_6$ alkyl, C$_2$-C$_6$ alkenyl, C$_2$-C$_6$ alkynyl, aryl, heteroaryl, heterocyclyl, cycloalkyl, and cycloalkenyl; wherein each R$^1$ C$_1$-C$_6$ alkyl, C$_2$-C$_6$ alkenyl, and C$_2$-C$_6$ alkynyl is optionally substituted with one or more substituents independently selected from the group consisting of R$^2$, OR$^2$, SR$^2$, S(O)R$^2$, SO$_2$R$^2$, C(O)R$^2$, CO(O)R$^2$, OC(O)R$^2$, OC(O)OR$^2$, NH$_2$, NHR$^2$, N(R$^2$)$_2$, NHC(O)R$^2$, NR$^2$C(O)R$^2$, NHS(O)$_2$R$^2$, NR$^2$S(O)$_2$R$^2$, NHC(O)OR$^2$, NR$^2$C(O)OR$^2$, NHC(O)NH$_2$, NHC(O)NHR$^2$, NHC(O)N(R$^2$)$_2$, NR$^2$C(O)NHR$^2$, NR$^2$C(O)N(R$^2$)$_2$, C(O)NH$_2$, C(O)NHR$^2$, C(O)N(R$^2$)$_2$, C(O)NHOH, C(O)NHOR$^2$, C(O)NHSO$_2$R$^2$, C(O)NR$^2$SO$_2$R$^2$, SO$_2$NH$_2$, SO$_2$NHR$^2$, SO$_2$N(R$^2$)$_2$, C(O)H, C(O)OH, OH, (O), CN, NO$_2$, CF$_3$, CF$_2$CF$_3$, OCF$_3$, OCF$_2$CF$_3$, F, Cl, Br and I; wherein each R$^1$ aryl, heteroaryl, heterocyclyl, cycloalkyl, and cycloalkenyl is optionally substituted with one or more substituents independently selected from the group consisting of R$^3$, OR$^3$, SR$^3$, S(O)R$^3$, SO$_2$R$^3$, C(O)R$^3$, CO(O)R$^3$, OC(O)R$^3$, OC(O)OR$^3$, NH$_2$, NHR$^3$, N(R$^3$)$_2$, NHC(O)R$^3$, NR$^3$C(O)R$^3$, NHS(O)$_2$R$^3$, NR$^3$S(O)$_2$R$^3$, NHC(O)OR$^3$, NR$^3$C(O)OR$^3$, NHC(O)NH$_2$, NHC(O)NHR$^3$, NHC(O)N(R$^3$)$_2$, NR$^3$C(O)NHR$^3$, NR$^3$C(O)N(R$^3$)$_2$, C(O)NH$_2$, C(O)NHR$^3$, C(O)N(R$^3$)$_2$, C(O)NHOH, C(O)NHOR$^3$, C(O)NHSO$_2$R$^3$, C(O)NR$^3$SO$_2$R$^3$, SO$_2$NH$_2$, SO$_2$NHR$^3$, SO$_2$N(R$^3$)$_2$, C(O)H, C(O)OH, C(O)C(O)NH$_2$, C(O)C(O)NHR$^3$, C(O)C(O)N(R$^3$)$_2$, C(N)NH$_2$, C(N)NHR$^3$, C(N)N(R$^3$)$_2$, CNOH, CNOCH$_3$, OH, (O), CN, NO$_2$, CF$_3$, CF$_2$CF$_3$, OCF$_3$, OCF$_2$CF$_3$, F, Cl, Br and I;

R$^2$, at each occurrence, is independently selected from the group consisting of C$_1$-C$_6$ alkyl, C$_2$-C$_6$ alkenyl, C$_2$-C$_6$ alkynyl, aryl, heteroaryl, heterocyclyl, cycloalkyl, and cycloalkenyl; wherein each R$^2$ C$_1$-C$_6$ alkyl, C$_2$-C$_6$ alkenyl, and C$_2$-C$_6$ alkynyl is optionally substituted with one or more substituents independently selected from the group consisting of $NH_2$, $C(O)NH_2$, $SO_2NH_2$, $C(O)H$, $C(O)OH$, $OH$, $(O)$, $CN$, $NO_2$, $CF_3$, $CF_2CF_3$, $OCF_3$, $OCF_2CF_3$, F, Cl, Br and I; wherein each $R^2$ aryl, heteroaryl, heterocyclyl, cycloalkyl, and cycloalkenyl is optionally substituted with one or more substituents independently selected from the group consisting of $NH_2$, $C(O)NH_2$, $SO_2NH_2$, $C(O)H$, $C(O)OH$, $OH$, $(O)$, $CN$, $NO_2$, $CF_3$, $CF_2CF_3$, $OCF_3$, $OCF_2CF_3$, F, Cl, Br and I;

$R^3$, at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^3$ $C_1$-$C_6$ alkyl, $C_2$-$C_6$ alkenyl, and $C_2$-$C_6$ alkynyl is optionally substituted with one or more substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $OH$, $(O)$, $CN$, $NO_2$, $CF_3$, $CF_2CF_3$, $OCF_3$, $OCF_2CF_3$, F, Cl, Br and I; wherein each $R^3$ aryl, heteroaryl, heterocyclyl, cycloalkyl, and cycloalkenyl is optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, $C(N)NH_2$, $C(N)NHR^5$, $C(N)N(R^5)_2$, $CNOH$, $CNOCH_3$, $OH$, $(O)$, $CN$, $NO_2$, $CF_3$, $CF_2CF_3$, $OCF_3$, $OCF_2CF_3$, F, Cl, Br and I;

$R^4$ is at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^4$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)NH_2$, $SO_2NH_2$, $C(O)H$, $C(O)OH$, $OH$, $(O)$, $CN$, $NO_2$, $CF_3$, $CF_2CF_3$, $OCF_3$, $OCF_2CF_3$, F, Cl, Br and I; wherein each $R^4$ aryl, heteroaryl, heterocyclyl, cycloalkyl, and cycloalkenyl is optionally substituted with one or more substituents independently selected from the group consisting of $NH_2$, $C(O)NH_2$, $SO_2NH_2$, $C(O)H$, $C(O)OH$, $OH$, $(O)$, $CN$, $NO_2$, $CF_3$, $CF_2CF_3$, $OCF_3$, $OCF_2CF_3$, F, Cl, Br and I;

$R^5$ is at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^5$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)NH_2$, $SO_2NH_2$, $C(O)H$, $C(O)OH$, $OH$, $(O)$, $CN$, $NO_2$, $CF_3$, $CF_2CF_3$, $OCF_3$, $OCF_2CF_3$, F, Cl, Br and I; wherein each $R^5$ aryl, heteroaryl, heterocyclyl, cycloalkyl, and cycloalkenyl is optionally substituted with one or more substituents independently selected from the group consisting of $NH_2$, $C(O)NH_2$, $SO_2NH_2$, $C(O)H$, $C(O)OH$, $OH$, $(O)$, $CN$, $NO_2$, $CF_3$, $CF_2CF_3$, $OCF_3$, $OCF_2CF_3$, F, Cl, Br and I;

n is 0, 1, or 2; and m is 0 or 1.

Another aspect pertains to compounds of Formula (I), or a pharmaceutically acceptable salt thereof, wherein $A^1$ and $A^2$ are each independently $C_1$-$C_2$ alkyl;

$A^3$ is heteroaryl, wherein the $A^3$ heteroaryl is optionally substituted with one or more substituents independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, $C(O)OH$, $CN$, F, Cl, Br and I;

$A^4$, at each occurrence, is a substituent on a substitutable position of the benzene ring of the indane independently selected from the group consisting of $C_1$-$C_6$ alkyl, OH, F, Cl, Br and I;

$A^5$ is a substituent on a substitutable position of the cyclopentane ring of the indane independently selected from the group consisting of $C_1$-$C_6$ alkyl, OH, F, Cl, Br and I;

$R^1$, at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^1$ $C_1$-$C_6$ alkyl, $C_2$-$C_6$ alkenyl, and $C_2$-$C_6$ alkynyl is optionally substituted with one or more substituents independently selected from the group consisting of $R^2$, $OR^2$, $SR^2$, $S(O)R^2$, $SO_2R^2$, $C(O)R^2$, $CO(O)R^2$, $OC(O)R^2$, $OC(O)OR^2$, $NH_2$, $NHR^2$, $N(R^2)_2$, $NHC(O)R^2$, $NR^2C(O)R^2$, $NHS(O)_2R^2$, $NR^2S(O)_2R^2$, $NHC(O)OR^2$, $NR^2C(O)OR^2$, $NHC(O)NH_2$, $NHC(O)NHR^2$, $NHC(O)N(R^2)_2$, $NR^2C(O)NHR^2$, $NR^2C(O)N(R^2)_2$, $C(O)NH_2$, $C(O)NHR^2$, $C(O)N(R^2)_2$, $C(O)NHOH$, $C(O)NHOR^2$, $C(O)NHSO_2R^2$, $C(O)NR^2SO_2R^2$, $SO_2NH_2$, $SO_2NHR^2$, $SO_2N(R^2)_2$, $C(O)H$, $C(O)OH$, $OH$, $(O)$, $CN$, $NO_2$, $CF_3$, $CF_2CF_3$, $OCF_3$, $OCF_2CF_3$, F, Cl, Br and I; wherein each $R^1$ aryl, heteroaryl, heterocyclyl, cycloalkyl, and cycloalkenyl is optionally substituted with one or more substituents independently selected from the group consisting of $R^3$, $OR^3$, $SR^3$, $S(O)R^3$, $SO_2R^3$, $C(O)R^3$, $CO(O)R^3$, $OC(O)R^3$, $OC(O)OR^3$, $NH_2$, $NHR^3$, $N(R^3)_2$, $NHC(O)R^3$, $NR^3C(O)R^3$, $NHS(O)_2R^3$, $NR^3S(O)_2R^3$, $NHC(O)OR^3$, $NR^3C(O)OR^3$, $NHC(O)NH_2$, $NHC(O)NHR^3$, $NHC(O)N(R^3)_2$, $NR^3C(O)NHR^3$, $NR^3C(O)N(R^3)_2$, $C(O)NH_2$, $C(O)NHR^3$, $C(O)N(R^3)_2$, $C(O)NHOH$, $C(O)NHOR^3$, $C(O)NHSO_2R^3$, $C(O)NR^3SO_2R^3$, $SO_2NH_2$, $SO_2NHR^3$, $SO_2N(R^3)_2$, $C(O)H$, $C(O)OH$, $C(O)C(O)NH_2$, $C(O)C(O)NHR^3$, $C(O)C(O)N(R^3)_2$, $C(N)NH_2$, $C(N)NHR^3$, $C(N)N(R^3)_2$, $CNOH$, $CNOCH_3$, $OH$, $(O)$, $CN$, $NO_2$, $CF_3$, $CF_2CF_3$, $OCF_3$, $OCF_2CF_3$, F, Cl, Br and I;

$R^2$, at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^2$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)NH_2$, $SO_2NH_2$, $C(O)H$, $C(O)OH$, $OH$, $(O)$, $CN$, $NO_2$, $CF_3$, $CF_2CF_3$, $OCF_3$, $OCF_2CF_3$, F, Cl, Br and I; wherein each $R^2$ aryl, heteroaryl, heterocyclyl, cycloalkyl, and cycloalkenyl is optionally substituted with one or more substituents independently selected from the group consisting of $NH_2$, $C(O)NH_2$, $SO_2NH_2$, $C(O)H$, $C(O)OH$, $OH$, $(O)$, $CN$, $NO_2$, $CF_3$, $CF_2CF_3$, $OCF_3$, $OCF_2CF_3$, F, Cl, Br and I;

$R^3$, at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^3$ $C_1$-$C_6$ alkyl, $C_2$-$C_6$ alkenyl, and $C_2$-$C_6$ alkynyl is optionally substituted with one or more substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)$ NR$^4$SO$_2$R$^4$, SO$_2$NH$_2$, SO$_2$NHR$^4$, SO$_2$N(R$^4$)$_2$, C(O)H, C(O)OH, OH, (O), CN, NO$_2$, CF$_3$, CF$_2$CF$_3$, OCF$_3$, OCF$_2$CF$_3$, F, Cl, Br and I; wherein each R$^3$ aryl, heteroaryl, heterocyclyl, cycloalkyl, and cycloalkenyl is optionally substituted with one or more substituents independently selected from the group consisting of R$^5$, OR$^5$, SR$^5$, S(O)R$^5$, SO$_2$R$^5$, C(O)R$^5$, CO(O)R$^5$, OC(O)R$^5$, OC(O)OR$^5$, NH$_2$, NHR$^5$, N(R$^5$)$_2$, NHC(O)R$^5$, NR$^5$C(O)R$^5$, NHS(O)$_2$R$^5$, NR$^5$S(O)$_2$R$^5$, NHC(O)OR$^5$, NR$^5$C(O)OR$^5$, NHC(O)NH$_2$, NHC(O)NHR$^5$, NHC(O)N(R$^5$)$_2$, NR$^5$C(O)NHR$^5$, NR$^5$C(O)N(R$^5$)$_2$, C(O)NH$_2$, C(O)NHR$^5$, C(O)N(R$^5$)$_2$, C(O)NHOH, C(O)NHOR$^5$, C(O)NHSO$_2$R$^5$, C(O)NR$^5$SO$_2$R$^5$, SO$_2$NH$_2$, SO$_2$NHR$^5$, SO$_2$N(R$^5$)$_2$, C(O)H, C(O)OH, C(N)NH$_2$, C(N)NHR$^5$, C(N)N(R$^5$)$_2$, CNOH, CNOCH$_3$, OH, (O), CN, NO$_2$, CF$_3$, CF$_2$CF$_3$, OCF$_3$, OCF$_2$CF$_3$, F, Cl, Br and I;

R$^4$ is at each occurrence, is independently selected from the group consisting of C$_1$-C$_6$ alkyl, C$_2$-C$_6$ alkenyl, C$_2$-C$_6$ alkynyl, aryl, heteroaryl, heterocyclyl, cycloalkyl, and cycloalkenyl; wherein each R$^4$ C$_1$-C$_6$ alkyl, C$_2$-C$_6$ alkenyl, and C$_2$-C$_6$ alkynyl is optionally substituted with one or more substituents independently selected from the group consisting of NH$_2$, C(O)NH$_2$, SO$_2$NH$_2$, C(O)H, C(O)OH, OH, (O), CN, NO$_2$, CF$_3$, CF$_2$CF$_3$, OCF$_3$, OCF$_2$CF$_3$, F, Cl, Br and I; wherein each R$^4$ aryl, heteroaryl, heterocyclyl, cycloalkyl, and cycloalkenyl is optionally substituted with one or more substituents independently selected from the group consisting of NH$_2$, C(O)NH$_2$, SO$_2$NH$_2$, C(O)H, C(O)OH, OH, (O), CN, NO$_2$, CF$_3$, CF$_2$CF$_3$, OCF$_3$, OCF$_2$CF$_3$, F, Cl, Br and I;

R$^5$ is at each occurrence, is independently selected from the group consisting of C$_1$-C$_6$ alkyl, C$_2$-C$_6$ alkenyl, C$_2$-C$_6$ alkynyl, aryl, heteroaryl, heterocyclyl, cycloalkyl, and cycloalkenyl; wherein each R$^5$ C$_1$-C$_6$ alkyl, C$_2$-C$_6$ alkenyl, and C$_2$-C$_6$ alkynyl is optionally substituted with one or more substituents independently selected from the group consisting of NH$_2$, C(O)NH$_2$, SO$_2$NH$_2$, C(O)H, C(O)OH, OH, (O), CN, NO$_2$, CF$_3$, CF$_2$CF$_3$, OCF$_3$, OCF$_2$CF$_3$, F, Cl, Br and I; wherein each R$^5$ aryl, heteroaryl, heterocyclyl, cycloalkyl, and cycloalkenyl is optionally substituted with one or more substituents independently selected from the group consisting of NH$_2$, C(O)NH$_2$, SO$_2$NH$_2$, C(O)H, C(O)OH, OH, (O), CN, NO$_2$, CF$_3$, CF$_2$CF$_3$, OCF$_3$, OCF$_2$CF$_3$, F, Cl, Br and I;

n is 0, 1, or 2; and m is 0 or 1.

Another aspect pertains to compounds of Formula (IIIa) or Formula (IIIb), or a pharmaceutically acceptable salt thereof, wherein A$^3$ is heteroaryl, wherein the A$^3$ heteroaryl is optionally substituted with one or more substituents independently selected from the group consisting of R$^1$, OR$^1$, SO$_2$R$^1$, C(O)R$^1$, CO(O)R$^1$, C(O)NH$_2$, C(O)NHR$^1$, C(O)N(R$^1$)$_2$, SO$_2$NH$_2$, C(O)OH, CN, F, Cl, Br and I;

R$^1$, at each occurrence, is independently selected from the group consisting of C$_1$-C$_6$ alkyl, C$_2$-C$_6$ alkenyl, C$_2$-C$_6$ alkynyl, aryl, heteroaryl, heterocyclyl, cycloalkyl, and cycloalkenyl; wherein each R$^1$ C$_1$-C$_6$ alkyl, C$_2$-C$_6$ alkenyl, and C$_2$-C$_6$ alkynyl is optionally substituted with one or more substituents independently selected from the group consisting of R$^2$, OR$^2$, SR$^2$, S(O)R$^2$, SO$_2$R$^2$, C(O)R$^2$, CO(O)R$^2$, OC(O)R$^2$, OC(O)OR$^2$, NH$_2$, NHR$^2$, N(R$^2$)$_2$, NHC(O)R$^2$, NR$^2$C(O)R$^2$, NHS(O)$_2$R$^2$, NR$^2$S(O)$_2$R$^2$, NHC(O)OR$^2$, NR$^2$C(O)OR$^2$, NHC(O)NH$_2$, NHC(O)NHR$^2$, NHC(O)N(R$^2$)$_2$, NR$^2$C(O)NHR$^2$, NR$^2$C(O)N(R$^2$)$_2$, C(O)NH$_2$, C(O)NHR$^2$, C(O)N(R$^2$)$_2$, C(O)NHOH, C(O)NHOR$^2$, C(O)NHSO$_2$R$^2$, C(O)NR$^2$SO$_2$R$^2$, SO$_2$NH$_2$, SO$_2$NHR$^2$, SO$_2$N(R$^2$)$_2$, C(O)H, C(O)OH, OH, (O), CN, NO$_2$, CF$_3$, CF$_2$CF$_3$, OCF$_3$, OCF$_2$CF$_3$, F, Cl, Br and I; wherein each R$^1$ aryl, heteroaryl, heterocyclyl, cycloalkyl, and cycloalkenyl is optionally substituted with one or more substituents independently selected from the group consisting of R$^3$, OR$^3$, SR$^3$, S(O)R$^3$, SO$_2$R$^3$, C(O)R$^3$, CO(O)R$^3$, OC(O)R$^3$, OC(O)OR$^3$, NH$_2$, NHR$^3$, N(R$^3$)$_2$, NHC(O)R$^3$, NR$^3$C(O)R$^3$, NHS(O)$_2$R$^3$, NR$^3$S(O)$_2$R$^3$, NHC(O)OR$^3$, NR$^3$C(O)OR$^3$, NHC(O)NH$_2$, NHC(O)NHR$^3$, NHC(O)N(R$^3$)$_2$, NR$^3$C(O)NHR$^3$, NR$^3$C(O)N(R$^3$)$_2$, C(O)NH$_2$, C(O)NHR$^3$, C(O)N(R$^3$)$_2$, C(O)NHOH, C(O)NHOR$^3$, C(O)NHSO$_2$R$^3$, C(O)NR$^3$SO$_2$R$^3$, SO$_2$NH$_2$, SO$_2$NHR$^3$, SO$_2$N(R$^3$)$_2$, C(O)H, C(O)OH, C(O)C(O)NH$_2$, C(O)C(O)NHR$^3$, C(O)C(O)N(R$^3$)$_2$, C(N)NH$_2$, C(N)NHR$^3$, C(N)N(R$^3$)$_2$, CNOH, CNOCH$_3$, OH, (O), CN, NO$_2$, CF$_3$, CF$_2$CF$_3$, OCF$_3$, OCF$_2$CF$_3$, F, Cl, Br and I;

R$^2$, at each occurrence, is independently selected from the group consisting of C$_1$-C$_6$ alkyl, C$_2$-C$_6$ alkenyl, C$_2$-C$_6$ alkynyl, aryl, heteroaryl, heterocyclyl, cycloalkyl, and cycloalkenyl; wherein each R$^2$ C$_1$-C$_6$ alkyl, C$_2$-C$_6$ alkenyl, and C$_2$-C$_6$ alkynyl is optionally substituted with one or more substituents independently selected from the group consisting of NH$_2$, C(O)NH$_2$, SO$_2$NH$_2$, C(O)H, C(O)OH, OH, (O), CN, NO$_2$, CF$_3$, CF$_2$CF$_3$, OCF$_3$, OCF$_2$CF$_3$, F, Cl, Br and I; wherein each R$^2$ aryl, heteroaryl, heterocyclyl, cycloalkyl, and cycloalkenyl is optionally substituted with one or more substituents independently selected from the group consisting of NH$_2$, C(O)NH$_2$, SO$_2$NH$_2$, C(O)H, C(O)OH, OH, (O), CN, NO$_2$, CF$_3$, CF$_2$CF$_3$, OCF$_3$, OCF$_2$CF$_3$, F, Cl, Br and I;

R$^3$, at each occurrence, is independently selected from the group consisting of C$_1$-C$_6$ alkyl, C$_2$-C$_6$ alkenyl, C$_2$-C$_6$ alkynyl, aryl, heteroaryl, heterocyclyl, cycloalkyl, and cycloalkenyl; wherein each R$^3$ C$_1$-C$_6$ alkyl, C$_2$-C$_6$ alkenyl, and C$_2$-C$_6$ alkynyl is optionally substituted with one or more substituents independently selected from the group consisting of R$^4$, OR$^4$, SR$^4$, S(O)R$^4$, SO$_2$R$^4$, C(O)R$^4$, CO(O)R$^4$, OC(O)R$^4$, OC(O)OR$^4$, NH$_2$, NHR$^4$, N(R$^4$)$_2$, NHC(O)R$^4$, NR$^4$C(O)R$^4$, NHS(O)$_2$R$^4$, NR$^4$S(O)$_2$R$^4$, NHC(O)OR$^4$, NR$^4$C(O)OR$^4$, NHC(O)NH$_2$, NHC(O)NHR$^4$, NHC(O)N(R$^4$)$_2$, NR$^4$C(O)NHR$^4$, NR$^4$C(O)N(R$^4$)$_2$, C(O)NH$_2$, C(O)NHR$^4$, C(O)N(R$^4$)$_2$, C(O)NHOH, C(O)NHOR$^4$, C(O)NHSO$_2$R$^4$, C(O)NR$^4$SO$_2$R$^4$, SO$_2$NH$_2$, SO$_2$NHR$^4$, SO$_2$N(R$^4$)$_2$, C(O)H, C(O)OH, OH, (O), CN, NO$_2$, CF$_3$, CF$_2$CF$_3$, OCF$_3$, OCF$_2$CF$_3$, F, Cl, Br and I; wherein each R$^3$ aryl, heteroaryl, heterocyclyl, cycloalkyl, and cycloalkenyl is optionally substituted with one or more substituents independently selected from the group consisting of R$^5$, OR$^5$, SR$^5$, S(O)R$^5$, SO$_2$R$^5$, C(O)R$^5$, CO(O)R$^5$, OC(O)R$^5$, OC(O)OR$^5$, NH$_2$, NHR$^5$, N(R$^5$)$_2$, NHC(O)R$^5$, NR$^5$C(O)R$^5$, NHS(O)$_2$R$^5$, NR$^5$S(O)$_2$R$^5$, NHC(O)OR$^5$, NR$^5$C(O)OR$^5$, NHC(O)NH$_2$, NHC(O)NHR$^5$, NHC(O)N(R$^5$)$_2$, NR$^5$C(O)NHR$^5$, NR$^5$C(O)N(R$^5$)$_2$, C(O)NH$_2$, C(O)NHR$^5$, C(O)N(R$^5$)$_2$, C(O)NHOH, C(O)NHOR$^5$, C(O)NHSO$_2$R$^5$, C(O)NR$^5$SO$_2$R$^5$, SO$_2$NH$_2$, SO$_2$NHR$^5$, SO$_2$N(R$^5$)$_2$, C(O)H, C(O)OH, C(N)NH$_2$, C(N)NHR$^5$, C(N)N(R$^5$)$_2$, CNOH, CNOCH$_3$, OH, (O), CN, NO$_2$, CF$_3$, CF$_2$CF$_3$, OCF$_3$, OCF$_2$CF$_3$, F, Cl, Br and I;

R$^4$ is at each occurrence, is independently selected from the group consisting of C$_1$-C$_6$ alkyl, C$_2$-C$_6$ alkenyl, C$_2$-C$_6$ alkynyl, aryl, heteroaryl, heterocyclyl, cycloalkyl, and cycloalkenyl; wherein each R$^4$ C$_1$-C$_6$ alkyl, C$_2$-C$_6$ alkenyl, and C$_2$-C$_6$ alkynyl is optionally substituted with one or more substituents independently selected from the group consisting of NH$_2$, C(O)NH$_2$, SO$_2$NH$_2$, C(O)H, C(O)OH, OH, (O), CN, NO$_2$, CF$_3$, CF$_2$CF$_3$, OCF$_3$, OCF$_2$CF$_3$, F, Cl, Br and I; wherein each R$^4$ aryl, heteroaryl, heterocyclyl, cycloalkyl, and cycloalkenyl is optionally substituted with one or more substituents independently selected from the group consisting of NH$_2$, C(O)NH$_2$, SO$_2$NH$_2$, C(O)H, C(O)OH, OH, (O), CN, NO$_2$, CF$_3$, CF$_2$CF$_3$, OCF$_3$, OCF$_2$CF$_3$, F, Cl, Br and I; and $R^5$ is at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^5$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)NH_2$, $SO_2NH_2$, $C(O)H$, $C(O)OH$, $OH$, $(O)$, $CN$, $NO_2$, $CF_3$, $CF_2CF_3$, $OCF_3$, $OCF_2CF_3$, F, Cl, Br and I; wherein each $R^5$ aryl, heteroaryl, heterocyclyl, cycloalkyl, and cycloalkenyl is optionally substituted with one or more substituents independently selected from the group consisting of $NH_2$, $C(O)NH_2$, $SO_2NH_2$, $C(O)H$, $C(O)OH$, $OH$, $(O)$, $CN$, $NO_2$, $CF_3$, $CF_2CF_3$, $OCF_3$, $OCF_2CF_3$, F, Cl, Br and I.

Another aspect pertains to compounds of Formula (I), or a pharmaceutically acceptable salt thereof,
wherein
$A^1$ and $A^2$ are each $CH_3$;
$A^3$ is heteroaryl, wherein the $A^3$ heteroaryl is optionally substituted with one or more substituents independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, $C(O)OH$, CN, F, Cl, Br and I;
$A^4$, at each occurrence, is a substituent on a substitutable position of the benzene ring of the indane independently selected from the group consisting of $C_1$-$C_6$ alkyl, OH, F, Cl, Br and I;
$A^5$ is a substituent on a substitutable position of the cyclopentane ring of the indane independently selected from the group consisting of $C_1$-$C_6$ alkyl, OH, F, Cl, Br and I;
$R^1$, at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^1$ $C_1$-$C_6$ alkyl, $C_2$-$C_6$ alkenyl, and $C_2$-$C_6$ alkynyl is optionally substituted with one or more substituents independently selected from the group consisting of $R^2$, $OR^2$, $SR^2$, $S(O)R^2$, $SO_2R^2$, $C(O)R^2$, $CO(O)R^2$, $OC(O)R^2$, $OC(O)OR^2$, $NH_2$, $NHR^2$, $N(R^2)_2$, $NHC(O)R^2$, $NR^2C(O)R^2$, $NHS(O)_2R^2$, $NR^2S(O)_2R^2$, $NHC(O)OR^2$, $NR^2C(O)OR^2$, $NHC(O)NH_2$, $NHC(O)NHR^2$, $NHC(O)N(R^2)_2$, $NR^2C(O)NHR^2$, $NR^2C(O)N(R^2)_2$, $C(O)NH_2$, $C(O)NHR^2$, $C(O)N(R^2)_2$, $C(O)NHOH$, $C(O)NHOR^2$, $C(O)NHSO_2R^2$, $C(O)NR^2SO_2R^2$, $SO_2NH_2$, $SO_2NHR^2$, $SO_2N(R^2)_2$, $C(O)H$, $C(O)OH$, OH, (O), CN, $NO_2$, $CF_3$, $CF_2CF_3$, $OCF_3$, $OCF_2CF_3$, F, Cl, Br and I; wherein each $R^1$ aryl, heteroaryl, heterocyclyl, cycloalkyl, and cycloalkenyl is optionally substituted with one or more substituents independently selected from the group consisting of $R^3$, $OR^3$, $SR^3$, $S(O)R^3$, $SO_2R^3$, $C(O)R^3$, $CO(O)R^3$, $OC(O)R^3$, $OC(O)OR^3$, $NH_2$, $NHR^3$, $N(R^3)_2$, $NHC(O)R^3$, $NR^3C(O)R^3$, $NHS(O)_2R^3$, $NR^3S(O)_2R^3$, $NHC(O)OR^3$, $NR^3C(O)OR^3$, $NHC(O)NH_2$, $NHC(O)NHR^3$, $NHC(O)N(R^3)_2$, $NR^3C(O)NHR^3$, $NR^3C(O)N(R^3)_2$, $C(O)NH_2$, $C(O)NHR^3$, $C(O)N(R^3)_2$, $C(O)NHOH$, $C(O)NHOR^3$, $C(O)NHSO_2R^3$, $C(O)NR^3SO_2R^3$, $SO_2NH_2$, $SO_2NHR^3$, $SO_2N(R^3)_2$, $C(O)H$, $C(O)OH$, $C(O)C(O)NH_2$, $C(O)C(O)NHR^3$, $C(O)C(O)N(R^3)_2$, $C(N)NH_2$, $C(N)NHR^3$, $C(N)N(R^3)_2$, CNOH, $CNOCH_3$, OH, (O), CN, $NO_2$, $CF_3$, $CF_2CF_3$, $OCF_3$, $OCF_2CF_3$, F, Cl, Br and I;
$R^2$, at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^2$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I; wherein each $R^2$ aryl, heteroaryl, heterocyclyl, and cycloalkenyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I;
$R^3$, at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^3$ $C_1$-$C_6$ alkyl, $C_2$-$C_6$ alkenyl, and $C_2$-$C_6$ alkynyl is optionally substituted with one or more substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, OH, (O), CN, $NO_2$, $CF_3$, $CF_2CF_3$, $OCF_3$, $OCF_2CF_3$, F, Cl, Br and I; wherein each $R^3$ aryl, heteroaryl, heterocyclyl, cycloalkyl, and cycloalkenyl is optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, $C(N)NH_2$, $C(N)NHR^5$, $C(N)N(R^5)_2$, CNOH, $CNOCH_3$, OH, (O), CN, $NO_2$, $CF_3$, $CF_2CF_3$, $OCF_3$, $OCF_2CF_3$, F, Cl, Br and I;
$R^4$ is at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^4$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I; wherein each $R^4$ aryl, heteroaryl, heterocyclyl, cycloalkyl, and cycloalkenyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I;
$R^5$ is at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^5$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I; wherein each $R^5$ aryl, heteroaryl, heterocyclyl, cycloalkyl, and cycloalkenyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I;
n is 0, 1, or 2; and
m is 0 or 1.

Another aspect pertains to a compound selected from the group consisting of
(3R,4S)-1-(7-fluoro-2,3-dihydro-1H-inden-1-yl)-4-{4-[4-(methanesulfonyl)piperazin-1-yl]phenyl}-N,N-dimethylpyrrolidin-3-amine;
rac-(3R,4S)-1-(7-fluoro-2,3-dihydro-1H-inden-1-yl)-4-{4-[4-(methanesulfonyl)piperazin-1-yl]phenyl}-N,N-dimethylpyrrolidin-3-amine;

(3S,4R)-1-(7-fluoro-2,3-dihydro-1H-inden-1-yl)-4-{4-[4-(methanesulfonyl)piperazin-1-yl]phenyl}-N,N-dimethyl-pyrrolidin-3-amine;

(3S,4R)-1-[(1S)-7-fluoro-2,3-dihydro-1H-inden-1-yl]-4-{4-[4-(methanesulfonyl)piperazin-1-yl]phenyl}-N,N-dim-ethylpyrrolidin-3-amine;

(3S,4R)-1-[(1R)-7-fluoro-2,3-dihydro-1H-inden-1-yl]-4-{4-[4-(methanesulfonyl)piperazin-1-yl]phenyl}-N,N-dim-ethylpyrrolidin-3-amine;

rac-(3S,4R)-4-(4-bromophenyl)-1-(7-fluoro-2,3-dihydro-1H-inden-1-yl)-N,N-dimethylpyrrolidin-3-amine;

rac-(3S,4R)-4-(4-chlorophenyl)-1-(7-fluoro-2,3-dihydro-1H-inden-1-yl)-N,N-dimethylpyrrolidin-3-amine;

rac-4-[(3S,4R)-4-(dimethylamino)-1-(7-fluoro-2,3-dihydro-1H-inden-1-yl)pyrrolidin-3-yl]benzene-1-sulfonamide;

(3R,4S)-1-[(1S)-2,3-dihydro-1H-inden-1-yl]-4-[4-(meth-anesulfonyl)phenyl]-N,N-dimethylpyrrolidin-3-amine;

(3S,4R)-1-[(1S)-2,3-dihydro-1H-inden-1-yl]-4-[4-(meth-anesulfonyl)phenyl]-N,N-dimethylpyrrolidin-3-amine;

(3R,4S)-1-[(1S)-7-fluoro-2,3-dihydro-1H-inden-1-yl]-4-[4-(methanesulfonyl)phenyl]-N,N-dimethylpyrrolidin-3-amine;

(3R,4S)-1-[(1R)-7-fluoro-2,3-dihydro-1H-inden-1-yl]-4-[4-(methanesulfonyl)phenyl]-N,N-dimethylpyrrolidin-3-amine;

(3S,4R)-1-[(1S)-7-fluoro-2,3-dihydro-1H-inden-1-yl]-4-[4-(methanesulfonyl)phenyl]-N,N-dimethylpyrrolidin-3-amine;

(3S,4R)-1-[(1R)-7-fluoro-2,3-dihydro-1H-inden-1-yl]-4-[4-(methanesulfonyl)phenyl]-N,N-dimethylpyrrolidin-3-amine;

rac-(1S)-1-{(3S,4R)-3-(dimethylamino)-4-[4-(methanesul-fonyl)phenyl]pyrrolidin-1-yl}-7-fluoro-2,3-dihydro-1H-inden-5-ol;

rac-(1R,3R)-3-{(3S,4R)-3-(dimethylamino)-4-[4-(methane-sulfonyl)phenyl]pyrrolidin-1-yl}-4-fluoro-2,3-dihydro-1H-inden-1-ol;

rac-(1R)-1-{(3S,4R)-3-(dimethylamino)-4-[4-(methanesul-fonyl)phenyl]pyrrolidin-1-yl}-7-fluoro-2,3-dihydro-1H-inden-5-ol;

rac-(1S,3S)-3-{(3R,4S)-3-(dimethylamino)-4-[4-(methane-sulfonyl)phenyl]pyrrolidin-1-yl}-4-fluoro-2,3-dihydro-1H-inden-1-ol;

rac-4-{(3R,4S)-4-(dimethylamino)-1-[(1R)-7-fluoro-2,3-di-hydro-1H-inden-1-yl]pyrrolidin-3-yl}benzonitrile;

rac-methyl 4-[(3R,4S)-1-[(1R)-2,3-dihydro-1H-inden-1-yl]-4-(dimethylamino)pyrrolidin-3-yl]benzoate;

rac-methyl 4-[(3S,4R)-1-(7-chloro-2,3-dihydro-1H-inden-1-yl)-4-(dimethylamino)pyrrolidin-3-yl]benzoate;

rac-methyl 4-[(3R,4S)-4-(dimethylamino)-1-(7-fluoro-2,3-dihydro-1H-inden-1-yl)pyrrolidin-3-yl]benzoate;

rac-(3S,4R)-4-(3,4-dimethoxyphenyl)-1-(7-fluoro-2,3-di-hydro-1H-inden-1-yl)-N,N-dimethylpyrrolidin-3-amine;

rac-4-[(3S,4R)-4-(dimethylamino)-1-(7-fluoro-2,3-dihydro-1H-inden-1-yl)pyrrolidin-3-yl]-N-methylbenzamide;

rac-4-[(3S,4R)-1-(7-chloro-2,3-dihydro-1H-inden-1-yl)-4-(dimethylamino)pyrrolidin-3-yl]-N,N-dimethylbenz-amide;

rac-4-[(3S,4R)-4-(dimethylamino)-1-(7-fluoro-2,3-dihydro-1H-inden-1-yl)pyrrolidin-3-yl]-N,N-dimethylbenzamide;

rac-(3R,4S)-4-(4-bromo-3-methylphenyl)-1-(7-fluoro-2,3-dihydro-1H-inden-1-yl)-N,N-dimethylpyrrolidin-3-amine;

rac-4-[(3S,4R)-1-(7-chloro-2,3-dihydro-1H-inden-1-yl)-4-(dimethylamino)pyrrolidin-3-yl]benzoic acid;

rac-4-[(3R,4S)-4-(dimethylamino)-1-(7-fluoro-2,3-dihydro-1H-inden-1-yl)pyrrolidin-3-yl]benzoic acid;

rac-(3R,4S)-1-[(3S)-3,7-difluoro-2,3-dihydro-1H-inden-1-yl]-4-[4-(methanesulfonyl)phenyl]-N,N-dimethylpyrroli-din-3-amine;

rac-(3R,4S)-1-[(1R,3S)-3,7-difluoro-2,3-dihydro-1H-inden-1-yl]-4-[4-(methanesulfonyl)phenyl]-N,N-dimethylpyr-rolidin-3-amine;

rac-(3R,4S)-1-[(1S,3S)-3,7-difluoro-2,3-dihydro-1H-inden-1-yl]-4-[4-(methanesulfonyl)phenyl]-N,N-dimethylpyr-rolidin-3-amine;

(3S)-3-{(3S,4R)-3-(dimethylamino)-4-[4-(methanesulfo-nyl)phenyl]pyrrolidin-1-yl}-4-fluoro-2,3-dihydro-1H-in-den-1-ol;

rac-(1R,3S)-3-{(3R,4S)-3-(dimethylamino)-4-[4-(methane-sulfonyl)phenyl]pyrrolidin-1-yl}-4-fluoro-2,3-dihydro-1H-inden-1-ol;

rac-4-[(3R,4S)-4-(dimethylamino)-1-(7-fluoro-2,3-dihydro-1H-inden-1-yl)pyrrolidin-3-yl]benzamide;

rac-4-[(3S,4R)-4-(dimethylamino)-1-(7-fluoro-2,3-dihydro-1H-inden-1-yl)pyrrolidin-3-yl]-2-methylbenzoic acid;

rac-4-[(3S,4R)-4-(dimethylamino)-1-(7-fluoro-2,3-dihydro-1H-inden-1-yl)pyrrolidin-3-yl]-2-methylbenzonitrile;

rac-4-[(3S,4R)-4-(dimethylamino)-1-(2-hydroxy-2,3-di-hydro-1H-inden-1-yl)pyrrolidin-3-yl]-2-methylbenzoni-trile;

rac-methyl 4-[(3S,4R)-4-(dimethylamino)-1-(7-fluoro-2,3-dihydro-1H-inden-1-yl)pyrrolidin-3-yl]-2-methylbenzo-ate;

rac-{4-[(3S,4R)-4-(dimethylamino)-1-(7-fluoro-2,3-di-hydro-1H-inden-1-yl)pyrrolidin-3-yl]phenyl}[(3S)-3-hy-droxypyrrolidin-1-yl]methanone;

rac-(3S,4R)-1-(7-fluoro-2,3-dihydro-1H-inden-1-yl)-N,N-dimethyl-4-[4-(piperazin-1-yl)phenyl]pyrrolidin-3-amine;

1-(4-{4-[(3S,4R)-1-(2,3-dihydro-1H-inden-1-yl)-4-(dimeth-ylamino)pyrrolidin-3-yl]phenyl}piperazin-1-yl)ethan-1-one;

1-(4-{4-[(3S,4R)-4-(dimethylamino)-1-(7-fluoro-2,3-di-hydro-1H-inden-1-yl)pyrrolidin-3-yl]phenyl}piperazin-1-yl)ethan-1-one;

rac-1-(4-{4-[(3S,4R)-4-(dimethylamino)-1-(7-fluoro-2,3-dihydro-1H-inden-1-yl)pyrrolidin-3-yl]phenyl}piperazin-1-yl)ethan-1-one;

1-[4-(4-{(3S,4R)-4-(dimethylamino)-1-[(1S)-7-fluoro-2,3-dihydro-1H-inden-1-yl]pyrrolidin-3-yl}phenyl)piper-azin-1-yl]ethan-1-one;

1-[4-(4-{(3S,4R)-4-(dimethylamino)-1-[(1R)-7-fluoro-2,3-dihydro-1H-inden-1-yl]pyrrolidin-3-yl}phenyl)piper-azin-1-yl]ethan-1-one;

1-[4-(4-{(3R,4S)-4-(dimethylamino)-1-[(1S)-7-fluoro-2,3-dihydro-1H-inden-1-yl]pyrrolidin-3-yl}phenyl)piper-azin-1-yl]ethan-1-one;

1-[4-(4-{(3R,4S)-4-(dimethylamino)-1-[(1R)-7-fluoro-2,3-dihydro-1H-inden-1-yl]pyrrolidin-3-yl}phenyl)piper-azin-1-yl]ethan-1-one;

rac-(3R,4S)-4-{4-[4-(ethanesulfonyl)piperazin-1-yl]phe-nyl}-1-(7-fluoro-2,3-dihydro-1H-inden-1-yl)-N,N-dim-ethylpyrrolidin-3-amine;

tert-butyl 4-{4-[(3R,4S)-4-(dimethylamino)-1-(7-fluoro-2,3-dihydro-1H-inden-1-yl)pyrrolidin-3-yl]phenyl}piperazine-1-carboxylate;

rac-4-{4-[(3S,4R)-4-(dimethylamino)-1-(7-fluoro-2,3-di-hydro-1H-inden-1-yl)pyrrolidin-3-yl]benzoyl}-1-methyl-piperazin-2-one;

rac-1-(4-{4-[(3R,4S)-4-(dimethylamino)-1-(7-fluoro-2,3-dihydro-1H-inden-1-yl)pyrrolidin-3-yl]phenyl}piperazin-1-yl)-2-hydroxyethan-1-one;

rac-{4-[(3S,4R)-4-(dimethylamino)-1-(7-fluoro-2,3-dihydro-1H-inden-1-yl)pyrrolidin-3-yl]phenyl}[4-(methanesulfonyl)piperazin-1-yl]methanone;
rac-2-(4-{4-[(3R,4S)-4-(dimethylamino)-1-(7-fluoro-2,3-dihydro-1H-inden-1-yl)pyrrolidin-3-yl]phenyl}piperazin-1-yl)-2-oxoacetamide;
rac-1-(4-{4-[(3S,4R)-4-(dimethylamino)-1-(7-fluoro-2,3-dihydro-1H-inden-1-yl)pyrrolidin-3-yl]benzoyl}piperazin-1-yl)ethan-1-one;
rac-4-{4-[(3S,4R)-4-(dimethylamino)-1-(7-fluoro-2,3-dihydro-1H-inden-1-yl)pyrrolidin-3-yl]phenyl}-1-methylpiperazin-2-one;
rac-{4-[(3S,4R)-4-(dimethylamino)-1-(7-fluoro-2,3-dihydro-1H-inden-1-yl)pyrrolidin-3-yl]phenyl}[4-(ethanesulfonyl)piperazin-1-yl]methanone;
rac-4-{4-[(3S,4R)-4-(dimethylamino)-1-(7-fluoro-2,3-dihydro-1H-inden-1-yl)pyrrolidin-3-yl]-2-methylphenyl}-1-methylpiperazin-2-one;
rac-2-(4-{4-[(3R,4S)-4-(dimethylamino)-1-(7-fluoro-2,3-dihydro-1H-inden-1-yl)pyrrolidin-3-yl]phenyl}piperazin-1-yl)-N,N-dimethyl-2-oxoacetamide;
rac-1-(4-{4-[(3S,4R)-4-(dimethylamino)-1-(7-fluoro-2,3-dihydro-1H-inden-1-yl)pyrrolidin-3-yl]-2-methylphenyl}piperazin-1-yl)ethan-1-one;
rac-(3R,4S)-1-(7-fluoro-2,3-dihydro-1H-inden-1-yl)-N,N-dimethyl-4-[4-(4-methylpiperazin-1-yl)phenyl]pyrrolidin-3-amine;
rac-(3R,4S)-4-{4-[4-(ethanesulfonyl)piperazin-1-yl]-3-methylphenyl}-1-(7-fluoro-2,3-dihydro-1H-inden-1-yl)-N,N-dimethylpyrrolidin-3-amine;
rac-4-{4-[(3S,4R)-4-(dimethylamino)-1-(7-fluoro-2,3-dihydro-1H-inden-1-yl)pyrrolidin-3-yl]phenyl}-N,N-dimethylpiperazine-1-carboxamide;
rac-(3R,4S)-4-[4-(4-cyclopropylpiperazin-1-yl)phenyl]-1-(7-fluoro-2,3-dihydro-1H-inden-1-yl)-N,N-dimethylpyrrolidin-3-amine;
rac-(3S,4R)-4-(2H-1,3-benzodioxol-5-yl)-1-(7-fluoro-2,3-dihydro-1H-inden-1-yl)-N,N-dimethylpyrrolidin-3-amine;
rac-(3S,4R)-1-(7-fluoro-2,3-dihydro-1H-inden-1-yl)-N,N-dimethyl-4-[4-(1,3-oxazol-2-yl)phenyl]pyrrolidin-3-amine;
rac-(3R,4S)-1-(7-fluoro-2,3-dihydro-1H-inden-1-yl)-N,N-dimethyl-4-[4-(3-methyl-1,2,4-oxadiazol-5-yl)phenyl]pyrrolidin-3-amine;
rac-(3S,4R)-1-(7-fluoro-2,3-dihydro-1H-inden-1-yl)-N,N-dimethyl-4-[4-(5-methyl-1,3,4-oxadiazol-2-yl)phenyl]pyrrolidin-3-amine;
rac-(3S,4R)-1-(7-fluoro-2,3-dihydro-1H-inden-1-yl)-N,N-dimethyl-4-[4-(4-methyl-1,3-oxazol-2-yl)phenyl]pyrrolidin-3-amine;
rac-(3R,4S)-1-(7-fluoro-2,3-dihydro-1H-inden-1-yl)-N,N-dimethyl-4-[4-(1-methyl-1H-pyrazol-4-yl)phenyl]pyrrolidin-3-amine;
rac-2-(4-{4-[(3S,4R)-4-(dimethylamino)-1-(7-fluoro-2,3-dihydro-1H-inden-1-yl)pyrrolidin-3-yl]phenyl}-1H-pyrazol-1-yl)acetamide;
rac-2-(4-{4-[(3S,4R)-4-(dimethylamino)-1-(7-fluoro-2,3-dihydro-1H-inden-1-yl)pyrrolidin-3-yl]phenyl}-1H-pyrazol-1-yl)-N-methylacetamide;
rac-(3S,4R)-1-(7-fluoro-2,3-dihydro-1H-inden-1-yl)-N,N-dimethyl-4-{4-[4-(1-methyl-1H-imidazole-4-sulfonyl)piperazin-1-yl]phenyl}pyrrolidin-3-amine;
rac-(3S,4R)-1-(7-fluoro-2,3-dihydro-1H-inden-1-yl)-N,N-dimethyl-4-{4-[4-(pyrimidin-4-yl)piperazin-1-yl]phenyl}pyrrolidin-3-amine;
rac-(3S,4R)-1-(7-fluoro-2,3-dihydro-1H-inden-1-yl)-N,N-dimethyl-4-{4-[4-(pyridin-2-yl)piperazin-1-yl]phenyl}pyrrolidin-3-amine;
(3R,4S)-1-(7-fluoro-2,3-dihydro-1H-inden-1-yl)-N,N-dimethyl-4-(1-methyl-1H-indol-3-yl)pyrrolidin-3-amine;
(3R,4S)-1-[(1S)-7-fluoro-2,3-dihydro-1H-inden-1-yl]-N,N-dimethyl-4-(1-methyl-1H-indol-3-yl)pyrrolidin-3-amine;
(3R,4S)-1-[(1R)-7-fluoro-2,3-dihydro-1H-inden-1-yl]-N,N-dimethyl-4-(1-methyl-1H-indol-3-yl)pyrrolidin-3-amine;
3-[(3S,4R)-4-(dimethylamino)-1-(7-fluoro-2,3-dihydro-1H-inden-1-yl)pyrrolidin-3-yl]-1-methyl-1H-indole-7-carboxylic acid;
rac-3-[(3S,4R)-4-(dimethylamino)-1-(7-fluoro-2,3-dihydro-1H-inden-1-yl)pyrrolidin-3-yl]-1-methyl-1H-indole-7-carboxylic acid;
3-[(3R,4S)-4-(dimethylamino)-1-(7-fluoro-2,3-dihydro-1H-inden-1-yl)pyrrolidin-3-yl]-1-methyl-1H-indole-7-carboxylic acid;
rac-methyl 3-[(3R,4S)-4-(dimethylamino)-1-(7-fluoro-2,3-dihydro-1H-inden-1-yl)pyrrolidin-3-yl]-1-methyl-1H-indole-6-carboxylate;
methyl 3-[(3S,4R)-4-(dimethylamino)-1-(7-fluoro-2,3-dihydro-1H-inden-1-yl)pyrrolidin-3-yl]-1-methyl-1H-indole-7-carboxylate;
rac-methyl 3-[(3S,4R)-4-(dimethylamino)-1-(7-fluoro-2,3-dihydro-1H-inden-1-yl)pyrrolidin-3-yl]-1-methyl-1H-indole-7-carboxylate;
methyl 3-[(3R,4S)-4-(dimethylamino)-1-(7-fluoro-2,3-dihydro-1H-inden-1-yl)pyrrolidin-3-yl]-1-methyl-1H-indole-7-carboxylate;
rac-3-[(3S,4R)-4-(dimethylamino)-1-(7-fluoro-2,3-dihydro-1H-inden-1-yl)pyrrolidin-3-yl]-N,N,1-trimethyl-1H-indole-6-carboxamide;
(3R,4S)-1-(2,3-dihydro-1H-inden-1-yl)-N,N-dimethyl-4-(1-methyl-1H-indol-3-yl)pyrrolidin-3-amine;
(3R,4S)-1-(7-chloro-2,3-dihydro-1H-inden-1-yl)-N,N-dimethyl-4-(1-methyl-1H-indol-3-yl)pyrrolidin-3-amine;
rac-(3R,4S)-1-(4-fluoro-2,3-dihydro-1H-inden-1-yl)-N,N-dimethyl-4-(1-methyl-1H-indol-3-yl)pyrrolidin-3-amine;
rac-(3R,4S)-1-(5-fluoro-2,3-dihydro-1H-inden-1-yl)-N,N-dimethyl-4-(1-methyl-1H-indol-3-yl)pyrrolidin-3-amine;
rac-(3R,4S)-1-(6-fluoro-2,3-dihydro-1H-inden-1-yl)-N,N-dimethyl-4-(1-methyl-1H-indol-3-yl)pyrrolidin-3-amine;
rac-(3R,4S)-4-(7-bromo-1-methyl-1H-indol-3-yl)-1-(7-fluoro-2,3-dihydro-1H-inden-1-yl)-N,N-dimethylpyrrolidin-3-amine;
rac-(3R,4S)-4-(6-bromo-1-methyl-1H-indol-3-yl)-1-(7-fluoro-2,3-dihydro-1H-inden-1-yl)-N,N-dimethylpyrrolidin-3-amine;
rac-(3R,4S)-1-(5,7-difluoro-2,3-dihydro-1H-inden-1-yl)-N,N-dimethyl-4-(1-methyl-1H-indol-3-yl)pyrrolidin-3-amine;
(3R,4S)-1-(6,7-difluoro-2,3-dihydro-1H-inden-1-yl)-N,N-dimethyl-4-(1-methyl-1H-indol-3-yl)pyrrolidin-3-amine;
3-[(3R,4S)-3-(dimethylamino)-4-(1-methyl-1H-indol-3-yl)pyrrolidin-1-yl]-2,3-dihydro-1H-inden-4-ol;
rac-3-[(3S,4R)-4-(dimethylamino)-1-(7-fluoro-2,3-dihydro-1H-inden-1-yl)pyrrolidin-3-yl]-N-(2-hydroxyethyl)-N,1-dimethyl-1H-indole-7-carboxamide;
rac-3-[(3S,4R)-4-(dimethylamino)-1-(7-fluoro-2,3-dihydro-1H-inden-1-yl)pyrrolidin-3-yl]-N,1-dimethyl-1H-indole-7-carboxamide;
(3R,4S)—N,N-dimethyl-1-(7-methyl-2,3-dihydro-1H-inden-1-yl)-4-(1-methyl-1H-indol-3-yl)pyrrolidin-3-amine;
rac-3-[(3S,4R)-4-(dimethylamino)-1-(7-fluoro-2,3-dihydro-1H-inden-1-yl)pyrrolidin-3-yl]-N,N,1-trimethyl-1H-indole-7-carboxamide;

{3-[(3S,4R)-4-(dimethylamino)-1-(7-fluoro-2,3-dihydro-1H-inden-1-yl)pyrrolidin-3-yl]-1-methyl-1H-indol-7-yl}(3-fluoroazetidin-1-yl)methanone;

rac-{3-[(3S,4R)-4-(dimethylamino)-1-(7-fluoro-2,3-dihydro-1H-inden-1-yl)pyrrolidin-3-yl]-1-methyl-1H-indol-7-yl}(3-fluoroazetidin-1-yl)methanone;

{3-[(3R,4S)-4-(dimethylamino)-1-(7-fluoro-2,3-dihydro-1H-inden-1-yl)pyrrolidin-3-yl]-1-methyl-1H-indol-7-yl}(3-fluoroazetidin-1-yl)methanone;

{3-[(3S,4R)-4-(dimethylamino)-1-(7-fluoro-2,3-dihydro-1H-inden-1-yl)pyrrolidin-3-yl]-1-methyl-1H-indol-7-yl}(3-hydroxyazetidin-1-yl)methanone;

rac-{3-[(3S,4R)-4-(dimethylamino)-1-(7-fluoro-2,3-dihydro-1H-inden-1-yl)pyrrolidin-3-yl]-1-methyl-1H-indol-7-yl}(3-hydroxyazetidin-1-yl)methanone;

rac-{3-[(3S,4R)-4-(dimethylamino)-1-(7-fluoro-2,3-dihydro-1H-inden-1-yl)pyrrolidin-3-yl]-1-methyl-1H-indol-6-yl}(3-hydroxyazetidin-1-yl)methanone;

rac-3-[(3S,4R)-4-(dimethylamino)-1-(7-fluoro-2,3-dihydro-1H-inden-1-yl)pyrrolidin-3-yl]-N-(3-hydroxycyclobutyl)-1-methyl-1H-indole-7-carboxamide;

rac-3-[(3S,4R)-4-(dimethylamino)-1-(7-fluoro-2,3-dihydro-1H-inden-1-yl)pyrrolidin-3-yl]-N-(3-hydroxycyclobutyl)-N,1-dimethyl-1H-indole-7-carboxamide;

rac-{3-[(3S,4R)-4-(dimethylamino)-1-(7-fluoro-2,3-dihydro-1H-inden-1-yl)pyrrolidin-3-yl]-1-methyl-1H-indol-7-yl}[3-(methanesulfonyl)azetidin-1-yl]methanone;

rac-{3-[(3S,4R)-4-(dimethylamino)-1-(7-fluoro-2,3-dihydro-1H-inden-1-yl)pyrrolidin-3-yl]-1-methyl-1H-indol-6-yl}[(3S)-3-hydroxypyrrolidin-1-yl]methanone;

rac-{3-[(3S,4R)-4-(dimethylamino)-1-(7-fluoro-2,3-dihydro-1H-inden-1-yl)pyrrolidin-3-yl]-1-methyl-1H-indol-6-yl}[(3R)-3-hydroxypyrrolidin-1-yl]methanone;

rac-[(3S,4S)-3,4-dihydroxypyrrolidin-1-yl]{3-[(3S,4R)-4-(dimethylamino)-1-(7-fluoro-2,3-dihydro-1H-inden-1-yl)pyrrolidin-3-yl]-1-methyl-1H-indol-7-yl}methanone;

rac-[(3S,4S)-3,4-dihydroxypyrrolidin-1-yl]{3-[(3S,4R)-4-(dimethylamino)-1-(7-fluoro-2,3-dihydro-1H-inden-1-yl)pyrrolidin-3-yl]-1-methyl-1H-indol-6-yl}methanone;

rac-3-[(3S,4R)-4-(dimethylamino)-1-(7-fluoro-2,3-dihydro-1H-inden-1-yl)pyrrolidin-3-yl]-N-(1,1-dioxo-1lambda~6~-thiolan-3-yl)-1-methyl-1H-indole-7-carboxamide;

rac-{3-[(3S,4R)-4-(dimethylamino)-1-(7-fluoro-2,3-dihydro-1H-inden-1-yl)pyrrolidin-3-yl]-1-methyl-1H-indol-7-yl}[(2S)-2-(hydroxymethyl)pyrrolidin-1-yl]methanone;

rac-1-{3-[(3S,4R)-4-(dimethylamino)-1-(7-fluoro-2,3-dihydro-1H-inden-1-yl)pyrrolidin-3-yl]-1-methyl-1H-indole-7-carbonyl}-L-prolinamide;

rac-{3-[(3S,4R)-4-(dimethylamino)-1-(7-fluoro-2,3-dihydro-1H-inden-1-yl)pyrrolidin-3-yl]-1-methyl-1H-indol-7-yl}[(3S)-3-hydroxypyrrolidin-1-yl]methanone;

rac-{3-[(3S,4R)-4-(dimethylamino)-1-(7-fluoro-2,3-dihydro-1H-inden-1-yl)pyrrolidin-3-yl]-1-methyl-1H-indol-7-yl}(piperazin-1-yl)methanone;

rac-(3R,4S)-1-(7-fluoro-2,3-dihydro-1H-inden-1-yl)-4-{6-[4-(methanesulfonyl)piperazin-1-yl]-1-methyl-1H-indol-3-yl}-N,N-dimethylpyrrolidin-3-amine;

rac-1-(4-{3-[(3S,4R)-4-(dimethylamino)-1-(7-fluoro-2,3-dihydro-1H-inden-1-yl)pyrrolidin-3-yl]-1-methyl-1H-indol-7-yl}piperazin-1-yl)ethan-1-one;

rac-{3-[(3S,4R)-4-(dimethylamino)-1-(7-fluoro-2,3-dihydro-1H-inden-1-yl)pyrrolidin-3-yl]-1-methyl-1H-indol-6-yl}[4-(methanesulfonyl)piperazin-1-yl]methanone;

rac-1-(4-{3-[(3S,4R)-4-(dimethylamino)-1-(7-fluoro-2,3-dihydro-1H-inden-1-yl)pyrrolidin-3-yl]-1-methyl-1H-indole-6-carbonyl}piperazin-1-yl)ethan-1-one;

rac-4-{3-[(3S,4R)-4-(dimethylamino)-1-(7-fluoro-2,3-dihydro-1H-inden-1-yl)pyrrolidin-3-yl]-1-methyl-1H-indole-7-carbonyl}-N,N-dimethylpiperazine-1-sulfonamide;

rac-4-{3-[(3S,4R)-4-(dimethylamino)-1-(7-fluoro-2,3-dihydro-1H-inden-1-yl)pyrrolidin-3-yl]-1-methyl-1H-indole-7-carbonyl}-1-methylpiperazin-2-one;

rac-{3-[(3S,4R)-4-(dimethylamino)-1-(7-fluoro-2,3-dihydro-1H-inden-1-yl)pyrrolidin-3-yl]-1-methyl-1H-indol-7-yl}[4-(methanesulfonyl)piperazin-1-yl]methanone;

rac-4-{3-[(3S,4R)-4-(dimethylamino)-1-(7-fluoro-2,3-dihydro-1H-inden-1-yl)pyrrolidin-3-yl]-1-methyl-1H-indole-7-carbonyl}-N,N-dimethylpiperazine-1-carboxamide;

rac-1-(4-{3-[(3S,4R)-4-(dimethylamino)-1-(7-fluoro-2,3-dihydro-1H-inden-1-yl)pyrrolidin-3-yl]-1-methyl-1H-indole-7-carbonyl}piperazin-1-yl)ethan-1-one;

rac-4-{3-[(3S,4R)-4-(dimethylamino)-1-(7-fluoro-2,3-dihydro-1H-inden-1-yl)pyrrolidin-3-yl]-1-methyl-1H-indol-7-yl}-1-methylpiperazin-2-one;

rac-{3-[(3S,4R)-4-(dimethylamino)-1-(7-fluoro-2,3-dihydro-1H-inden-1-yl)pyrrolidin-3-yl]-1-methyl-1H-indol-7-yl}[4-(ethanesulfonyl)piperazin-1-yl]methanone;

rac-4-{3-[(3S,4R)-4-(dimethylamino)-1-(7-fluoro-2,3-dihydro-1H-inden-1-yl)pyrrolidin-3-yl]-1-methyl-1H-indol-7-yl}-N,N-dimethylpiperazine-1-carboxamide;

[4-(azetidine-1-sulfonyl)piperazin-1-yl]{3-[(3S,4R)-4-(dimethylamino)-1-(7-fluoro-2,3-dihydro-1H-inden-1-yl)pyrrolidin-3-yl]-1-methyl-1H-indol-7-yl}methanone;

1-(4-{3-[(3S,4R)-4-(dimethylamino)-1-(7-fluoro-2,3-dihydro-1H-inden-1-yl)pyrrolidin-3-yl]-1-methyl-1H-indole-7-carbonyl}piperazine-1-sulfonyl)azetidine-3-carbonitrile;

rac-8-{3-[(3S,4R)-4-(dimethylamino)-1-(7-fluoro-2,3-dihydro-1H-inden-1-yl)pyrrolidin-3-yl]-1-methyl-1H-indole-7-carbonyl}hexahydro-2H-pyrazino[1,2-a]pyrazin-1(6H)-one;

rac-{3-[(3S,4R)-4-(dimethylamino)-1-(7-fluoro-2,3-dihydro-1H-inden-1-yl)pyrrolidin-3-yl]-1-methyl-1H-indol-7-yl}[4-(1-methyl-1H-imidazole-5-sulfonyl)piperazin-1-yl]methanone;

rac-{3-[(3S,4R)-4-(dimethylamino)-1-(7-fluoro-2,3-dihydro-1H-inden-1-yl)pyrrolidin-3-yl]-1-methyl-1H-indol-7-yl}[4-(3,5-dimethyl-1H-pyrazole-4-sulfonyl)piperazin-1-yl]methanone;

rac-{3-[(3S,4R)-4-(dimethylamino)-1-(7-fluoro-2,3-dihydro-1H-inden-1-yl)pyrrolidin-3-yl]-1-methyl-1H-indol-7-yl}[4-(pyridazin-3-yl)piperazin-1-yl]methanone;

rac-(3R,4S)-1-[(1S)-7-fluoro-2,3-dihydro-1H-inden-1-yl]-N,N-dimethyl-4-(1-methyl-1H-pyrrolo[3,2-b]pyridin-3-yl)pyrrolidin-3-amine;

rac-(3S,4R)-4-(2,3-dihydro-1-benzofuran-3-yl)-1-[(1R)-7-fluoro-2,3-dihydro-1H-inden-1-yl]-N,N-dimethylpyrrolidin-3-amine;

rac-(3S,4R)-1-(7-fluoro-2,3-dihydro-1H-inden-1-yl)-N,N-dimethyl-4-(5,6,7,8-tetrahydroimidazo[1,2-a]pyridin-3-yl)pyrrolidin-3-amine;

rac-(3R,4S)-1-(7-fluoro-2,3-dihydro-1H-inden-1-yl)-N,N-dimethyl-4-(1-methyl-1H-pyrrolo[3,2-c]pyridin-3-yl)pyrrolidin-3-amine;

rac-(3R,4S)-4-(2,3-dihydro-1-benzofuran-3-yl)-1-[(1R)-7-fluoro-2,3-dihydro-1H-inden-1-yl]-N,N-dimethylpyrrolidin-3-amine;

rac-(3R,4S)-1-[(1R)-7-fluoro-2,3-dihydro-1H-inden-1-yl]-N,N-dimethyl-4-(1-methyl-1H-pyrrolo[3,2-b]pyridin-3-yl)pyrrolidin-3-amine;
rac-(3R,4S)-1-(7-fluoro-2,3-dihydro-1H-inden-1-yl)-N,N-dimethyl-4-(oxan-4-yl)pyrrolidin-3-amine;
rac-(3S,4R)-1-(7-fluoro-2,3-dihydro-1H-inden-1-yl)-N,N-dimethyl-4-[6-(piperazin-1-yl)pyridin-3-yl]pyrrolidin-3-amine;
rac-(3R,4S)-1-(7-fluoro-2,3-dihydro-1H-inden-1-yl)-N,N-dimethyl-4-(1-phenylpiperidin-4-yl)pyrrolidin-3-amine;
rac-2-(4-{5-[(3R,4S)-4-(dimethylamino)-1-(7-fluoro-2,3-dihydro-1H-inden-1-yl)pyrrolidin-3-yl]pyridin-2-yl}piperazin-1-yl)-N,N-dimethylacetamide;
rac-(3R,4S)-1-(7-fluoro-2,3-dihydro-1H-inden-1-yl)-N,N-dimethyl-4-(1-methyl-1H-pyrrolo[2,3-c]pyridin-3-yl)pyrrolidin-3-amine;
rac-(3R,4S)-1-(7-fluoro-2,3-dihydro-1H-inden-1-yl)-N,N-dimethyl-4-[1-(pyridin-3-yl)piperidin-4-yl]pyrrolidin-3-amine;
rac-2-(4-{5-[(3R,4S)-4-(dimethylamino)-1-(7-fluoro-2,3-dihydro-1H-inden-1-yl)pyrrolidin-3-yl]pyridin-2-yl}-1H-pyrazol-1-yl)-1-(3-hydroxyazetidin-1-yl)ethan-1-one;
rac-(4-{5-[(3R,4S)-4-(dimethylamino)-1-(7-fluoro-2,3-dihydro-1H-inden-1-yl)pyrrolidin-3-yl]pyridin-2-yl}piperazin-1-yl)(oxetan-3-yl)methanone;
rac-(3R,4S)-1-(7-fluoro-2,3-dihydro-1H-inden-1-yl)-N,N-dimethyl-4-[1-(pyridin-2-yl)piperidin-4-yl]pyrrolidin-3-amine;
rac-2-(4-{5-[(3R,4S)-4-(dimethylamino)-1-(7-fluoro-2,3-dihydro-1H-inden-1-yl)pyrrolidin-3-yl]pyridin-2-yl}-1H-pyrazol-1-yl)-1-(3-fluoroazetidin-1-yl)ethan-1-one;
rac-6-{4-[(3S,4R)-4-(dimethylamino)-1-(7-fluoro-2,3-dihydro-1H-inden-1-yl)pyrrolidin-3-yl]piperidin-1-yl}-N-methylpyridine-3-carboxamide;
rac-N-[2-(4-{5-[(3R,4S)-4-(dimethylamino)-1-(7-fluoro-2,3-dihydro-1H-inden-1-yl)pyrrolidin-3-yl]pyridin-2-yl}piperazin-1-yl)-2-oxoethyl]methanesulfonamide;
rac-(3R,4S)-1-(7-fluoro-2,3-dihydro-1H-inden-1-yl)-N,N-dimethyl-4-(1-methyl-1H-indazol-3-yl)pyrrolidin-3-amine;
rac-1-(4-{5-[(3R,4S)-4-(dimethylamino)-1-(7-fluoro-2,3-dihydro-1H-inden-1-yl)pyrrolidin-3-yl]pyridin-2-yl}piperazin-1-yl)-2-(methanesulfonyl)ethan-1-one;
rac-2-(4-{5-[(3R,4S)-4-(dimethylamino)-1-(7-fluoro-2,3-dihydro-1H-inden-1-yl)pyrrolidin-3-yl]pyridin-2-yl}-1H-pyrazol-1-yl)acetamide;
rac-2-(4-{5-[(3R,4S)-4-(dimethylamino)-1-(7-fluoro-2,3-dihydro-1H-inden-1-yl)pyrrolidin-3-yl]pyridin-2-yl}-1H-pyrazol-1-yl)-N,N-dimethylacetamide;
rac-2-(4-{5-[(3R,4S)-4-(dimethylamino)-1-(7-fluoro-2,3-dihydro-1H-inden-1-yl)pyrrolidin-3-yl]pyridin-2-yl}piperazin-1-yl)-2-oxoethane-1-sulfonamide;
rac-2-(4-{5-[(3R,4S)-4-(dimethylamino)-1-(7-fluoro-2,3-dihydro-1H-inden-1-yl)pyrrolidin-3-yl]pyridin-2-yl}-1H-pyrazol-1-yl)-N-methylacetamide;
rac-2-{4-[(3S,4R)-4-(dimethylamino)-1-(7-fluoro-2,3-dihydro-1H-inden-1-yl)pyrrolidin-3-yl]piperidin-1-yl}-1,3-thiazole-5-carboxamide;
rac-5-{4-[(3S,4R)-4-(dimethylamino)-1-(7-fluoro-2,3-dihydro-1H-inden-1-yl)pyrrolidin-3-yl]piperidin-1-yl}pyrazine-2-carboxamide;
rac-(3R,4S)-1-(7-fluoro-2,3-dihydro-1H-inden-1-yl)-N,N-dimethyl-4-(1-methyl-1H-pyrrolo[2,3-b]pyridin-3-yl)pyrrolidin-3-amine;
rac-6-{4-[(3S,4R)-4-(dimethylamino)-1-(7-fluoro-2,3-dihydro-1H-inden-1-yl)pyrrolidin-3-yl]piperidin-1-yl}pyridazine-3-carboxamide;
rac-4-{4-[(3S,4R)-4-(dimethylamino)-1-(7-fluoro-2,3-dihydro-1H-inden-1-yl)pyrrolidin-3-yl]piperidin-1-yl}benzamide;
rac-6-{4-[(3S,4R)-4-(dimethylamino)-1-(7-fluoro-2,3-dihydro-1H-inden-1-yl)pyrrolidin-3-yl]piperidin-1-yl}pyridine-3-carboxamide; and pharmaceutically acceptable salts thereof.

Another aspect pertains to a pharmaceutical composition comprising a pharmaceutically acceptable excipient and a therapeutically effective amount of a compound of Formula (I) or a pharmaceutically acceptable salt thereof.

Another aspect pertains to a method of treating cancer in a patient, comprising administering to a patient suffering from a cancer a therapeutically effective amount of a compound of Formula (I), or a pharmaceutically acceptable salt thereof.

DETAILED DESCRIPTION OF THE INVENTION

Abbreviations and Definitions

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition. In this application, the use of "or" means "and/or" unless stated otherwise. Furthermore, the use of the term "including", as well as other forms, such as "includes" and "included", is not limiting. With reference to the use of the words "comprise" or "comprises" or "comprising" in this patent application (including the claims), Applicants note that unless the context requires otherwise, those words are used on the basis and clear understanding that they are to be interpreted inclusively, rather than exclusively, and that Applicants intend each of those words to be so interpreted in construing this patent application, including the claims below. For a variable that occurs more than one time in any substituent or in the compound of the invention or any other formulae herein, its definition on each occurrence is independent of its definition at every other occurrence. Combinations of substituents are permissible only if such combinations result in stable compounds. Stable compounds are compounds which can be isolated in a useful degree of purity from a reaction mixture.

It is meant to be understood that proper valences are maintained for all combinations herein, that monovalent moieties having more than one atom are attached through their left ends, and that divalent moieties are drawn from left to right.

It is noted that, as used in this specification and the intended claims, the singular form "a," "an," and "the" include plural referents unless the context clearly dictates otherwise. Thus, for example, reference to "a compound" includes a single compound as well as one or more of the same or different compounds; reference to "optionally a pharmaceutically acceptable carrier" refers to a single optional pharmaceutically acceptable carrier as well as one or more pharmaceutically acceptable carriers, and the like.

As used in the specification and the appended claims, unless specified to the contrary, the following terms have the meaning indicated:

The term "alkenyl" as used herein, means a straight or branched hydrocarbon chain containing from 2 to 10 carbons and containing at least one carbon-carbon double bond.

Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" means a divalent group derived from a straight or branched chain hydrocarbon of from 2 to 10 carbon atoms containing at least one double bond. Representative examples of alkenylene include, but are not limited to, —CH═CH—, —CH═CH$_2$CH$_2$—, and —CH═C(CH$_3$)CH$_2$—.

The term "alkoxy" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkyl" as used herein, and likewise the term "alkyl" in alkylcarbonyl, alkylcarbonylamino, alkylsulfonyl and alkylsulfonylamino, means a straight or branched, saturated hydrocarbon chain containing from 1 to 10 carbon atoms. The term "lower alkyl" or "$C_1$-$C_6$ alkyl" means a straight or branched chain hydrocarbon containing from 1 to 6 carbon atoms. The term "$C_1$-$C_3$ alkyl" means a straight or branched chain hydrocarbon containing from 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene" denotes a divalent group derived from a straight or branched chain hydrocarbon containing from 1 to 10 carbon atoms. Representative examples of alkylene include, but are not limited to, —CH$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkynyl" as used herein, means a straight or branched chain hydrocarbon group containing from 2 to 10 carbon atoms and containing at least one carbon-carbon triple bond. Representative examples of alkynyl include, but are not limited to, acetylenyl, 1-propynyl, 2-propynyl, 3-butynyl, 2-pentynyl, and 1-butynyl.

The term "aryl" as used herein, means phenyl or a bicyclic aryl. The bicyclic aryl is naphthyl, or a phenyl fused to a monocyclic cycloalkyl, or a phenyl fused to a monocyclic cycloalkenyl. Representative examples of the aryl groups include, but are not limited to, dihydroindenyl, indenyl, naphthyl, dihydronaphthalenyl, and tetrahydronaphthalenyl. The bicyclic aryl is attached to the parent molecular moiety through any carbon atom contained within the bicyclic ring system. The aryl groups of the present invention can be unsubstituted or substituted.

The term "arylalkyl" as used herein, means an aryl group, as defined herein, appended to the parent molecular moiety through an alkylene group, as defined herein. Representative examples of arylalkyl include, but are not limited to, benzyl, 1-phenylethyl, 2-phenylethyl, 3-phenylpropyl, and 2-naphth-2-ylethyl.

The term "carbonyl" as used herein means a —C(═O)— group.

The term "cyano" as used herein, means a —CN group.

The term "cycloalkyl" or "cycloalkane" as used herein, means a monocyclic, a bicyclic, a tricyclic, or a spirocyclic cycloalkyl. The monocyclic cycloalkyl is a carbocyclic ring system containing three to eight carbon atoms, zero heteroatoms and zero double bonds. Examples of monocyclic ring systems include cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl ring, or a bridged monocyclic ring system in which two non-adjacent carbon atoms of the monocyclic ring are linked by an alkylene bridge containing one, two, three, or four carbon atoms. Representative examples of bicyclic ring systems include, but are not limited to, bicyclo [3.1.1]heptane, bicyclo[2.2.1]heptane, bicyclo[2.2.2]octane, bicyclo[3.2.2]nonane, bicyclo[3.3.1]nonane, and bicyclo [4.2.1]nonane. Tricyclic cycloalkyls are exemplified by a bicyclic cycloalkyl fused to a monocyclic cycloalkyl, or a bicyclic cycloalkyl in which two non-adjacent carbon atoms of the ring systems are linked by an alkylene bridge of 1, 2, 3, or 4 carbon atoms. Representative examples of tricyclic-ring systems include, but are not limited to, tricyclo[3.3.1.0$^{3,7}$]nonane (octahydro-2,5-methanopentalene or noradamantane), and tricyclo[3.3.1.1$^{3,7}$]decane (adamantane). The monocyclic, bicyclic, and tricyclic cycloalkyls can be unsubstituted or substituted, and are attached to the parent molecular moiety through any substitutable atom contained within the ring system. Spirocyclic cycloalkyl is exemplified by a monocyclic or a bicyclic cycloalkyl, wherein two of the substituents on the same carbon atom of the ring, together with said carbon atom, form a 4-, 5-, or 6-membered monocyclic cycloalkyl. An example of a spirocyclic cycloalkyl is spiro[2.5]octane. The spirocyclic cycloalkyl groups of the present invention can be appended to the parent molecular moiety through any substitutable carbon atom of the groups.

The term "cycloalkenyl" or "cycloalkene" as used herein, means a monocyclic, a bicyclic, a tricyclic, or a spirocyclic cycloalkenyl. The monocyclic cycloalkenyl is a partially unsaturated carbocyclic ring system containing from 4 or more carbon ring atoms ("ring atoms" are the atoms bound together to form the ring or rings of a cyclic substituent). A cycloalkenyl may be a single carbon ring, which typically contains from 4 to 8 carbon ring atoms and more typically from 4 to 6 ring atoms. Examples of single-ring cycloalkenyls include cyclobutenyl, cyclopentenyl, and cyclohexenyl. A cycloalkenyl may alternatively be polycyclic (contain more than one ring). Examples of polycyclic cycloalkenyls include bridged, fused, and spirocyclic cycloalkenyls.

The term "fluoroalkyl" as used herein, means an alkyl group, as defined herein, in which one, two, three, four, five, six, seven or eight hydrogen atoms are replaced by fluorine. Representative examples of haloalkyl include, but are not limited to, fluoromethyl, 2-fluoroethyl, 2,2-difluoroethyl, 2,2,2-trifluoroethyl, trifluoromethyl, difluoromethyl, pentafluoroethyl, 1,1,2-trifluoroisopropyl, and trifluoropropyl such as 3,3,3-trifluoropropyl.

The term "halo" or "halogen" as used herein, means Cl, Br, I, or F.

The term "haloalkyl" as used herein, means an alkyl group, as defined herein, in which one, two, three, four, five, six, seven or eight hydrogen atoms are replaced by halogen. Representative examples of haloalkyl include, but are not limited to, chloromethyl, 2-fluoroethyl, 2,2,2-trifluoroethyl, trifluoromethyl, difluoromethyl, pentafluoroethyl, 2-chloro-3-fluoropentyl, and trifluoropropyl such as 3,3,3-trifluoropropyl.

The term "heteroaryl" as used herein, means a heterocyclic aromatic radical and includes monocyclic heteroaryl and bicyclic heteroaryl. The monocyclic heteroaryl is a five- or six-membered ring. The five-membered ring contains two double bonds. The five-membered ring may contain one heteroatom selected from O or S; or one, two, three, or four nitrogen atoms and optionally one oxygen or sulfur atom. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl groups include, but are not limited to, benzofuranyl, benzothienyl, benzoxazolyl, benzimidazolyl, benzoxadiazolyl, 6,7-dihydro-1,3-benzothiazolyl, imidazo[1,2-a]pyridinyl, indazolyl, indolyl, isoindolyl, isoquinolinyl, naphthyridinyl, pyridoimidazolyl, quinolinyl, thiazolo[5,4-b]pyridin-2-yl, thiazolo[5,4-d]pyrimidin-2-yl, and 5,6,7,8-tetrahydroquinolin-5-yl. The monocyclic and bicyclic heteroaryl groups of the present invention can be substituted or unsubstituted and are connected to the parent molecular moiety through any carbon atom or any nitrogen atom contained within the ring systems.

The term "heteroarylalkyl", as used herein, refers to refers to a heteroaryl group attached to the parent molecular moiety through an alkyl group.

The term "heterocyclyl", "heterocycle" or "heterocyclic" as used herein, means a non-aromatic heterocyclic radical and includes a monocyclic heterocycle, a bicyclic heterocycle, a tricyclic heterocycle, or a spirocyclic heterocycle. If not stated otherwise, the heterocyclic radical is saturated or has one or two non-conjugated endocyclic double bounds, e.g. a C=N or C=C double bond. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.1$^{3,7}$]decane), oxa-adamantane (2-oxatricyclo[3.3.1.1$^{3,7}$]decane), and octahydro-1H-4,7-epiminoisoindole. The spirocyclic heterocycles are exemplified by a monocyclic heterocycle as defined herein wherein one carbon atom of the monocyclic heterocycle is bridged by two ends of an alkylene chain. In the spirocyclic heterocycle, one or more carbon atoms in the bridging alkylene chain may be replaced with a heteroatom. Examples of spirocyclic heterocycles include, but are not limited to, 4,7-diazaspiro[2.5]octane, 2-oxa-6-azaspiro[3.3]heptane, 2,6-diazaspiro[3.3]heptane, 2-oxa-5,8-diazaspiro[3.5]nonane, 2,7-diazaspiro[3.5]nonane, 1,4-dioxa-8-azaspiro[4.5]decane, 1,6-diazaspiro[3.3]heptane, 1-azaspiro[4.4]nonane, 7-azaspiro[3.5]nonane, 1,4-dioxa-7-azaspiro[4.4]nonane, 5,8-diazaspiro[3.5]nonane, 5,8-dioxa-2-azaspiro[3.4]octane, 2-oxa-6-azaspiro[3.4]octane, 6-oxa-1-azaspiro[3.3]heptane, 6-oxa-2-azaspiro[3.4]octane, 6-oxa-2-azaspiro[3.5]nonane, and 7-oxa-2-azaspiro[3.5]nonane. The monocyclic, bicyclic, tricyclic, and spirocyclic heterocycles are connected to the parent molecular moiety through any carbon atom or any nitrogen atom contained within the rings, and can be unsubstituted or substituted.

The term "heterocyclealkyl", as used herein, refers to refers to a heterocycle group attached to the parent molecular moiety through an alkyl group.

The term "heterocyclecarbonyl" refers to a heterocycle, as defined herein, appended to the parent molecular moiety through a carbonyl group, as defined herein. Representative examples of heterocyclecarbonyl include, but are not limited to, piperidine-1-carbonyl, morpholine-4-carbonyl, and pyrrolidine-1-carbonyl.

The term "heteroatom" as used herein, means a nitrogen, oxygen, or sulfur atom.

The term "hydroxyl" or "hydroxy" as used herein, means an —OH group.

The term "oxo" as used herein means (=O).

In some instances, the number of carbon atoms in a hydrocarbyl substituent (e.g., alkyl, alkenyl, alkynyl, cycloalkyl, haloalkyl, alkoxy, and haloalkoxy, etc.) is indicated by the prefix "$C_x$-$C_y$", wherein x is the minimum and y is the maximum number of carbon atoms in the substituent. Thus, for example, "$C_1$-$C_6$ alkyl" refers to an alkyl substituent containing from 1 to 6 carbon atoms. Illustrating further, $C_3$-$C_6$ cycloalkyl means a saturated hydrocarbyl ring containing from 3 to 6 carbon ring atoms.

As used herein, the term "radiolabel" refers to a compound of the invention in which at least one of the atoms is a radioactive atom or radioactive isotope, wherein the radioactive atom or isotope spontaneously emits gamma rays or energetic particles, for example alpha particles or beta particles, or positrons. Examples of such radioactive atoms include, but are not limited to, $^3$H (tritium), $^{14}$C, $^{11}$C, $^{15}$O, $^{18}$F, $^{35}$S, $^{123}$I, and $^{125}$I.

If a moiety is described as "substituted", a non-hydrogen radical is in the place of hydrogen radical of any substitutable atom of the moiety. Thus, for example, a substituted heterocycle moiety is a heterocycle moiety in which at least one non-hydrogen radical is in the place of a hydrogen radical on the heterocycle. It should be recognized that if there are more than one substitution on a moiety, each non-hydrogen radical may be identical or different (unless otherwise stated).

If a moiety is described as being "optionally substituted," the moiety may be either (1) not substituted or (2) substituted. If a moiety is described as being optionally substituted with up to a particular number of non-hydrogen radicals, that moiety may be either (1) not substituted; or (2) substituted by up to that particular number of non-hydrogen radicals or by up to the maximum number of substitutable positions on the moiety, whichever is less. Thus, for example, if a moiety is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

The terms "treat", "treating", and "treatment" refer to a method of alleviating or abrogating a disease and/or its attendant symptoms.

The terms "prevent", "preventing", and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

The phrase "therapeutically effective amount" means an amount of a compound, or a pharmaceutically acceptable salt thereof, sufficient to prevent the development of or to alleviate to some extent one or more of the symptoms of the condition or disorder being treated when administered alone or in conjunction with another therapeutic agent or treatment in a particular subject or subject population. For example in a human or other mammal, a therapeutically effective amount can be determined experimentally in a laboratory or clinical setting, or may be the amount required by the guidelines of the United States Food and Drug Administration, or equivalent foreign agency, for the particular disease and subject being treated.

The term "subject" is defined herein to refer to animals such as mammals, including, but not limited to, primates (e.g., humans), cows, sheep, goats, pigs, horses, dogs, cats, rabbits, rats, mice and the like. In some embodiments, the subject is a human.

The phrase "substituted with one or more substituents" means the moiety can be substituted by up to the maximum number of substitutable positions on the moiety.

Compounds

Geometric isomers may exist in the present compounds. Compounds of this invention may contain carbon-carbon double bonds or carbon-nitrogen double bonds in the E or Z configuration, wherein the term "E" represents higher order substituents on opposite sides of the carbon-carbon or carbon-nitrogen double bond and the term "Z" represents higher order substituents on the same side of the carbon-carbon or carbon-nitrogen double bond as determined by the Cahn-Ingold-Prelog Priority Rules. The compounds of this invention may also exist as a mixture of "E" and "Z" isomers. Substituents around a cycloalkyl or heterocycloalkyl may also be designated as being of cis or trans configuration.

Compounds of this invention may contain asymmetrically substituted carbon atoms in the R or S configuration, in which the terms "R" and "S" are as defined by the IUPAC 1974 Recommendations for Section E, Fundamental Stereochemistry, Pure Appl. Chem. (1976) 45, 13-10. Compounds having asymmetrically substituted carbon atoms with equal amounts of R and S configurations are racemic at those carbon atoms. Atoms with an excess of one configuration over the other are assigned the configuration present in the higher amount, preferably an excess of about 85%-90%, more preferably an excess of about 95%-99%, and still more preferably an excess greater than about 99%. Accordingly, this invention includes racemic mixtures, relative and absolute stereoisomers, and mixtures of relative and absolute stereoisomers.

Isotope Enriched or Labeled Compounds

Compounds of the invention can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to, $^2$H, $^3$H, $^{13}$C, $^{14}$C, $^{15}$N, $^{18}$O, $^{32}$P, $^{35}$S, $^{18}$F, $^{36}$Cl, and $^{125}$I. Compounds that contain other isotopes of these and/or other atoms are within the scope of this invention.

In another embodiment, the isotope-labeled compounds contain deuterium ($^2$H), tritium ($^3$H) or $^{14}$C isotopes. Isotope-labeled compounds of this invention can be prepared by the general methods well known to persons having ordinary skill in the art. Such isotope-labeled compounds can be conveniently prepared by carrying out the procedures disclosed in the Examples disclosed herein and Schemes by substituting a readily available isotope-labeled reagent for a non-labeled reagent. In some instances, compounds may be treated with isotope-labeled reagents to exchange a normal atom with its isotope, for example, hydrogen for deuterium can be exchanged by the action of a deuteric acid such as $D_2SO_4/D_2O$. In addition to the above, relevant procedures and intermediates are disclosed, for instance, in Lizondo, J et al., *Drugs Fut*, 21(11), 1116 (1996); Brickner, S J et al., *J Med Chem*, 39(3), 673 (1996); Mallesham, B et al., *Org Lett*, 5(7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; and 20090082471, the methods are hereby incorporated by reference.

The isotope-labeled compounds of the invention may be used as standards to determine the effectiveness of EED inhibitors in binding assays. Isotope containing compounds have been used in pharmaceutical research to investigate the in vivo metabolic fate of the compounds by evaluation of the mechanism of action and metabolic pathway of the nonisotope-labeled parent compound (Blake et al. *J. Pharm. Sci.* 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., *J. Labelled Comp. Radiopharmaceut.*, 36(10):927-932 (1995); Kushner et al., *Can. J. Physiol. Pharmacol.*, 77, 79-88 (1999).

In addition, non-radioactive isotope containing drugs, such as deuterated drugs called "heavy drugs," can be used for the treatment of diseases and conditions related to EED activity. Increasing the amount of an isotope present in a compound above its natural abundance is called enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Replacement of up to about 15% of normal atom with a heavy isotope has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci 1960 84: 736; Czajka D M et al., Am. J. Physiol. 1961 201: 357). Acute replacement of as high as 15%-23% in human fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Stable isotope labeling of a drug can alter its physicochemical properties such as pKa and lipid solubility. These effects and alterations can affect the pharmacodynamic response of the drug molecule if the isotopic substitution affects a region involved in a ligand-receptor interaction. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. Accordingly, the incorporation of an isotope at a site of metabolism or enzymatic transformation will slow said reactions potentially altering the pharmacokinetic profile or efficacy relative to the non-isotopic compound.

EMBODIMENTS

Suitable groups for $A^1$, $A^2$, $A^3$, $A^4$, $A^5$, n, and m in compounds of Formula (I), $A^3$, $A^4$, $A^5$, n, and m in compounds of Formula (IIa) and (IIb), and $A^3$ in compounds of Formulas (IIIa), (IIIb), (IVa), (IVb), (Va), (Vb), (VI), (VII), (VIII) and (IX) are independently selected. The described embodiments of the present invention may be combined. Such combination is contemplated and within the scope of the present invention. For example, it is contemplated that embodiments for any of $A^1$, $A^2$, $A^3$, $A^4$, $A^5$, n, and m, in compounds of Formula (I) can be combined with embodiments defined for any other of $A^1$, $A^2$, $A^3$, $A^4$, $A^5$, n, and m in compounds of Formula (I).

One embodiment pertains to compounds or pharmaceutically acceptable salts thereof, which are useful as inhibitors of EED, the compounds having Formula (I)

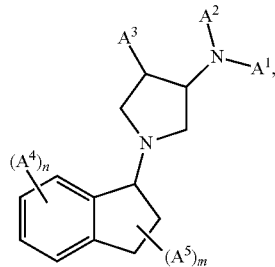

Formula (I)

wherein $A^1$ and $A^2$ are each independently $C_1$-$C_2$ alkyl;

$A^3$ is selected from the group consisting of aryl, heterocyclyl, and heteroaryl, wherein the $A^3$ aryl, heterocyclyl, and heteroaryl are optionally substituted with one or more substituents independently selected from the group consisting of $R^1$, $OR^1$, $SR^1$, $S(O)R^1$, $SO_2R^1$, $C(O)R^1$, $CO(O)R^1$, $OC(O)R^1$, $OC(O)OR^1$, $NH_2$, $NHR^1$, $N(R^1)_2$, $NHC(O)R^1$, $NR^1C(O)R^1$, $NHS(O)_2R^1$, $NR^1S(O)_2R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $C(O)NH_2$, $C(O)NHR^1$, $C(O)N(R^1)_2$, $C(O)NHOH$, $C(O)NHOR^1$, $C(O)NHSO_2R^1$, $C(O)NR^1SO_2R^1$, $SO_2NH_2$, $SO_2NHR^1$, $SO_2N(R^1)_2$, $C(O)H$, $C(O)OH$, $C(N)NH_2$, $C(N)NHR^1$, $C(N)N(R^1)_2$, CNOH, $CNOCH_3$, OH, (O), CN, $NO_2$, $CF_3$, $CF_2CF_3$, $OCF_3$, $OCF_2CF_3$, F, Cl, Br and I;

$A^4$, at each occurrence, is a substituent on a substitutable position of the benzene ring of the indane independently selected from the group consisting of $C_1$-$C_6$ alkyl, OH, F, Cl, Br and I;

$A^5$ is a substituent on a substitutable position of the cyclopentane ring of the indane independently selected from the group consisting of $C_1$-$C_6$ alkyl, OH, F, Cl, Br and I;

$R^1$, at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^1$ $C_1$-$C_6$ alkyl, $C_2$-$C_6$ alkenyl, and $C_2$-$C_6$ alkynyl is optionally substituted with one or more substituents independently selected from the group consisting of $R^2$, $OR^2$, $SR^2$, $S(O)R^2$, $SO_2R^2$, $C(O)R^2$, $CO(O)R^2$, $OC(O)R^2$, $OC(O)OR^2$, $NH_2$, $NHR^2$, $N(R^2)_2$, $NHC(O)R^2$, $NR^2C(O)R^2$, $NHS(O)_2R^2$, $NR^2S(O)_2R^2$, $NHC(O)OR^2$, $NR^2C(O)OR^2$, $NHC(O)NH_2$, $NHC(O)NHR^2$, $NHC(O)N(R^2)_2$, $NR^2C(O)NHR^2$, $NR^2C(O)N(R^2)_2$, $C(O)NH_2$, $C(O)NHR^2$, $C(O)N(R^2)_2$, $C(O)NHOH$, $C(O)NHOR^2$, $C(O)NHSO_2R^2$, $C(O)NR^2SO_2R^2$, $SO_2NH_2$, $SO_2NHR^2$, $SO_2N(R^2)_2$, $C(O)H$, $C(O)OH$, OH, (O), CN, $NO_2$, $CF_3$, $CF_2CF_3$, $OCF_3$, $OCF_2CF_3$, F, Cl, Br and I; wherein each $R^1$ aryl, heteroaryl, heterocyclyl, cycloalkyl, and cycloalkenyl is optionally substituted with one or more substituents independently selected from the group consisting of $R^3$, $OR^3$, $SR^3$, $S(O)R^3$, $SO_2R^3$, $C(O)R^3$, $CO(O)R^3$, $OC(O)R^3$, $OC(O)OR^3$, $NH_2$, $NHR^3$, $N(R^3)_2$, $NHC(O)R^3$, $NR^3C(O)R^3$, $NHS(O)_2R^3$, $NR^3S(O)_2R^3$, $NHC(O)OR^3$, $NR^3C(O)OR^3$, $NHC(O)NH_2$, $NHC(O)NHR^3$, $NHC(O)N(R^3)_2$, $NR^3C(O)NHR^3$, $NR^3C(O)N(R^3)_2$, $C(O)NH_2$, $C(O)NHR^3$, $C(O)N(R^3)_2$, $C(O)NHOH$, $C(O)NHOR^3$, $C(O)NHSO_2R^3$, $C(O)NR^3SO_2R^3$, $SO_2NH_2$, $SO_2NHR^3$, $SO_2N(R^3)_2$, $C(O)H$, $C(O)OH$, $C(O)C(O)NH_2$, $C(O)C(O)NHR^3$, $C(O)C(O)N(R^3)_2$, $C(N)NH_2$, $C(N)NHR^3$, $C(N)N$ $(R^3)_2$, CNOH, CNOCH$_3$, OH, (O), CN, NO$_2$, CF$_3$, CF$_2$CF$_3$, OCF$_3$, OCF$_2$CF$_3$, F, Cl, Br and I;

R$^2$, at each occurrence, is independently selected from the group consisting of C$_1$-C$_6$ alkyl, C$_2$-C$_6$ alkenyl, C$_2$-C$_6$ alkynyl, aryl, heteroaryl, heterocyclyl, cycloalkyl, and cycloalkenyl; wherein each R$^2$ C$_1$-C$_6$ alkyl, C$_2$-C$_6$ alkenyl, and C$_2$-C$_6$ alkynyl is optionally substituted with one or more substituents independently selected from the group consisting of NH$_2$, C(O)NH$_2$, SO$_2$NH$_2$, C(O)H, C(O)OH, OH, (O), CN, NO$_2$, CF$_3$, CF$_2$CF$_3$, OCF$_3$, OCF$_2$CF$_3$, F, Cl, Br and I; wherein each R$^2$ aryl, heteroaryl, heterocyclyl, cycloalkyl, and cycloalkenyl is optionally substituted with one or more substituents independently selected from the group consisting of NH$_2$, C(O)NH$_2$, SO$_2$NH$_2$, C(O)H, C(O)OH, OH, (O), CN, NO$_2$, CF$_3$, CF$_2$CF$_3$, OCF$_3$, OCF$_2$CF$_3$, F, Cl, Br and I;

R$^3$, at each occurrence, is independently selected from the group consisting of C$_1$-C$_6$ alkyl, C$_2$-C$_6$ alkenyl, C$_2$-C$_6$ alkynyl, aryl, heteroaryl, heterocyclyl, cycloalkyl, and cycloalkenyl; wherein each R$^3$ C$_1$-C$_6$ alkyl, C$_2$-C$_6$ alkenyl, and C$_2$-C$_6$ alkynyl is optionally substituted with one or more substituents independently selected from the group consisting of R$^4$, OR$^4$, SR$^4$, S(O)R$^4$, SO$_2$R$^4$, C(O)R$^4$, CO(O)R$^4$, OC(O)R$^4$, OC(O)OR$^4$, NH$_2$, NHR$^4$, N(R$^4$)$_2$, NHC(O)R$^4$, NR$^4$C(O)R$^4$, NHS(O)$_2$R$^4$, NR$^4$S(O)$_2$R$^4$, NHC(O)OR$^4$, NR$^4$C(O)OR$^4$, NHC(O)NH$_2$, NHC(O)NHR$^4$, NHC(O)N(R$^4$)$_2$, NR$^4$C(O)NHR$^4$, NR$^4$C(O)N(R$^4$)$_2$, C(O)NH$_2$, C(O)NHR$^4$, C(O)N(R$^4$)$_2$, C(O)NHOH, C(O)NHOR$^4$, C(O)NHSO$_2$R$^4$, C(O)NR$^4$SO$_2$R$^4$, SO$_2$NH$_2$, SO$_2$NHR$^4$, SO$_2$N(R$^4$)$_2$, C(O)H, C(O)OH, OH, (O), CN, NO$_2$, CF$_3$, CF$_2$CF$_3$, OCF$_3$, OCF$_2$CF$_3$, F, Cl, Br and I; wherein each R$^3$ aryl, heteroaryl, heterocyclyl, cycloalkyl, and cycloalkenyl is optionally substituted with one or more substituents independently selected from the group consisting of R$^5$, OR$^5$, SR$^5$, S(O)R$^5$, SO$_2$R$^5$, C(O)R$^5$, CO(O)R$^5$, OC(O)R$^5$, OC(O)OR$^5$, NH$_2$, NHR$^5$, N(R$^5$)$_2$, NHC(O)R$^5$, NR$^5$C(O)R$^5$, NHS(O)$_2$R$^5$, NR$^5$S(O)$_2$R$^5$, NHC(O)OR$^5$, NR$^5$C(O)OR$^5$, NHC(O)NH$_2$, NHC(O)NHR$^5$, NHC(O)N(R$^5$)$_2$, NR$^5$C(O)NHR$^5$, NR$^5$C(O)N(R$^5$)$_2$, C(O)NH$_2$, C(O)NHR$^5$, C(O)N(R$^5$)$_2$, C(O)NHOH, C(O)NHOR$^5$, C(O)NHSO$_2$R$^5$, C(O)NR$^5$SO$_2$R$^5$, SO$_2$NH$_2$, SO$_2$NHR$^5$, SO$_2$N(R$^5$)$_2$, C(O)H, C(O)OH, C(N)NH$_2$, C(N)NHR$^5$, C(N)N(R$^5$)$_2$, CNOH, CNOCH$_3$, OH, (O), CN, NO$_2$, CF$_3$, CF$_2$CF$_3$, OCF$_3$, OCF$_2$CF$_3$, F, Cl, Br and I;

R$^4$ is at each occurrence, is independently selected from the group consisting of C$_1$-C$_6$ alkyl, C$_2$-C$_6$ alkenyl, C$_2$-C$_6$ alkynyl, aryl, heteroaryl, heterocyclyl, cycloalkyl, and cycloalkenyl; wherein each R$^4$ C$_1$-C$_6$ alkyl, C$_2$-C$_6$ alkenyl, and C$_2$-C$_6$ alkynyl is optionally substituted with one or more substituents independently selected from the group consisting of NH$_2$, C(O)NH$_2$, SO$_2$NH$_2$, C(O)H, C(O)OH, OH, (O), CN, NO$_2$, CF$_3$, CF$_2$CF$_3$, OCF$_3$, OCF$_2$CF$_3$, F, Cl, Br and I; wherein each R$^4$ aryl, heteroaryl, heterocyclyl, cycloalkyl, and cycloalkenyl is optionally substituted with one or more substituents independently selected from the group consisting of NH$_2$, C(O)NH$_2$, SO$_2$NH$_2$, C(O)H, C(O)OH, OH, (O), CN, NO$_2$, CF$_3$, CF$_2$CF$_3$, OCF$_3$, OCF$_2$CF$_3$, F, Cl, Br and I;

R$^5$ is at each occurrence, is independently selected from the group consisting of C$_1$-C$_6$ alkyl, C$_2$-C$_6$ alkenyl, C$_2$-C$_6$ alkynyl, aryl, heteroaryl, heterocyclyl, cycloalkyl, and cycloalkenyl; wherein each R$^5$ C$_1$-C$_6$ alkyl, C$_2$-C$_6$ alkenyl, and C$_2$-C$_6$ alkynyl is optionally substituted with one or more substituents independently selected from the group consisting of NH$_2$, C(O)NH$_2$, SO$_2$NH$_2$, C(O)H, C(O)OH, OH, (O), CN, NO$_2$, CF$_3$, CF$_2$CF$_3$, OCF$_3$, OCF$_2$CF$_3$, F, Cl, Br and I; wherein each R$^5$ aryl, heteroaryl, heterocyclyl, cycloalkyl, and cycloalkenyl is optionally substituted with one or more substituents independently selected from the group consisting of NH$_2$, C(O)NH$_2$, SO$_2$NH$_2$, C(O)H, C(O)OH, OH, (O), CN, NO$_2$, CF$_3$, CF$_2$CF$_3$, OCF$_3$, OCF$_2$CF$_3$, F, Cl, Br and I;

n is 0, 1, or 2; and m is 0 or 1.

In one embodiment of Formula (I), A$^1$ and A$^2$ are each independently C$_1$-C$_2$ alkyl. In another embodiment of Formula (I), A$^1$ and A$^2$ are each independently C$_2$ alkyl. In another embodiment of Formula (I), A$^1$ and A$^2$ are each independently C$_1$ alkyl. In another embodiment of Formula (I), one of A$^1$ and A$^2$ is independently C$_1$ alkyl; and the other is C$_2$ alkyl.

In one embodiment of Formula (I), A$^3$ is selected from the group consisting of aryl, heterocyclyl, and heteroaryl, wherein the A$^3$ aryl, heterocyclyl, and heteroaryl are optionally substituted with one or more substituents independently selected from the group consisting of R$^1$, OR$^1$, SR$^1$, S(O)R$^1$, SO$_2$R$^1$, C(O)R$^1$, CO(O)R$^1$, OC(O)R$^1$, OC(O)OR$^1$, NH$_2$, NHR$^1$, N(R$^1$)$_2$, NHC(O)R$^1$, NR$^1$C(O)R$^1$, NHS(O)$_2$R$^1$, NR$^1$S(O)$_2$R$^1$, NHC(O)OR$^1$, NR$^1$C(O)OR$^1$, NHC(O)NH$_2$, NHC(O)NHR$^1$, NHC(O)N(R$^1$)$_2$, NR$^1$C(O)NHR$^1$, NR$^1$C(O)N(R$^1$)$_2$, C(O)NH$_2$, C(O)NHR$^1$, C(O)N(R$^1$)$_2$, C(O)NHOH, C(O)NHOR$^1$, C(O)NHSO$_2$R$^1$, C(O)NR$^1$SO$_2$R$^1$, SO$_2$NH$_2$, SO$_2$NHR$^1$, SO$_2$N(R$^1$)$_2$, C(O)H, C(O)OH, C(N)NH$_2$, C(N)NHR$^1$, C(N)N(R$^1$)$_2$, CNOH, CNOCH$_3$, OH, (O), CN, NO$_2$, CF$_3$, CF$_2$CF$_3$, OCF$_3$, OCF$_2$CF$_3$, F, Cl, Br and I. In another embodiment of Formula (I), A$^3$ is selected from the group consisting of aryl, heterocyclyl, and heteroaryl, wherein the A$^3$ aryl, heterocyclyl, and heteroaryl are optionally substituted with one or more substituents independently selected from the group consisting of R$^1$, OR$^1$, SO$_2$R$^1$, C(O)R$^1$, CO(O)R$^1$, C(O)NH$_2$, C(O)NHR$^1$, C(O)N(R$^1$)$_2$, SO$_2$NH$_2$, C(O)OH, CN, F, Cl, Br and I. In another embodiment of Formula (I), A$^3$ is aryl, wherein the A$^3$ aryl is optionally substituted with one or more substituents independently selected from the group consisting of R$^1$, OR$^1$, SO$_2$R$^1$, C(O)R$^1$, CO(O)R$^1$, C(O)NH$_2$, C(O)NHR$^1$, C(O)N(R$^1$)$_2$, SO$_2$NH$_2$, C(O)OH, CN, F, Cl, Br and I. In another embodiment of Formula (I), A$^3$ is aryl, wherein the A$^3$ aryl is substituted with one substituent independently selected from the group consisting of R$^1$, OR$^1$, SO$_2$R$^1$, C(O)R$^1$, CO(O)R$^1$, C(O)NH$_2$, C(O)NHR$^1$, C(O)N(R$^1$)$_2$, SO$_2$NH$_2$, C(O)OH, CN, F, Cl, Br and I. In another embodiment of Formula (I), A$^3$ is aryl, wherein the A$^3$ aryl is substituted with two substituents independently selected from the group consisting of R$^1$, OR$^1$, SO$_2$R$^1$, C(O)R$^1$, CO(O)R$^1$, C(O)NH$_2$, C(O)NHR$^1$, C(O)N(R$^1$)$_2$, SO$_2$NH$_2$, C(O)OH, CN, F, Cl, Br and I. In another embodiment of Formula (I), A$^3$ is heterocyclyl, wherein the A$^3$ heterocyclyl is optionally substituted with one or more substituents independently selected from the group consisting of R$^1$, OR$^1$, SO$_2$R$^1$, C(O)R$^1$, CO(O)R$^1$, C(O)NH$_2$, C(O)NHR$^1$, C(O)N(R$^1$)$_2$, SO$_2$NH$_2$, C(O)OH, CN, F, Cl, Br and I. In another embodiment of Formula (I), A$^3$ is heterocyclyl, wherein the A$^3$ heterocyclyl is unsubstituted. In another embodiment of Formula (I), A$^3$ is heterocyclyl, wherein the A$^3$ heterocyclyl is substituted with one substituent independently selected from the group consisting of R$^1$, OR$^1$, SO$_2$R$^1$, C(O)R$^1$, CO(O)R$^1$, C(O)NH$_2$, C(O)NHR$^1$, C(O)N(R$^1$)$_2$, SO$_2$NH$_2$, C(O)OH, CN, F, Cl, Br and I. In another embodiment of Formula (I), A$^3$ is heterocyclyl, wherein the A$^3$ heterocyclyl is substituted with two substituents independently selected from the group consisting of R$^1$, OR$^1$, SO$_2$R$^1$, C(O)R$^1$, CO(O)R$^1$, C(O)NH$_2$, C(O)NHR$^1$, C(O)N(R$^1$)$_2$, SO$_2$NH$_2$, C(O)OH, CN, F, Cl, Br and I. In another embodiment of Formula (I), A$^3$ is heteroaryl, wherein the A$^3$ heteroaryl is optionally substituted with one or more substituents independently selected from the group consisting of R$^1$, OR$^1$, SO$_2$R$^1$, C(O)R$^1$, CO(O)R$^1$, C(O)

NH$_2$, C(O)NHR$^1$, C(O)N(R$^1$)$_2$, SO$_2$NH$_2$, C(O)OH, CN, F, Cl, Br and I. In another embodiment of Formula (I), A$^3$ is heteroaryl, wherein the A$^3$ heteroaryl is unsubstituted. In another embodiment of Formula (I), A$^3$ is heteroaryl, wherein the A$^3$ heteroaryl is substituted with one substituent independently selected from the group consisting of R$^1$, OR$^1$, SO$_2$R$^1$, C(O)R$^1$, CO(O)R$^1$, C(O)NH$_2$, C(O)NHR$^1$, C(O)N(R$^1$)$_2$, SO$_2$NH$_2$, C(O)OH, CN, F, Cl, Br and I. In another embodiment of Formula (I), A$^3$ is heteroaryl, wherein the A$^3$ heteroaryl is substituted with two substituents independently selected from the group consisting of R$^1$, OR$^1$, SO$_2$R$^1$, C(O)R$^1$, CO(O)R$^1$, C(O)NH$_2$, C(O)NHR$^1$, C(O)N(R$^1$)$_2$, SO$_2$NH$_2$, C(O)OH, CN, F, Cl, Br and I.

In one embodiment of Formula (I), n is 0, 1, or 2; and A$^4$, at each occurrence, is a substituent on a substitutable position of the benzene ring of the indane independently selected from the group consisting of C$_1$-C$_6$ alkyl, OH, F, Cl, Br and I. In another embodiment of Formula (I), n is 0. In another embodiment of Formula (I), n is 1; and A$^4$ is a substituent on a substitutable position of the benzene ring of the indane independently selected from the group consisting of C$_1$-C$_6$ alkyl, OH, F, Cl, Br and I. In another embodiment of Formula (I), n is 2; and A$^4$, at each occurrence, is a substituent on a substitutable position of the benzene ring of the indane independently selected from the group consisting of OH and F. In another embodiment of Formula (I), n is 2; and A$^4$, at each occurrence, is F.

In one embodiment of Formula (I), m is 0 or 1; and A$^5$ is a substituent on a substitutable position of the cyclopentane ring of the indane independently selected from the group consisting of C$_1$-C$_6$ alkyl, OH, F, Cl, Br and I. In another embodiment of Formula (I), m is 0. In another embodiment of Formula (I), m is 1; and A$^5$ is a substituent on a substitutable position of the cyclopentane ring of the indane independently selected from the group consisting of C$_1$-C$_6$ alkyl, OH, F, Cl, Br and I. In another embodiment of Formula (I), m is 1; and A$^5$ is a substituent on a substitutable position of the cyclopentane ring of the indane independently selected from the group consisting of OH and F. In another embodiment of Formula (I), m is 1; and A$^5$ is OH. In another embodiment of Formula (I), m is 1; and A$^5$ is F.

In one embodiment of Formula (I), R$^1$, at each occurrence, is independently selected from the group consisting of C$_1$-C$_6$ alkyl, C$_2$-C$_6$ alkenyl, C$_2$-C$_6$ alkynyl, aryl, heteroaryl, heterocyclyl, cycloalkyl, and cycloalkenyl; wherein each R$^1$ C$_1$-C$_6$ alkyl, C$_2$-C$_6$ alkenyl, and C$_2$-C$_6$ alkynyl is optionally substituted with one or more substituents independently selected from the group consisting of R$^2$, OR$^2$, SR$^2$, S(O)R$^2$, SO$_2$R$^2$, C(O)R$^2$, CO(O)R$^2$, OC(O)R$^2$, OC(O)OR$^2$, NH$_2$, NHR$^2$, N(R$^2$)$_2$, NHC(O)R$^2$, NR$^2$C(O)R$^2$, NHS(O)$_2$R$^2$, NR$^2$S(O)$_2$R$^2$, NHC(O)OR$^2$, NR$^2$C(O)OR$^2$, NHC(O)NH$_2$, NHC(O)NHR$^2$, NHC(O)N(R$^2$)$_2$, NR$^2$C(O)NHR$^2$, NR$^2$C(O)N(R$^2$)$_2$, C(O)NH$_2$, C(O)NHR$^2$, C(O)N(R$^2$)$_2$, C(O)NHOH, C(O)NHOR$^2$, C(O)NHSO$_2$R$^2$, C(O)NR$^2$SO$_2$R$^2$, SO$_2$NH$_2$, SO$_2$NHR$^2$, SO$_2$N(R$^2$)$_2$, C(O)H, C(O)OH, OH, (O), CN, NO$_2$, CF$_3$, CF$_2$CF$_3$, OCF$_3$, OCF$_2$CF$_3$, F, Cl, Br and I; wherein each R$^1$ aryl, heteroaryl, heterocyclyl, cycloalkyl, and cycloalkenyl is optionally substituted with one or more substituents independently selected from the group consisting of R$^3$, OR$^3$, SR$^3$, S(O)R$^3$, SO$_2$R$^3$, C(O)R$^3$, CO(O)R$^3$, OC(O)R$^3$, OC(O)OR$^3$, NH$_2$, NHR$^3$, N(R$^3$)$_2$, NHC(O)R$^3$, NR$^3$C(O)R$^3$, NHS(O)$_2$R$^3$, NR$^3$S(O)$_2$R$^3$, NHC(O)OR$^3$, NR$^3$C(O)OR$^3$, NHC(O)NH$_2$, NHC(O)NHR$^3$, NHC(O)N(R$^3$)$_2$, NR$^3$C(O)NHR$^3$, NR$^3$C(O)N(R$^3$)$_2$, C(O)NH$_2$, C(O)NHR$^3$, C(O)N(R$^3$)$_2$, C(O)NHOH, C(O)NHOR$^3$, C(O)NHSO$_2$R$^3$, C(O)NR$^3$SO$_2$R$^3$, SO$_2$NH$_2$, SO$_2$NHR$^3$, SO$_2$N(R$^3$)$_2$, C(O)H, C(O)OH, C(O)C(O)NH$_2$, C(O)C(O)NHR$^3$, C(O)C(O)N(R$^3$)$_2$, C(N)NH$_2$, C(N)NHR$^3$, C(N)N(R$^3$)$_2$, CNOH, CNOCH$_3$, OH, (O), CN, NO$_2$, CF$_3$, CF$_2$CF$_3$, OCF$_3$, OCF$_2$CF$_3$, F, Cl, Br and I. In another embodiment of Formula (I), R$^1$, at each occurrence, is C$_1$-C$_6$ alkyl; wherein each R$^1$ C$_1$-C$_6$ alkyl is optionally substituted with one or more substituents independently selected from the group consisting of C(O)OH and OH. In another embodiment of Formula (I), R$^1$, at each occurrence, is independently selected from the group consisting of aryl, heteroaryl, heterocyclyl, and cycloalkyl; wherein each R$^1$ aryl, heteroaryl, heterocyclyl, and cycloalkyl is optionally substituted with one or more substituents independently selected from the group consisting of R$^3$, SO$_2$R$^3$, C(O)R$^3$, CO(O)R$^3$, C(O)NH$_2$, C(O)NHR$^3$, C(O)N(R$^3$)$_2$, SO$_2$N(R$^3$)$_2$, C(O)C(O)NH$_2$, C(O)C(O)N(R$^3$)$_2$, OH, (O), and F.

In one embodiment of Formula (I), R$^3$, at each occurrence, is independently selected from the group consisting of C$_1$-C$_6$ alkyl, C$_2$-C$_6$ alkenyl, C$_2$-C$_6$ alkynyl, aryl, heteroaryl, heterocyclyl, cycloalkyl, and cycloalkenyl; wherein each R$^3$ C$_1$-C$_6$ alkyl, C$_2$-C$_6$ alkenyl, and C$_2$-C$_6$ alkynyl is optionally substituted with one or more substituents independently selected from the group consisting of R$^4$, OR$^4$, SR$^4$, S(O)R$^4$, SO$_2$R$^4$, C(O)R$^4$, CO(O)R$^4$, OC(O)R$^4$, OC(O)OR$^4$, NH$_2$, NHR$^4$, N(R$^4$)$_2$, NHC(O)R$^4$, NR$^4$C(O)R$^4$, NHS(O)$_2$R$^4$, NR$^4$S(O)$_2$R$^4$, NHC(O)OR$^4$, NR$^4$C(O)OR$^4$, NHC(O)NH$_2$, NHC(O)NHR$^4$, NHC(O)N(R$^4$)$_2$, NR$^4$C(O)NHR$^4$, NR$^4$C(O)N(R$^4$)$_2$, C(O)NH$_2$, C(O)NHR$^4$, C(O)N(R$^4$)$_2$, C(O)NHOH, C(O)NHOR$^4$, C(O)NHSO$_2$R$^4$, C(O)NR$^4$SO$_2$R$^4$, SO$_2$NH$_2$, SO$_2$NHR$^4$, SO$_2$N(R$^4$)$_2$, C(O)H, C(O)OH, OH, (O), CN, NO$_2$, CF$_3$, CF$_2$CF$_3$, OCF$_3$, OCF$_2$CF$_3$, F, Cl, Br and I; wherein each R$^3$ aryl, heteroaryl, heterocyclyl, cycloalkyl, and cycloalkenyl is optionally substituted with one or more substituents independently selected from the group consisting of R$^5$, OR$^5$, SR$^5$, S(O)R$^5$, SO$_2$R$^5$, C(O)R$^5$, CO(O)R$^5$, OC(O)R$^5$, OC(O)OR$^5$, NH$_2$, NHR$^5$, N(R$^5$)$_2$, NHC(O)R$^5$, NR$^5$C(O)R$^5$, NHS(O)$_2$R$^5$, NR$^5$S(O)$_2$R$^5$, NHC(O)OR$^5$, NR$^5$C(O)OR$^5$, NHC(O)NH$_2$, NHC(O)NHR$^5$, NHC(O)N(R$^5$)$_2$, NR$^5$C(O)NHR$^5$, NR$^5$C(O)N(R$^5$)$_2$, C(O)NH$_2$, C(O)NHR$^5$, C(O)N(R$^5$)$_2$, C(O)NHOH, C(O)NHOR$^5$, C(O)NHSO$_2$R$^5$, C(O)NR$^5$SO$_2$R$^5$, SO$_2$NH$_2$, SO$_2$NHR$^5$, SO$_2$N(R$^5$)$_2$, C(O)H, C(O)OH, C(N)NH$_2$, C(N)NHR$^5$, C(N)N(R$^5$)$_2$, CNOH, CNOCH$_3$, OH, (O), CN, NO$_2$, CF$_3$, CF$_2$CF$_3$, OCF$_3$, OCF$_2$CF$_3$, F, Cl, Br and I. In another embodiment of Formula (I), R$^3$, at each occurrence, is independently C$_1$-C$_6$ alkyl; wherein each R$^3$ C$_1$-C$_6$ alkyl is optionally substituted with one or more substituents independently selected from the group consisting of SO$_2$R$^4$, C(O)R$^4$, NHS(O)$_2$R$^4$, C(O)NH$_2$, C(O)NHR$^4$, C(O)N(R$^4$)$_2$, SO$_2$NH$_2$, and OH. In another embodiment of Formula (I), R$^3$, at each occurrence, is independently selected from the group consisting of heteroaryl, heterocyclyl, and cycloalkyl; wherein each R$^3$ heteroaryl, heterocyclyl, and cycloalkyl is optionally substituted with one or more substituents independently selected from the group consisting of R$^5$ and CN.

In one embodiment of Formula (I), R$^4$ is at each occurrence, is independently selected from the group consisting of C$_1$-C$_6$ alkyl, C$_2$-C$_6$ alkenyl, C$_2$-C$_6$ alkynyl, aryl, heteroaryl, heterocyclyl, cycloalkyl, and cycloalkenyl; wherein each R$^4$ C$_1$-C$_6$ alkyl, C$_2$-C$_6$ alkenyl, and C$_2$-C$_6$ alkynyl is optionally substituted with one or more substituents independently selected from the group consisting of NH$_2$, C(O)NH$_2$, SO$_2$NH$_2$, C(O)H, C(O)OH, OH, (O), CN, NO$_2$, CF$_3$, CF$_2$CF$_3$, OCF$_3$, OCF$_2$CF$_3$, F, Cl, Br and I; wherein each R$^4$ aryl, heteroaryl, heterocyclyl, cycloalkyl, and cycloalkenyl is optionally substituted with one or more substituents independently selected from the group consisting of NH$_2$, C(O)NH$_2$, SO$_2$NH$_2$, C(O)H, C(O)OH, OH, (O), CN, NO$_2$, CF₃, CF₂CF₃, OCF₃, OCF₂CF₃, F, Cl, Br and I. In another embodiment of Formula (I), R⁴ at each occurrence, is $C_1$-$C_6$ alkyl. In another embodiment of Formula (I), R⁴ at each occurrence, is heterocyclyl; wherein each R⁴ heterocyclyl is optionally substituted with one or more substituents independently selected from the group consisting of OH, and F.

In one embodiment of Formula (I), R⁵ is at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each R⁵ $C_1$-$C_6$ alkyl, $C_2$-$C_6$ alkenyl, and $C_2$-$C_6$ alkynyl is optionally substituted with one or more substituents independently selected from the group consisting of NH₂, C(O)NH₂, SO₂NH₂, C(O)H, C(O)OH, OH, (O), CN, NO₂, CF₃, CF₂CF₃, OCF₃, OCF₂CF₃, F, Cl, Br and I; wherein each R⁵ aryl, heteroaryl, heterocyclyl, cycloalkyl, and cycloalkenyl is optionally substituted with one or more substituents independently selected from the group consisting of NH₂, C(O)NH₂, SO₂NH₂, C(O)H, C(O)OH, OH, (O), CN, NO₂, CF₃, CF₂CF₃, OCF₃, OCF₂CF₃, F, Cl, Br and I. In another embodiment of Formula (I), R⁵ is at each occurrence, is independently $C_1$-$C_6$ alkyl.

In one embodiment of Formula (I),

A¹ and A² are each independently $C_1$-$C_2$ alkyl;

A³ is selected from the group consisting of aryl, heterocyclyl, and heteroaryl, wherein the A³ aryl, heterocyclyl, and heteroaryl are optionally substituted with one or more substituents independently selected from the group consisting of R¹, OR¹, SO₂R¹, C(O)R¹, CO(O)R¹, C(O)NH₂, C(O)NHR¹, C(O)N(R¹)₂, SO₂NH₂, C(O)OH, CN, F, Cl, Br and I;

A⁴, at each occurrence, is a substituent on a substitutable position of the benzene ring of the indane independently selected from the group consisting of $C_1$-$C_6$ alkyl, OH, F, Cl, Br and I;

A⁵ is a substituent on a substitutable position of the cyclopentane ring of the indane independently selected from the group consisting of OH, F, Cl, Br and I;

R¹, at each occurrence, is independently selected from the group consisting of $C_1$-$C_6$ alkyl, aryl, heteroaryl, heterocyclyl, and cycloalkyl; wherein each R¹ $C_1$-$C_6$ alkyl is optionally substituted with one or more substituents independently selected from the group consisting of C(O)OH, OH, F, Cl, Br and I; wherein each R¹ aryl, heteroaryl, heterocyclyl, cycloalkyl, and cycloalkenyl is optionally substituted with one or more substituents independently selected from the group consisting of R³, SO₂R³, C(O)R³, CO(O)R³, C(O)NH₂, C(O)NHR³, C(O)N(R³)₂, SO₂N(R³)₂, C(O)C(O)NH₂, C(O)C(O)N(R³)₂, OH, (O), F, Cl, Br and I;

R³, at each occurrence, is independently selected from the group consisting of $C_1$-$C_6$ alkyl, heteroaryl, heterocyclyl, and cycloalkyl; wherein each R³ $C_1$-$C_6$ alkyl is optionally substituted with one or more substituents independently selected from the group consisting of SO₂R⁴, C(O)R⁴, NHS(O)₂R⁴, C(O)NH₂, C(O)NHR⁴, C(O)N(R⁴)₂, SO₂NH₂, F, Cl, Br and I; wherein each R³ heteroaryl and heterocyclyl is optionally substituted with one or more substituents independently selected from the group consisting of R⁵, CN, F, Cl, Br and I;

R⁴ is at each occurrence, is independently selected from the group consisting of $C_1$-$C_6$ alkyl and heterocyclyl; wherein each R⁴ heterocyclyl is optionally substituted with one or more substituents independently selected from the group consisting of OH, F, Cl, Br and I;

R⁵ is at each occurrence, is independently $C_1$-$C_6$ alkyl;

n is 0, 1, or 2; and m is 0 or 1.

Still another embodiment pertains to compounds of Formula (I), selected from the group consisting of:

(3R,4S)-1-(7-fluoro-2,3-dihydro-1H-inden-1-yl)-4-{4-[4-(methanesulfonyl)piperazin-1-yl]phenyl}-N,N-dimethylpyrrolidin-3-amine;

rac-(3R,4S)-1-(7-fluoro-2,3-dihydro-1H-inden-1-yl)-4-{4-[4-(methanesulfonyl)piperazin-1-yl]phenyl}-N,N-dimethylpyrrolidin-3-amine;

(3S,4R)-1-(7-fluoro-2,3-dihydro-1H-inden-1-yl)-4-{4-[4-(methanesulfonyl)piperazin-1-yl]phenyl}-N,N-dimethylpyrrolidin-3-amine;

(3S,4R)-1-[(1S)-7-fluoro-2,3-dihydro-1H-inden-1-yl]-4-{4-[4-(methanesulfonyl)piperazin-1-yl]phenyl}-N,N-dimethylpyrrolidin-3-amine;

(3S,4R)-1-[(1R)-7-fluoro-2,3-dihydro-1H-inden-1-yl]-4-{4-[4-(methanesulfonyl)piperazin-1-yl]phenyl}-N,N-dimethylpyrrolidin-3-amine;

rac-(3S,4R)-4-(4-bromophenyl)-1-(7-fluoro-2,3-dihydro-1H-inden-1-yl)-N,N-dimethylpyrrolidin-3-amine;

rac-(3S,4R)-4-(4-chlorophenyl)-1-(7-fluoro-2,3-dihydro-1H-inden-1-yl)-N,N-dimethylpyrrolidin-3-amine;

rac-4-[(3S,4R)-4-(dimethylamino)-1-(7-fluoro-2,3-dihydro-1H-inden-1-yl)pyrrolidin-3-yl]benzene-1-sulfonamide;

(3R,4S)-1-[(1S)-2,3-dihydro-1H-inden-1-yl]-4-[4-(methanesulfonyl)phenyl]-N,N-dimethylpyrrolidin-3-amine;

(3S,4R)-1-[(1S)-2,3-dihydro-1H-inden-1-yl]-4-[4-(methanesulfonyl)phenyl]-N,N-dimethylpyrrolidin-3-amine;

(3R,4S)-1-[(1S)-7-fluoro-2,3-dihydro-1H-inden-1-yl]-4-[4-(methanesulfonyl)phenyl]-N,N-dimethylpyrrolidin-3-amine;

(3R,4S)-1-[(1R)-7-fluoro-2,3-dihydro-1H-inden-1-yl]-4-[4-(methanesulfonyl)phenyl]-N-dimethylpyrrolidin-3-amine;

(3S,4R)-1-[(1S)-7-fluoro-2,3-dihydro-1H-inden-1-yl]-4-[4-(methanesulfonyl)phenyl]-N,N-dimethylpyrrolidin-3-amine;

(3S,4R)-1-[(1R)-7-fluoro-2,3-dihydro-1H-inden-1-yl]-4-[4-(methanesulfonyl)phenyl]-N,N-dimethylpyrrolidin-3-amine;

rac-(1S)-1-{(3S,4R)-3-(dimethylamino)-4-[4-(methanesulfonyl)phenyl]pyrrolidin-1-yl}-7-fluoro-2,3-dihydro-1H-inden-5-ol;

rac-(1R,3R)-3-{(3R,4S)-3-(dimethylamino)-4-[4-(methanesulfonyl)phenyl]pyrrolidin-1-yl}-4-fluoro-2,3-dihydro-1H-inden-1-ol;

rac-(1R)-1-{(3S,4R)-3-(dimethylamino)-4-[4-(methanesulfonyl)phenyl]pyrrolidin-1-yl}-7-fluoro-2,3-dihydro-1H-inden-5-ol;

rac-(1S,3S)-3-{(3R,4S)-3-(dimethylamino)-4-[4-(methanesulfonyl)phenyl]pyrrolidin-1-yl}-4-fluoro-2,3-dihydro-1H-inden-1-ol;

rac-4-{(3R,4S)-4-(dimethylamino)-1-[(1R)-7-fluoro-2,3-dihydro-1H-inden-1-yl]pyrrolidin-3-yl}benzonitrile;

rac-methyl 4-[(3R,4S)-1-[(1R)-2,3-dihydro-1H-inden-1-yl]-4-(dimethylamino)pyrrolidin-3-yl]benzoate;

rac-methyl 4-[(3S,4R)-1-(7-chloro-2,3-dihydro-1H-inden-1-yl)-4-(dimethylamino)pyrrolidin-3-yl]benzoate;

rac-methyl 4-[(3R,4S)-4-(dimethylamino)-1-(7-fluoro-2,3-dihydro-1H-inden-1-yl)pyrrolidin-3-yl]benzoate;

rac-(3S,4R)-4-(3,4-dimethoxyphenyl)-1-(7-fluoro-2,3-dihydro-1H-inden-1-yl)-N,N-dimethylpyrrolidin-3-amine;

rac-4-[(3S,4R)-4-(dimethylamino)-1-(7-fluoro-2,3-dihydro-1H-inden-1-yl)pyrrolidin-3-yl]-N-methylbenzamide;

rac-4-[(3S,4R)-1-(7-chloro-2,3-dihydro-1H-inden-1-yl)-4-(dimethylamino)pyrrolidin-3-yl]-N,N-dimethylbenzamide;

rac-4-[(3S,4R)-4-(dimethylamino)-1-(7-fluoro-2,3-dihydro-1H-inden-1-yl)pyrrolidin-3-yl]-N,N-dimethylbenzamide;
rac-(3R,4S)-4-(4-bromo-3-methylphenyl)-1-(7-fluoro-2,3-dihydro-1H-inden-1-yl)-N,N-dimethylpyrrolidin-3-amine;
rac-4-[(3S,4R)-1-(7-chloro-2,3-dihydro-1H-inden-1-yl)-4-(dimethylamino)pyrrolidin-3-yl]benzoic acid;
rac-4-[(3R,4S)-4-(dimethylamino)-1-(7-fluoro-2,3-dihydro-1H-inden-1-yl)pyrrolidin-3-yl]benzoic acid;
rac-(3R,4S)-1-[(3S)-3,7-difluoro-2,3-dihydro-1H-inden-1-yl]-4-[4-(methanesulfonyl)phenyl]-N,N-dimethylpyrrolidin-3-amine;
rac-(3R,4S)-1-[(1R,3S)-3,7-difluoro-2,3-dihydro-1H-inden-1-yl]-4-[4-(methanesulfonyl)phenyl]-N,N-dimethylpyrrolidin-3-amine;
rac-(3R,4S)-1-[(1S,3S)-3,7-difluoro-2,3-dihydro-1H-inden-1-yl]-4-[4-(methanesulfonyl)phenyl]-N,N-dimethylpyrrolidin-3-amine;
(3S)-3-{(3S,4R)-3-(dimethylamino)-4-[4-(methanesulfonyl)phenyl]pyrrolidin-1-yl}-4-fluoro-2,3-dihydro-1H-inden-1-ol;
rac-(1R,3S)-3-{(3R,4S)-3-(dimethylamino)-4-[4-(methanesulfonyl)phenyl]pyrrolidin-1-yl}-4-fluoro-2,3-dihydro-1H-inden-1-ol;
rac-4-[(3R,4S)-4-(dimethylamino)-1-(7-fluoro-2,3-dihydro-1H-inden-1-yl)pyrrolidin-3-yl]benzamide;
rac-4-[(3S,4R)-4-(dimethylamino)-1-(7-fluoro-2,3-dihydro-1H-inden-1-yl)pyrrolidin-3-yl]-2-methylbenzoic acid;
rac-4-[(3S,4R)-4-(dimethylamino)-1-(7-fluoro-2,3-dihydro-1H-inden-1-yl)pyrrolidin-3-yl]-2-methylbenzonitrile;
rac-4-[(3S,4R)-4-(dimethylamino)-1-(2-hydroxy-2,3-dihydro-1H-inden-1-yl)pyrrolidin-3-yl]-2-methylbenzonitrile;
rac-methyl 4-[(3S,4R)-4-(dimethylamino)-1-(7-fluoro-2,3-dihydro-1H-inden-1-yl)pyrrolidin-3-yl]-2-methylbenzoate;
rac-{4-[(3S,4R)-4-(dimethylamino)-1-(7-fluoro-2,3-dihydro-1H-inden-1-yl)pyrrolidin-3-yl]phenyl}[(3S)-3-hydroxypyrrolidin-1-yl]methanone;
rac-(3S,4R)-1-(7-fluoro-2,3-dihydro-1H-inden-1-yl)-N,N-dimethyl-4-[4-(piperazin-1-yl)phenyl]pyrrolidin-3-amine;
1-(4-{4-[(3S,4R)-1-(2,3-dihydro-1H-inden-1-yl)-4-(dimethylamino)pyrrolidin-3-yl]phenyl}piperazin-1-yl)ethan-1-one;
1-(4-{4-[(3S,4R)-4-(dimethylamino)-1-(7-fluoro-2,3-dihydro-1H-inden-1-yl)pyrrolidin-3-yl]phenyl}piperazin-1-yl)ethan-1-one;
rac-1-(4-{4-[(3S,4R)-4-(dimethylamino)-1-(7-fluoro-2,3-dihydro-1H-inden-1-yl)pyrrolidin-3-yl]phenyl}piperazin-1-yl)ethan-1-one;
1-[4-(4-{(3S,4R)-4-(dimethylamino)-1-[(1S)-7-fluoro-2,3-dihydro-1H-inden-1-yl]pyrrolidin-3-yl}phenyl)piperazin-1-yl]ethan-1-one;
1-[4-(4-{(3S,4R)-4-(dimethylamino)-1-[(1R)-7-fluoro-2,3-dihydro-1H-inden-1-yl]pyrrolidin-3-yl}phenyl)piperazin-1-yl]ethan-1-one;
1-[4-(4-{(3R,4S)-4-(dimethylamino)-1-[(1S)-7-fluoro-2,3-dihydro-1H-inden-1-yl]pyrrolidin-3-yl}phenyl)piperazin-1-yl]ethan-1-one;
1-[4-(4-{(3R,4S)-4-(dimethylamino)-1-[(1R)-7-fluoro-2,3-dihydro-1H-inden-1-yl]pyrrolidin-3-yl}phenyl)piperazin-1-yl]ethan-1-one;
rac-(3R,4S)-4-{4-[4-(ethanesulfonyl)piperazin-1-yl]phenyl}-1-(7-fluoro-2,3-dihydro-1H-inden-1-yl)-N,N-dimethylpyrrolidin-3-amine;
tert-butyl 4-{4-[(3R,4S)-4-(dimethylamino)-1-(7-fluoro-2,3-dihydro-1H-inden-1-yl)pyrrolidin-3-yl]phenyl}piperazine-1-carboxylate;
rac-4-{4-[(3S,4R)-4-(dimethylamino)-1-(7-fluoro-2,3-dihydro-1H-inden-1-yl)pyrrolidin-3-yl]benzoyl}-1-methylpiperazin-2-one;
rac-1-(4-{4-[(3R,4S)-4-(dimethylamino)-1-(7-fluoro-2,3-dihydro-1H-inden-1-yl)pyrrolidin-3-yl]phenyl}piperazin-1-yl)-2-hydroxyethan-1-one;
rac-{4-[(3S,4R)-4-(dimethylamino)-1-(7-fluoro-2,3-dihydro-1H-inden-1-yl)pyrrolidin-3-yl]phenyl}[4-(methanesulfonyl)piperazin-1-yl]methanone;
rac-2-(4-{4-[(3S,4R)-4-(dimethylamino)-1-(7-fluoro-2,3-dihydro-1H-inden-1-yl)pyrrolidin-3-yl]phenyl}piperazin-1-yl)-2-oxoacetamide;
rac-1-(4-{4-[(3S,4R)-4-(dimethylamino)-1-(7-fluoro-2,3-dihydro-1H-inden-1-yl)pyrrolidin-3-yl]benzoyl}piperazin-1-yl)ethan-1-one;
rac-4-{4-[(3S,4R)-4-(dimethylamino)-1-(7-fluoro-2,3-dihydro-1H-inden-1-yl)pyrrolidin-3-yl]phenyl}-1-methylpiperazin-2-one;
rac-{4-[(3S,4R)-4-(dimethylamino)-1-(7-fluoro-2,3-dihydro-1H-inden-1-yl)pyrrolidin-3-yl]phenyl}[4-(ethanesulfonyl)piperazin-1-yl]methanone;
rac-4-{4-[(3S,4R)-4-(dimethylamino)-1-(7-fluoro-2,3-dihydro-1H-inden-1-yl)pyrrolidin-3-yl]-2-methylphenyl}-1-methylpiperazin-2-one;
rac-2-(4-{4-[(3R,4S)-4-(dimethylamino)-1-(7-fluoro-2,3-dihydro-1H-inden-1-yl)pyrrolidin-3-yl]phenyl}piperazin-1-yl)-N,N-dimethyl-2-oxoacetamide;
rac-1-(4-{4-[(3S,4R)-4-(dimethylamino)-1-(7-fluoro-2,3-dihydro-1H-inden-1-yl)pyrrolidin-3-yl]-2-methylphenyl}piperazin-1-yl)ethan-1-one;
rac-(3R,4S)-1-(7-fluoro-2,3-dihydro-1H-inden-1-yl)-N,N-dimethyl-4-[4-(4-methylpiperazin-1-yl)phenyl]pyrrolidin-3-amine;
rac-(3R,4S)-4-{4-[4-(ethanesulfonyl)piperazin-1-yl]-3-methylphenyl}-1-(7-fluoro-2,3-dihydro-1H-inden-1-yl)-N,N-dimethylpyrrolidin-3-amine;
rac-4-{4-[(3R,4S)-4-(dimethylamino)-1-(7-fluoro-2,3-dihydro-1H-inden-1-yl)pyrrolidin-3-yl]phenyl}-N,N-dimethylpiperazine-1-carboxamide;
rac-(3R,4S)-4-[4-(4-cyclopropylpiperazin-1-yl)phenyl]-1-(7-fluoro-2,3-dihydro-1H-inden-1-yl)-N,N-dimethylpyrrolidin-3-amine;
rac-(3S,4R)-4-(2H-1,3-benzodioxol-5-yl)-1-(7-fluoro-2,3-dihydro-1H-inden-1-yl)-N,N-dimethylpyrrolidin-3-amine;
rac-(3S,4R)-1-(7-fluoro-2,3-dihydro-1H-inden-1-yl)-N,N-dimethyl-4-[4-(1,3-oxazol-2-yl)phenyl]pyrrolidin-3-amine;
rac-(3R,4S)-1-(7-fluoro-2,3-dihydro-1H-inden-1-yl)-N,N-dimethyl-4-[4-(3-methyl-1,2,4-oxadiazol-5-yl)phenyl]pyrrolidin-3-amine;
rac-(3S,4R)-1-(7-fluoro-2,3-dihydro-1H-inden-1-yl)-N,N-dimethyl-4-[4-(5-methyl-1,3,4-oxadiazol-2-yl)phenyl]pyrrolidin-3-amine;
rac-(3S,4R)-1-(7-fluoro-2,3-dihydro-1H-inden-1-yl)-N,N-dimethyl-4-[4-(4-methyl-1,3-oxazol-2-yl)phenyl]pyrrolidin-3-amine;
rac-(3R,4S)-1-(7-fluoro-2,3-dihydro-1H-inden-1-yl)-N,N-dimethyl-4-[4-(1-methyl-1H-pyrazol-4-yl)phenyl]pyrrolidin-3-amine;
rac-2-(4-{4-[(3S,4R)-4-(dimethylamino)-1-(7-fluoro-2,3-dihydro-1H-inden-1-yl)pyrrolidin-3-yl]phenyl}-1H-pyrazol-1-yl)acetamide;

rac-2-(4-{4-[(3S,4R)-4-(dimethylamino)-1-(7-fluoro-2,3-dihydro-1H-inden-1-yl)pyrrolidin-3-yl]phenyl}-1H-pyrazol-1-yl)-N-methylacetamide;

rac-(3S,4R)-1-(7-fluoro-2,3-dihydro-1H-inden-1-yl)-N,N-dimethyl-4-{4-[4-(1-methyl-1H-imidazole-4-sulfonyl)piperazin-1-yl]phenyl}pyrrolidin-3-amine;

rac-(3S,4R)-1-(7-fluoro-2,3-dihydro-1H-inden-1-yl)-N,N-dimethyl-4-{4-[4-(pyrimidin-4-yl)piperazin-1-yl]phenyl}pyrrolidin-3-amine;

rac-(3S,4R)-1-(7-fluoro-2,3-dihydro-1H-inden-1-yl)-N,N-dimethyl-4-{4-[4-(pyridin-2-yl)piperazin-1-yl]phenyl}pyrrolidin-3-amine;

(3R,4S)-1-(7-fluoro-2,3-dihydro-1H-inden-1-yl)-N,N-dimethyl-4-(1-methyl-1H-indol-3-yl)pyrrolidin-3-amine;

(3R,4S)-1-[(1S)-7-fluoro-2,3-dihydro-1H-inden-1-yl]-N,N-dimethyl-4-(1-methyl-1H-indol-3-yl)pyrrolidin-3-amine;

(3R,4S)-1-[(1R)-7-fluoro-2,3-dihydro-1H-inden-1-yl]-N,N-dimethyl-4-(1-methyl-1H-indol-3-yl)pyrrolidin-3-amine;

3-[(3S,4R)-4-(dimethylamino)-1-(7-fluoro-2,3-dihydro-1H-inden-1-yl)pyrrolidin-3-yl]-1-methyl-1H-indole-7-carboxylic acid;

rac-3-[(3S,4R)-4-(dimethylamino)-1-(7-fluoro-2,3-dihydro-1H-inden-1-yl)pyrrolidin-3-yl]-1-methyl-1H-indole-7-carboxylic acid;

3-[(3R,4S)-4-(dimethylamino)-1-(7-fluoro-2,3-dihydro-1H-inden-1-yl)pyrrolidin-3-yl]-1-methyl-1H-indole-7-carboxylic acid;

rac-methyl 3-[(3R,4S)-4-(dimethylamino)-1-(7-fluoro-2,3-dihydro-1H-inden-1-yl)pyrrolidin-3-yl]-1-methyl-1H-indole-6-carboxylate;

methyl 3-[(3S,4R)-4-(dimethylamino)-1-(7-fluoro-2,3-dihydro-1H-inden-1-yl)pyrrolidin-3-yl]-1-methyl-1H-indole-7-carboxylate;

rac-methyl 3-[(3S,4R)-4-(dimethylamino)-1-(7-fluoro-2,3-dihydro-1H-inden-1-yl)pyrrolidin-3-yl]-1-methyl-1H-indole-7-carboxylate;

methyl 3-[(3R,4S)-4-(dimethylamino)-1-(7-fluoro-2,3-dihydro-1H-inden-1-yl)pyrrolidin-3-yl]-1-methyl-1H-indole-7-carboxylate;

rac-3-[(3S,4R)-4-(dimethylamino)-1-(7-fluoro-2,3-dihydro-1H-inden-1-yl)pyrrolidin-3-yl]-N,N,1-trimethyl-1H-indole-6-carboxamide;

(3R,4S)-1-(2,3-dihydro-1H-inden-1-yl)-N,N-dimethyl-4-(1-methyl-1H-indol-3-yl)pyrrolidin-3-amine;

(3R,4S)-1-(7-chloro-2,3-dihydro-1H-inden-1-yl)-N,N-dimethyl-4-(1-methyl-1H-indol-3-yl)pyrrolidin-3-amine;

rac-(3R,4S)-1-(4-fluoro-2,3-dihydro-1H-inden-1-yl)-N,N-dimethyl-4-(1-methyl-1H-indol-3-yl)pyrrolidin-3-amine;

rac-(3R,4S)-1-(5-fluoro-2,3-dihydro-1H-inden-1-yl)-N,N-dimethyl-4-(1-methyl-1H-indol-3-yl)pyrrolidin-3-amine;

rac-(3R,4S)-1-(6-fluoro-2,3-dihydro-1H-inden-1-yl)-N,N-dimethyl-4-(1-methyl-1H-indol-3-yl)pyrrolidin-3-amine;

rac-(3R,4S)-4-(7-bromo-1-methyl-1H-indol-3-yl)-1-(7-fluoro-2,3-dihydro-1H-inden-1-yl)-N,N-dimethylpyrrolidin-3-amine;

rac-(3R,4S)-4-(6-bromo-1-methyl-1H-indol-3-yl)-1-(7-fluoro-2,3-dihydro-1H-inden-1-yl)-N,N-dimethylpyrrolidin-3-amine;

rac-(3R,4S)-1-(5,7-difluoro-2,3-dihydro-1H-inden-1-yl)-N,N-dimethyl-4-(1-methyl-1H-indol-3-yl)pyrrolidin-3-amine;

(3R,4S)-1-(6,7-difluoro-2,3-dihydro-1H-inden-1-yl)-N,N-dimethyl-4-(1-methyl-1H-indol-3-yl)pyrrolidin-3-amine;

3-[(3R,4S)-3-(dimethylamino)-4-(1-methyl-1H-indol-3-yl)pyrrolidin-1-yl]-2,3-dihydro-1H-inden-4-ol;

rac-3-[(3S,4R)-4-(dimethylamino)-1-(7-fluoro-2,3-dihydro-1H-inden-1-yl)pyrrolidin-3-yl]-N-(2-hydroxyethyl)-N,1-dimethyl-1H-indole-7-carboxamide;

rac-3-[(3S,4R)-4-(dimethylamino)-1-(7-fluoro-2,3-dihydro-1H-inden-1-yl)pyrrolidin-3-yl]-N,1-dimethyl-1H-indole-7-carboxamide;

(3R,4S)—N,N-dimethyl-1-(7-methyl-2,3-dihydro-1H-inden-1-yl)-4-(1-methyl-1H-indol-3-yl)pyrrolidin-3-amine;

rac-3-[(3S,4R)-4-(dimethylamino)-1-(7-fluoro-2,3-dihydro-1H-inden-1-yl)pyrrolidin-3-yl]-N,N,1-trimethyl-1H-indole-7-carboxamide;

{3-[(3S,4R)-4-(dimethylamino)-1-(7-fluoro-2,3-dihydro-1H-inden-1-yl)pyrrolidin-3-yl]-1-methyl-1H-indol-7-yl}(3-fluoroazetidin-1-yl)methanone;

rac-{3-[(3S,4R)-4-(dimethylamino)-1-(7-fluoro-2,3-dihydro-1H-inden-1-yl)pyrrolidin-3-yl]-1-methyl-1H-indol-7-yl}(3-fluoroazetidin-1-yl)methanone;

{3-[(3R,4S)-4-(dimethylamino)-1-(7-fluoro-2,3-dihydro-1H-inden-1-yl)pyrrolidin-3-yl]-1-methyl-1H-indol-7-yl}(3-fluoroazetidin-1-yl)methanone;

{3-[(3S,4R)-4-(dimethylamino)-1-(7-fluoro-2,3-dihydro-1H-inden-1-yl)pyrrolidin-3-yl]-1-methyl-1H-indol-7-yl}(3-hydroxyazetidin-1-yl)methanone;

rac-{3-[(3S,4R)-4-(dimethylamino)-1-(7-fluoro-2,3-dihydro-1H-inden-1-yl)pyrrolidin-3-yl]-1-methyl-1H-indol-7-yl}(3-hydroxyazetidin-1-yl)methanone;

rac-{3-[(3S,4R)-4-(dimethylamino)-1-(7-fluoro-2,3-dihydro-1H-inden-1-yl)pyrrolidin-3-yl]-1-methyl-1H-indol-6-yl}(3-hydroxyazetidin-1-yl)methanone;

rac-3-[(3S,4R)-4-(dimethylamino)-1-(7-fluoro-2,3-dihydro-1H-inden-1-yl)pyrrolidin-3-yl]-N-(3-hydroxycyclobutyl)-1-methyl-1H-indole-7-carboxamide;

rac-3-[(3S,4R)-4-(dimethylamino)-1-(7-fluoro-2,3-dihydro-1H-inden-1-yl)pyrrolidin-3-yl]-N-(3-hydroxycyclobutyl)-N,1-dimethyl-1H-indole-7-carboxamide;

rac-{3-[(3S,4R)-4-(dimethylamino)-1-(7-fluoro-2,3-dihydro-1H-inden-1-yl)pyrrolidin-3-yl]-1-methyl-1H-indol-7-yl}[3-(methanesulfonyl)azetidin-1-yl]methanone;

rac-{3-[(3S,4R)-4-(dimethylamino)-1-(7-fluoro-2,3-dihydro-1H-inden-1-yl)pyrrolidin-3-yl]-1-methyl-1H-indol-6-yl}[(3S)-3-hydroxypyrrolidin-1-yl]methanone;

rac-{3-[(3S,4R)-4-(dimethylamino)-1-(7-fluoro-2,3-dihydro-1H-inden-1-yl)pyrrolidin-3-yl]-1-methyl-1H-indol-6-yl}[(3R)-3-hydroxypyrrolidin-1-yl]methanone;

rac-[(3S,4S)-3,4-dihydroxypyrrolidin-1-yl]{3-[(3S,4R)-4-(dimethylamino)-1-(7-fluoro-2,3-dihydro-1H-inden-1-yl)pyrrolidin-3-yl]-1-methyl-1H-indol-7-yl}methanone;

rac-[(3S,4S)-3,4-dihydroxypyrrolidin-1-yl]{3-[(3S,4R)-4-(dimethylamino)-1-(7-fluoro-2,3-dihydro-1H-inden-1-yl)pyrrolidin-3-yl]-1-methyl-1H-indol-6-yl}methanone;

rac-3-[(3S,4R)-4-(dimethylamino)-1-(7-fluoro-2,3-dihydro-1H-inden-1-yl)pyrrolidin-3-yl]-N-(1,1-dioxo-1lambda~6~-thiolan-3-yl)-1-methyl-1H-indole-7-carboxamide;

rac-{3-[(3S,4R)-4-(dimethylamino)-1-(7-fluoro-2,3-dihydro-1H-inden-1-yl)pyrrolidin-3-yl]-1-methyl-1H-indol-7-yl}[(2S)-2-(hydroxymethyl)pyrrolidin-1-yl]methanone;

rac-1-{3-[(3S,4R)-4-(dimethylamino)-1-(7-fluoro-2,3-dihydro-1H-inden-1-yl)pyrrolidin-3-yl]-1-methyl-1H-indole-7-carbonyl}-L-prolinamide;

rac-{3-[(3S,4R)-4-(dimethylamino)-1-(7-fluoro-2,3-dihydro-1H-inden-1-yl)pyrrolidin-3-yl]-1-methyl-1H-indol-7-yl}[(3S)-3-hydroxypyrrolidin-1-yl]methanone;

rac-{3-[(3S,4R)-4-(dimethylamino)-1-(7-fluoro-2,3-dihydro-1H-inden-1-yl)pyrrolidin-3-yl]-1-methyl-1H-indol-7-yl}(piperazin-1-yl)methanone;

rac-(3R,4S)-1-(7-fluoro-2,3-dihydro-1H-inden-1-yl)-4-{6-[4-(methanesulfonyl)piperazin-1-yl]-1-methyl-1H-indol-3-yl}-N,N-dimethylpyrrolidin-3-amine;

rac-1-(4-{3-[(3S,4R)-4-(dimethylamino)-1-(7-fluoro-2,3-dihydro-1H-inden-1-yl)pyrrolidin-3-yl]-1-methyl-1H-indol-6-yl}piperazin-1-yl)ethan-1-one;

rac-{3-[(3S,4R)-4-(dimethylamino)-1-(7-fluoro-2,3-dihydro-1H-inden-1-yl)pyrrolidin-3-yl]-1-methyl-1H-indol-6-yl}[4-(methanesulfonyl)piperazin-1-yl]methanone;

rac-1-(4-{3-[(3S,4R)-4-(dimethylamino)-1-(7-fluoro-2,3-dihydro-1H-inden-1-yl)pyrrolidin-3-yl]-1-methyl-1H-indole-6-carbonyl}piperazin-1-yl)ethan-1-one;

rac-4-{3-[(3S,4R)-4-(dimethylamino)-1-(7-fluoro-2,3-dihydro-1H-inden-1-yl)pyrrolidin-3-yl]-1-methyl-1H-indole-7-carbonyl}-N,N-dimethylpiperazine-1-sulfonamide;

rac-4-{3-[(3S,4R)-4-(dimethylamino)-1-(7-fluoro-2,3-dihydro-1H-inden-1-yl)pyrrolidin-3-yl]-1-methyl-1H-indole-7-carbonyl}-1-methylpiperazin-2-one;

rac-{3-[(3S,4R)-4-(dimethylamino)-1-(7-fluoro-2,3-dihydro-1H-inden-1-yl)pyrrolidin-3-yl]-1-methyl-1H-indol-7-yl}[4-(methanesulfonyl)piperazin-1-yl]methanone;

rac-4-{3-[(3S,4R)-4-(dimethylamino)-1-(7-fluoro-2,3-dihydro-1H-inden-1-yl)pyrrolidin-3-yl]-1-methyl-1H-indole-7-carbonyl}-N,N-dimethylpiperazine-1-carboxamide;

rac-1-(4-{3-[(3S,4R)-4-(dimethylamino)-1-(7-fluoro-2,3-dihydro-1H-inden-1-yl)pyrrolidin-3-yl]-1-methyl-1H-indole-7-carbonyl}piperazin-1-yl)ethan-1-one;

rac-4-{3-[(3S,4R)-4-(dimethylamino)-1-(7-fluoro-2,3-dihydro-1H-inden-1-yl)pyrrolidin-3-yl]-1-methyl-1H-indol-7-yl}-1-methylpiperazin-2-one;

rac-{3-[(3S,4R)-4-(dimethylamino)-1-(7-fluoro-2,3-dihydro-1H-inden-1-yl)pyrrolidin-3-yl]-1-methyl-1H-indol-7-yl}[4-(ethanesulfonyl)piperazin-1-yl]methanone;

rac-4-{3-[(3S,4R)-4-(dimethylamino)-1-(7-fluoro-2,3-dihydro-1H-inden-1-yl)pyrrolidin-3-yl]-1-methyl-1H-indol-7-yl}-N,N-dimethylpiperazine-1-carboxamide;

[4-(azetidine-1-sulfonyl)piperazin-1-yl]{3-[(3S,4R)-4-(dimethylamino)-1-(7-fluoro-2,3-dihydro-1H-inden-1-yl)pyrrolidin-3-yl]-1-methyl-1H-indol-7-yl}methanone;

1-(4-{3-[(3S,4R)-4-(dimethylamino)-1-(7-fluoro-2,3-dihydro-1H-inden-1-yl)pyrrolidin-3-yl]-1-methyl-1H-indole-7-carbonyl}piperazine-1-sulfonyl)azetidine-3-carbonitrile;

rac-8-{3-[(3S,4R)-4-(dimethylamino)-1-(7-fluoro-2,3-dihydro-1H-inden-1-yl)pyrrolidin-3-yl]-1-methyl-1H-indole-7-carbonyl}hexahydro-2H-pyrazino[1,2-a]pyrazin-1(6H)-one;

rac-{3-[(3S,4R)-4-(dimethylamino)-1-(7-fluoro-2,3-dihydro-1H-inden-1-yl)pyrrolidin-3-yl]-1-methyl-1H-indol-7-yl}[4-(1-methyl-1H-imidazole-5-sulfonyl)piperazin-1-yl]methanone;

rac-{3-[(3S,4R)-4-(dimethylamino)-1-(7-fluoro-2,3-dihydro-1H-inden-1-yl)pyrrolidin-3-yl]-1-methyl-1H-indol-7-yl}[4-(3,5-dimethyl-1H-pyrazole-4-sulfonyl)piperazin-1-yl]methanone;

rac-{3-[(3S,4R)-4-(dimethylamino)-1-(7-fluoro-2,3-dihydro-1H-inden-1-yl)pyrrolidin-3-yl]-1-methyl-1H-indol-7-yl}[4-(pyridazin-3-yl)piperazin-1-yl]methanone;

rac-(3R,4S)-1-[(1S)-7-fluoro-2,3-dihydro-1H-inden-1-yl]-N,N-dimethyl-4-(1-methyl-1H-pyrrolo[3,2-b]pyridin-3-yl)pyrrolidin-3-amine;

rac-(3S,4R)-4-(2,3-dihydro-1-benzofuran-3-yl)-1-[(1R)-7-fluoro-2,3-dihydro-1H-inden-1-yl]-N,N-dimethylpyrrolidin-3-amine;

rac-(3S,4R)-1-(7-fluoro-2,3-dihydro-1H-inden-1-yl)-N,N-dimethyl-4-(5,6,7,8-tetrahydroimidazo[1,2-a]pyridin-3-yl)pyrrolidin-3-amine;

rac-(3R,4S)-1-(7-fluoro-2,3-dihydro-1H-inden-1-yl)-N,N-dimethyl-4-(1-methyl-1H-pyrrolo[3,2-c]pyridin-3-yl)pyrrolidin-3-amine;

rac-(3S,4R)-4-(2,3-dihydro-1-benzofuran-3-yl)-1-[(1R)-7-fluoro-2,3-dihydro-1H-inden-1-yl]-N,N-dimethylpyrrolidin-3-amine;

rac-(3S,4R)-1-[(1R)-7-fluoro-2,3-dihydro-1H-inden-1-yl]-N,N-dimethyl-4-(1-methyl-1H-pyrrolo[3,2-b]pyridin-3-yl)pyrrolidin-3-amine;

rac-(3R,4S)-1-(7-fluoro-2,3-dihydro-1H-inden-1-yl)-N,N-dimethyl-4-(oxan-4-yl)pyrrolidin-3-amine;

rac-(3S,4R)-1-(7-fluoro-2,3-dihydro-1H-inden-1-yl)-N,N-dimethyl-4-[6-(piperazin-1-yl)pyridin-3-yl]pyrrolidin-3-amine;

rac-(3R,4S)-1-(7-fluoro-2,3-dihydro-1H-inden-1-yl)-N,N-dimethyl-4-(1-phenylpiperidin-4-yl)pyrrolidin-3-amine;

rac-2-(4-{5-[(3R,4S)-4-(dimethylamino)-1-(7-fluoro-2,3-dihydro-1H-inden-1-yl)pyrrolidin-3-yl]pyridin-2-yl}piperazin-1-yl)-N,N-dimethylacetamide;

rac-(3R,4S)-1-(7-fluoro-2,3-dihydro-1H-inden-1-yl)-N,N-dimethyl-4-(1-methyl-1H-pyrrolo[2,3-c]pyridin-3-yl)pyrrolidin-3-amine;

rac-(3R,4S)-1-(7-fluoro-2,3-dihydro-1H-inden-1-yl)-N,N-dimethyl-4-[1-(pyridin-3-yl)piperidin-4-yl]pyrrolidin-3-amine;

rac-2-(4-{5-[(3R,4S)-4-(dimethylamino)-1-(7-fluoro-2,3-dihydro-1H-inden-1-yl)pyrrolidin-3-yl]pyridin-2-yl}-1H-pyrazol-1-yl)-1-(3-hydroxyazetidin-1-yl)ethan-1-one;

rac-(4-{5-[(3R,4S)-4-(dimethylamino)-1-(7-fluoro-2,3-dihydro-1H-inden-1-yl)pyrrolidin-3-yl]pyridin-2-yl}piperazin-1-yl)(oxetan-3-yl)methanone;

rac-(3R,4S)-1-(7-fluoro-2,3-dihydro-1H-inden-1-yl)-N,N-dimethyl-4-[1-(pyridin-2-yl)piperidin-4-yl]pyrrolidin-3-amine;

rac-2-(4-{5-[(3R,4S)-4-(dimethylamino)-1-(7-fluoro-2,3-dihydro-1H-inden-1-yl)pyrrolidin-3-yl]pyridin-2-yl}-1H-pyrazol-1-yl)-1-(3-fluoroazetidin-1-yl)ethan-1-one;

rac-6-{4-[(3R,4S)-4-(dimethylamino)-1-(7-fluoro-2,3-dihydro-1H-inden-1-yl)pyrrolidin-3-yl]piperidin-1-yl}-N-methylpyridine-3-carboxamide;

rac-N-[2-(4-{5-[(3R,4S)-4-(dimethylamino)-1-(7-fluoro-2,3-dihydro-1H-inden-1-yl)pyrrolidin-3-yl]pyridin-2-yl}piperazin-1-yl)-2-oxoethyl]methanesulfonamide;

rac-(3R,4S)-1-(7-fluoro-2,3-dihydro-1H-inden-1-yl)-N,N-dimethyl-4-(1-methyl-1H-indazol-3-yl)pyrrolidin-3-amine;

rac-1-(4-{5-[(3R,4S)-4-(dimethylamino)-1-(7-fluoro-2,3-dihydro-1H-inden-1-yl)pyrrolidin-3-yl]pyridin-2-yl}piperazin-1-yl)-2-(methanesulfonyl)ethan-1-one;

rac-2-(4-{5-[(3R,4S)-4-(dimethylamino)-1-(7-fluoro-2,3-dihydro-1H-inden-1-yl)pyrrolidin-3-yl]pyridin-2-yl}-1H-pyrazol-1-yl)acetamide;

rac-2-(4-{5-[(3R,4S)-4-(dimethylamino)-1-(7-fluoro-2,3-dihydro-1H-inden-1-yl)pyrrolidin-3-yl]pyridin-2-yl}-1H-pyrazol-1-yl)-N,N-dimethylacetamide;

rac-2-(4-{5-[(3R,4S)-4-(dimethylamino)-1-(7-fluoro-2,3-dihydro-1H-inden-1-yl)pyrrolidin-3-yl]pyridin-2-yl}piperazin-1-yl)-2-oxoethane-1-sulfonamide;

rac-2-(4-{5-[(3R,4S)-4-(dimethylamino)-1-(7-fluoro-2,3-dihydro-1H-inden-1-yl)pyrrolidin-3-yl]pyridin-2-yl}-1H-pyrazol-1-yl)-N-methylacetamide;

rac-2-{4-[(3S,4R)-4-(dimethylamino)-1-(7-fluoro-2,3-dihydro-1H-inden-1-yl)pyrrolidin-3-yl]piperidin-1-yl}-1,3-thiazole-5-carboxamide;

rac-5-{4-[(3S,4R)-4-(dimethylamino)-1-(7-fluoro-2,3-di-hydro-1H-inden-1-yl)pyrrolidin-3-yl]piperidin-1-yl}pyrazine-2-carboxamide;

rac-(3R,4S)-1-(7-fluoro-2,3-dihydro-1H-inden-1-yl)-N,N-dimethyl-4-(1-methyl-1H-pyrrolo[2,3-b]pyridin-3-yl)pyrrolidin-3-amine;

rac-6-{4-[(3S,4R)-4-(dimethylamino)-1-(7-fluoro-2,3-di-hydro-1H-inden-1-yl)pyrrolidin-3-yl]piperidin-1-yl}pyridazine-3-carboxamide;

rac-4-{4-[(3S,4R)-4-(dimethylamino)-1-(7-fluoro-2,3-di-hydro-1H-inden-1-yl)pyrrolidin-3-yl]piperidin-1-yl}benzamide;

rac-6-{4-[(3S,4R)-4-(dimethylamino)-1-(7-fluoro-2,3-di-hydro-1H-inden-1-yl)pyrrolidin-3-yl]piperidin-1-yl}pyridine-3-carboxamide; and pharmaceutically acceptable salts thereof.

One embodiment pertains to compounds or pharmaceutically acceptable salts thereof, which are useful as inhibitors of EED, the compounds having Formula (IIa) or Formula (IIb)

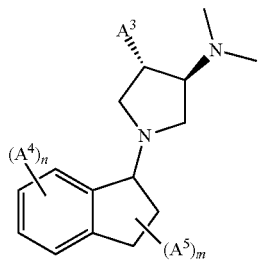

Formula (IIa)

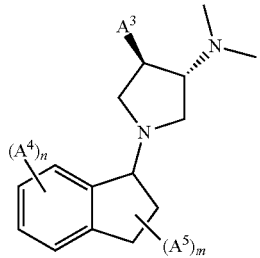

Formula (IIb)

wherein $A^3$ is selected from the group consisting of aryl, heterocyclyl, and heteroaryl, wherein the $A^3$ aryl, heterocyclyl, and heteroaryl are optionally substituted with one or more substituents independently selected from the group consisting of $R^1$, $OR^1$, $SR^1$, $S(O)R^1$, $SO_2R^1$, $C(O)R^1$, $CO(O)R^1$, $OC(O)R^1$, $OC(O)OR^1$, $NH_2$, $NHR^1$, $N(R^1)_2$, $NHC(O)R^1$, $NR^1C(O)R^1$, $NHS(O)_2R^1$, $NR^1S(O)_2R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $C(O)NH_2$, $C(O)NHR^1$, $C(O)N(R^1)_2$, $C(O)NHOH$, $C(O)NHOR^1$, $C(O)NHSO_2R^1$, $C(O)NR^1SO_2R^1$, $SO_2NH_2$, $SO_2NHR^1$, $SO_2N(R^1)_2$, $C(O)H$, $C(O)OH$, $C(N)NH_2$, $C(N)NHR^1$, $C(N)N(R^1)_2$, $CNOH$, $CNOCH_3$, $OH$, $(O)$, $CN$, $NO_2$, $CF_3$, $CF_2CF_3$, $OCF_3$, $OCF_2CF_3$, $F$, $Cl$, $Br$ and $I$;

$A^4$, at each occurrence, is a substituent on a substitutable position of the benzene ring of the indane independently selected from the group consisting of $C_1$-$C_6$ alkyl, OH, F, Cl, Br and I;

$A^5$ is a substituent on a substitutable position of the cyclopentane ring of the indane independently selected from the group consisting of $C_1$-$C_6$ alkyl, OH, F, Cl, Br and I;

$R^1$, at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^1$ $C_1$-$C_6$ alkyl, $C_2$-$C_6$ alkenyl, and $C_2$-$C_6$ alkynyl is optionally substituted with one or more substituents independently selected from the group consisting of $R^2$, $OR^2$, $SR^2$, $S(O)R^2$, $SO_2R^2$, $C(O)R^2$, $CO(O)R^2$, $OC(O)R^2$, $OC(O)OR^2$, $NH_2$, $NHR^2$, $N(R^2)_2$, $NHC(O)R^2$, $NR^2C(O)R^2$, $NHS(O)_2R^2$, $NR^2S(O)_2R^2$, $NHC(O)OR^2$, $NR^2C(O)OR^2$, $NHC(O)NH_2$, $NHC(O)NHR^2$, $NHC(O)N(R^2)_2$, $NR^2C(O)NHR^2$, $NR^2C(O)N(R^2)_2$, $C(O)NH_2$, $C(O)NHR^2$, $C(O)N(R^2)_2$, $C(O)NHOH$, $C(O)NHOR^2$, $C(O)NHSO_2R^2$, $C(O)NR^2SO_2R^2$, $SO_2NH_2$, $SO_2NHR^2$, $SO_2N(R^2)_2$, $C(O)H$, $C(O)OH$, $OH$, $(O)$, $CN$, $NO_2$, $CF_3$, $CF_2CF_3$, $OCF_3$, $OCF_2CF_3$, $F$, $Cl$, $Br$ and $I$; wherein each $R^1$ aryl, heteroaryl, heterocyclyl, cycloalkyl, and cycloalkenyl is optionally substituted with one or more substituents independently selected from the group consisting of $R^3$, $OR^3$, $SR^3$, $S(O)R^3$, $SO_2R^3$, $C(O)R^3$, $CO(O)R^3$, $OC(O)R^3$, $OC(O)OR^3$, $NH_2$, $NHR^3$, $N(R^3)_2$, $NHC(O)R^3$, $NR^3C(O)R^3$, $NHS(O)_2R^3$, $NR^3S(O)_2R^3$, $NHC(O)OR^3$, $NR^3C(O)OR^3$, $NHC(O)NH_2$, $NHC(O)NHR^3$, $NHC(O)N(R^3)_2$, $NR^3C(O)NHR^3$, $NR^3C(O)N(R^3)_2$, $C(O)NH_2$, $C(O)NHR^3$, $C(O)N(R^3)_2$, $C(O)NHOH$, $C(O)NHOR^3$, $C(O)NHSO_2R^3$, $C(O)NR^3SO_2R^3$, $SO_2NH_2$, $SO_2NHR^3$, $SO_2N(R^3)_2$, $C(O)H$, $C(O)OH$, $C(O)C(O)NH_2$, $C(O)C(O)NHR^3$, $C(O)C(O)N(R^3)_2$, $C(N)NH_2$, $C(N)NHR^3$, $C(N)N(R^3)_2$, $CNOH$, $CNOCH_3$, $OH$, $(O)$, $CN$, $NO_2$, $CF_3$, $CF_2CF_3$, $OCF_3$, $OCF_2CF_3$, $F$, $Cl$, $Br$ and $I$;

$R^2$, at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^2$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)NH_2$, $SO_2NH_2$, $C(O)H$, $C(O)OH$, $OH$, $(O)$, $CN$, $NO_2$, $CF_3$, $CF_2CF_3$, $OCF_3$, $OCF_2CF_3$, $F$, $Cl$, $Br$ and $I$; wherein each $R^2$ aryl, heteroaryl, heterocyclyl, cycloalkyl, and cycloalkenyl is optionally substituted with one or more substituents independently selected from the group consisting of $NH_2$, $C(O)NH_2$, $SO_2NH_2$, $C(O)H$, $C(O)OH$, $OH$, $(O)$, $CN$, $NO_2$, $CF_3$, $CF_2CF_3$, $OCF_3$, $OCF_2CF_3$, $F$, $Cl$, $Br$ and $I$;

$R^3$, at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^3$ $C_1$-$C_6$ alkyl, $C_2$-$C_6$ alkenyl, and $C_2$-$C_6$ alkynyl is optionally substituted with one or more substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $(O)$, $CN$, $NO_2$, $CF_3$, $CF_2CF_3$, $OCF_3$, $OCF_2CF_3$, $F$, $Cl$, $Br$ and $I$; wherein each $R^3$ aryl, heteroaryl, heterocyclyl, cycloalkyl, and cycloalkenyl is optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, $C(N)NH_2$, $C(N)NHR^5$, $C(N)N $N(R^5)_2$, CNOH, CNOCH$_3$, OH, (O), CN, NO$_2$, CF$_3$, CF$_2$CF$_3$, OCF$_3$, OCF$_2$CF$_3$, F, Cl, Br and I;

$R^4$ is at each occurrence, is independently selected from the group consisting of C$_1$-C$_6$ alkyl, C$_2$-C$_6$ alkenyl, C$_2$-C$_6$ alkynyl, aryl, heteroaryl, heterocyclyl, cycloalkyl, and cycloalkenyl; wherein each $R^4$ C$_1$-C$_6$ alkyl, C$_2$-C$_6$ alkenyl, and C$_2$-C$_6$ alkynyl is optionally substituted with one or more substituents independently selected from the group consisting of NH$_2$, C(O)NH$_2$, SO$_2$NH$_2$, C(O)H, C(O)OH, OH, (O), CN, NO$_2$, CF$_3$, CF$_2$CF$_3$, OCF$_3$, OCF$_2$CF$_3$, F, Cl, Br and I; wherein each $R^4$ aryl, heteroaryl, heterocyclyl, cycloalkyl, and cycloalkenyl is optionally substituted with one or more substituents independently selected from the group consisting of NH$_2$, C(O)NH$_2$, SO$_2$NH$_2$, C(O)H, C(O)OH, OH, (O), CN, NO$_2$, CF$_3$, CF$_2$CF$_3$, OCF$_3$, OCF$_2$CF$_3$, F, Cl, Br and I;

$R^5$ is at each occurrence, is independently selected from the group consisting of C$_1$-C$_6$ alkyl, C$_2$-C$_6$ alkenyl, C$_2$-C$_6$ alkynyl, aryl, heteroaryl, heterocyclyl, cycloalkyl, and cycloalkenyl; wherein each $R^5$ C$_1$-C$_6$ alkyl, C$_2$-C$_6$ alkenyl, and C$_2$-C$_6$ alkynyl is optionally substituted with one or more substituents independently selected from the group consisting of NH$_2$, C(O)NH$_2$, SO$_2$NH$_2$, C(O)H, C(O)OH, OH, (O), CN, NO$_2$, CF$_3$, CF$_2$CF$_3$, OCF$_3$, OCF$_2$CF$_3$, F, Cl, Br and I; wherein each $R^5$ aryl, heteroaryl, heterocyclyl, cycloalkyl, and cycloalkenyl is optionally substituted with one or more substituents independently selected from the group consisting of NH$_2$, C(O)NH$_2$, SO$_2$NH$_2$, C(O)H, C(O)OH, OH, (O), CN, NO$_2$, CF$_3$, CF$_2$CF$_3$, OCF$_3$, OCF$_2$CF$_3$, F, Cl, Br and I;

n is 0, 1, or 2; and m is 0 or 1.

In one embodiment of Formula (IIa) or Formula (IIb), $A^3$ is selected from the group consisting of aryl, heterocyclyl, and heteroaryl, wherein the $A^3$ aryl, heterocyclyl, and heteroaryl are optionally substituted with one or more substituents independently selected from the group consisting of $R^1$, OR$^1$, SR$^1$, S(O)R$^1$, SO$_2$R$^1$, C(O)R$^1$, CO(O)R$^1$, OC(O)R$^1$, OC(O)OR$^1$, NH$_2$, NHR$^1$, N(R$^1$)$_2$, NHC(O)R$^1$, NR$^1$C(O)R$^1$, NHS(O)$_2$R$^1$, NR$^1$S(O)$_2$R$^1$, NHC(O)OR$^1$, NR$^1$C(O)OR$^1$, NHC(O)NH$_2$, NHC(O)NHR$^1$, NHC(O)N(R$^1$)$_2$, NR$^1$C(O)NHR$^1$, NR$^1$C(O)N(R$^1$)$_2$, C(O)NH$_2$, C(O)NHR$^1$, C(O)N(R$^1$)$_2$, C(O)NHOH, C(O)NHOR$^1$, C(O)NHSO$_2$R$^1$, C(O)NR$^1$SO$_2$R$^1$, SO$_2$NH$_2$, SO$_2$NHR$^1$, SO$_2$N(R$^1$)$_2$, C(O)H, C(O)OH, C(N)NH$_2$, C(N)NHR$^1$, C(N)N(R$^1$)$_2$, CNOH, CNOCH$_3$, OH, (O), CN, NO$_2$, CF$_3$, CF$_2$CF$_3$, OCF$_3$, OCF$_2$CF$_3$, F, Cl, Br and I. In another embodiment of Formula (IIa) or Formula (IIb), $A^3$ is selected from the group consisting of aryl, heterocyclyl, and heteroaryl, wherein the $A^3$ aryl, heterocyclyl, and heteroaryl are optionally substituted with one or more substituents independently selected from the group consisting of $R^1$, OR$^1$, SO$_2$R$^1$, C(O)R$^1$, CO(O)R$^1$, C(O)NH$_2$, C(O)NHR$^1$, C(O)N(R$^1$)$_2$, SO$_2$NH$_2$, C(O)OH, CN, F, Cl, Br and I. In another embodiment of Formula (IIa) or Formula (IIb), $A^3$ is aryl, wherein the $A^3$ aryl is optionally substituted with one or more substituents independently selected from the group consisting of $R^1$, OR$^1$, SO$_2$R$^1$, C(O)R$^1$, CO(O)R$^1$, C(O)NH$_2$, C(O)NHR$^1$, C(O)N(R$^1$)$_2$, SO$_2$NH$_2$, C(O)OH, CN, F, Cl, Br and I. In another embodiment of Formula (IIa) or Formula (IIb), $A^3$ is aryl, wherein the $A^3$ aryl is substituted with one substituent independently selected from the group consisting of $R^1$, OR$^1$, SO$_2$R$^1$, C(O)R$^1$, CO(O)R$^1$, C(O)NH$_2$, C(O)NHR$^1$, C(O)N(R$^1$)$_2$, SO$_2$NH$_2$, C(O)OH, CN, F, Cl, Br and I. In another embodiment of Formula (IIa) or Formula (IIb), $A^3$ is aryl, wherein the $A^3$ aryl is substituted with two substituents independently selected from the group consisting of $R^1$, OR$^1$, SO$_2$R$^1$, C(O)R$^1$, CO(O)R$^1$, C(O)NH$_2$, C(O)NHR$^1$, C(O)N(R$^1$)$_2$, SO$_2$NH$_2$, C(O)OH, CN, F, Cl, Br and I. In another embodiment of Formula (IIa) or Formula (IIb), $A^3$ is heterocyclyl, wherein the $A^3$ heterocyclyl is optionally substituted with one or more substituents independently selected from the group consisting of $R^1$, OR$^1$, SO$_2$R$^1$, C(O)R$^1$, CO(O)R$^1$, C(O)NH$_2$, C(O)NHR$^1$, C(O)N(R$^1$)$_2$, SO$_2$NH$_2$, C(O)OH, CN, F, Cl, Br and I. In another embodiment of Formula (IIa) or Formula (IIb), $A^3$ is heterocyclyl, wherein the $A^3$ heterocyclyl is unsubstituted. In another embodiment of Formula (IIa) or Formula (IIb), $A^3$ is heterocyclyl, wherein the $A^3$ heterocyclyl is substituted with one substituent independently selected from the group consisting of $R^1$, OR$^1$, SO$_2$R$^1$, C(O)R$^1$, CO(O)R$^1$, C(O)NH$_2$, C(O)NHR$^1$, C(O)N(R$^1$)$_2$, SO$_2$NH$_2$, C(O)OH, CN, F, Cl, Br and I. In another embodiment of Formula (IIa) or Formula (IIb), $A^3$ is heterocyclyl, wherein the $A^3$ heterocyclyl is substituted with two substituents independently selected from the group consisting of $R^1$, OR$^1$, SO$_2$R$^1$, C(O)R$^1$, CO(O)R$^1$, C(O)NH$_2$, C(O)NHR$^1$, C(O)N(R$^1$)$_2$, SO$_2$NH$_2$, C(O)OH, CN, F, Cl, Br and I. In another embodiment of Formula (IIa) or Formula (IIb), $A^3$ is heteroaryl, wherein the $A^3$ heteroaryl is optionally substituted with one or more substituents independently selected from the group consisting of $R^1$, OR$^1$, SO$_2$R$^1$, C(O)R$^1$, CO(O)R$^1$, C(O)NH$_2$, C(O)NHR$^1$, C(O)N(R$^1$)$_2$, SO$_2$NH$_2$, C(O)OH, CN, F, Cl, Br and I. In another embodiment of Formula (IIa) or Formula (IIb), $A^3$ is heteroaryl, wherein the $A^3$ heteroaryl is unsubstituted. In another embodiment of Formula (IIa) or Formula (IIb), $A^3$ is heteroaryl, wherein the $A^3$ heteroaryl is substituted with one substituent independently selected from the group consisting of $R^1$, OR$^1$, SO$_2$R$^1$, C(O)R$^1$, CO(O)R$^1$, C(O)NH$_2$, C(O)NHR$^1$, C(O)N(R$^1$)$_2$, SO$_2$NH$_2$, C(O)OH, CN, F, Cl, Br and I. In another embodiment of Formula (IIa) or Formula (IIb), $A^3$ is heteroaryl, wherein the $A^3$ heteroaryl is substituted with two substituents independently selected from the group consisting of $R^1$, OR$^1$, SO$_2$R$^1$, C(O)R$^1$, CO(O)R$^1$, C(O)NH$_2$, C(O)NHR$^1$, C(O)N(R$^1$)$_2$, SO$_2$NH$_2$, C(O)OH, CN, F, Cl, Br and I.

In one embodiment of Formula (IIa) or Formula (IIb), n is 0, 1, or 2; and $A^4$, at each occurrence, is a substituent on a substitutable position of the benzene ring of the indane independently selected from the group consisting of C$_1$-C$_6$ alkyl, OH, F, Cl, Br and I. In another embodiment of Formula (IIa) or Formula (IIb), n is 0. In another embodiment of Formula (IIa) or Formula (IIb), n is 1; and $A^4$ is a substituent on a substitutable position of the benzene ring of the indane independently selected from the group consisting of C$_1$-C$_6$ alkyl, OH, F, Cl, Br and I. In another embodiment of Formula (IIa) or Formula (IIb), n is 2; and $A^4$, at each occurrence, is a substituent on a substitutable position of the benzene ring of the indane independently selected from the group consisting of OH and F. In another embodiment of Formula (IIa) or Formula (IIb), n is 2; and $A^4$, at each occurrence, is F.

In one embodiment of Formula (IIa) or Formula (IIb), m is 0 or 1; and $A^5$ is a substituent on a substitutable position of the cyclopentane ring of the indane independently selected from the group consisting of C$_1$-C$_6$ alkyl, OH, F, Cl, Br and I. In another embodiment of Formula (IIa) or Formula (IIb), m is 0. In another embodiment of Formula (IIa) or Formula (IIb), m is 1; and $A^5$ is a substituent on a substitutable position of the cyclopentane ring of the indane independently selected from the group consisting of C$_1$-C$_6$ alkyl, OH, F, Cl, Br and I. In another embodiment of Formula (IIa) or Formula (IIb), m is 1; and $A^5$ is a substituent on a substitutable position of the cyclopentane ring of the indane independently selected from the group consisting of OH and F. In another embodiment of Formula (IIa) or Formula (IIb), m is 1; and $A^5$ is OH. In another embodiment of Formula (IIa) or Formula (IIb), m is 1; and $A^5$ is F.

In one embodiment of Formula (IIa) or Formula (IIb), $R^1$, at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^1$ $C_1$-$C_6$ alkyl, $C_2$-$C_6$ alkenyl, and $C_2$-$C_6$ alkynyl is optionally substituted with one or more substituents independently selected from the group consisting of $R^2$, $OR^2$, $SR^2$, $S(O)R^2$, $SO_2R^2$, $C(O)R^2$, $CO(O)R^2$, $OC(O)R^2$, $OC(O)OR^2$, $NH_2$, $NHR^2$, $N(R^2)_2$, $NHC(O)R^2$, $NR^2C(O)R^2$, $NHS(O)_2R^2$, $NR^2S(O)_2R^2$, $NHC(O)OR^2$, $NR^2C(O)OR^2$, $NHC(O)NH_2$, $NHC(O)NHR^2$, $NHC(O)N(R^2)_2$, $NR^2C(O)NHR^2$, $NR^2C(O)N(R^2)_2$, $C(O)NH_2$, $C(O)NHR^2$, $C(O)N(R^2)_2$, $C(O)NHOH$, $C(O)NHOR^2$, $C(O)NHSO_2R^2$, $C(O)NR^2SO_2R^2$, $SO_2NH_2$, $SO_2NHR^2$, $SO_2N(R^2)_2$, $C(O)H$, $C(O)OH$, OH, (O), CN, $NO_2$, $CF_3$, $CF_2CF_3$, $OCF_3$, $OCF_2CF_3$, F, Cl, Br and I; wherein each $R^1$ aryl, heteroaryl, heterocyclyl, cycloalkyl, and cycloalkenyl is optionally substituted with one or more substituents independently selected from the group consisting of $R^3$, $OR^3$, $SR^3$, $S(O)R^3$, $SO_2R^3$, $C(O)R^3$, $CO(O)R^3$, $OC(O)R^3$, $OC(O)OR^3$, $NH_2$, $NHR^3$, $N(R^3)_2$, $NHC(O)R^3$, $NR^3C(O)R^3$, $NHS(O)_2R^3$, $NR^3S(O)_2R^3$, $NHC(O)OR^3$, $NR^3C(O)OR^3$, $NHC(O)NH_2$, $NHC(O)NHR^3$, $NHC(O)N(R^3)_2$, $NR^3C(O)NHR^3$, $NR^3C(O)N(R^3)_2$, $C(O)NH_2$, $C(O)NHR^3$, $C(O)N(R^3)_2$, $C(O)NHOH$, $C(O)NHOR^3$, $C(O)NHSO_2R^3$, $C(O)NR^3SO_2R^3$, $SO_2NH_2$, $SO_2NHR^3$, $SO_2N(R^3)_2$, $C(O)H$, $C(O)OH$, $C(O)C(O)NH_2$, $C(O)C(O)NHR^3$, $C(O)C(O)N(R^3)_2$, $C(N)NH_2$, $C(N)NHR^3$, $C(N)N(R^3)_2$, CNOH, $CNOCH_3$, OH, (O), CN, $NO_2$, $CF_3$, $CF_2CF_3$, $OCF_3$, $OCF_2CF_3$, F, Cl, Br and I. In another embodiment of Formula (IIa) or Formula (IIb), $R^1$, at each occurrence, is $C_1$-$C_6$ alkyl; wherein each $R^1$ $C_1$-$C_6$ alkyl is optionally substituted with one or more substituents independently selected from the group consisting of C(O)OH and OH. In another embodiment of Formula (IIa) or Formula (IIb), $R^1$, at each occurrence, is independently selected from the group consisting of aryl, heteroaryl, heterocyclyl, and cycloalkyl; wherein each $R^1$ aryl, heteroaryl, heterocyclyl, and cycloalkyl is optionally substituted with one or more substituents independently selected from the group consisting of $R^3$, $SO_2R^3$, $C(O)R^3$, $CO(O)R^3$, $C(O)NH_2$, $C(O)NHR^3$, $C(O)N(R^3)_2$, $SO_2N(R^3)_2$, $C(O)C(O)NH_2$, $C(O)C(O)N(R^3)_2$, OH, (O), and F.

In one embodiment of Formula (IIa) or Formula (IIb), $R^3$, at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^3$ $C_1$-$C_6$ alkyl, $C_2$-$C_6$ alkenyl, and $C_2$-$C_6$ alkynyl is optionally substituted with one or more substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, OH, (O), CN, $NO_2$, $CF_3$, $CF_2CF_3$, $OCF_3$, $OCF_2CF_3$, F, Cl, Br and I; wherein each $R^3$ aryl, heteroaryl, heterocyclyl, cycloalkyl, and cycloalkenyl is optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)$ $NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, $C(N)NH_2$, $C(N)NHR^5$, $C(N)N(R^5)_2$, CNOH, $CNOCH_3$, OH, (O), CN, $NO_2$, $CF_3$, $CF_2CF_3$, $OCF_3$, $OCF_2CF_3$, F, Cl, Br and I. In another embodiment of Formula (IIa) or Formula (IIb), $R^3$, at each occurrence, is independently $C_1$-$C_6$ alkyl; wherein each $R^3$ $C_1$-$C_6$ alkyl is optionally substituted with one or more substituents independently selected from the group consisting of $SO_2R^4$, $C(O)R^4$, $NHS(O)_2R^4$, $C(O)NH_2$, $C(O)NHR^4$, $C(O)N(R^4)_2$, $SO_2NH_2$, and OH. In another embodiment of Formula (IIa) or Formula (IIb), $R^3$, at each occurrence, is independently selected from the group consisting of heteroaryl, heterocyclyl, and cycloalkyl; wherein each $R^3$ heteroaryl, heterocyclyl, and cycloalkyl is optionally substituted with one or more substituents independently selected from the group consisting of $R^5$ and CN.

In one embodiment of Formula (IIa) or Formula (IIb), $R^4$ is at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^4$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I; wherein each $R^4$ aryl, heteroaryl, heterocyclyl, cycloalkyl, and cycloalkenyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I. In another embodiment of Formula (IIa) or Formula (IIb), $R^4$ at each occurrence, is $C_1$-$C_6$ alkyl. In another embodiment of Formula (IIa) or Formula (IIb), $R^4$ at each occurrence, is heterocyclyl; wherein each $R^4$ heterocyclyl is optionally substituted with one or more substituents independently selected from the group consisting of OH, and F.

In one embodiment of Formula (IIa) or Formula (IIb), $R^5$ is at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^5$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I; wherein each $R^5$ aryl, heteroaryl, heterocyclyl, cycloalkyl, and cycloalkenyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I. In another embodiment of Formula (IIa) or Formula (IIb), $R^5$ is at each occurrence, is independently $C_1$-$C_6$ alkyl.

In one embodiment of Formula (IIa) or Formula (IIb), $A^3$ is selected from the group consisting of aryl, heterocyclyl, and heteroaryl, wherein the $A^3$ aryl, heterocyclyl, and heteroaryl are optionally substituted with one or more substituents independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, C(O)OH, CN, F, Cl, Br and I;

$A^4$, at each occurrence, is a substituent on a substitutable position of the benzene ring of the indane independently selected from the group consisting of $C_1$-$C_6$ alkyl, OH, F, Cl, Br and I;

$A^5$ is a substituent on a substitutable position of the cyclopentane ring of the indane independently selected from the group consisting of OH, F, Cl, Br and I;

R¹, at each occurrence, is independently selected from the group consisting of $C_1$-$C_6$ alkyl, aryl, heteroaryl, heterocyclyl, and cycloalkyl; wherein each R¹ $C_1$-$C_6$ alkyl is optionally substituted with one or more substituents independently selected from the group consisting of C(O)OH, OH, F, Cl, Br and I; wherein each R¹ aryl, heteroaryl, heterocyclyl, cycloalkyl, and cycloalkenyl is optionally substituted with one or more substituents independently selected from the group consisting of R³, $SO_2R^3$, C(O)R³, CO(O)R³, C(O)NH₂, C(O)NHR³, C(O)N(R³)₂, $SO_2N(R^3)_2$, C(O)C(O)NH₂, C(O)C(O)N(R³)₂, OH, (O), F, Cl, Br and I;

R³, at each occurrence, is independently selected from the group consisting of $C_1$-$C_6$ alkyl, heteroaryl, heterocyclyl, and cycloalkyl; wherein each R³ $C_1$-$C_6$ alkyl is optionally substituted with one or more substituents independently selected from the group consisting of $SO_2R^4$, C(O)R⁴, NHS(O)₂R⁴, C(O)NH₂, C(O)NHR⁴, C(O)N(R⁴)₂, $SO_2NH_2$, F, Cl, Br and I; wherein each R³ heteroaryl and heterocyclyl is optionally substituted with one or more substituents independently selected from the group consisting of R⁵, CN, F, Cl, Br and I;

R⁴ is at each occurrence, is independently selected from the group consisting of $C_1$-$C_6$ alkyl and heterocyclyl; wherein each R⁴ heterocyclyl is optionally substituted with one or more substituents independently selected from the group consisting of OH, F, Cl, Br and I;

R⁵ is at each occurrence, is independently $C_1$-$C_6$ alkyl;

n is 0, 1, or 2; and m is 0 or 1.

Still another embodiment pertains to compounds of Formula (IIa) or Formula (IIb), selected from the group consisting of:

(3R,4S)-1-(7-fluoro-2,3-dihydro-1H-inden-1-yl)-4-{4-[4-(methanesulfonyl)piperazin-1-yl]phenyl}-N,N-dimethylpyrrolidin-3-amine;

rac-(3R,4S)-1-(7-fluoro-2,3-dihydro-1H-inden-1-yl)-4-{4-[4-(methanesulfonyl)piperazin-1-yl]phenyl}-N,N-dimethylpyrrolidin-3-amine;

(3S,4R)-1-(7-fluoro-2,3-dihydro-1H-inden-1-yl)-4-{4-[4-(methanesulfonyl)piperazin-1-yl]phenyl}-N,N-dimethylpyrrolidin-3-amine;

(3S,4R)-1-[(1S)-7-fluoro-2,3-dihydro-1H-inden-1-yl]-4-{4-[4-(methanesulfonyl)piperazin-1-yl]phenyl}-N,N-dimethylpyrrolidin-3-amine;

(3S,4R)-1-[(1R)-7-fluoro-2,3-dihydro-1H-inden-1-yl]-4-{4-[4-(methanesulfonyl)piperazin-1-yl]phenyl}-N,N-dimethylpyrrolidin-3-amine;

rac-(3S,4R)-4-(4-bromophenyl)-1-(7-fluoro-2,3-dihydro-1H-inden-1-yl)-N,N-dimethylpyrrolidin-3-amine;

rac-(3S,4R)-4-(4-chlorophenyl)-1-(7-fluoro-2,3-dihydro-1H-inden-1-yl)-N,N-dimethylpyrrolidin-3-amine;

rac-4-[(3S,4R)-4-(dimethylamino)-1-(7-fluoro-2,3-dihydro-1H-inden-1-yl)pyrrolidin-3-yl]benzene-1-sulfonamide;

(3R,4S)-1-[(1S)-2,3-dihydro-1H-inden-1-yl]-4-[4-(methanesulfonyl)phenyl]-N,N-dimethylpyrrolidin-3-amine;

(3S,4R)-1-[(1S)-2,3-dihydro-1H-inden-1-yl]-4-[4-(methanesulfonyl)phenyl]-N,N-dimethylpyrrolidin-3-amine;

(3R,4S)-1-[(1S)-7-fluoro-2,3-dihydro-1H-inden-1-yl]-4-[4-(methanesulfonyl)phenyl]-N,N-dimethylpyrrolidin-3-amine;

(3R,4S)-1-[(1R)-7-fluoro-2,3-dihydro-1H-inden-1-yl]-4-[4-(methanesulfonyl)phenyl]-N,N-dimethylpyrrolidin-3-amine;

(3S,4R)-1-[(1S)-7-fluoro-2,3-dihydro-1H-inden-1-yl]-4-[4-(methanesulfonyl)phenyl]-N,N-dimethylpyrrolidin-3-amine;

(3S,4R)-1-[(1R)-7-fluoro-2,3-dihydro-1H-inden-1-yl]-4-[4-(methanesulfonyl)phenyl]-N,N-dimethylpyrrolidin-3-amine;

rac-(1S)-1-{(3S,4R)-3-(dimethylamino)-4-[4-(methanesulfonyl)phenyl]pyrrolidin-1-yl}-7-fluoro-2,3-dihydro-1H-inden-5-ol;

rac-(1R,3R)-3-{(3R,4S)-3-(dimethylamino)-4-[4-(methanesulfonyl)phenyl]pyrrolidin-1-yl}-4-fluoro-2,3-dihydro-1H-inden-1-ol;

rac-(1R)-1-{(3S,4R)-3-(dimethylamino)-4-[4-(methanesulfonyl)phenyl]pyrrolidin-1-yl}-7-fluoro-2,3-dihydro-1H-inden-5-ol;

rac-(1S,3S)-3-{(3R,4S)-3-(dimethylamino)-4-[4-(methanesulfonyl)phenyl]pyrrolidin-1-yl}-4-fluoro-2,3-dihydro-1H-inden-1-ol;

rac-4-{(3R,4S)-4-(dimethylamino)-1-[(1R)-7-fluoro-2,3-dihydro-1H-inden-1-yl]pyrrolidin-3-yl}benzonitrile;

rac-methyl 4-[(3R,4S)-1-[(1R)-2,3-dihydro-1H-inden-1-yl]-4-(dimethylamino)pyrrolidin-3-yl]benzoate;

rac-methyl 4-[(3S,4R)-1-(7-chloro-2,3-dihydro-1H-inden-1-yl)-4-(dimethylamino)pyrrolidin-3-yl]benzoate;

rac-methyl 4-[(3R,4S)-4-(dimethylamino)-1-(7-fluoro-2,3-dihydro-1H-inden-1-yl)pyrrolidin-3-yl]benzoate;

rac-(3S,4R)-4-(3,4-dimethoxyphenyl)-1-(7-fluoro-2,3-dihydro-1H-inden-1-yl)-N,N-dimethylpyrrolidin-3-amine;

rac-4-[(3S,4R)-4-(dimethylamino)-1-(7-fluoro-2,3-dihydro-1H-inden-1-yl)pyrrolidin-3-yl]-N-methylbenzamide;

rac-4-[(3S,4R)-1-(7-chloro-2,3-dihydro-1H-inden-1-yl)-4-(dimethylamino)pyrrolidin-3-yl]-N,N-dimethylbenzamide;

rac-4-[(3S,4R)-4-(dimethylamino)-1-(7-fluoro-2,3-dihydro-1H-inden-1-yl)pyrrolidin-3-yl]-N,N-dimethylbenzamide;

rac-(3R,4S)-4-(4-bromo-3-methylphenyl)-1-(7-fluoro-2,3-dihydro-1H-inden-1-yl)-N,N-dimethylpyrrolidin-3-amine;

rac-4-[(3S,4R)-1-(7-chloro-2,3-dihydro-1H-inden-1-yl)-4-(dimethylamino)pyrrolidin-3-yl]benzoic acid;

rac-4-[(3R,4S)-4-(dimethylamino)-1-(7-fluoro-2,3-dihydro-1H-inden-1-yl)pyrrolidin-3-yl]benzoic acid;

rac-(3R,4S)-1-[(3S)-3,7-difluoro-2,3-dihydro-1H-inden-1-yl]-4-[4-(methanesulfonyl)phenyl]-N,N-dimethylpyrrolidin-3-amine;

rac-(3R,4S)-1-[(1R,3S)-3,7-difluoro-2,3-dihydro-1H-inden-1-yl]-4-[4-(methanesulfonyl)phenyl]-N,N-dimethylpyrrolidin-3-amine;

rac-(3R,4S)-1-[(1S,3S)-3,7-difluoro-2,3-dihydro-1H-inden-1-yl]-4-[4-(methanesulfonyl)phenyl]-N,N-dimethylpyrrolidin-3-amine;

(3S)-3-{(3S,4R)-3-(dimethylamino)-4-[4-(methanesulfonyl)phenyl]pyrrolidin-1-yl}-4-fluoro-2,3-dihydro-1H-inden-1-ol;

rac-(1R,3S)-3-{(3R,4S)-3-(dimethylamino)-4-[4-(methanesulfonyl)phenyl]pyrrolidin-1-yl}-4-fluoro-2,3-dihydro-1H-inden-1-ol;

rac-4-[(3R,4S)-4-(dimethylamino)-1-(7-fluoro-2,3-dihydro-1H-inden-1-yl)pyrrolidin-3-yl]benzamide;

rac-4-[(3S,4R)-4-(dimethylamino)-1-(7-fluoro-2,3-dihydro-1H-inden-1-yl)pyrrolidin-3-yl]-2-methylbenzoic acid;

rac-4-[(3S,4R)-4-(dimethylamino)-1-(7-fluoro-2,3-dihydro-1H-inden-1-yl)pyrrolidin-3-yl]-2-methylbenzonitrile;

rac-4-[(3S,4R)-4-(dimethylamino)-1-(2-hydroxy-2,3-dihydro-1H-inden-1-yl)pyrrolidin-3-yl]-2-methylbenzonitrile;

rac-methyl 4-[(3S,4R)-4-(dimethylamino)-1-(7-fluoro-2,3-dihydro-1H-inden-1-yl)pyrrolidin-3-yl]-2-methylbenzoate;

rac-{4-[(3S,4R)-4-(dimethylamino)-1-(7-fluoro-2,3-dihydro-1H-inden-1-yl)pyrrolidin-3-yl]phenyl}[(3S)-3-hydroxypyrrolidin-1-yl]methanone;

rac-(3S,4R)-1-(7-fluoro-2,3-dihydro-1H-inden-1-yl)-N,N-dimethyl-4-[(piperazin-1-yl)phenyl]pyrrolidin-3-amine;

1-(4-{4-[(3S,4R)-1-(2,3-dihydro-1H-inden-1-yl)-4-(dimethylamino)pyrrolidin-3-yl]phenyl}piperazin-1-yl)ethan-1-one;

1-(4-{4-[(3S,4R)-4-(dimethylamino)-1-(7-fluoro-2,3-dihydro-1H-inden-1-yl)pyrrolidin-3-yl]phenyl}piperazin-1-yl)ethan-1-one;

rac-1-(4-{4-[(3S,4R)-4-(dimethylamino)-1-(7-fluoro-2,3-dihydro-1H-inden-1-yl)pyrrolidin-3-yl]phenyl}piperazin-1-yl)ethan-1-one;

1-[4-(4-{(3S,4R)-4-(dimethylamino)-1-[(1S)-7-fluoro-2,3-dihydro-1H-inden-1-yl]pyrrolidin-3-yl}phenyl)piperazin-1-yl]ethan-1-one;

1-[4-(4-{(3S,4R)-4-(dimethylamino)-1-[(1R)-7-fluoro-2,3-dihydro-1H-inden-1-yl]pyrrolidin-3-yl}phenyl)piperazin-1-yl]ethan-1-one;

1-[4-(4-{(3R,4S)-4-(dimethylamino)-1-[(1S)-7-fluoro-2,3-dihydro-1H-inden-1-yl]pyrrolidin-3-yl}phenyl)piperazin-1-yl]ethan-1-one;

1-[4-(4-{(3R,4S)-4-(dimethylamino)-1-[(1R)-7-fluoro-2,3-dihydro-1H-inden-1-yl]pyrrolidin-3-yl}phenyl)piperazin-1-yl]ethan-1-one;

rac-(3R,4S)-4-{4-[4-(ethanesulfonyl)piperazin-1-yl]phenyl}-1-(7-fluoro-2,3-dihydro-1H-inden-1-yl)-N,N-dimethylpyrrolidin-3-amine;

tert-butyl 4-{4-[(3R,4S)-4-(dimethylamino)-1-(7-fluoro-2,3-dihydro-1H-inden-1-yl)pyrrolidin-3-yl]phenyl}piperazine-1-carboxylate;

rac-4-{4-[(3S,4R)-4-(dimethylamino)-1-(7-fluoro-2,3-dihydro-1H-inden-1-yl)pyrrolidin-3-yl]benzoyl}-1-methylpiperazin-2-one;

rac-1-(4-{4-[(3R,4S)-4-(dimethylamino)-1-(7-fluoro-2,3-dihydro-1H-inden-1-yl)pyrrolidin-3-yl]phenyl}piperazin-1-yl)-2-hydroxyethan-1-one;

rac-{4-[(3S,4R)-4-(dimethylamino)-1-(7-fluoro-2,3-dihydro-1H-inden-1-yl)pyrrolidin-3-yl]phenyl}[4-(methanesulfonyl)piperazin-1-yl]methanone;

rac-2-(4-{4-[(3R,4S)-4-(dimethylamino)-1-(7-fluoro-2,3-dihydro-1H-inden-1-yl)pyrrolidin-3-yl]phenyl}piperazin-1-yl)-2-oxoacetamide;

rac-1-(4-{4-[(3S,4R)-4-(dimethylamino)-1-(7-fluoro-2,3-dihydro-1H-inden-1-yl)pyrrolidin-3-yl]benzoyl}piperazin-1-yl)ethan-1-one;

rac-4-{4-[(3S,4R)-4-(dimethylamino)-1-(7-fluoro-2,3-dihydro-1H-inden-1-yl)pyrrolidin-3-yl]phenyl}-1-methylpiperazin-2-one;

rac-{4-[(3S,4R)-4-(dimethylamino)-1-(7-fluoro-2,3-dihydro-1H-inden-1-yl)pyrrolidin-3-yl]phenyl}[4-(ethanesulfonyl)piperazin-1-yl]methanone;

rac-4-{4-[(3S,4R)-4-(dimethylamino)-1-(7-fluoro-2,3-dihydro-1H-inden-1-yl)pyrrolidin-3-yl]-2-methylphenyl}-1-methylpiperazin-2-one;

rac-2-(4-{4-[(3R,4S)-4-(dimethylamino)-1-(7-fluoro-2,3-dihydro-1H-inden-1-yl)pyrrolidin-3-yl]phenyl}piperazin-1-yl)-N,N-dimethyl-2-oxoacetamide;

rac-1-(4-{4-[(3R,4S)-4-(dimethylamino)-1-(7-fluoro-2,3-dihydro-1H-inden-1-yl)pyrrolidin-3-yl]-2-methylphenyl}piperazin-1-yl)ethan-1-one;

rac-(3R,4S)-1-(7-fluoro-2,3-dihydro-1H-inden-1-yl)-N,N-dimethyl-4-[4-(4-methylpiperazin-1-yl)phenyl]pyrrolidin-3-amine;

rac-(3R,4S)-4-{4-[4-(ethanesulfonyl)piperazin-1-yl]-3-methylphenyl}-1-(7-fluoro-2,3-dihydro-1H-inden-1-yl)-N,N-dimethylpyrrolidin-3-amine;

rac-4-{4-[(3S,4R)-4-(dimethylamino)-1-(7-fluoro-2,3-dihydro-1H-inden-1-yl)pyrrolidin-3-yl]phenyl}-N,N-dimethylpiperazine-1-carboxamide;

rac-(3R,4S)-4-[4-(4-cyclopropylpiperazin-1-yl)phenyl]-1-(7-fluoro-2,3-dihydro-1H-inden-1-yl)-N,N-dimethylpyrrolidin-3-amine;

rac-(3S,4R)-4-(2H-1,3-benzodioxol-5-yl)-1-(7-fluoro-2,3-dihydro-1H-inden-1-yl)-N,N-dimethylpyrrolidin-3-amine;

rac-(3S,4R)-1-(7-fluoro-2,3-dihydro-1H-inden-1-yl)-N,N-dimethyl-4-[4-(1,3-oxazol-2-yl)phenyl]pyrrolidin-3-amine;

rac-(3R,4S)-1-(7-fluoro-2,3-dihydro-1H-inden-1-yl)-N,N-dimethyl-4-[4-(3-methyl-1,2,4-oxadiazol-5-yl)phenyl]pyrrolidin-3-amine;

rac-(3S,4R)-1-(7-fluoro-2,3-dihydro-1H-inden-1-yl)-N,N-dimethyl-4-[4-(5-methyl-1,3,4-oxadiazol-2-yl)phenyl]pyrrolidin-3-amine;

rac-(3S,4R)-1-(7-fluoro-2,3-dihydro-1H-inden-1-yl)-N,N-dimethyl-4-[4-(4-methyl-1,3-oxazol-2-yl)phenyl]pyrrolidin-3-amine;

rac-(3R,4S)-1-(7-fluoro-2,3-dihydro-1H-inden-1-yl)-N,N-dimethyl-4-[4-(1-methyl-1H-pyrazol-4-yl)phenyl]pyrrolidin-3-amine;

rac-2-(4-{4-[(3S,4R)-4-(dimethylamino)-1-(7-fluoro-2,3-dihydro-1H-inden-1-yl)pyrrolidin-3-yl]phenyl}-1H-pyrazol-1-yl)acetamide;

rac-2-(4-{4-[(3S,4R)-4-(dimethylamino)-1-(7-fluoro-2,3-dihydro-1H-inden-1-yl)pyrrolidin-3-yl]phenyl}-1H-pyrazol-1-yl)-N-methylacetamide;

rac-(3S,4R)-1-(7-fluoro-2,3-dihydro-1H-inden-1-yl)-N,N-dimethyl-4-{4-[4-(1-methyl-1H-imidazole-4-sulfonyl)piperazin-1-yl]phenyl}pyrrolidin-3-amine;

rac-(3S,4R)-1-(7-fluoro-2,3-dihydro-1H-inden-1-yl)-N,N-dimethyl-4-{4-[4-(pyrimidin-4-yl)piperazin-1-yl]phenyl}pyrrolidin-3-amine;

rac-(3S,4R)-1-(7-fluoro-2,3-dihydro-1H-inden-1-yl)-N,N-dimethyl-4-{4-[4-(pyridin-2-yl)piperazin-1-yl]phenyl}pyrrolidin-3-amine;

(3R,4S)-1-(7-fluoro-2,3-dihydro-1H-inden-1-yl)-N,N-dimethyl-4-(1-methyl-1H-indol-3-yl)pyrrolidin-3-amine;

(3R,4S)-1-[(1S)-7-fluoro-2,3-dihydro-1H-inden-1-yl]-N,N-dimethyl-4-(1-methyl-1H-indol-3-yl)pyrrolidin-3-amine;

(3R,4S)-1-[(1R)-7-fluoro-2,3-dihydro-1H-inden-1-yl]-N,N-dimethyl-4-(1-methyl-1H-indol-3-yl)pyrrolidin-3-amine;

3-[(3S,4R)-4-(dimethylamino)-1-(7-fluoro-2,3-dihydro-1H-inden-1-yl)pyrrolidin-3-yl]-1-methyl-1H-indole-7-carboxylic acid;

rac-3-[(3S,4R)-4-(dimethylamino)-1-(7-fluoro-2,3-dihydro-1H-inden-1-yl)pyrrolidin-3-yl]-1-methyl-1H-indole-7-carboxylic acid;

3-[(3R,4S)-4-(dimethylamino)-1-(7-fluoro-2,3-dihydro-1H-inden-1-yl)pyrrolidin-3-yl]-1-methyl-1H-indole-7-carboxylic acid;

rac-methyl 3-[(3R,4S)-4-(dimethylamino)-1-(7-fluoro-2,3-dihydro-1H-inden-1-yl)pyrrolidin-3-yl]-1-methyl-1H-indole-6-carboxylate;

methyl 3-[(3S,4R)-4-(dimethylamino)-1-(7-fluoro-2,3-dihydro-1H-inden-1-yl)pyrrolidin-3-yl]-1-methyl-1H-indole-7-carboxylate;

rac-methyl 3-[(3S,4R)-4-(dimethylamino)-1-(7-fluoro-2,3-dihydro-1H-inden-1-yl)pyrrolidin-3-yl]-1-methyl-1H-indole-7-carboxylate;

methyl 3-[(3R,4S)-4-(dimethylamino)-1-(7-fluoro-2,3-dihydro-1H-inden-1-yl)pyrrolidin-3-yl]-1-methyl-1H-indole-7-carboxylate;
rac-3-[(3S,4R)-4-(dimethylamino)-1-(7-fluoro-2,3-dihydro-1H-inden-1-yl)pyrrolidin-3-yl]-N,N,1-trimethyl-1H-indole-6-carboxamide;
(3R,4S)-1-(2,3-dihydro-1H-inden-1-yl)-N,N-dimethyl-4-(1-methyl-1H-indol-3-yl)pyrrolidin-3-amine;
(3R,4S)-1-(7-chloro-2,3-dihydro-1H-inden-1-yl)-N,N-dimethyl-4-(1-methyl-1H-indol-3-yl)pyrrolidin-3-amine;
rac-(3R,4S)-1-(4-fluoro-2,3-dihydro-1H-inden-1-yl)-N,N-dimethyl-4-(1-methyl-1H-indol-3-yl)pyrrolidin-3-amine;
rac-(3R,4S)-1-(5-fluoro-2,3-dihydro-1H-inden-1-yl)-N,N-dimethyl-4-(1-methyl-1H-indol-3-yl)pyrrolidin-3-amine;
rac-(3R,4S)-1-(6-fluoro-2,3-dihydro-1H-inden-1-yl)-N,N-dimethyl-4-(1-methyl-1H-indol-3-yl)pyrrolidin-3-amine;
rac-(3R,4S)-4-(7-bromo-1-methyl-1H-indol-3-yl)-1-(7-fluoro-2,3-dihydro-1H-inden-1-yl)-N,N-dimethylpyrrolidin-3-amine;
rac-(3R,4S)-4-(6-bromo-1-methyl-1H-indol-3-yl)-1-(7-fluoro-2,3-dihydro-1H-inden-1-yl)-N,N-dimethylpyrrolidin-3-amine;
rac-(3R,4S)-1-(5,7-difluoro-2,3-dihydro-1H-inden-1-yl)-N,N-dimethyl-4-(1-methyl-1H-indol-3-yl)pyrrolidin-3-amine;
(3R,4S)-1-(6,7-difluoro-2,3-dihydro-1H-inden-1-yl)-N,N-dimethyl-4-(1-methyl-1H-indol-3-yl)pyrrolidin-3-amine;
3-[(3R,4S)-3-(dimethylamino)-4-(1-methyl-1H-indol-3-yl)pyrrolidin-1-yl]-2,3-dihydro-1H-inden-4-ol;
rac-3-[(3S,4R)-4-(dimethylamino)-1-(7-fluoro-2,3-dihydro-1H-inden-1-yl)pyrrolidin-3-yl]-N-(2-hydroxyethyl)-N,1-dimethyl-1H-indole-7-carboxamide;
rac-3-[(3S,4R)-4-(dimethylamino)-1-(7-fluoro-2,3-dihydro-1H-inden-1-yl)pyrrolidin-3-yl]-N,1-dimethyl-1H-indole-7-carboxamide;
(3R,4S)—N,N-dimethyl-1-(7-methyl-2,3-dihydro-1H-inden-1-yl)-4-(1-methyl-1H-indol-3-yl)pyrrolidin-3-amine;
rac-3-[(3S,4R)-4-(dimethylamino)-1-(7-fluoro-2,3-dihydro-1H-inden-1-yl)pyrrolidin-3-yl]-N,N,1-trimethyl-1H-indole-7-carboxamide;
{3-[(3S,4R)-4-(dimethylamino)-1-(7-fluoro-2,3-dihydro-1H-inden-1-yl)pyrrolidin-3-yl]-1-methyl-1H-indol-7-yl}(3-fluoroazetidin-1-yl)methanone;
rac-{3-[(3S,4R)-4-(dimethylamino)-1-(7-fluoro-2,3-dihydro-1H-inden-1-yl)pyrrolidin-3-yl]-1-methyl-1H-indol-7-yl}(3-fluoroazetidin-1-yl)methanone;
{3-[(3R,4S)-4-(dimethylamino)-1-(7-fluoro-2,3-dihydro-1H-inden-1-yl)pyrrolidin-3-yl]-1-methyl-1H-indol-7-yl}(3-fluoroazetidin-1-yl)methanone;
{3-[(3S,4R)-4-(dimethylamino)-1-(7-fluoro-2,3-dihydro-1H-inden-1-yl)pyrrolidin-3-yl]-1-methyl-1H-indol-7-yl}(3-hydroxyazetidin-1-yl)methanone;
rac-{3-[(3S,4R)-4-(dimethylamino)-1-(7-fluoro-2,3-dihydro-1H-inden-1-yl)pyrrolidin-3-yl]-1-methyl-1H-indol-7-yl}(3-hydroxyazetidin-1-yl)methanone;
rac-{3-[(3S,4R)-4-(dimethylamino)-1-(7-fluoro-2,3-dihydro-1H-inden-1-yl)pyrrolidin-3-yl]-1-methyl-1H-indol-6-yl}(3-hydroxyazetidin-1-yl)methanone;
rac-3-[(3S,4R)-4-(dimethylamino)-1-(7-fluoro-2,3-dihydro-1H-inden-1-yl)pyrrolidin-3-yl]-N-(3-hydroxycyclobutyl)-1-methyl-1H-indole-7-carboxamide;
rac-3-[(3S,4R)-4-(dimethylamino)-1-(7-fluoro-2,3-dihydro-1H-inden-1-yl)pyrrolidin-3-yl]-N-(3-hydroxycyclobutyl)-N,1-dimethyl-1H-indole-7-carboxamide;
rac-{3-[(3S,4R)-4-(dimethylamino)-1-(7-fluoro-2,3-dihydro-1H-inden-1-yl)pyrrolidin-3-yl]-1-methyl-1H-indol-7-yl}[3-(methanesulfonyl)azetidin-1-yl]methanone;
rac-{3-[(3S,4R)-4-(dimethylamino)-1-(7-fluoro-2,3-dihydro-1H-inden-1-yl)pyrrolidin-3-yl]-1-methyl-1H-indol-6-yl}[(3S)-3-hydroxypyrrolidin-1-yl]methanone;
rac-{3-[(3S,4R)-4-(dimethylamino)-1-(7-fluoro-2,3-dihydro-1H-inden-1-yl)pyrrolidin-3-yl]-1-methyl-1H-indol-6-yl}[(3R)-3-hydroxypyrrolidin-1-yl]methanone;
rac-[(3S,4S)-3,4-dihydroxypyrrolidin-1-yl]{3-[(3S,4R)-4-(dimethylamino)-1-(7-fluoro-2,3-dihydro-1H-inden-1-yl)pyrrolidin-3-yl]-1-methyl-1H-indol-7-yl}methanone;
rac-[(3S,4S)-3,4-dihydroxypyrrolidin-1-yl]{3-[(3S,4R)-4-(dimethylamino)-1-(7-fluoro-2,3-dihydro-1H-inden-1-yl)pyrrolidin-3-yl]-1-methyl-1H-indol-6-yl}methanone;
rac-3-[(3S,4R)-4-(dimethylamino)-1-(7-fluoro-2,3-dihydro-1H-inden-1-yl)pyrrolidin-3-yl]-N-(1,1-dioxo-1lambda~6~-thiolan-3-yl)-1-methyl-1H-indole-7-carboxamide;
rac-{3-[(3S,4R)-4-(dimethylamino)-1-(7-fluoro-2,3-dihydro-1H-inden-1-yl)pyrrolidin-3-yl]-1-methyl-1H-indol-7-yl}[(2S)-2-(hydroxymethyl)pyrrolidin-1-yl]methanone;
rac-1-{3-[(3S,4R)-4-(dimethylamino)-1-(7-fluoro-2,3-dihydro-1H-inden-1-yl)pyrrolidin-3-yl]-1-methyl-1H-indole-7-carbonyl}-L-prolinamide;
rac-{3-[(3S,4R)-4-(dimethylamino)-1-(7-fluoro-2,3-dihydro-1H-inden-1-yl)pyrrolidin-3-yl]-1-methyl-1H-indol-7-yl}[(3S)-3-hydroxypyrrolidin-1-yl]methanone;
rac-{3-[(3S,4R)-4-(dimethylamino)-1-(7-fluoro-2,3-dihydro-1H-inden-1-yl)pyrrolidin-3-yl]-1-methyl-1H-indol-7-yl}(piperazin-1-yl)methanone;
rac-(3R,4S)-1-(7-fluoro-2,3-dihydro-1H-inden-1-yl)-4-{6-[4-(methanesulfonyl)piperazin-1-yl]-1-methyl-1H-indol-3-yl}-N,N-dimethylpyrrolidin-3-amine;
rac-1-(4-{3-[(3S,4R)-4-(dimethylamino)-1-(7-fluoro-2,3-dihydro-1H-inden-1-yl)pyrrolidin-3-yl]-1-methyl-1H-indol-6-yl}piperazin-1-yl)ethan-1-one;
rac-{3-[(3S,4R)-4-(dimethylamino)-1-(7-fluoro-2,3-dihydro-1H-inden-1-yl)pyrrolidin-3-yl]-1-methyl-1H-indol-6-yl}[4-(methanesulfonyl)piperazin-1-yl]methanone;
rac-1-(4-{3-[(3S,4R)-4-(dimethylamino)-1-(7-fluoro-2,3-dihydro-1H-inden-1-yl)pyrrolidin-3-yl]-1-methyl-1H-indole-6-carbonyl}piperazin-1-yl)ethan-1-one;
rac-4-{3-[(3S,4R)-4-(dimethylamino)-1-(7-fluoro-2,3-dihydro-1H-inden-1-yl)pyrrolidin-3-yl]-1-methyl-1H-indole-7-carbonyl}-N,N-dimethylpiperazine-1-sulfonamide;
rac-4-{3-[(3S,4R)-4-(dimethylamino)-1-(7-fluoro-2,3-dihydro-1H-inden-1-yl)pyrrolidin-3-yl]-1-methyl-1H-indole-7-carbonyl}-1-methylpiperazin-2-one;
rac-{3-[(3S,4R)-4-(dimethylamino)-1-(7-fluoro-2,3-dihydro-1H-inden-1-yl)pyrrolidin-3-yl]-1-methyl-1H-indol-7-yl}[4-(methanesulfonyl)piperazin-1-yl]methanone;
rac-4-{3-[(3S,4R)-4-(dimethylamino)-1-(7-fluoro-2,3-dihydro-1H-inden-1-yl)pyrrolidin-3-yl]-1-methyl-1H-indole-7-carbonyl}-N,N-dimethylpiperazine-1-carboxamide;
rac-1-(4-{3-[(3S,4R)-4-(dimethylamino)-1-(7-fluoro-2,3-dihydro-1H-inden-1-yl)pyrrolidin-3-yl]-1-methyl-1H-indole-7-carbonyl}piperazin-1-yl)ethan-1-one;
rac-4-{3-[(3S,4R)-4-(dimethylamino)-1-(7-fluoro-2,3-dihydro-1H-inden-1-yl)pyrrolidin-3-yl]-1-methyl-1H-indol-7-yl}-1-methylpiperazin-2-one;
rac-{3-[(3S,4R)-4-(dimethylamino)-1-(7-fluoro-2,3-dihydro-1H-inden-1-yl)pyrrolidin-3-yl]-1-methyl-1H-indol-7-yl}[4-(ethanesulfonyl)piperazin-1-yl]methanone;
rac-4-{3-[(3S,4R)-4-(dimethylamino)-1-(7-fluoro-2,3-dihydro-1H-inden-1-yl)pyrrolidin-3-yl]-1-methyl-1H-indol-7-yl}-N,N-dimethylpiperazine-1-carboxamide;

[4-(azetidine-1-sulfonyl)piperazin-1-yl]{3-[(3S,4R)-4-(dimethylamino)-1-(7-fluoro-2,3-dihydro-1H-inden-1-yl)pyrrolidin-3-yl]-1-methyl-1H-indol-7-yl}methanone;

1-(4-{3-[(3S,4R)-4-(dimethylamino)-1-(7-fluoro-2,3-dihydro-1H-inden-1-yl)pyrrolidin-3-yl]-1-methyl-1H-indole-7-carbonyl}piperazine-1-sulfonyl)azetidine-3-carbonitrile;

rac-8-{3-[(3S,4R)-4-(dimethylamino)-1-(7-fluoro-2,3-dihydro-1H-inden-1-yl)pyrrolidin-3-yl]-1-methyl-1H-indole-7-carbonyl}hexahydro-2H-pyrazino[1,2-a]pyrazin-1(6H)-one;

rac-{3-[(3S,4R)-4-(dimethylamino)-1-(7-fluoro-2,3-dihydro-1H-inden-1-yl)pyrrolidin-3-yl]-1-methyl-1H-indol-7-yl}[4-(1-methyl-1H-imidazole-5-sulfonyl)piperazin-1-yl]methanone;

rac-{3-[(3S,4R)-4-(dimethylamino)-1-(7-fluoro-2,3-dihydro-1H-inden-1-yl)pyrrolidin-3-yl]-1-methyl-1H-indol-7-yl}[4-(3,5-dimethyl-1H-pyrazole-4-sulfonyl)piperazin-1-yl]methanone;

rac-{3-[(3S,4R)-4-(dimethylamino)-1-(7-fluoro-2,3-dihydro-1H-inden-1-yl)pyrrolidin-3-yl]-1-methyl-1H-indol-7-yl}[4-(pyridazin-3-yl)piperazin-1-yl]methanone;

rac-(3R,4S)-1-[(1S)-7-fluoro-2,3-dihydro-1H-inden-1-yl]-N,N-dimethyl-4-(1-methyl-1H-pyrrolo[3,2-b]pyridin-3-yl)pyrrolidin-3-amine;

rac-(3S,4R)-4-(2,3-dihydro-1-benzofuran-3-yl)-1-[(1R)-7-fluoro-2,3-dihydro-1H-inden-1-yl]-N,N-dimethylpyrrolidin-3-amine;

rac-(3S,4R)-1-(7-fluoro-2,3-dihydro-1H-inden-1-yl)-N,N-dimethyl-4-(5,6,7,8-tetrahydroimidazo[1,2-a]pyridin-3-yl)pyrrolidin-3-amine;

rac-(3R,4S)-1-(7-fluoro-2,3-dihydro-1H-inden-1-yl)-N,N-dimethyl-4-(1-methyl-1H-pyrrolo[3,2-c]pyridin-3-yl)pyrrolidin-3-amine;

rac-(3R,4S)-4-(2,3-dihydro-1-benzofuran-3-yl)-1-[(1R)-7-fluoro-2,3-dihydro-1H-inden-1-yl]-N,N-dimethylpyrrolidin-3-amine;

rac-(3R,4S)-1-[(1R)-7-fluoro-2,3-dihydro-1H-inden-1-yl]-N,N-dimethyl-4-(1-methyl-1H-pyrrolo[3,2-b]pyridin-3-yl)pyrrolidin-3-amine;

rac-(3R,4S)-1-(7-fluoro-2,3-dihydro-1H-inden-1-yl)-N,N-dimethyl-4-(oxan-4-yl)pyrrolidin-3-amine;

rac-(3S,4R)-1-(7-fluoro-2,3-dihydro-1H-inden-1-yl)-N,N-dimethyl-4-[6-(piperazin-1-yl)pyridin-3-yl]pyrrolidin-3-amine;

rac-(3R,4S)-1-(7-fluoro-2,3-dihydro-1H-inden-1-yl)-N,N-dimethyl-4-(1-phenylpiperidin-4-yl)pyrrolidin-3-amine;

rac-2-(4-{5-[(3R,4S)-4-(dimethylamino)-1-(7-fluoro-2,3-dihydro-1H-inden-1-yl)pyrrolidin-3-yl]pyridin-2-yl}piperazin-1-yl)-N,N-dimethylacetamide;

rac-(3R,4S)-1-(7-fluoro-2,3-dihydro-1H-inden-1-yl)-N,N-dimethyl-4-(1-methyl-1H-pyrrolo[2,3-c]pyridin-3-yl)pyrrolidin-3-amine;

rac-(3R,4S)-1-(7-fluoro-2,3-dihydro-1H-inden-1-yl)-N,N-dimethyl-4-[1-(pyridin-3-yl)piperidin-4-yl]pyrrolidin-3-amine;

rac-2-(4-{5-[(3R,4S)-4-(dimethylamino)-1-(7-fluoro-2,3-dihydro-1H-inden-1-yl)pyrrolidin-3-yl]pyridin-2-yl}-1H-pyrazol-1-yl)-1-(3-hydroxyazetidin-1-yl)ethan-1-one;

rac-(4-{5-[(3R,4S)-4-(dimethylamino)-1-(7-fluoro-2,3-dihydro-1H-inden-1-yl)pyrrolidin-3-yl]pyridin-2-yl}piperazin-1-yl)(oxetan-3-yl)methanone;

rac-(3R,4S)-1-(7-fluoro-2,3-dihydro-1H-inden-1-yl)-N,N-dimethyl-4-[1-(pyridin-2-yl)piperidin-4-yl]pyrrolidin-3-amine;

rac-2-(4-{5-[(3R,4S)-4-(dimethylamino)-1-(7-fluoro-2,3-dihydro-1H-inden-1-yl)pyrrolidin-3-yl]pyridin-2-yl}-1H-pyrazol-1-yl)-1-(3-fluoroazetidin-1-yl)ethan-1-one;

rac-6-{4-[(3S,4R)-4-(dimethylamino)-1-(7-fluoro-2,3-dihydro-1H-inden-1-yl)pyrrolidin-3-yl]piperidin-1-yl}-N-methylpyridine-3-carboxamide;

rac-N-[2-(4-{5-[(3R,4S)-4-(dimethylamino)-1-(7-fluoro-2,3-dihydro-1H-inden-1-yl)pyrrolidin-3-yl]pyridin-2-yl}piperazin-1-yl)-2-oxoethyl]methanesulfonamide;

rac-(3R,4S)-1-(7-fluoro-2,3-dihydro-1H-inden-1-yl)-N,N-dimethyl-4-(1-methyl-1H-indazol-3-yl)pyrrolidin-3-amine;

rac-1-(4-{5-[(3R,4S)-4-(dimethylamino)-1-(7-fluoro-2,3-dihydro-1H-inden-1-yl)pyrrolidin-3-yl]pyridin-2-yl}piperazin-1-yl)-2-(methanesulfonyl)ethan-1-one;

rac-2-(4-{5-[(3R,4S)-4-(dimethylamino)-1-(7-fluoro-2,3-dihydro-1H-inden-1-yl)pyrrolidin-3-yl]pyridin-2-yl}-1H-pyrazol-1-yl)acetamide;

rac-2-(4-{5-[(3R,4S)-4-(dimethylamino)-1-(7-fluoro-2,3-dihydro-1H-inden-1-yl)pyrrolidin-3-yl]pyridin-2-yl}-1H-pyrazol-1-yl)-N,N-dimethylacetamide;

rac-2-(4-{5-[(3R,4S)-4-(dimethylamino)-1-(7-fluoro-2,3-dihydro-1H-inden-1-yl)pyrrolidin-3-yl]pyridin-2-yl}piperazin-1-yl)-2-oxoethane-1-sulfonamide;

rac-2-(4-{5-[(3R,4S)-4-(dimethylamino)-1-(7-fluoro-2,3-dihydro-1H-inden-1-yl)pyrrolidin-3-yl]pyridin-2-yl}-1H-pyrazol-1-yl)-N-methylacetamide;

rac-2-{4-[(3S,4R)-4-(dimethylamino)-1-(7-fluoro-2,3-dihydro-1H-inden-1-yl)pyrrolidin-3-yl]piperidin-1-yl}-1,3-thiazole-5-carboxamide;

rac-5-{4-[(3S,4R)-4-(dimethylamino)-1-(7-fluoro-2,3-dihydro-1H-inden-1-yl)pyrrolidin-3-yl]piperidin-1-yl}pyrazine-2-carboxamide;

rac-(3R,4S)-1-(7-fluoro-2,3-dihydro-1H-inden-1-yl)-N,N-dimethyl-4-(1-methyl-1H-pyrrolo[2,3-b]pyridin-3-yl)pyrrolidin-3-amine;

rac-6-{4-[(3S,4R)-4-(dimethylamino)-1-(7-fluoro-2,3-dihydro-1H-inden-1-yl)pyrrolidin-3-yl]piperidin-1-yl}pyridazine-3-carboxamide;

rac-4-{4-[(3S,4R)-4-(dimethylamino)-1-(7-fluoro-2,3-dihydro-1H-inden-1-yl)pyrrolidin-3-yl]piperidin-1-yl}benzamide;

rac-6-{4-[(3S,4R)-4-(dimethylamino)-1-(7-fluoro-2,3-dihydro-1H-inden-1-yl)pyrrolidin-3-yl]piperidin-1-yl}pyridine-3-carboxamide; and pharmaceutically acceptable salts thereof.

One embodiment pertains to compounds or pharmaceutically acceptable salts thereof, which are useful as inhibitors of EED, the compounds having Formula (IIIa) or Formula (IIIb)

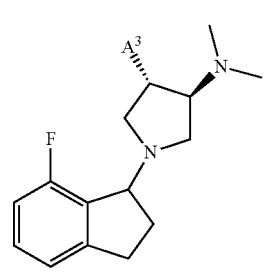

Formula (IIIa)

Formula (IIIb)

wherein

A³ is selected from the group consisting of aryl, heterocyclyl, and heteroaryl, wherein the A³ aryl, heterocyclyl, and heteroaryl are optionally substituted with one or more substituents independently selected from the group consisting of R¹, OR¹, SR¹, S(O)R¹, SO₂R¹, C(O)R¹, CO(O)R¹, OC(O)R¹, OC(O)OR¹, NH₂, NHR¹, N(R¹)₂, NHC(O)R¹, NR¹C(O)R¹, NHS(O)₂R¹, NR¹S(O)₂R¹, NHC(O)OR¹, NR¹C(O)OR¹, NHC(O)NH₂, NHC(O)NHR¹, NHC(O)N(R¹)₂, NR¹C(O)NHR¹, NR¹C(O)N(R¹)₂, C(O)NH₂, C(O)NHR¹, C(O)N(R¹)₂, C(O)NHOH, C(O)NHOR¹, C(O)NHSO₂R¹, C(O)NR¹SO₂R¹, SO₂NH₂, SO₂NHR¹, SO₂N(R¹)₂, C(O)H, C(O)OH, C(N)NH₂, C(N)NHR¹, C(N)N(R¹)₂, CNOH, CNOCH₃, OH, (O), CN, NO₂, CF₃, CF₂CF₃, OCF₃, OCF₂CF₃, F, Cl, Br and I;

R¹, at each occurrence, is independently selected from the group consisting of C₁-C₆ alkyl, C₂-C₆ alkenyl, C₂-C₆ alkynyl, aryl, heteroaryl, heterocyclyl, cycloalkyl, and cycloalkenyl; wherein each R¹ C₁-C₆ alkyl, C₂-C₆ alkenyl, and C₂-C₆ alkynyl is optionally substituted with one or more substituents independently selected from the group consisting of R², OR², SR², S(O)R², SO₂R², C(O)R², CO(O)R², OC(O)R², OC(O)OR², NH₂, NHR², N(R²)₂, NHC(O)R², NR²C(O)R², NHS(O)₂R², NR²S(O)₂R², NHC(O)OR², NR²C(O)OR², NHC(O)NH₂, NHC(O)NHR², NHC(O)N(R²)₂, NR²C(O)NHR², NR²C(O)N(R²)₂, C(O)NH₂, C(O)NHR², C(O)N(R²)₂, C(O)NHOH, C(O)NHOR², C(O)NHSO₂R², C(O)NR²SO₂R², SO₂NH₂, SO₂NHR², SO₂N(R²)₂, C(O)H, C(O)OH, OH, (O), CN, NO₂, CF₃, CF₂CF₃, OCF₃, OCF₂CF₃, F, Cl, Br and I; wherein each R¹ aryl, heteroaryl, heterocyclyl, cycloalkyl, and cycloalkenyl is optionally substituted with one or more substituents independently selected from the group consisting of R³, OR³, SR³, S(O)R³, SO₂R³, C(O)R³, CO(O)R³, OC(O)R³, OC(O)OR³, NH₂, NHR³, N(R³)₂, NHC(O)R³, NR³C(O)R³, NHS(O)₂R³, NR³S(O)₂R³, NHC(O)OR³, NR³C(O)OR³, NHC(O)NH₂, NHC(O)NHR³, NHC(O)N(R³)₂, NR³C(O)NHR³, NR³C(O)N(R³)₂, C(O)NH₂, C(O)NHR³, C(O)N(R³)₂, C(O)NHOH, C(O)NHOR³, C(O)NHSO₂R³, C(O)NR³SO₂R³, SO₂NH₂, SO₂NHR³, SO₂N(R³)₂, C(O)H, C(O)OH, C(O)C(O)NH₂, C(O)C(O)NHR³, C(O)C(O)N(R³)₂, C(N)NH₂, C(N)NHR³, C(N)N(R³)₂, CNOH, CNOCH₃, OH, (O), CN, NO₂, CF₃, CF₂CF₃, OCF₃, OCF₂CF₃, F, Cl, Br and I;

R², at each occurrence, is independently selected from the group consisting of C₁-C₆ alkyl, C₂-C₆ alkenyl, C₂-C₆ alkynyl, aryl, heteroaryl, heterocyclyl, cycloalkyl, and cycloalkenyl; wherein each R² C₁-C₆ alkyl, C₂-C₆ alkenyl, and C₂-C₆ alkynyl is optionally substituted with one or more substituents independently selected from the group consisting of NH₂, C(O)NH₂, SO₂NH₂, C(O)H, C(O)OH, OH, (O), CN, NO₂, CF₃, CF₂CF₃, OCF₃, OCF₂CF₃, F, Cl, Br and I; wherein each R² aryl, heteroaryl, heterocyclyl, cycloalkyl, and cycloalkenyl is optionally substituted with one or more substituents independently selected from the group consisting of NH₂, C(O)NH₂, SO₂NH₂, C(O)H, C(O)OH, OH, (O), CN, NO₂, CF₃, CF₂CF₃, OCF₃, OCF₂CF₃, F, Cl, Br and I;

R³, at each occurrence, is independently selected from the group consisting of C₁-C₆ alkyl, C₂-C₆ alkenyl, C₂-C₆ alkynyl, aryl, heteroaryl, heterocyclyl, cycloalkyl, and cycloalkenyl; wherein each R³ C₁-C₆ alkyl, C₂-C₆ alkenyl, and C₂-C₆ alkynyl is optionally substituted with one or more substituents independently selected from the group consisting of R⁴, OR⁴, SR⁴, S(O)R⁴, SO₂R⁴, C(O)R⁴, CO(O)R⁴, OC(O)R⁴, OC(O)OR⁴, NH₂, NHR⁴, N(R⁴)₂, NHC(O)R⁴, NR⁴C(O)R⁴, NHS(O)₂R⁴, NR⁴S(O)₂R⁴, NHC(O)OR⁴, NR⁴C(O)OR⁴, NHC(O)NH₂, NHC(O)NHR⁴, NHC(O)N(R⁴)₂, NR⁴C(O)NHR⁴, NR⁴C(O)N(R⁴)₂, C(O)NH₂, C(O)NHR⁴, C(O)N(R⁴)₂, C(O)NHOH, C(O)NHOR⁴, C(O)NHSO₂R⁴, C(O)NR⁴SO₂R⁴, SO₂NH₂, SO₂NHR⁴, SO₂N(R⁴)₂, C(O)H, C(O)OH, OH, (O), CN, NO₂, CF₃, CF₂CF₃, OCF₃, OCF₂CF₃, F, Cl, Br and I; wherein each R³ aryl, heteroaryl, heterocyclyl, cycloalkyl, and cycloalkenyl is optionally substituted with one or more substituents independently selected from the group consisting of R⁵, OR⁵, SR⁵, S(O)R⁵, SO₂R⁵, C(O)R⁵, CO(O)R⁵, OC(O)R⁵, OC(O)OR⁵, NH₂, NHR⁵, N(R⁵)₂, NHC(O)R⁵, NR⁵C(O)R⁵, NHS(O)₂R⁵, NR⁵S(O)₂R⁵, NHC(O)OR⁵, NR⁵C(O)OR⁵, NHC(O)NH₂, NHC(O)NHR⁵, NHC(O)N(R⁵)₂, NR⁵C(O)NHR⁵, NR⁵C(O)N(R⁵)₂, C(O)NH₂, C(O)NHR⁵, C(O)N(R⁵)₂, C(O)NHOH, C(O)NHOR⁵, C(O)NHSO₂R⁵, C(O)NR⁵SO₂R⁵, SO₂NH₂, SO₂NHR⁵, SO₂N(R⁵)₂, C(O)H, C(O)OH, C(N)NH₂, C(N)NHR⁵, C(N)N(R⁵)₂, CNOH, CNOCH₃, OH, (O), CN, NO₂, CF₃, CF₂CF₃, OCF₃, OCF₂CF₃, F, Cl, Br and I;

R⁴ is at each occurrence, is independently selected from the group consisting of C₁-C₆ alkyl, C₂-C₆ alkenyl, C₂-C₆ alkynyl, aryl, heteroaryl, heterocyclyl, cycloalkyl, and cycloalkenyl; wherein each R⁴ C₁-C₆ alkyl, C₂-C₆ alkenyl, and C₂-C₆ alkynyl is optionally substituted with one or more substituents independently selected from the group consisting of NH₂, C(O)NH₂, SO₂NH₂, C(O)H, C(O)OH, OH, (O), CN, NO₂, CF₃, CF₂CF₃, OCF₃, OCF₂CF₃, F, Cl, Br and I; wherein each R⁴ aryl, heteroaryl, heterocyclyl, cycloalkyl, and cycloalkenyl is optionally substituted with one or more substituents independently selected from the group consisting of NH₂, C(O)NH₂, SO₂NH₂, C(O)H, C(O)OH, OH, (O), CN, NO₂, CF₃, CF₂CF₃, OCF₃, OCF₂CF₃, F, Cl, Br and I; and R⁵ is at each occurrence, is independently selected from the group consisting of C₁-C₆ alkyl, C₂-C₆ alkenyl, C₂-C₆ alkynyl, aryl, heteroaryl, heterocyclyl, cycloalkyl, and cycloalkenyl; wherein each R⁵ C₁-C₆ alkyl, C₂-C₆ alkenyl, and C₂-C₆ alkynyl is optionally substituted with one or more substituents independently selected from the group consisting of NH₂, C(O)NH₂, SO₂NH₂, C(O)H, C(O)OH, OH, (O), CN, NO₂, CF₃, CF₂CF₃, OCF₃, OCF₂CF₃, F, Cl, Br and I; wherein each R⁵ aryl, heteroaryl, heterocyclyl, cycloalkyl, and cycloalkenyl is optionally substituted with one or more substituents independently selected from the group consisting of NH₂, C(O)NH₂, SO₂NH₂, C(O)H, C(O)OH, OH, (O), CN, NO₂, CF₃, CF₂CF₃, OCF₃, OCF₂CF₃, F, Cl, Br and I.

In one embodiment of Formula (IIIa) or Formula (IIIb), A³ is selected from the group consisting of aryl, heterocyclyl, and heteroaryl, wherein the A³ aryl, heterocyclyl, and heteroaryl are optionally substituted with one or more substituents independently selected from the group consisting of R¹, OR¹, SR¹, S(O)R¹, SO₂R¹, C(O)R¹, CO(O)R¹, OC(O)R¹, OC(O)OR¹, NH₂, NHR¹, N(R¹)₂, NHC(O)R¹, NR¹C(O)R¹, NHS(O)₂R¹, NR¹S(O)₂R¹, NHC(O)OR¹, NR¹C(O)OR¹, NHC(O)NH₂, NHC(O)NHR¹, NHC(O)N(R¹)₂, NR¹C(O)NHR¹, NR¹C(O)N(R¹)₂, C(O)NH₂, C(O)NHR¹, C(O)N(R¹)₂, C(O)NHOH, C(O)NHOR¹, C(O)NHSO₂R¹, C(O)

$NR^1SO_2R^1$, $SO_2NH_2$, $SO_2NHR^1$, $SO_2N(R^1)_2$, C(O)H, C(O)OH, $C(N)NH_2$, $C(N)NHR^1$, $C(N)N(R^1)_2$, CNOH, $CNOCH_3$, OH, (O), CN, $NO_2$, $CF_3$, $CF_2CF_3$, $OCF_3$, $OCF_2CF_3$, F, Cl, Br and I. In another embodiment of Formula (IIIa) or Formula (IIIb), $A^3$ is selected from the group consisting of aryl, heterocyclyl, and heteroaryl, wherein the $A^3$ aryl, heterocyclyl, and heteroaryl are optionally substituted with one or more substituents independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, C(O)OH, CN, F, Cl, Br and I. In another embodiment of Formula (IIIa) or Formula (IIIb), $A^3$ is aryl, wherein the $A^3$ aryl is optionally substituted with one or more substituents independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, C(O)OH, CN, F, Cl, Br and I. In another embodiment of Formula (IIIa) or Formula (IIIb), $A^3$ is aryl, wherein the $A^3$ aryl is substituted with one substituent independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, C(O)OH, CN, F, Cl, Br and I. In another embodiment of Formula (IIIa) or Formula (IIIb), $A^3$ is aryl, wherein the $A^3$ aryl is substituted with two substituents independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, C(O)OH, CN, F, Cl, Br and I. In another embodiment of Formula (IIIa) or Formula (IIIb), $A^3$ is heterocyclyl, wherein the $A^3$ heterocyclyl is optionally substituted with one or more substituents independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, C(O)OH, CN, F, Cl, Br and I. In another embodiment of Formula (IIIa) or Formula (IIIb), $A^3$ is heterocyclyl, wherein the $A^3$ heterocyclyl is unsubstituted. In another embodiment of Formula (IIIa) or Formula (IIIb), $A^3$ is heterocyclyl, wherein the $A^3$ heterocyclyl is substituted with one substituent independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, C(O)OH, CN, F, Cl, Br and I. In another embodiment of Formula (IIIa) or Formula (IIIb), $A^3$ is heterocyclyl, wherein the $A^3$ heterocyclyl is substituted with two substituents independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, C(O)OH, CN, F, Cl, Br and I. In another embodiment of Formula (IIIa) or Formula (IIIb), $A^3$ is heteroaryl, wherein the $A^3$ heteroaryl is optionally substituted with one or more substituents independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, C(O)OH, CN, F, Cl, Br and I. In another embodiment of Formula (IIIa) or Formula (IIIb), $A^3$ is heteroaryl, wherein the $A^3$ heteroaryl is unsubstituted. In another embodiment of Formula (IIIa) or Formula (IIIb), $A^3$ is heteroaryl, wherein the $A^3$ heteroaryl is substituted with one substituent independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, C(O)OH, CN, F, Cl, Br and I. In another embodiment of Formula (IIIa) or Formula (IIIb), $A^3$ is heteroaryl, wherein the $A^3$ heteroaryl is substituted with two substituents independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, C(O)OH, CN, F, Cl, Br and I.

In one embodiment of Formula (IIIa) or Formula (IIIb), $R^1$, at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^1$ $C_1$-$C_6$ alkyl, $C_2$-$C_6$ alkenyl, and $C_2$-$C_6$ alkynyl is optionally substituted with one or more substituents independently selected from the group consisting of $R^2$, $OR^2$, $SR^2$, $S(O)R^2$, $SO_2R^2$, $C(O)R^2$, $CO(O)R^2$, $OC(O)R^2$, $OC(O)OR^2$, $NH_2$, $NHR^2$, $N(R^2)_2$, $NHC(O)R^2$, $NR^2C(O)R^2$, $NHS(O)_2R^2$, $NR^2S(O)_2R^2$, $NHC(O)OR^2$, $NR^2C(O)OR^2$, $NHC(O)NH_2$, $NHC(O)NHR^2$, $NHC(O)N(R^2)_2$, $NR^2C(O)NHR^2$, $NR^2C(O)N(R^2)_2$, $C(O)NH_2$, $C(O)NHR^2$, $C(O)N(R^2)_2$, C(O)NHOH, $C(O)NHOR^2$, $C(O)NHSO_2R^2$, $C(O)NR^2SO_2R^2$, $SO_2NH_2$, $SO_2NHR^2$, $SO_2N(R^2)_2$, C(O)H, C(O)OH, OH, (O), CN, $NO_2$, $CF_3$, $CF_2CF_3$, $OCF_3$, $OCF_2CF_3$, F, Cl, Br and I; wherein each $R^1$ aryl, heteroaryl, heterocyclyl, cycloalkyl, and cycloalkenyl is optionally substituted with one or more substituents independently selected from the group consisting of $R^3$, $OR^3$, $SR^3$, $S(O)R^3$, $SO_2R^3$, $C(O)R^3$, $CO(O)R^3$, $OC(O)R^3$, $OC(O)OR^3$, $NH_2$, $NHR^3$, $N(R^3)_2$, $NHC(O)R^3$, $NR^3C(O)R^3$, $NHS(O)_2R^3$, $NR^3S(O)_2R^3$, $NHC(O)OR^3$, $NR^3C(O)OR^3$, $NHC(O)NH_2$, $NHC(O)NHR^3$, $NHC(O)N(R^3)_2$, $NR^3C(O)NHR^3$, $NR^3C(O)N(R^3)_2$, $C(O)NH_2$, $C(O)NHR^3$, $C(O)N(R^3)_2$, C(O)NHOH, $C(O)NHOR^3$, $C(O)NHSO_2R^3$, $C(O)NR^3SO_2R^3$, $SO_2NH_2$, $SO_2NHR^3$, $SO_2N(R^3)_2$, C(O)H, C(O)OH, $C(O)C(O)NH_2$, $C(O)C(O)NHR^3$, $C(O)C(O)N(R^3)_2$, $C(N)NH_2$, $C(N)NHR^3$, $C(N)N(R^3)_2$, CNOH, $CNOCH_3$, OH, (O), CN, $NO_2$, $CF_3$, $CF_2CF_3$, $OCF_3$, $OCF_2CF_3$, F, Cl, Br and I. In another embodiment of Formula (IIIa) or Formula (IIIb), $R^1$, at each occurrence, is $C_1$-$C_6$ alkyl; wherein each $R^1$ $C_1$-$C_6$ alkyl is optionally substituted with one or more substituents independently selected from the group consisting of C(O)OH and OH. In another embodiment of Formula (IIIa) or Formula (IIIb), $R^1$, at each occurrence, is independently selected from the group consisting of aryl, heteroaryl, heterocyclyl, and cycloalkyl; wherein each $R^1$ aryl, heteroaryl, heterocyclyl, and cycloalkyl is optionally substituted with one or more substituents independently selected from the group consisting of $R^3$, $SO_2R^3$, $C(O)R^3$, $CO(O)R^3$, $C(O)NH_2$, $C(O)NHR^3$, $C(O)N(R^3)_2$, $SO_2N(R^3)_2$, $C(O)C(O)NH_2$, $C(O)C(O)N(R^3)_2$, OH, (O), and F.

In one embodiment of Formula (IIIa) or Formula (IIIb), $R^3$, at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^3$ $C_1$-$C_6$ alkyl, $C_2$-$C_6$ alkenyl, and $C_2$-$C_6$ alkynyl is optionally substituted with one or more substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, C(O)NHOH, $C(O)NHOR^4$, $C(O)NHSO_2R^4$, $C(O)NR^4SO_2R^4$, $SO_2NH_2$, $SO_2NHR^4$, $SO_2N(R^4)_2$, C(O)H, C(O)OH, OH, (O), CN, $NO_2$, $CF_3$, $CF_2CF_3$, $OCF_3$, $OCF_2CF_3$, F, Cl, Br and I; wherein each $R^3$ aryl, heteroaryl, heterocyclyl, cycloalkyl, and cycloalkenyl is optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, NHC(O)$OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, C(O)NHOH, $C(O)NHOR^5$, $C(O)NHSO_2R^5$, $C(O)NR^5SO_2R^5$, $SO_2NH_2$, $SO_2NHR^5$, $SO_2N(R^5)_2$, C(O)H, C(O)OH, $C(N)NH_2$, $C(N)NHR^5$, $C(N)N(R^5)_2$, CNOH, $CNOCH_3$, OH, (O), CN, $NO_2$, $CF_3$, $CF_2CF_3$, $OCF_3$, $OCF_2CF_3$, F, Cl, Br and I. In another embodiment of Formula (IIIa) or Formula (IIIb), $R^3$, at each occurrence, is independently $C_1$-$C_6$ alkyl; wherein each $R^3$ $C_1$-$C_6$ alkyl is optionally substituted with one or more substituents independently selected from the group consisting of $SO_2R^4$, $C(O)R^4$, $NHS(O)_2R^4$, $C(O)NH_2$, $C(O)NHR^4$, $C(O)N(R^4)_2$, $SO_2NH_2$, and OH. In another embodiment of Formula (IIIa) or Formula (IIIb), $R^3$, at each occurrence, is independently selected from the group consisting of heteroaryl, heterocyclyl, and cycloalkyl; wherein each $R^3$ heteroaryl, heterocyclyl, and cycloalkyl is optionally substituted with one or more substituents independently selected from the group consisting of $R^5$ and CN.

In one embodiment of Formula (IIIa) or Formula (IIIb), $R^4$ is at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^4$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I; wherein each $R^4$ aryl, heteroaryl, heterocyclyl, cycloalkyl, and cycloalkenyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I. In another embodiment of Formula (IIIa) or Formula (IIIb), $R^4$ at each occurrence, is $C_1$-$C_6$ alkyl. In another embodiment of Formula (IIIa) or Formula (IIIb), $R^4$ at each occurrence, is heterocyclyl; wherein each $R^4$ heterocyclyl is optionally substituted with one or more substituents independently selected from the group consisting of OH, and F.

In one embodiment of Formula (IIIa) or Formula (IIIb), $R^5$ is at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^5$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I; wherein each $R^5$ aryl, heteroaryl, heterocyclyl, cycloalkyl, and cycloalkenyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I. In another embodiment of Formula (IIIa) or Formula (IIIb), $R^5$ is at each occurrence, is independently $C_1$-$C_6$ alkyl.

In one embodiment of Formula (IIIa) or Formula (IIIb), $A^3$ is selected from the group consisting of aryl, heterocyclyl, and heteroaryl, wherein the $A^3$ aryl, heterocyclyl, and heteroaryl are optionally substituted with one or more substituents independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, $C(O)OH$, CN, F, Cl, Br and I;

$R^1$, at each occurrence, is independently selected from the group consisting of $C_1$-$C_6$ alkyl, aryl, heteroaryl, heterocyclyl, and cycloalkyl; wherein each $R^1$ $C_1$-$C_6$ alkyl is optionally substituted with one or more substituents independently selected from the group consisting of C(O)OH, OH, F, Cl, Br and I; wherein each $R^1$ aryl, heteroaryl, heterocyclyl, cycloalkyl, and cycloalkenyl is optionally substituted with one or more substituents independently selected from the group consisting of $R^3$, $SO_2R^3$, $C(O)R^3$, $CO(O)R^3$, $C(O)NH_2$, $C(O)NHR^3$, $C(O)N(R^3)_2$, $SO_2N(R^3)_2$, $C(O)C(O)NH_2$, $C(O)C(O)N(R^3)_2$, OH, (O), F, Cl, Br and I;

$R^3$, at each occurrence, is independently selected from the group consisting of $C_1$-$C_6$ alkyl, heteroaryl, heterocyclyl, and cycloalkyl; wherein each $R^3$ $C_1$-$C_6$ alkyl is optionally substituted with one or more substituents independently selected from the group consisting of $SO_2R^4$, $C(O)R^4$, $NHS(O)_2R^4$, $C(O)NH_2$, $C(O)NHR^4$, $C(O)N(R^4)_2$, $SO_2NH_2$, F, Cl, Br and I; wherein each $R^3$ heteroaryl and heterocyclyl is optionally substituted with one or more substituents independently selected from the group consisting of $R^5$, CN, F, Cl, Br and I;

$R^4$ is at each occurrence, is independently selected from the group consisting of $C_1$-$C_6$ alkyl and heterocyclyl; wherein each $R^4$ heterocyclyl is optionally substituted with one or more substituents independently selected from the group consisting of OH, F, Cl, Br and I; and $R^5$ is at each occurrence, is independently $C_1$-$C_6$ alkyl.

Still another embodiment pertains to compounds of Formula (IIIa) or Formula (IIIb), selected from the group consisting of:

rac-(3R,4S)-1-(7-fluoro-2,3-dihydro-1H-inden-1-yl)-4-{4-[4-(methanesulfonyl)piperazin-1-yl]phenyl}-N,N-dimethylpyrrolidin-3-amine;

rac-(3S,4R)-4-(4-bromophenyl)-1-(7-fluoro-2,3-dihydro-1H-inden-1-yl)-N,N-dimethylpyrrolidin-3-amine;

rac-(3S,4R)-4-(4-chlorophenyl)-1-(7-fluoro-2,3-dihydro-1H-inden-1-yl)-N,N-dimethylpyrrolidin-3-amine;

rac-4-[(3S,4R)-4-(dimethylamino)-1-(7-fluoro-2,3-dihydro-1H-inden-1-yl)pyrrolidin-3-yl]benzene-1-sulfonamide;

rac-4-{(3R,4S)-4-(dimethylamino)-1-[(1R)-7-fluoro-2,3-dihydro-1H-inden-1-yl]pyrrolidin-3-yl}benzonitrile;

rac-methyl 4-[(3R,4S)-4-(dimethylamino)-1-(7-fluoro-2,3-dihydro-1H-inden-1-yl)pyrrolidin-3-yl]benzoate;

rac-(3S,4R)-4-(3,4-dimethoxyphenyl)-1-(7-fluoro-2,3-dihydro-1H-inden-1-yl)-N,N-dimethylpyrrolidin-3-amine;

rac-4-[(3S,4R)-4-(dimethylamino)-1-(7-fluoro-2,3-dihydro-1H-inden-1-yl)pyrrolidin-3-yl]-N-methylbenzamide;

rac-4-[(3S,4R)-4-(dimethylamino)-1-(7-fluoro-2,3-dihydro-1H-inden-1-yl)pyrrolidin-3-yl]-N,N-dimethylbenzamide;

rac-(3R,4S)-4-(4-bromo-3-methylphenyl)-1-(7-fluoro-2,3-dihydro-1H-inden-1-yl)-N,N-dimethylpyrrolidin-3-amine;

rac-4-[(3S,4R)-4-(dimethylamino)-1-(7-fluoro-2,3-dihydro-1H-inden-1-yl)pyrrolidin-3-yl]benzoic acid;

rac-4-[(3R,4S)-4-(dimethylamino)-1-(7-fluoro-2,3-dihydro-1H-inden-1-yl)pyrrolidin-3-yl]benzamide;

rac-4-[(3S,4R)-4-(dimethylamino)-1-(7-fluoro-2,3-dihydro-1H-inden-1-yl)pyrrolidin-3-yl]-2-methylbenzoic acid;

rac-4-[(3S,4R)-4-(dimethylamino)-1-(7-fluoro-2,3-dihydro-1H-inden-1-yl)pyrrolidin-3-yl]-2-methylbenzonitrile;

rac-methyl 4-[(3S,4R)-4-(dimethylamino)-1-(7-fluoro-2,3-dihydro-1H-inden-1-yl)pyrrolidin-3-yl]-2-methylbenzoate;

rac-{4-[(3S,4R)-4-(dimethylamino)-1-(7-fluoro-2,3-dihydro-1H-inden-1-yl)pyrrolidin-3-yl]phenyl}[(3S)-3-hydroxypyrrolidin-1-yl]methanone;

rac-(3S,4R)-1-(7-fluoro-2,3-dihydro-1H-inden-1-yl)-N,N-dimethyl-4-[4-(piperazin-1-yl)phenyl]pyrrolidin-3-amine;

rac-1-(4-{4-[(3S,4R)-4-(dimethylamino)-1-(7-fluoro-2,3-dihydro-1H-inden-1-yl)pyrrolidin-3-yl]phenyl}piperazin-1-yl)ethan-1-one;

rac-(3R,4S)-4-{4-[4-(ethanesulfonyl)piperazin-1-yl]phenyl}-1-(7-fluoro-2,3-dihydro-1H-inden-1-yl)-N,N-dimethylpyrrolidin-3-amine;

rac-4-{4-[(3S,4R)-4-(dimethylamino)-1-(7-fluoro-2,3-dihydro-1H-inden-1-yl)pyrrolidin-3-yl]benzoyl}-1-methylpiperazin-2-one;

rac-1-(4-{4-[(3R,4S)-4-(dimethylamino)-1-(7-fluoro-2,3-dihydro-1H-inden-1-yl)pyrrolidin-3-yl]phenyl}piperazin-1-yl)-2-hydroxyethan-1-one;

rac-{4-[(3S,4R)-4-(dimethylamino)-1-(7-fluoro-2,3-dihydro-1H-inden-1-yl)pyrrolidin-3-yl]phenyl}[4-(methanesulfonyl)piperazin-1-yl]methanone;

rac-2-(4-{4-[(3R,4S)-4-(dimethylamino)-1-(7-fluoro-2,3-dihydro-1H-inden-1-yl)pyrrolidin-3-yl]phenyl}piperazin-1-yl)-2-oxoacetamide;

rac-1-(4-{4-[(3S,4R)-4-(dimethylamino)-1-(7-fluoro-2,3-dihydro-1H-inden-1-yl)pyrrolidin-3-yl]benzoyl}piperazin-1-yl)ethan-1-one;

rac-4-{4-[(3S,4R)-4-(dimethylamino)-1-(7-fluoro-2,3-dihydro-1H-inden-1-yl)pyrrolidin-3-yl]phenyl}-1-methylpiperazin-2-one;

rac-{4-[(3S,4R)-4-(dimethylamino)-1-(7-fluoro-2,3-dihydro-1H-inden-1-yl)pyrrolidin-3-yl]phenyl}[4-(ethanesulfonyl)piperazin-1-yl]methanone;

rac-4-{4-[(3S,4R)-4-(dimethylamino)-1-(7-fluoro-2,3-dihydro-1H-inden-1-yl)pyrrolidin-3-yl]-2-methylphenyl}-1-methylpiperazin-2-one;

rac-2-(4-{4-[(3R,4S)-4-(dimethylamino)-1-(7-fluoro-2,3-dihydro-1H-inden-1-yl)pyrrolidin-3-yl]phenyl}piperazin-1-yl)-N,N-dimethyl-2-oxoacetamide;

rac-1-(4-{4-[(3S,4R)-4-(dimethylamino)-1-(7-fluoro-2,3-dihydro-1H-inden-1-yl)pyrrolidin-3-yl]-2-methylphenyl}piperazin-1-yl)ethan-1-one;

rac-(3R,4S)-1-(7-fluoro-2,3-dihydro-1H-inden-1-yl)-N,N-dimethyl-4-[4-(4-methylpiperazin-1-yl)phenyl]pyrrolidin-3-amine;

rac-(3R,4S)-4-{4-[4-(ethanesulfonyl)piperazin-1-yl]-3-methylphenyl}-1-(7-fluoro-2,3-dihydro-1H-inden-1-yl)-N,N-dimethylpyrrolidin-3-amine;

rac-4-{4-[(3S,4R)-4-(dimethylamino)-1-(7-fluoro-2,3-dihydro-1H-inden-1-yl)pyrrolidin-3-yl]phenyl}-N,N-dimethylpiperazine-1-carboxamide;

rac-(3R,4S)-4-[4-(4-cyclopropylpiperazin-1-yl)phenyl]-1-(7-fluoro-2,3-dihydro-1H-inden-1-yl)-N,N-dimethylpyrrolidin-3-amine;

rac-(3S,4R)-4-(2H-1,3-benzodioxol-5-yl)-1-(7-fluoro-2,3-dihydro-1H-inden-1-yl)-N,N-dimethylpyrrolidin-3-amine;

rac-(3S,4R)-1-(7-fluoro-2,3-dihydro-1H-inden-1-yl)-N,N-dimethyl-4-[4-(1,3-oxazol-2-yl)phenyl]pyrrolidin-3-amine;

rac-(3R,4S)-1-(7-fluoro-2,3-dihydro-1H-inden-1-yl)-N,N-dimethyl-4-[4-(3-methyl-1,2,4-oxadiazol-5-yl)phenyl]pyrrolidin-3-amine;

rac-(3S,4R)-1-(7-fluoro-2,3-dihydro-1H-inden-1-yl)-N,N-dimethyl-4-[4-(5-methyl-1,3,4-oxadiazol-2-yl)phenyl]pyrrolidin-3-amine;

rac-(3S,4R)-1-(7-fluoro-2,3-dihydro-1H-inden-1-yl)-N,N-dimethyl-4-[4-(4-methyl-1,3-oxazol-2-yl)phenyl]pyrrolidin-3-amine;

rac-(3R,4S)-1-(7-fluoro-2,3-dihydro-1H-inden-1-yl)-N,N-dimethyl-4-[4-(1-methyl-1H-pyrazol-4-yl)phenyl]pyrrolidin-3-amine;

rac-2-(4-{4-[(3S,4R)-4-(dimethylamino)-1-(7-fluoro-2,3-dihydro-1H-inden-1-yl)pyrrolidin-3-yl]phenyl}-1H-pyrazol-1-yl)acetamide;

rac-2-(4-{4-[(3S,4R)-4-(dimethylamino)-1-(7-fluoro-2,3-dihydro-1H-inden-1-yl)pyrrolidin-3-yl]phenyl}-1H-pyrazol-1-yl)-N-methylacetamide;

rac-(3S,4R)-1-(7-fluoro-2,3-dihydro-1H-inden-1-yl)-N,N-dimethyl-4-{4-[4-(1-methyl-1H-imidazole-4-sulfonyl)piperazin-1-yl]phenyl}pyrrolidin-3-amine;

rac-(3S,4R)-1-(7-fluoro-2,3-dihydro-1H-inden-1-yl)-N,N-dimethyl-4-{4-[4-(pyrimidin-4-yl)piperazin-1-yl]phenyl}pyrrolidin-3-amine;

rac-(3S,4R)-1-(7-fluoro-2,3-dihydro-1H-inden-1-yl)-N,N-dimethyl-4-{4-[4-(pyridin-2-yl)piperazin-1-yl]phenyl}pyrrolidin-3-amine;

rac-3-[(3S,4R)-4-(dimethylamino)-1-(7-fluoro-2,3-dihydro-1H-inden-1-yl)pyrrolidin-3-yl]-1-methyl-1H-indole-7-carboxylic acid;

rac-methyl 3-[(3R,4S)-4-(dimethylamino)-1-(7-fluoro-2,3-dihydro-1H-inden-1-yl)pyrrolidin-3-yl]-1-methyl-1H-indole-6-carboxylate;

rac-methyl 3-[(3S,4R)-4-(dimethylamino)-1-(7-fluoro-2,3-dihydro-1H-inden-1-yl)pyrrolidin-3-yl]-1-methyl-1H-indole-7-carboxylate;

rac-3-[(3S,4R)-4-(dimethylamino)-1-(7-fluoro-2,3-dihydro-1H-inden-1-yl)pyrrolidin-3-yl]-N,N,1-trimethyl-1H-indole-6-carboxamide;

rac-(3R,4S)-4-(7-bromo-1-methyl-1H-indol-3-yl)-1-(7-fluoro-2,3-dihydro-1H-inden-1-yl)-N,N-dimethylpyrrolidin-3-amine;

rac-(3R,4S)-4-(6-bromo-1-methyl-1H-indol-3-yl)-1-(7-fluoro-2,3-dihydro-1H-inden-1-yl)-N,N-dimethylpyrrolidin-3-amine;

rac-3-[(3S,4R)-4-(dimethylamino)-1-(7-fluoro-2,3-dihydro-1H-inden-1-yl)pyrrolidin-3-yl]-N-(2-hydroxyethyl)-N,1-dimethyl-1H-indole-7-carboxamide;

rac-3-[(3S,4R)-4-(dimethylamino)-1-(7-fluoro-2,3-dihydro-1H-inden-1-yl)pyrrolidin-3-yl]-N,1-dimethyl-1H-indole-7-carboxamide;

rac-3-[(3S,4R)-4-(dimethylamino)-1-(7-fluoro-2,3-dihydro-1H-inden-1-yl)pyrrolidin-3-yl]-N,N,1-trimethyl-1H-indole-7-carboxamide;

rac-{3-[(3S,4R)-4-(dimethylamino)-1-(7-fluoro-2,3-dihydro-1H-inden-1-yl)pyrrolidin-3-yl]-1-methyl-1H-indol-7-yl}(3-fluoroazetidin-1-yl)methanone;

rac-{3-[(3S,4R)-4-(dimethylamino)-1-(7-fluoro-2,3-dihydro-1H-inden-1-yl)pyrrolidin-3-yl]-1-methyl-1H-indol-7-yl}(3-hydroxyazetidin-1-yl)methanone;

rac-{3-[(3S,4R)-4-(dimethylamino)-1-(7-fluoro-2,3-dihydro-1H-inden-1-yl)pyrrolidin-3-yl]-1-methyl-1H-indol-6-yl}(3-hydroxyazetidin-1-yl)methanone;

rac-3-[(3S,4R)-4-(dimethylamino)-1-(7-fluoro-2,3-dihydro-1H-inden-1-yl)pyrrolidin-3-yl]-N-(3-hydroxycyclobutyl)-1-methyl-1H-indole-7-carboxamide;

rac-3-[(3S,4R)-4-(dimethylamino)-1-(7-fluoro-2,3-dihydro-1H-inden-1-yl)pyrrolidin-3-yl]-N-(3-hydroxycyclobutyl)-N,1-dimethyl-1H-indole-7-carboxamide;

rac-{3-[(3S,4R)-4-(dimethylamino)-1-(7-fluoro-2,3-dihydro-1H-inden-1-yl)pyrrolidin-3-yl]-1-methyl-1H-indol-7-yl}[3-(methanesulfonyl)azetidin-1-yl]methanone;

rac-{3-[(3S,4R)-4-(dimethylamino)-1-(7-fluoro-2,3-dihydro-1H-inden-1-yl)pyrrolidin-3-yl]-1-methyl-1H-indol-6-yl}[(3S)-3-hydroxypyrrolidin-1-yl]methanone;

rac-{3-[(3S,4R)-4-(dimethylamino)-1-(7-fluoro-2,3-dihydro-1H-inden-1-yl)pyrrolidin-3-yl]-1-methyl-1H-indol-6-yl}[(3R)-3-hydroxypyrrolidin-1-yl]methanone;

rac-[(3S,4S)-3,4-dihydroxypyrrolidin-1-yl]{3-[(3S,4R)-4-(dimethylamino)-1-(7-fluoro-2,3-dihydro-1H-inden-1-yl)pyrrolidin-3-yl]-1-methyl-1H-indol-7-yl}methanone;

rac-[(3S,4S)-3,4-dihydroxypyrrolidin-1-yl]{3-[(3S,4R)-4-(dimethylamino)-1-(7-fluoro-2,3-dihydro-1H-inden-1-yl)pyrrolidin-3-yl]-1-methyl-1H-indol-6-yl}methanone;

rac-3-[(3S,4R)-4-(dimethylamino)-1-(7-fluoro-2,3-dihydro-1H-inden-1-yl)pyrrolidin-3-yl]-N-(1,1-dioxo-1lambda~6~-thiolan-3-yl)-1-methyl-1H-indole-7-carboxamide;

rac-{3-[(3S,4R)-4-(dimethylamino)-1-(7-fluoro-2,3-dihydro-1H-inden-1-yl)pyrrolidin-3-yl]-1-methyl-1H-indol-7-yl}[(2S)-2-(hydroxymethyl)pyrrolidin-1-yl]methanone;

rac-1-{3-[(3S,4R)-4-(dimethylamino)-1-(7-fluoro-2,3-dihydro-1H-inden-1-yl)pyrrolidin-3-yl]-1-methyl-1H-indole-7-carbonyl}-L-prolinamide;

rac-{3-[(3S,4R)-4-(dimethylamino)-1-(7-fluoro-2,3-dihydro-1H-inden-1-yl)pyrrolidin-3-yl]-1-methyl-1H-indol-7-yl}[(3S)-3-hydroxypyrrolidin-1-yl]methanone;

rac-{3-[(3S,4R)-4-(dimethylamino)-1-(7-fluoro-2,3-dihydro-1H-inden-1-yl)pyrrolidin-3-yl]-1-methyl-1H-indol-7-yl}(piperazin-1-yl)methanone;

rac-(3R,4S)-1-(7-fluoro-2,3-dihydro-1H-inden-1-yl)-4-{6-[4-(methanesulfonyl)piperazin-1-yl]-1-methyl-1H-indol-3-yl}-N,N-dimethylpyrrolidin-3-amine;

rac-1-(4-{3-[(3S,4R)-4-(dimethylamino)-1-(7-fluoro-2,3-dihydro-1H-inden-1-yl)pyrrolidin-3-yl]-1-methyl-1H-indol-6-yl}piperazin-1-yl)ethan-1-one;

rac-{3-[(3S,4R)-4-(dimethylamino)-1-(7-fluoro-2,3-dihydro-1H-inden-1-yl)pyrrolidin-3-yl]-1-methyl-1H-indol-6-yl}[4-(methanesulfonyl)piperazin-1-yl]methanone;

rac-1-(4-{3-[(3S,4R)-4-(dimethylamino)-1-(7-fluoro-2,3-dihydro-1H-inden-1-yl)pyrrolidin-3-yl]-1-methyl-1H-indole-6-carbonyl}piperazin-1-yl)ethan-1-one;

rac-4-{3-[(3S,4R)-4-(dimethylamino)-1-(7-fluoro-2,3-dihydro-1H-inden-1-yl)pyrrolidin-3-yl]-1-methyl-1H-indole-7-carbonyl}-N,N-dimethylpiperazine-1-sulfonamide;

rac-4-{3-[(3S,4R)-4-(dimethylamino)-1-(7-fluoro-2,3-dihydro-1H-inden-1-yl)pyrrolidin-3-yl]-1-methyl-1H-indole-7-carbonyl}-1-methylpiperazin-2-one;

rac-{3-[(3S,4R)-4-(dimethylamino)-1-(7-fluoro-2,3-dihydro-1H-inden-1-yl)pyrrolidin-3-yl]-1-methyl-1H-indol-7-yl}[4-(methanesulfonyl)piperazin-1-yl]methanone;

rac-4-{3-[(3S,4R)-4-(dimethylamino)-1-(7-fluoro-2,3-dihydro-1H-inden-1-yl)pyrrolidin-3-yl]-1-methyl-1H-indole-7-carbonyl}-N,N-dimethylpiperazine-1-carboxamide;

rac-1-(4-{3-[(3S,4R)-4-(dimethylamino)-1-(7-fluoro-2,3-dihydro-1H-inden-1-yl)pyrrolidin-3-yl]-1-methyl-1H-indole-7-carbonyl}piperazin-1-yl)ethan-1-one;

rac-4-{3-[(3S,4R)-4-(dimethylamino)-1-(7-fluoro-2,3-dihydro-1H-inden-1-yl)pyrrolidin-3-yl]-1-methyl-1H-indol-7-yl}-1-methylpiperazin-2-one;

rac-{3-[(3S,4R)-4-(dimethylamino)-1-(7-fluoro-2,3-dihydro-1H-inden-1-yl)pyrrolidin-3-yl]-1-methyl-1H-indol-7-yl}[4-(ethane sulfonyl)piperazin-1-yl]methanone;

rac-4-{3-[(3S,4R)-4-(dimethylamino)-1-(7-fluoro-2,3-dihydro-1H-inden-1-yl)pyrrolidin-3-yl]-1-methyl-1H-indol-7-yl}-N,N-dimethylpiperazine-1-carboxamide;

rac-8-{3-[(3S,4R)-4-(dimethylamino)-1-(7-fluoro-2,3-dihydro-1H-inden-1-yl)pyrrolidin-3-yl]-1-methyl-1H-indole-7-carbonyl}hexahydro-2H-pyrazino[1,2-a]pyrazin-1(6H)-one;

rac-{3-[(3S,4R)-4-(dimethylamino)-1-(7-fluoro-2,3-dihydro-1H-inden-1-yl)pyrrolidin-3-yl]-1-methyl-1H-indol-7-yl}[4-(1-methyl-1H-imidazole-5-sulfonyl)piperazin-1-yl]methanone;

rac-{3-[(3S,4R)-4-(dimethylamino)-1-(7-fluoro-2,3-dihydro-1H-inden-1-yl)pyrrolidin-3-yl]-1-methyl-1H-indol-7-yl}[4-(3,5-dimethyl-1H-pyrazole-4-sulfonyl)piperazin-1-yl]methanone;

rac-{3-[(3S,4R)-4-(dimethylamino)-1-(7-fluoro-2,3-dihydro-1H-inden-1-yl)pyrrolidin-3-yl]-1-methyl-1H-indol-7-yl}[4-(pyridazin-3-yl)piperazin-1-yl]methanone;

rac-(3S,4R)-1-(7-fluoro-2,3-dihydro-1H-inden-1-yl)-N,N-dimethyl-4-(5,6,7,8-tetrahydroimidazo[1,2-a]pyridin-3-yl)pyrrolidin-3-amine;

rac-(3R,4S)-1-(7-fluoro-2,3-dihydro-1H-inden-1-yl)-N,N-dimethyl-4-(1-methyl-1H-pyrrolo[3,2-c]pyridin-3-yl)pyrrolidin-3-amine;

rac-(3S,4R)-1-(7-fluoro-2,3-dihydro-1H-inden-1-yl)-N,N-dimethyl-4-(oxan-4-yl)pyrrolidin-3-amine;

rac-(3S,4R)-1-(7-fluoro-2,3-dihydro-1H-inden-1-yl)-N,N-dimethyl-4-[6-(piperazin-1-yl)pyridin-3-yl]pyrrolidin-3-amine;

rac-(3R,4S)-1-(7-fluoro-2,3-dihydro-1H-inden-1-yl)-N,N-dimethyl-4-(1-phenylpiperidin-4-yl)pyrrolidin-3-amine;

rac-2-(4-{5-[(3R,4S)-4-(dimethylamino)-1-(7-fluoro-2,3-dihydro-1H-inden-1-yl)pyrrolidin-3-yl]pyridin-2-yl}piperazin-1-yl)-N,N-dimethylacetamide;

rac-(3R,4S)-1-(7-fluoro-2,3-dihydro-1H-inden-1-yl)-N,N-dimethyl-4-(1-methyl-1H-pyrrolo[2,3-c]pyridin-3-yl)pyrrolidin-3-amine;

rac-(3R,4S)-1-(7-fluoro-2,3-dihydro-1H-inden-1-yl)-N,N-dimethyl-4-[1-(pyridin-3-yl)piperidin-4-yl]pyrrolidin-3-amine;

rac-2-(4-{5-[(3R,4S)-4-(dimethylamino)-1-(7-fluoro-2,3-dihydro-1H-inden-1-yl)pyrrolidin-3-yl]pyridin-2-yl}-1H-pyrazol-1-yl)-1-(3-hydroxyazetidin-1-yl)ethan-1-one;

rac-(4-{5-[(3R,4S)-4-(dimethylamino)-1-(7-fluoro-2,3-dihydro-1H-inden-1-yl)pyrrolidin-3-yl]pyridin-2-yl}piperazin-1-yl)(oxetan-3-yl)methanone;

rac-(3R,4S)-1-(7-fluoro-2,3-dihydro-1H-inden-1-yl)-N,N-dimethyl-4-[1-(pyridin-2-yl)piperidin-4-yl]pyrrolidin-3-amine;

rac-2-(4-{5-[(3R,4S)-4-(dimethylamino)-1-(7-fluoro-2,3-dihydro-1H-inden-1-yl)pyrrolidin-3-yl]pyridin-2-yl}-1H-pyrazol-1-yl)-1-(3-fluoroazetidin-1-yl)ethan-1-one;

rac-6-{4-[(3S,4R)-4-(dimethylamino)-1-(7-fluoro-2,3-dihydro-1H-inden-1-yl)pyrrolidin-3-yl]piperidin-1-yl}-N-methylpyridine-3-carboxamide;

rac-N-[2-(4-{5-[(3R,4S)-4-(dimethylamino)-1-(7-fluoro-2,3-dihydro-1H-inden-1-yl)pyrrolidin-3-yl]pyridin-2-yl}piperazin-1-yl)-2-oxoethyl]methanesulfonamide;

rac-(3R,4S)-1-(7-fluoro-2,3-dihydro-1H-inden-1-yl)-N,N-dimethyl-4-(1-methyl-1H-indazol-3-yl)pyrrolidin-3-amine;

rac-1-(4-{5-[(3R,4S)-4-(dimethylamino)-1-(7-fluoro-2,3-dihydro-1H-inden-1-yl)pyrrolidin-3-yl]pyridin-2-yl}piperazin-1-yl)-2-(methanesulfonyl)ethan-1-one;

rac-2-(4-{5-[(3R,4S)-4-(dimethylamino)-1-(7-fluoro-2,3-dihydro-1H-inden-1-yl)pyrrolidin-3-yl]pyridin-2-yl}-1H-pyrazol-1-yl)acetamide;

rac-2-(4-{5-[(3R,4S)-4-(dimethylamino)-1-(7-fluoro-2,3-dihydro-1H-inden-1-yl)pyrrolidin-3-yl]pyridin-2-yl}-1H-pyrazol-1-yl)-N,N-dimethylacetamide;

rac-2-(4-{5-[(3R,4S)-4-(dimethylamino)-1-(7-fluoro-2,3-dihydro-1H-inden-1-yl)pyrrolidin-3-yl]pyridin-2-yl}piperazin-1-yl)-2-oxoethane-1-sulfonamide;

rac-2-(4-{5-[(3R,4S)-4-(dimethylamino)-1-(7-fluoro-2,3-dihydro-1H-inden-1-yl)pyrrolidin-3-yl]pyridin-2-yl}-1H-pyrazol-1-yl)-N-methylacetamide;

rac-2-{4-[(3S,4R)-4-(dimethylamino)-1-(7-fluoro-2,3-dihydro-1H-inden-1-yl)pyrrolidin-3-yl]piperidin-1-yl}-1,3-thiazole-5-carboxamide;

rac-5-{4-[(3S,4R)-4-(dimethylamino)-1-(7-fluoro-2,3-dihydro-1H-inden-1-yl)pyrrolidin-3-yl]piperidin-1-yl}pyrazine-2-carboxamide;

rac-(3R,4S)-1-(7-fluoro-2,3-dihydro-1H-inden-1-yl)-N,N-dimethyl-4-(1-methyl-1H-pyrrolo[2,3-b]pyridin-3-yl)pyrrolidin-3-amine;

rac-6-{4-[(3S,4R)-4-(dimethylamino)-1-(7-fluoro-2,3-dihydro-1H-inden-1-yl)pyrrolidin-3-yl]piperidin-1-yl}pyridazine-3-carboxamide;
rac-4-{4-[(3S,4R)-4-(dimethylamino)-1-(7-fluoro-2,3-dihydro-1H-inden-1-yl)pyrrolidin-3-yl]piperidin-1-yl}benzamide;
rac-6-{4-[(3S,4R)-4-(dimethylamino)-1-(7-fluoro-2,3-dihydro-1H-inden-1-yl)pyrrolidin-3-yl]piperidin-1-yl}pyridine-3-carboxamide; and pharmaceutically acceptable salts thereof.

One embodiment pertains to compounds or pharmaceutically acceptable salts thereof, which are useful as inhibitors of EED, the compounds having Formula (IVa) or Formula (IVb)

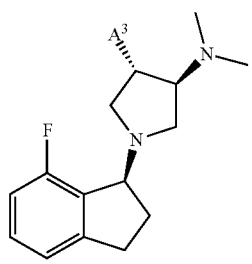

Formula (IVa)

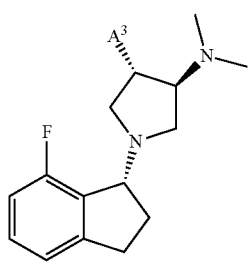

Formula (IVb)

wherein $A^3$ is selected from the group consisting of aryl, heterocyclyl, and heteroaryl, wherein the $A^3$ aryl, heterocyclyl, and heteroaryl are optionally substituted with one or more substituents independently selected from the group consisting of $R^1$, $OR^1$, $SR^1$, $S(O)R^1$, $SO_2R^1$, $C(O)R^1$, $CO(O)R^1$, $OC(O)R^1$, $OC(O)OR^1$, $NH_2$, $NHR^1$, $N(R^1)_2$, $NHC(O)R^1$, $NR^1C(O)R^1$, $NHS(O)_2R^1$, $NR^1S(O)_2R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $C(O)NH_2$, $C(O)NHR^1$, $C(O)N(R^1)_2$, $C(O)NHOH$, $C(O)NHOR^1$, $C(O)NHSO_2R^1$, $C(O)NR^1SO_2R^1$, $SO_2NH_2$, $SO_2NHR^1$, $SO_2N(R^1)_2$, $C(O)H$, $C(O)OH$, $C(N)NH_2$, $C(N)NHR^1$, $C(N)N(R^1)_2$, $CNOH$, $CNOCH_3$, OH, (O), CN, $NO_2$, $CF_3$, $CF_2CF_3$, $OCF_3$, $OCF_2CF_3$, F, Cl, Br and I;

$R^1$, at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^1$ $C_1$-$C_6$ alkyl, $C_2$-$C_6$ alkenyl, and $C_2$-$C_6$ alkynyl is optionally substituted with one or more substituents independently selected from the group consisting of $R^2$, $OR^2$, $SR^2$, $S(O)R^2$, $SO_2R^2$, $C(O)R^2$, $CO(O)R^2$, $OC(O)R^2$, $OC(O)OR^2$, $NH_2$, $NHR^2$, $N(R^2)_2$, $NHC(O)R^2$, $NR^2C(O)R^2$, $NHS(O)_2R^2$, $NR^2S(O)_2R^2$, $NHC(O)OR^2$, $NR^2C(O)OR^2$, $NHC(O)NH_2$, $NHC(O)NHR^2$, $NHC(O)N(R^2)_2$, $NR^2C(O)NHR^2$, $NR^2C(O)N(R^2)_2$, $C(O)NH_2$, $C(O)NHR^2$, $C(O)N(R^2)_2$, $C(O)NHOH$, $C(O)NHOR^2$, $C(O)NHSO_2R^2$, $C(O)NR^2SO_2R^2$, $SO_2NH_2$, $SO_2NHR^2$, $SO_2N(R^2)_2$, $C(O)H$, $C(O)OH$, OH, (O), CN, $NO_2$, $CF_3$, $CF_2CF_3$, $OCF_3$, $OCF_2CF_3$, F, Cl, Br and I; wherein each $R^1$ aryl, heteroaryl, heterocyclyl, cycloalkyl, and cycloalkenyl is optionally substituted with one or more substituents independently selected from the group consisting of $R^3$, $OR^3$, $SR^3$, $S(O)R^3$, $SO_2R^3$, $C(O)R^3$, $CO(O)R^3$, $OC(O)R^3$, $OC(O)OR^3$, $NH_2$, $NHR^3$, $N(R^3)_2$, $NHC(O)R^3$, $NR^3C(O)R^3$, $NHS(O)_2R^3$, $NR^3S(O)_2R^3$, $NHC(O)OR^3$, $NR^3C(O)OR^3$, $NHC(O)NH_2$, $NHC(O)NHR^3$, $NHC(O)N(R^3)_2$, $NR^3C(O)NHR^3$, $NR^3C(O)N(R^3)_2$, $C(O)NH_2$, $C(O)NHR^3$, $C(O)N(R^3)_2$, $C(O)NHOH$, $C(O)NHOR^3$, $C(O)NHSO_2R^3$, $C(O)NR^3SO_2R^3$, $SO_2NH_2$, $SO_2NHR^3$, $SO_2N(R^3)_2$, $C(O)H$, $C(O)OH$, $C(O)C(O)NH_2$, $C(O)C(O)NHR^3$, $C(O)C(O)N(R^3)_2$, $C(N)NH_2$, $C(N)NHR^3$, $C(N)N(R^3)_2$, $CNOH$, $CNOCH_3$, OH, (O), CN, $NO_2$, $CF_3$, $CF_2CF_3$, $OCF_3$, $OCF_2CF_3$, F, Cl, Br and I;

$R^2$, at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^2$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I; wherein each $R^2$ aryl, heteroaryl, heterocyclyl, cycloalkyl, and cycloalkenyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I;

$R^3$, at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^3$ $C_1$-$C_6$ alkyl, $C_2$-$C_6$ alkenyl, and $C_2$-$C_6$ alkynyl is optionally substituted with one or more substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, (O), CN, $NO_2$, $CF_3$, $CF_2CF_3$, $OCF_3$, $OCF_2CF_3$, F, Cl, Br and I; wherein each $R^3$ aryl, heteroaryl, heterocyclyl, cycloalkyl, and cycloalkenyl is optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, $C(N)NH_2$, $C(N)NHR^5$, $C(N)N(R^5)_2$, $CNOH$, $CNOCH_3$, OH, (O), CN, $NO_2$, $CF_3$, $CF_2CF_3$, $OCF_3$, $OCF_2CF_3$, F, Cl, Br and I;

$R^4$ is at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^4$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I; wherein each $R^4$ aryl, heteroaryl, heterocyclyl, cycloalkyl, and cycloalkenyl is optionally substituted with one or more substituents independently selected from the group consisting of $NH_2$, $C(O)NH_2$, $SO_2NH_2$, $C(O)H$, $C(O)OH$, $OH$, $(O)$, $CN$, $NO_2$, $CF_3$, $CF_2CF_3$, $OCF_3$, $OCF_2CF_3$, $F$, $Cl$, $Br$ and $I$; and $R^5$ is at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^5$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)NH_2$, $SO_2NH_2$, $C(O)H$, $C(O)OH$, $OH$, $(O)$, $CN$, $NO_2$, $CF_3$, $CF_2CF_3$, $OCF_3$, $OCF_2CF_3$, $F$, $Cl$, $Br$ and $I$; wherein each $R^5$ aryl, heteroaryl, heterocyclyl, cycloalkyl, and cycloalkenyl is optionally substituted with one or more substituents independently selected from the group consisting of $NH_2$, $C(O)NH_2$, $SO_2NH_2$, $C(O)H$, $C(O)OH$, $OH$, $(O)$, $CN$, $NO_2$, $CF_3$, $CF_2CF_3$, $OCF_3$, $OCF_2CF_3$, $F$, $Cl$, $Br$ and $I$.

In one embodiment of Formula (IVa) or Formula (IVb), $A^3$ is selected from the group consisting of aryl, heterocyclyl, and heteroaryl, wherein the $A^3$ aryl, heterocyclyl, and heteroaryl are optionally substituted with one or more substituents independently selected from the group consisting of $R^1$, $OR^1$, $SR^1$, $S(O)R^1$, $SO_2R^1$, $C(O)R^1$, $CO(O)R^1$, $OC(O)R^1$, $OC(O)OR^1$, $NH_2$, $NHR^1$, $N(R^1)_2$, $NHC(O)R^1$, $NR^1C(O)R^1$, $NHS(O)_2R^1$, $NR^1S(O)_2R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $C(O)NH_2$, $C(O)NHR^1$, $C(O)N(R^1)_2$, $C(O)NHOH$, $C(O)NHOR^1$, $C(O)NHSO_2R^1$, $C(O)NR^1SO_2R^1$, $SO_2NH_2$, $SO_2NHR^1$, $SO_2N(R^1)_2$, $C(O)H$, $C(O)OH$, $C(N)NH_2$, $C(N)NHR^1$, $C(N)N(R^1)_2$, $CNOH$, $CNOCH_3$, $OH$, $(O)$, $CN$, $NO_2$, $CF_3$, $CF_2CF_3$, $OCF_3$, $OCF_2CF_3$, $F$, $Cl$, $Br$ and $I$. In another embodiment of Formula (IVa) or Formula (IVb), $A^3$ is selected from the group consisting of aryl, heterocyclyl, and heteroaryl, wherein the $A^3$ aryl, heterocyclyl, and heteroaryl are optionally substituted with one or more substituents independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, $C(O)OH$, $CN$, $F$, $Cl$, $Br$ and $I$. In another embodiment of Formula (IVa) or Formula (IVb), $A^3$ is aryl, wherein the $A^3$ aryl is optionally substituted with one or more substituents independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, $C(O)OH$, $CN$, $F$, $Cl$, $Br$ and $I$. In another embodiment of Formula (IVa) or Formula (IVb), $A^3$ is aryl, wherein the $A^3$ aryl is substituted with one substituent independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, $C(O)OH$, $CN$, $F$, $Cl$, $Br$ and $I$. In another embodiment of Formula (IVa) or Formula (IVb), $A^3$ is aryl, wherein the $A^3$ aryl is substituted with two substituents independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, $C(O)OH$, $CN$, $F$, $Cl$, $Br$ and $I$. In another embodiment of Formula (IVa) or Formula (IVb), $A^3$ is heterocyclyl, wherein the $A^3$ heterocyclyl is optionally substituted with one or more substituents independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, $C(O)OH$, $CN$, $F$, $Cl$, $Br$ and $I$. In another embodiment of Formula (IVa) or Formula (IVb), $A^3$ is heterocyclyl, wherein the $A^3$ heterocyclyl is unsubstituted. In another embodiment of Formula (IVa) or Formula (IVb), $A^3$ is heterocyclyl, wherein the $A^3$ heterocyclyl is substituted with one substituent independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, $C(O)OH$, $CN$, $F$, $Cl$, $Br$ and $I$. In another embodiment of Formula (IVa) or Formula (IVb), $A^3$ is heterocyclyl, wherein the $A^3$ heterocyclyl is substituted with two substituents independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, $C(O)OH$, $CN$, $F$, $Cl$, $Br$ and $I$. In another embodiment of Formula (IVa) or Formula (IVb), $A^3$ is heteroaryl, wherein the $A^3$ heteroaryl is optionally substituted with one or more substituents independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, $C(O)OH$, $CN$, $F$, $Cl$, $Br$ and $I$. In another embodiment of Formula (IVa) or Formula (IVb), $A^3$ is heteroaryl, wherein the $A^3$ heteroaryl is unsubstituted. In another embodiment of Formula (IVa) or Formula (IVb), $A^3$ is heteroaryl, wherein the $A^3$ heteroaryl is substituted with one substituent independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, $C(O)OH$, $CN$, $F$, $Cl$, $Br$ and $I$. In another embodiment of Formula (IVa) or Formula (IVb), $A^3$ is heteroaryl, wherein the $A^3$ heteroaryl is substituted with two substituents independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, $C(O)OH$, $CN$, $F$, $Cl$, $Br$ and $I$.

In one embodiment of Formula (IVa) or Formula (IVb), $R^1$, at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^1$ $C_1$-$C_6$ alkyl, $C_2$-$C_6$ alkenyl, and $C_2$-$C_6$ alkynyl is optionally substituted with one or more substituents independently selected from the group consisting of $R^2$, $OR^2$, $SR^2$, $S(O)R^2$, $SO_2R^2$, $C(O)R^2$, $CO(O)R^2$, $OC(O)R^2$, $OC(O)OR^2$, $NH_2$, $NHR^2$, $N(R^2)_2$, $NHC(O)R^2$, $NR^2C(O)R^2$, $NHS(O)_2R^2$, $NR^2S(O)_2R^2$, $NHC(O)OR^2$, $NR^2C(O)OR^2$, $NHC(O)NH_2$, $NHC(O)NHR^2$, $NHC(O)N(R^2)_2$, $NR^2C(O)NHR^2$, $NR^2C(O)N(R^2)_2$, $C(O)NH_2$, $C(O)NHR^2$, $C(O)N(R^2)_2$, $C(O)NHOH$, $C(O)NHOR^2$, $C(O)NHSO_2R^2$, $C(O)NR^2SO_2R^2$, $SO_2NH_2$, $SO_2NHR^2$, $SO_2N(R^2)_2$, $C(O)H$, $C(O)OH$, $OH$, $(O)$, $CN$, $NO_2$, $CF_3$, $CF_2CF_3$, $OCF_3$, $OCF_2CF_3$, $F$, $Cl$, $Br$ and $I$; wherein each $R^1$ aryl, heteroaryl, heterocyclyl, cycloalkyl, and cycloalkenyl is optionally substituted with one or more substituents independently selected from the group consisting of $R^3$, $OR^3$, $SR^3$, $S(O)R^3$, $SO_2R^3$, $C(O)R^3$, $CO(O)R^3$, $OC(O)R^3$, $OC(O)OR^3$, $NH_2$, $NHR^3$, $N(R^3)_2$, $NHC(O)R^3$, $NR^3C(O)R^3$, $NHS(O)_2R^3$, $N R^3S(O)_2R^3$, $NHC(O)OR^3$, $NR^3C(O)OR^3$, $NHC(O)NH_2$, $NHC(O)NHR^3$, $NHC(O)N(R^3)_2$, $NR^3C(O)NHR^3$, $NR^3C(O)N(R^3)_2$, $C(O)NH_2$, $C(O)NHR^3$, $C(O)N(R^3)_2$, $C(O)NHOH$, $C(O)NHOR^3$, $C(O)NHSO_2R^3$, $C(O)NR^3SO_2R^3$, $SO_2NH_2$, $SO_2NHR^3$, $SO_2N(R^3)_2$, $C(O)H$, $C(O)OH$, $C(O)C(O)NH_2$, $C(O)C(O)NHR^3$, $C(O)C(O)N(R^3)_2$, $C(N)NH_2$, $C(N)NHR^3$, $C(N)N(R^3)_2$, $CNOH$, $CNOCH_3$, $OH$, $(O)$, $CN$, $NO_2$, $CF_3$, $CF_2CF_3$, $OCF_3$, $OCF_2CF_3$, $F$, $Cl$, $Br$ and $I$. In another embodiment of Formula (IVa) or Formula (IVb), $R^1$, at each occurrence, is $C_1$-$C_6$ alkyl; wherein each $R^1$ $C_1$-$C_6$ alkyl is optionally substituted with one or more substituents independently selected from the group consisting of $C(O)OH$ and $OH$. In another embodiment of Formula (IVa) or Formula (IVb), $R^1$, at each occurrence, is independently selected from the group consisting of aryl, heteroaryl, heterocyclyl, and cycloalkyl; wherein each $R^1$ aryl, heteroaryl, heterocyclyl, and cycloalkyl is optionally substituted with one or more substituents independently selected from the group consisting of $R^3$, $SO_2R^3$, $C(O)R^3$, $CO(O)R^3$, $C(O)NH_2$, $C(O)NHR^3$, $C(O)N(R^3)_2$, $SO_2N(R^3)_2$, $C(O)C(O)NH_2$, $C(O)C(O)N(R^3)_2$, $OH$, $(O)$, and $F$.

In one embodiment of Formula (IVa) or Formula (IVb), $R^3$, at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^3$ $C_1$-$C_6$ alkyl, $C_2$-$C_6$ alkenyl, and $C_2$-$C_6$ alkynyl is optionally substituted with one or more substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $OH$, $(O)$, $CN$, $NO_2$, $CF_3$, $CF_2CF_3$, $OCF_3$, $OCF_2CF_3$, F, Cl, Br and I; wherein each $R^3$ aryl, heteroaryl, heterocyclyl, cycloalkyl, and cycloalkenyl is optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, $C(N)NH_2$, $C(N)NHR^5$, $C(N)N(R^5)_2$, $CNOH$, $CNOCH_3$, $OH$, $(O)$, $CN$, $NO_2$, $CF_3$, $CF_2CF_3$, $OCF_3$, $OCF_2CF_3$, F, Cl, Br and I. In another embodiment of Formula (IVa) or Formula (IVb), $R^3$, at each occurrence, is independently $C_1$-$C_6$ alkyl; wherein each $R^3$ $C_1$-$C_6$ alkyl is optionally substituted with one or more substituents independently selected from the group consisting of $SO_2R^4$, $C(O)R^4$, $NHS(O)_2R^4$, $C(O)NH_2$, $C(O)NHR^4$, $C(O)N(R^4)_2$, $SO_2NH_2$, and OH. In another embodiment of Formula (IVa) or Formula (IVb), $R^3$, at each occurrence, is independently selected from the group consisting of heteroaryl, heterocyclyl, and cycloalkyl; wherein each $R^3$ heteroaryl, heterocyclyl, and cycloalkyl is optionally substituted with one or more substituents independently selected from the group consisting of $R^5$ and CN.

In one embodiment of Formula (IVa) or Formula (IVb), $R^4$ is at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^4$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I; wherein each $R^4$ aryl, heteroaryl, heterocyclyl, cycloalkyl, and cycloalkenyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I. In another embodiment of Formula (IVa) or Formula (IVb), $R^4$ at each occurrence, is $C_1$-$C_6$ alkyl. In another embodiment of Formula (IVa) or Formula (IVb), $R^4$ at each occurrence, is heterocyclyl; wherein each $R^4$ heterocyclyl is optionally substituted with one or more substituents independently selected from the group consisting of OH, and F.

In one embodiment of Formula (IVa) or Formula (IVb), $R^5$ is at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^5$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I; wherein each $R^5$ aryl, heteroaryl, heterocyclyl, cycloalkyl, and cycloalkenyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I. In another embodiment of Formula (IVa) or Formula (IVb), $R^5$ is at each occurrence, is independently $C_1$-$C_6$ alkyl.

In one embodiment of Formula (IVa) or Formula (IVb), $A^3$ is selected from the group consisting of aryl, heterocyclyl, and heteroaryl, wherein the $A^3$ aryl, heterocyclyl, and heteroaryl are optionally substituted with one or more substituents independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, $C(O)OH$, CN, F, Cl, Br and I;

$R^1$, at each occurrence, is independently selected from the group consisting of $C_1$-$C_6$ alkyl, aryl, heteroaryl, heterocyclyl, and cycloalkyl; wherein each $R^1$ $C_1$-$C_6$ alkyl is optionally substituted with one or more substituents independently selected from the group consisting of $C(O)OH$, OH, F, Cl, Br and I; wherein each $R^1$ aryl, heteroaryl, heterocyclyl, cycloalkyl, and cycloalkenyl is optionally substituted with one or more substituents independently selected from the group consisting of $R^3$, $SO_2R^3$, $C(O)R^3$, $CO(O)R^3$, $C(O)NH_2$, $C(O)NHR^3$, $C(O)N(R^3)_2$, $SO_2N(R^3)_2$, $C(O)C(O)NH_2$, $C(O)C(O)N(R^3)_2$, OH, (O), F, Cl, Br and I;

$R^3$, at each occurrence, is independently selected from the group consisting of $C_1$-$C_6$ alkyl, heteroaryl, heterocyclyl, and cycloalkyl; wherein each $R^3$ $C_1$-$C_6$ alkyl is optionally substituted with one or more substituents independently selected from the group consisting of $SO_2R^4$, $C(O)R^4$, $NHS(O)_2R^4$, $C(O)NH_2$, $C(O)NHR^4$, $C(O)N(R^4)_2$, $SO_2NH_2$, F, Cl, Br and I; wherein each $R^3$ heteroaryl and heterocyclyl is optionally substituted with one or more substituents independently selected from the group consisting of $R^5$, CN, F, Cl, Br and I;

$R^4$ is at each occurrence, is independently selected from the group consisting of $C_1$-$C_6$ alkyl and heterocyclyl; wherein each $R^4$ heterocyclyl is optionally substituted with one or more substituents independently selected from the group consisting of OH, F, Cl, Br and I; and $R^5$ is at each occurrence, is independently $C_1$-$C_6$ alkyl.

Still another embodiment pertains to compounds of Formula (IVa) or Formula (IVb), selected from the group consisting of:

(3R,4S)-1-(7-fluoro-2,3-dihydro-1H-inden-1-yl)-4-{4-[4-(methanesulfonyl)piperazin-1-yl]phenyl}-N,N-dimethylpyrrolidin-3-amine;

1-(4-{4-[(3S,4R)-4-(dimethylamino)-1-(7-fluoro-2,3-dihydro-1H-inden-1-yl)pyrrolidin-3-yl]phenyl}piperazin-1-yl)ethan-1-one;

(3R,4S)-1-(7-fluoro-2,3-dihydro-1H-inden-1-yl)-N,N-dimethyl-4-(1-methyl-1H-indol-3-yl)pyrrolidin-3-amine;

3-[(3S,4R)-4-(dimethylamino)-1-(7-fluoro-2,3-dihydro-1H-inden-1-yl)pyrrolidin-3-yl]-1-methyl-1H-indole-7-carboxylic acid;

methyl 3-[(3S,4R)-4-(dimethylamino)-1-(7-fluoro-2,3-dihydro-1H-inden-1-yl)pyrrolidin-3-yl]-1-methyl-1H-indole-7-carboxylate;

{3-[(3S,4R)-4-(dimethylamino)-1-(7-fluoro-2,3-dihydro-1H-inden-1-yl)pyrrolidin-3-yl]-1-methyl-1H-indol-7-yl}(3-fluoroazetidin-1-yl)methanone;

{3-[(3S,4R)-4-(dimethylamino)-1-(7-fluoro-2,3-dihydro-1H-inden-1-yl)pyrrolidin-3-yl]-1-methyl-1H-indol-7-yl}(3-hydroxyazetidin-1-yl)methanone;

[4-(azetidine-1-sulfonyl)piperazin-1-yl]{3-[(3S,4R)-4-(dimethylamino)-1-(7-fluoro-2,3-dihydro-1H-inden-1-yl)pyrrolidin-3-yl]-1-methyl-1H-indol-7-yl}methanone;

1-(4-{3-[(3S,4R)-4-(dimethylamino)-1-(7-fluoro-2,3-dihydro-1H-inden-1-yl)pyrrolidin-3-yl]-1-methyl-1H-indole-7-carbonyl}piperazine-1-sulfonyl)azetidine-3-carbonitrile; and pharmaceutically acceptable salts thereof.

One embodiment pertains to compounds or pharmaceutically acceptable salts thereof, which are useful as inhibitors of EED, the compounds having Formula (Va) or Formula (Vb)

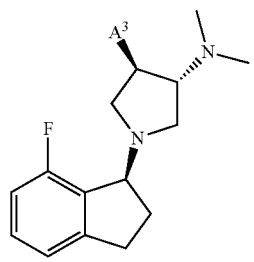

Formula (Va)

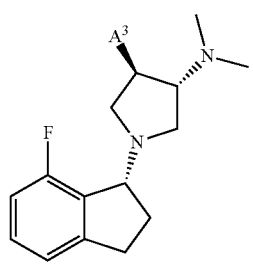

Formula (Vb)

wherein $A^3$ is selected from the group consisting of aryl, heterocyclyl, and heteroaryl, wherein the $A^3$ aryl, heterocyclyl, and heteroaryl are optionally substituted with one or more substituents independently selected from the group consisting of $R^1$, $OR^1$, $SR^1$, $S(O)R^1$, $SO_2R^1$, $C(O)R^1$, $CO(O)R^1$, $OC(O)R^1$, $OC(O)OR^1$, $NH_2$, $NHR^1$, $N(R^1)_2$, $NHC(O)R^1$, $NR^1C(O)R^1$, $NHS(O)_2R^1$, $NR^1S(O)_2R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $C(O)NH_2$, $C(O)NHR^1$, $C(O)N(R^1)_2$, $C(O)NHOH$, $C(O)NHOR^1$, $C(O)NHSO_2R^1$, $C(O)NR^1SO_2R^1$, $SO_2NH_2$, $SO_2NHR^1$, $SO_2N(R^1)_2$, $C(O)H$, $C(O)OH$, $C(N)NH_2$, $C(N)NHR^1$, $C(N)N(R^1)_2$, CNOH, $CNOCH_3$, OH, (O), CN, $NO_2$, $CF_3$, $CF_2CF_3$, $OCF_3$, $OCF_2CF_3$, F, Cl, Br and I;

$R^1$, at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^1$ $C_1$-$C_6$ alkyl, $C_2$-$C_6$ alkenyl, and $C_2$-$C_6$ alkynyl is optionally substituted with one or more substituents independently selected from the group consisting of $R^2$, $OR^2$, $SR^2$, $S(O)R^2$, $SO_2R^2$, $C(O)R^2$, $CO(O)R^2$, $OC(O)R^2$, $OC(O)OR^2$, $NH_2$, $NHR^2$, $N(R^2)_2$, $NHC(O)R^2$, $NR^2C(O)R^2$, $NHS(O)_2R^2$, $NR^2S(O)_2R^2$, $NHC(O)OR^2$, $NR^2C(O)OR^2$, $NHC(O)NH_2$, $NHC(O)NHR^2$, $NHC(O)N(R^2)_2$, $NR^2C(O)NHR^2$, $NR^2C(O)N(R^2)_2$, $C(O)NH_2$, $C(O)NHR^2$, $C(O)N(R^2)_2$, $C(O)NHOH$, $C(O)NHOR^2$, $C(O)NHSO_2R^2$, $C(O)NR^2SO_2R^2$, $SO_2NH_2$, $SO_2NHR^2$, $SO_2N(R^2)_2$, $C(O)H$, $C(O)OH$, OH, (O), CN, $NO_2$, $CF_3$, $CF_2CF_3$, $OCF_3$, $OCF_2CF_3$, F, Cl, Br and I; wherein each $R^1$ aryl, heteroaryl, heterocyclyl, cycloalkyl, and cycloalkenyl is optionally substituted with one or more substituents independently selected from the group consisting of $R^3$, $OR^3$, $SR^3$, $S(O)R^3$, $SO_2R^3$, $C(O)R^3$, $CO(O)R^3$, $OC(O)R^3$, $OC(O)OR^3$, $NH_2$, $NHR^3$, $N(R^3)_2$, $NHC(O)R^3$, $NR^3C(O)R^3$, $NHS(O)_2R^3$, $NR^3S(O)_2R^3$, $NHC(O)OR^3$, $NR^3C(O)OR^3$, $NHC(O)NH_2$, $NHC(O)NHR^3$, $NHC(O)N(R^3)_2$, $NR^3C(O)NHR^3$, $NR^3C(O)N(R^3)_2$, $C(O)NH_2$, $C(O)NHR^3$, $C(O)N(R^3)_2$, $C(O)NHOH$, $C(O)NHOR^3$, $C(O)NHSO_2R^3$, $C(O)NR^3SO_2R^3$, $SO_2NH_2$, $SO_2NHR^3$, $SO_2N(R^3)_2$, $C(O)H$, $C(O)OH$, $C(O)C(O)NH_2$, $C(O)C(O)NHR^3$, $C(O)C(O)N(R^3)_2$, $C(N)NH_2$, $C(N)NHR^3$, $C(N)N(R^3)_2$, CNOH, $CNOCH_3$, OH, (O), CN, $NO_2$, $CF_3$, $CF_2CF_3$, $OCF_3$, $OCF_2CF_3$, F, Cl, Br and I;

$R^2$, at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^2$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I; wherein each $R^2$ aryl, heteroaryl, heterocyclyl, cycloalkyl, and cycloalkenyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I;

$R^3$, at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^3$ $C_1$-$C_6$ alkyl, $C_2$-$C_6$ alkenyl, and $C_2$-$C_6$ alkynyl is optionally substituted with one or more substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, OH, (O), CN, $NO_2$, $CF_3$, $CF_2CF_3$, $OCF_3$, $OCF_2CF_3$, F, Cl, Br and I; wherein each $R^3$ aryl, heteroaryl, heterocyclyl, cycloalkyl, and cycloalkenyl is optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, $C(N)NH_2$, $C(N)NHR^5$, $C(N)N(R^5)_2$, CNOH, $CNOCH_3$, OH, (O), CN, $NO_2$, $CF_3$, $CF_2CF_3$, $OCF_3$, $OCF_2CF_3$, F, Cl, Br and I;

$R^4$ is at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^4$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I; wherein each $R^4$ aryl, heteroaryl, heterocyclyl, cycloalkyl, and cycloalkenyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I; and $R^5$ is at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^5$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)NH_2$, $SO_2NH_2$, $C(O)H$, $C(O)OH$, $OH$, $(O)$, $CN$, $NO_2$, $CF_3$, $CF_2CF_3$, $OCF_3$, $OCF_2CF_3$, $F$, $Cl$, $Br$ and $I$; wherein each $R^5$ aryl, heteroaryl, heterocyclyl, cycloalkyl, and cycloalkenyl is optionally substituted with one or more substituents independently selected from the group consisting of $NH_2$, $C(O)NH_2$, $SO_2NH_2$, $C(O)H$, $C(O)OH$, $OH$, $(O)$, $CN$, $NO_2$, $CF_3$, $CF_2CF_3$, $OCF_3$, $OCF_2CF_3$, $F$, $Cl$, $Br$ and $I$.

In one embodiment of Formula (Va) or Formula (Vb), $A^3$ is selected from the group consisting of aryl, heterocyclyl, and heteroaryl, wherein the $A^3$ aryl, heterocyclyl, and heteroaryl are optionally substituted with one or more substituents independently selected from the group consisting of $R^1$, $OR^1$, $SR^1$, $S(O)R^1$, $SO_2R^1$, $C(O)R^1$, $CO(O)R^1$, $OC(O)R^1$, $OC(O)OR^1$, $NH_2$, $NHR^1$, $N(R^1)_2$, $NHC(O)R^1$, $NR^1C(O)R^1$, $NHS(O)_2R^1$, $NR^1S(O)_2R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $C(O)NH_2$, $C(O)NHR^1$, $C(O)N(R^1)_2$, $C(O)NHOH$, $C(O)NHOR^1$, $C(O)NHSO_2R^1$, $C(O)NR^1SO_2R^1$, $SO_2NH_2$, $SO_2NHR^1$, $SO_2N(R^1)_2$, $C(O)H$, $C(O)OH$, $C(N)NH_2$, $C(N)NHR^1$, $C(N)N(R^1)_2$, $CNOH$, $CNOCH_3$, $OH$, $(O)$, $CN$, $NO_2$, $CF_3$, $CF_2CF_3$, $OCF_3$, $OCF_2CF_3$, $F$, $Cl$, $Br$ and $I$. In another embodiment of Formula (Va) or Formula (Vb), $A^3$ is selected from the group consisting of aryl, heterocyclyl, and heteroaryl, wherein the $A^3$ aryl, heterocyclyl, and heteroaryl are optionally substituted with one or more substituents independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, $C(O)OH$, $CN$, $F$, $Cl$, $Br$ and $I$. In another embodiment of Formula (Va) or Formula (Vb), $A^3$ is aryl, wherein the $A^3$ aryl is optionally substituted with one or more substituents independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, $C(O)OH$, $CN$, $F$, $Cl$, $Br$ and $I$. In another embodiment of Formula (Va) or Formula (Vb), $A^3$ is aryl, wherein the $A^3$ aryl is substituted with one substituent independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, $C(O)OH$, $CN$, $F$, $Cl$, $Br$ and $I$. In another embodiment of Formula (Va) or Formula (Vb), $A^3$ is aryl, wherein the $A^3$ aryl is substituted with two substituents independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, $C(O)OH$, $CN$, $F$, $Cl$, $Br$ and $I$. In another embodiment of Formula (Va) or Formula (Vb), $A^3$ is heterocyclyl, wherein the $A^3$ heterocyclyl is optionally substituted with one or more substituents independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, $C(O)OH$, $CN$, $F$, $Cl$, $Br$ and $I$. In another embodiment of Formula (Va) or Formula (Vb), $A^3$ is heterocyclyl, wherein the $A^3$ heterocyclyl is unsubstituted. In another embodiment of Formula (Va) or Formula (Vb), $A^3$ is heterocyclyl, wherein the $A^3$ heterocyclyl is substituted with one substituent independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, $C(O)OH$, $CN$, $F$, $Cl$, $Br$ and $I$. In another embodiment of Formula (Va) or Formula (Vb), $A^3$ is heterocyclyl, wherein the $A^3$ heterocyclyl is substituted with two substituents independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, $C(O)OH$, $CN$, $F$, $Cl$, $Br$ and $I$. In another embodiment of Formula (Va) or Formula (Vb), $A^3$ is heteroaryl, wherein the $A^3$ heteroaryl is optionally substituted with one or more substituents independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, $C(O)OH$, $CN$, $F$, $Cl$, $Br$ and $I$. In another embodiment of Formula (Va) or Formula (Vb), $A^3$ is heteroaryl, wherein the $A^3$ heteroaryl is unsubstituted. In another embodiment of Formula (Va) or Formula (Vb), $A^3$ is heteroaryl, wherein the $A^3$ heteroaryl is substituted with one substituent independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, $C(O)OH$, $CN$, $F$, $Cl$, $Br$ and $I$. In another embodiment of Formula (Va) or Formula (Vb), $A^3$ is heteroaryl, wherein the $A^3$ heteroaryl is substituted with two substituents independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, $C(O)OH$, $CN$, $F$, $Cl$, $Br$ and $I$.

In one embodiment of Formula (Va) or Formula (Vb), $R^1$, at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^1$ $C_1$-$C_6$ alkyl, $C_2$-$C_6$ alkenyl, and $C_2$-$C_6$ alkynyl is optionally substituted with one or more substituents independently selected from the group consisting of $R^2$, $OR^2$, $SR^2$, $S(O)R^2$, $SO_2R^2$, $C(O)R^2$, $CO(O)R^2$, $OC(O)R^2$, $OC(O)OR^2$, $NH_2$, $NHR^2$, $N(R^2)_2$, $NHC(O)R^2$, $NR^2C(O)R^2$, $NHS(O)_2R^2$, $NR^2S(O)_2R^2$, $NHC(O)OR^2$, $NR^2C(O)OR^2$, $NHC(O)NH_2$, $NHC(O)NHR^2$, $NHC(O)N(R^2)_2$, $NR^2C(O)NHR^2$, $NR^2C(O)N(R^2)_2$, $C(O)NH_2$, $C(O)NHR^2$, $C(O)N(R^2)_2$, $C(O)NHOH$, $C(O)NHOR^2$, $C(O)NHSO_2R^2$, $C(O)NR^2SO_2R^2$, $SO_2NH_2$, $SO_2NHR^2$, $SO_2N(R^2)_2$, $C(O)H$, $C(O)OH$, $OH$, $(O)$, $CN$, $NO_2$, $CF_3$, $CF_2CF_3$, $OCF_3$, $OCF_2CF_3$, $F$, $Cl$, $Br$ and $I$; wherein each $R^1$ aryl, heteroaryl, heterocyclyl, cycloalkyl, and cycloalkenyl is optionally substituted with one or more substituents independently selected from the group consisting of $R^3$, $OR^3$, $SR^3$, $S(O)R^3$, $SO_2R^3$, $C(O)R^3$, $CO(O)R^3$, $OC(O)R^3$, $OC(O)OR^3$, $NH_2$, $NHR^3$, $N(R^3)_2$, $NHC(O)R^3$, $NR^3C(O)R^3$, $NHS(O)_2R^3$, $NR^3S(O)_2R^3$, $NHC(O)OR^3$, $NR^3C(O)OR^3$, $NHC(O)NH_2$, $NHC(O)NHR^3$, $NHC(O)N(R^3)_2$, $NR^3C(O)NHR^3$, $NR^3C(O)N(R^3)_2$, $C(O)NH_2$, $C(O)NHR^3$, $C(O)N(R^3)_2$, $C(O)NHOH$, $C(O)NHOR^3$, $C(O)NHSO_2R^3$, $C(O)NR^3SO_2R^3$, $SO_2NH_2$, $SO_2NHR^3$, $SO_2N(R^3)_2$, $C(O)H$, $C(O)OH$, $C(O)C(O)NH_2$, $C(O)C(O)NHR^3$, $C(O)C(O)N(R^3)_2$, $C(N)NH_2$, $C(N)NHR^3$, $C(N)N(R^3)_2$, $CNOH$, $CNOCH_3$, $OH$, $(O)$, $CN$, $NO_2$, $CF_3$, $CF_2CF_3$, $OCF_3$, $OCF_2CF_3$, $F$, $Cl$, $Br$ and $I$. In another embodiment of Formula (Va) or Formula (Vb), $R^1$, at each occurrence, is $C_1$-$C_6$ alkyl; wherein each $R^1$ $C_1$-$C_6$ alkyl is optionally substituted with one or more substituents independently selected from the group consisting of $C(O)OH$ and $OH$. In another embodiment of Formula (Va) or Formula (Vb), $R^1$, at each occurrence, is independently selected from the group consisting of aryl, heteroaryl, heterocyclyl, and cycloalkyl; wherein each $R^1$ aryl, heteroaryl, heterocyclyl, and cycloalkyl is optionally substituted with one or more substituents independently selected from the group consisting of $R^3$, $SO_2R^3$, $C(O)R^3$, $CO(O)R^3$, $C(O)NH_2$, $C(O)NHR^3$, $C(O)N(R^3)_2$, $SO_2N(R^3)_2$, $C(O)C(O)NH_2$, $C(O)C(O)N(R^3)_2$, $OH$, $(O)$, and $F$.

In one embodiment of Formula (Va) or Formula (Vb), $R^3$, at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^3$ $C_1$-$C_6$ alkyl, $C_2$-$C_6$ alkenyl, and $C_2$-$C_6$ alkynyl is optionally substituted with one or more substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, NHC(O)NH$_2$, NHC(O)NHR$^4$, NHC(O)N(R$^4$)$_2$, NR$^4$C(O)NHR$^4$, NR$^4$C(O)N(R$^4$)$_2$, C(O)NH$_2$, C(O)NHR$^4$, C(O)N(R$^4$)$_2$, C(O)NHOH, C(O)NHOR$^4$, C(O)NHSO$_2$R$^4$, C(O)NR$^4$SO$_2$R$^4$, SO$_2$NH$_2$, SO$_2$NHR$^4$, SO$_2$N(R$^4$)$_2$, C(O)H, C(O)OH, OH, (O), CN, NO$_2$, CF$_3$, CF$_2$CF$_3$, OCF$_3$, OCF$_2$CF$_3$, F, Cl, Br and I; wherein each R$^3$ aryl, heteroaryl, heterocyclyl, cycloalkyl, and cycloalkenyl is optionally substituted with one or more substituents independently selected from the group consisting of R$^5$, OR$^5$, SR$^5$, S(O)R$^5$, SO$_2$R$^5$, C(O)R$^5$, CO(O)R$^5$, OC(O)R$^5$, OC(O)OR$^5$, NH$_2$, NHR$^5$, N(R$^5$)$_2$, NHC(O)R$^5$, NR$^5$C(O)R$^5$, NHS(O)$_2$R$^5$, NR$^5$S(O)$_2$R$^5$, NHC(O)OR$^5$, NR$^5$C(O)OR$^5$, NHC(O)NH$_2$, NHC(O)NHR$^5$, NHC(O)N(R$^5$)$_2$, NR$^5$C(O)NHR$^5$, NR$^5$C(O)N(R$^5$)$_2$, C(O)NH$_2$, C(O)NHR$^5$, C(O)N(R$^5$)$_2$, C(O)NHOH, C(O)NHOR$^5$, C(O)NHSO$_2$R$^5$, C(O)NR$^5$SO$_2$R$^5$, SO$_2$NH$_2$, SO$_2$NHR$^5$, SO$_2$N(R$^5$)$_2$, C(O)H, C(O)OH, C(N)NH$_2$, C(N)NHR$^5$, C(N)N(R$^5$)$_2$, CNOH, CNOCH$_3$, OH, (O), CN, NO$_2$, CF$_3$, CF$_2$CF$_3$, OCF$_3$, OCF$_2$CF$_3$, F, Cl, Br and I. In another embodiment of Formula (Va) or Formula (Vb), R$^3$, at each occurrence, is independently C$_1$-C$_6$ alkyl; wherein each R$^3$ C$_1$-C$_6$ alkyl is optionally substituted with one or more substituents independently selected from the group consisting of SO$_2$R$^4$, C(O)R$^4$, NHS(O)$_2$R$^4$, C(O)NH$_2$, C(O)NHR$^4$, C(O)N(R$^4$)$_2$, SO$_2$NH$_2$, and OH. In another embodiment of Formula (Va) or Formula (Vb), R$^3$, at each occurrence, is independently selected from the group consisting of heteroaryl, heterocyclyl, and cycloalkyl; wherein each R$^3$ heteroaryl, heterocyclyl, and cycloalkyl is optionally substituted with one or more substituents independently selected from the group consisting of R$^5$ and CN.

In one embodiment of Formula (Va) or Formula (Vb), R$^4$ is at each occurrence, is independently selected from the group consisting of C$_1$-C$_6$ alkyl, C$_2$-C$_6$ alkenyl, C$_2$-C$_6$ alkynyl, aryl, heteroaryl, heterocyclyl, cycloalkyl, and cycloalkenyl; wherein each R$^4$ C$_1$-C$_6$ alkyl, C$_2$-C$_6$ alkenyl, and C$_2$-C$_6$ alkynyl is optionally substituted with one or more substituents independently selected from the group consisting of NH$_2$, C(O)NH$_2$, SO$_2$NH$_2$, C(O)H, C(O)OH, OH, (O), CN, NO$_2$, CF$_3$, CF$_2$CF$_3$, OCF$_3$, OCF$_2$CF$_3$, F, Cl, Br and I; wherein each R$^4$ aryl, heteroaryl, heterocyclyl, cycloalkyl, and cycloalkenyl is optionally substituted with one or more substituents independently selected from the group consisting of NH$_2$, C(O)NH$_2$, SO$_2$NH$_2$, C(O)H, C(O)OH, OH, (O), CN, NO$_2$, CF$_3$, CF$_2$CF$_3$, OCF$_3$, OCF$_2$CF$_3$, F, Cl, Br and I. In another embodiment of Formula (Va) or Formula (Vb), R$^4$ at each occurrence, is C$_1$-C$_6$ alkyl. In another embodiment of Formula (Va) or Formula (Vb), R$^4$ at each occurrence, is heterocyclyl; wherein each R$^4$ heterocyclyl is optionally substituted with one or more substituents independently selected from the group consisting of OH, and F.

In one embodiment of Formula (Va) or Formula (Vb), R$^5$ is at each occurrence, is independently selected from the group consisting of C$_1$-C$_6$ alkyl, C$_2$-C$_6$ alkenyl, C$_2$-C$_6$ alkynyl, aryl, heteroaryl, heterocyclyl, cycloalkyl, and cycloalkenyl; wherein each R$^5$ C$_1$-C$_6$ alkyl, C$_2$-C$_6$ alkenyl, and C$_2$-C$_6$ alkynyl is optionally substituted with one or more substituents independently selected from the group consisting of NH$_2$, C(O)NH$_2$, SO$_2$NH$_2$, C(O)H, C(O)OH, OH, (O), CN, NO$_2$, CF$_3$, CF$_2$CF$_3$, OCF$_3$, OCF$_2$CF$_3$, F, Cl, Br and I; wherein each R$^5$ aryl, heteroaryl, heterocyclyl, cycloalkyl, and cycloalkenyl is optionally substituted with one or more substituents independently selected from the group consisting of NH$_2$, C(O)NH$_2$, SO$_2$NH$_2$, C(O)H, C(O)OH, OH, (O), CN, NO$_2$, CF$_3$, CF$_2$CF$_3$, OCF$_3$, OCF$_2$CF$_3$, F, Cl, Br and I. In another embodiment of Formula (Va) or Formula (Vb), R$^5$ is at each occurrence, is independently C$_1$-C$_6$ alkyl.

In one embodiment of Formula (Va) or Formula (Vb), A$^3$ is selected from the group consisting of aryl, heterocyclyl, and heteroaryl, wherein the A$^3$ aryl, heterocyclyl, and heteroaryl are optionally substituted with one or more substituents independently selected from the group consisting of R$^1$, OR$^1$, SO$_2$R$^1$, C(O)R$^1$, CO(O)R$^1$, C(O)NH$_2$, C(O)NHR$^1$, C(O)N(R$^1$)$_2$, SO$_2$NH$_2$, C(O)OH, CN, F, Cl, Br and I;

R$^1$, at each occurrence, is independently selected from the group consisting of C$_1$-C$_6$ alkyl, aryl, heteroaryl, heterocyclyl, and cycloalkyl; wherein each R$^1$ C$_1$-C$_6$ alkyl is optionally substituted with one or more substituents independently selected from the group consisting of C(O)OH, OH, F, Cl, Br and I; wherein each R$^1$ aryl, heteroaryl, heterocyclyl, cycloalkyl, and cycloalkenyl is optionally substituted with one or more substituents independently selected from the group consisting of R$^3$, SO$_2$R$^3$, C(O)R$^3$, CO(O)R$^3$, C(O)NH$_2$, C(O)NHR$^3$, C(O)N(R$^3$)$_2$, SO$_2$N(R$^3$)$_2$, C(O)C(O)NH$_2$, C(O)C(O)N(R$^3$)$_2$, OH, (O), F, Cl, Br and I;

R$^3$, at each occurrence, is independently selected from the group consisting of C$_1$-C$_6$ alkyl, heteroaryl, heterocyclyl, and cycloalkyl; wherein each R$^3$ C$_1$-C$_6$ alkyl is optionally substituted with one or more substituents independently selected from the group consisting of SO$_2$R$^4$, C(O)R$^4$, NHS(O)$_2$R$^4$, C(O)NH$_2$, C(O)NHR$^4$, C(O)N(R$^4$)$_2$, SO$_2$NH$_2$, F, Cl, Br and I; wherein each R$^3$ heteroaryl and heterocyclyl is optionally substituted with one or more substituents independently selected from the group consisting of R$^5$, CN, F, Cl, Br and I;

R$^4$ is at each occurrence, is independently selected from the group consisting of C$_1$-C$_6$ alkyl and heterocyclyl; wherein each R$^4$ heterocyclyl is optionally substituted with one or more substituents independently selected from the group consisting of OH, F, Cl, Br and I; and R$^5$ is at each occurrence, is independently C$_1$-C$_6$ alkyl.

Still another embodiment pertains to compounds of Formula (Va) or Formula (Vb), selected from the group consisting of:

(3S,4R)-1-(7-fluoro-2,3-dihydro-1H-inden-1-yl)-4-{4-[4-(methanesulfonyl)piperazin-1-yl]phenyl}-N,N-dimethylpyrrolidin-3-amine;

tert-butyl 4-{4-[(3R,4S)-4-(dimethylamino)-1-(7-fluoro-2,3-dihydro-1H-inden-1-yl)pyrrolidin-3-yl]phenyl}piperazine-1-carboxylate;

3-[(3R,4S)-4-(dimethylamino)-1-(7-fluoro-2,3-dihydro-1H-inden-1-yl)pyrrolidin-3-yl]-1-methyl-1H-indole-7-carboxylic acid;

methyl 3-[(3R,4S)-4-(dimethylamino)-1-(7-fluoro-2,3-dihydro-1H-inden-1-yl)pyrrolidin-3-yl]-1-methyl-1H-indole-7-carboxylate;

{3-[(3R,4S)-4-(dimethylamino)-1-(7-fluoro-2,3-dihydro-1H-inden-1-yl)pyrrolidin-3-yl]-1-methyl-1H-indol-7-yl}(3-fluoroazetidin-1-yl)methanone; and pharmaceutically acceptable salts thereof.

One embodiment pertains to compounds or pharmaceutically acceptable salts thereof, which are useful as inhibitors of EED, the compounds having Formula (VI)

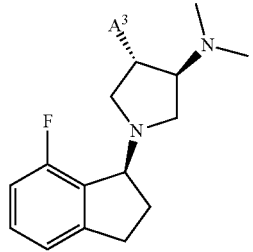

Formula (VI)

wherein $A^3$ is selected from the group consisting of aryl, heterocyclyl, and heteroaryl, wherein the $A^3$ aryl, heterocyclyl, and heteroaryl are optionally substituted with one or more substituents independently selected from the group consisting of $R^1$, $OR^1$, $SR^1$, $S(O)R^1$, $SO_2R^1$, $C(O)R^1$, $CO(O)R^1$, $OC(O)R^1$, $OC(O)OR^1$, $NH_2$, $NHR^1$, $N(R^1)_2$, $NHC(O)R^1$, $NR^1C(O)R^1$, $NHS(O)_2R^1$, $NR^1S(O)_2R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $C(O)NH_2$, $C(O)NHR^1$, $C(O)N(R^1)_2$, $C(O)NHOH$, $C(O)NHOR^1$, $C(O)NHSO_2R^1$, $C(O)NR^1SO_2R^1$, $SO_2NH_2$, $SO_2NHR^1$, $SO_2N(R^1)_2$, $C(O)H$, $C(O)OH$, $C(N)NH_2$, $C(N)NHR^1$, $C(N)N(R^1)_2$, CNOH, $CNOCH_3$, OH, (O), CN, $NO_2$, $CF_3$, $CF_2CF_3$, $OCF_3$, $OCF_2CF_3$, F, Cl, Br and I;

$R^1$, at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^1$ $C_1$-$C_6$ alkyl, $C_2$-$C_6$ alkenyl, and $C_2$-$C_6$ alkynyl is optionally substituted with one or more substituents independently selected from the group consisting of $R^2$, $OR^2$, $SR^2$, $S(O)R^2$, $SO_2R^2$, $C(O)R^2$, $CO(O)R^2$, $OC(O)R^2$, $OC(O)OR^2$, $NH_2$, $NHR^2$, $N(R^2)_2$, $NHC(O)R^2$, $NR^2C(O)R^2$, $NHS(O)_2R^2$, $NR^2S(O)_2R^2$, $NHC(O)OR^2$, $NR^2C(O)OR^2$, $NHC(O)NH_2$, $NHC(O)NHR^2$, $NHC(O)N(R^2)_2$, $NR^2C(O)NHR^2$, $NR^2C(O)N(R^2)_2$, $C(O)NH_2$, $C(O)NHR^2$, $C(O)N(R^2)_2$, $C(O)NHOH$, $C(O)NHOR^2$, $C(O)NHSO_2R^2$, $C(O)NR^2SO_2R^2$, $SO_2NH_2$, $SO_2NHR^2$, $SO_2N(R^2)_2$, $C(O)H$, $C(O)OH$, OH, (O), CN, $NO_2$, $CF_3$, $CF_2CF_3$, $OCF_3$, $OCF_2CF_3$, F, Cl, Br and I; wherein each $R^1$ aryl, heteroaryl, heterocyclyl, cycloalkyl, and cycloalkenyl is optionally substituted with one or more substituents independently selected from the group consisting of $R^3$, $OR^3$, $SR^3$, $S(O)R^3$, $SO_2R^3$, $C(O)R^3$, $CO(O)R^3$, $OC(O)R^3$, $OC(O)OR^3$, $NH_2$, $NHR^3$, $N(R^3)_2$, $NHC(O)R^3$, $NR^3C(O)R^3$, $NHS(O)_2R^3$, $NR^3S(O)_2R^3$, $NHC(O)OR^3$, $NR^3C(O)OR^3$, $NHC(O)NH_2$, $NHC(O)NHR^3$, $NHC(O)N(R^3)_2$, $NR^3C(O)NHR^3$, $NR^3C(O)N(R^3)_2$, $C(O)NH_2$, $C(O)NHR^3$, $C(O)N(R^3)_2$, $C(O)NHOH$, $C(O)NHOR^3$, $C(O)NHSO_2R^3$, $C(O)NR^3SO_2R^3$, $SO_2NH_2$, $SO_2NHR^3$, $SO_2N(R^3)_2$, $C(O)H$, $C(O)OH$, $C(O)C(O)NH_2$, $C(O)C(O)NHR^3$, $C(O)C(O)N(R^3)_2$, $C(N)NH_2$, $C(N)NHR^3$, $C(N)N(R^3)_2$, CNOH, $CNOCH_3$, OH, (O), CN, $NO_2$, $CF_3$, $CF_2CF_3$, $OCF_3$, $OCF_2CF_3$, F, Cl, Br and I;

$R^2$, at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^2$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I; wherein each $R^2$ aryl, heteroaryl, heterocyclyl, cycloalkyl, and cycloalkenyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I;

$R^3$, at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^3$ $C_1$-$C_6$ alkyl, $C_2$-$C_6$ alkenyl, and $C_2$-$C_6$ alkynyl is optionally substituted with one or more substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, OH, (O), CN, $NO_2$, $CF_3$, $CF_2CF_3$, $OCF_3$, $OCF_2CF_3$, F, Cl, Br and I; wherein each $R^3$ aryl, heteroaryl, heterocyclyl, cycloalkyl, and cycloalkenyl is optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, $C(N)NH_2$, $C(N)NHR^5$, $C(N)N(R^5)_2$, CNOH, $CNOCH_3$, OH, (O), CN, $NO_2$, $CF_3$, $CF_2CF_3$, $OCF_3$, $OCF_2CF_3$, F, Cl, Br and I;

$R^4$ is at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^4$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I; wherein each $R^4$ aryl, heteroaryl, heterocyclyl, cycloalkyl, and cycloalkenyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I; and $R^5$ is at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^5$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I; wherein each $R^5$ aryl, heteroaryl, heterocyclyl, cycloalkyl, and cycloalkenyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I.

In one embodiment of Formula (VI), $A^3$ is selected from the group consisting of aryl, heterocyclyl, and heteroaryl, wherein the $A^3$ aryl, heterocyclyl, and heteroaryl are optionally substituted with one or more substituents independently selected from the group consisting of $R^1$, $OR^1$, $SR^1$, $S(O)R^1$, $SO_2R^1$, $C(O)R^1$, $CO(O)R^1$, $OC(O)R^1$, $OC(O)OR^1$, $NH_2$, $NHR^1$, $N(R^1)_2$, $NHC(O)R^1$, $NR^1C(O)R^1$, $NHS(O)_2R^1$, $NR^1S(O)_2R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $C(O)NH_2$, $C(O)NHR^1$, $C(O)N(R^1)_2$, $C(O)NHOH$, $C(O)NHOR^1$, $C(O)NHSO_2R^1$, $C(O)NR^1SO_2R^1$, $SO_2NH_2$, $SO_2NHR^1$, $SO_2N(R^1)_2$, $C(O)H$, $C(O)OH$, $C(N)NH_2$, $C(N)NHR^1$, $C(N)N(R^1)_2$, CNOH, $CNOCH_3$, OH, (O), CN, $NO_2$, $CF_3$, $CF_2CF_3$, $OCF_3$, $OCF_2CF_3$, F, Cl, Br and I. In another embodiment of Formula (VI), $A^3$ is selected from the group consisting of aryl, heterocyclyl, and heteroaryl, wherein the $A^3$ aryl, heterocyclyl, and heteroaryl are optionally substituted with one or more substituents independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, $C(O)OH$, CN, F, Cl, Br and I. In another embodiment of Formula (VI), $A^3$ is aryl, wherein the $A^3$ aryl is optionally substituted with one or more substituents independently selected from the group consisting of $R^1$, $OR^1$, $SO_2R^1$, C(O)R$^1$, CO(O)R$^1$, C(O)NH$_2$, C(O)NHR$^1$, C(O)N(R$^1$)$_2$, SO$_2$NH$_2$, C(O)OH, CN, F, Cl, Br and I. In another embodiment of Formula (VI), A$^3$ is aryl, wherein the A$^3$ aryl is substituted with one substituent independently selected from the group consisting of R$^1$, OR$^1$, SO$_2$R$^1$, C(O)R$^1$, CO(O)R$^1$, C(O)NH$_2$, C(O)NHR$^1$, C(O)N(R$^1$)$_2$, SO$_2$NH$_2$, C(O)OH, CN, F, Cl, Br and I. In another embodiment of Formula (VI), A$^3$ is aryl, wherein the A$^3$ aryl is substituted with two substituents independently selected from the group consisting of R$^1$, OR$^1$, SO$_2$R$^1$, C(O)R$^1$, CO(O)R$^1$, C(O)NH$_2$, C(O)NHR$^1$, C(O)N(R$^1$)$_2$, SO$_2$NH$_2$, C(O)OH, CN, F, Cl, Br and I. In another embodiment of Formula (VI), A$^3$ is heterocyclyl, wherein the A$^3$ heterocyclyl is optionally substituted with one or more substituents independently selected from the group consisting of R$^1$, OR$^1$, SO$_2$R$^1$, C(O)R$^1$, CO(O)R$^1$, C(O)NH$_2$, C(O)NHR$^1$, C(O)N(R$^1$)$_2$, SO$_2$NH$_2$, C(O)OH, CN, F, Cl, Br and I. In another embodiment of Formula (VI), A$^3$ is heterocyclyl, wherein the A$^3$ heterocyclyl is unsubstituted. In another embodiment of Formula (VI), A$^3$ is heterocyclyl, wherein the A$^3$ heterocyclyl is substituted with one substituent independently selected from the group consisting of R$^1$, OR$^1$, SO$_2$R$^1$, C(O)R$^1$, CO(O)R$^1$, C(O)NH$_2$, C(O)NHR$^1$, C(O)N(R$^1$)$_2$, SO$_2$NH$_2$, C(O)OH, CN, F, Cl, Br and I. In another embodiment of Formula (VI), A$^3$ is heterocyclyl, wherein the A$^3$ heterocyclyl is substituted with two substituents independently selected from the group consisting of R$^1$, OR$^1$, SO$_2$R$^1$, C(O)R$^1$, CO(O)R$^1$, C(O)NH$_2$, C(O)NHR$^1$, C(O)N(R$^1$)$_2$, SO$_2$NH$_2$, C(O)OH, CN, F, Cl, Br and I. In another embodiment of Formula (VI), A$^3$ is heteroaryl, wherein the A$^3$ heteroaryl is optionally substituted with one or more substituents independently selected from the group consisting of R$^1$, OR$^1$, SO$_2$R$^1$, C(O)R$^1$, CO(O)R$^1$, C(O)NH$_2$, C(O)NHR$^1$, C(O)N(R$^1$)$_2$, SO$_2$NH$_2$, C(O)OH, CN, F, Cl, Br and I. In another embodiment of Formula (VI), A$^3$ is heteroaryl, wherein the A$^3$ heteroaryl is unsubstituted. In another embodiment of Formula (VI), A$^3$ is heteroaryl, wherein the A$^3$ heteroaryl is substituted with one substituent independently selected from the group consisting of R$^1$, OR$^1$, SO$_2$R$^1$, C(O)R$^1$, CO(O)R$^1$, C(O)NH$_2$, C(O)NHR$^1$, C(O)N(R$^1$)$_2$, SO$_2$NH$_2$, C(O)OH, CN, F, Cl, Br and I. In another embodiment of Formula (VI), A$^3$ is heteroaryl, wherein the A$^3$ heteroaryl is substituted with two substituents independently selected from the group consisting of R$^1$, OR$^1$, SO$_2$R$^1$, C(O)R$^1$, CO(O)R$^1$, C(O)NH$_2$, C(O)NHR$^1$, C(O)N(R$^1$)$_2$, SO$_2$NH$_2$, C(O)OH, CN, F, Cl, Br and I.

In one embodiment of Formula (VI), R$^1$, at each occurrence, is independently selected from the group consisting of C$_1$-C$_6$ alkyl, C$_2$-C$_6$ alkenyl, C$_2$-C$_6$ alkynyl, aryl, heteroaryl, heterocyclyl, cycloalkyl, and cycloalkenyl; wherein each R$^1$ C$_1$-C$_6$ alkyl, C$_2$-C$_6$ alkenyl, and C$_2$-C$_6$ alkynyl is optionally substituted with one or more substituents independently selected from the group consisting of R$^2$, OR$^2$, SR$^2$, S(O)R$^2$, SO$_2$R$^2$, C(O)R$^2$, CO(O)R$^2$, OC(O)R$^2$, OC(O)OR$^2$, NH$_2$, NHR$^2$, N(R$^2$)$_2$, NHC(O)R$^2$, NR$^2$C(O)R$^2$, NHS(O)$_2$R$^2$, NR$^2$S(O)$_2$R$^2$, NHC(O)OR$^2$, NR$^2$C(O)OR$^2$, NHC(O)NH$_2$, NHC(O)NHR$^2$, NHC(O)N(R$^2$)$_2$, NR$^2$C(O)NHR$^2$, NR$^2$C(O)N(R$^2$)$_2$, C(O)NH$_2$, C(O)NHR$^2$, C(O)N(R$^2$)$_2$, C(O)NHOH, C(O)NHOR$^2$, C(O)NHSO$_2$R$^2$, C(O)NR$^2$SO$_2$R$^2$, SO$_2$NH$_2$, SO$_2$NHR$^2$, SO$_2$N(R$^2$)$_2$, C(O)H, C(O)OH, OH, (O), CN, NO$_2$, CF$_3$, CF$_2$CF$_3$, OCF$_3$, OCF$_2$CF$_3$, F, Cl, Br and I; wherein each R$^1$ aryl, heteroaryl, heterocyclyl, cycloalkyl, and cycloalkenyl is optionally substituted with one or more substituents independently selected from the group consisting of R$^3$, OR$^3$, SR$^3$, S(O)R$^3$, SO$_2$R$^3$, C(O)R$^3$, CO(O)R$^3$, OC(O)R$^3$, OC(O)OR$^3$, NH$_2$, NHR$^3$, N(R$^3$)$_2$, NHC(O)R$^3$, NR$^3$C(O)R$^3$, NHS(O)$_2$R$^3$, NR$^3$S(O)$_2$R$^3$, NHC(O)OR$^3$, NR$^3$C(O)OR$^3$, NHC(O)NH$_2$, NHC(O)NHR$^3$, NHC(O)N(R$^3$)$_2$, NR$^3$C(O)NHR$^3$, NR$^3$C(O)N(R$^3$)$_2$, C(O)NH$_2$, C(O)NHR$^3$, C(O)N(R$^3$)$_2$, C(O)NHOH, C(O)NHOR$^3$, C(O)NHSO$_2$R$^3$, C(O)NR$^3$SO$_2$R$^3$, SO$_2$NH$_2$, SO$_2$NHR$^3$, SO$_2$N(R$^3$)$_2$, C(O)H, C(O)OH, C(O)C(O)NH$_2$, C(O)C(O)NHR$^3$, C(O)C(O)N(R$^3$)$_2$, C(N)NH$_2$, C(N)NHR$^3$, C(N)N(R$^3$)$_2$, CNOH, CNOCH$_3$, OH, (O), CN, NO$_2$, CF$_3$, CF$_2$CF$_3$, OCF$_3$, OCF$_2$CF$_3$, F, Cl, Br and I. In another embodiment of Formula (VI), R$^1$, at each occurrence, is C$_1$-C$_6$ alkyl; wherein each R$^1$ C$_1$-C$_6$ alkyl is optionally substituted with one or more substituents independently selected from the group consisting of C(O)OH and OH. In another embodiment of Formula (VI), R$^1$, at each occurrence, is independently selected from the group consisting of aryl, heteroaryl, heterocyclyl, and cycloalkyl; wherein each R$^1$ aryl, heteroaryl, heterocyclyl, and cycloalkyl is optionally substituted with one or more substituents independently selected from the group consisting of R$^3$, SO$_2$R$^3$, C(O)R$^3$, CO(O)R$^3$, C(O)NH$_2$, C(O)NHR$^3$, C(O)N(R$^3$)$_2$, SO$_2$N(R$^3$)$_2$, C(O)C(O)NH$_2$, C(O)C(O)N(R$^3$)$_2$, OH, (O), and F.

In one embodiment of Formula (VI), R$^3$, at each occurrence, is independently selected from the group consisting of C$_1$-C$_6$ alkyl, C$_2$-C$_6$ alkenyl, C$_2$-C$_6$ alkynyl, aryl, heteroaryl, heterocyclyl, cycloalkyl, and cycloalkenyl; wherein each R$^3$ C$_1$-C$_6$ alkyl, C$_2$-C$_6$ alkenyl, and C$_2$-C$_6$ alkynyl is optionally substituted with one or more substituents independently selected from the group consisting of R$^4$, OR$^4$, SR$^4$, S(O)R$^4$, SO$_2$R$^4$, C(O)R$^4$, CO(O)R$^4$, OC(O)R$^4$, OC(O)OR$^4$, NH$_2$, NHR$^4$, N(R$^4$)$_2$, NHC(O)R$^4$, NR$^4$C(O)R$^4$, NHS(O)$_2$R$^4$, NR$^4$S(O)$_2$R$^4$, NHC(O)OR$^4$, NR$^4$C(O)OR$^4$, NHC(O)NH$_2$, NHC(O)NHR$^4$, NHC(O)N(R$^4$)$_2$, NR$^4$C(O)NHR$^4$, NR$^4$C(O)N(R$^4$)$_2$, C(O)NH$_2$, C(O)NHR$^4$, C(O)N(R$^4$)$_2$, C(O)NHOH, C(O)NHOR$^4$, C(O)NHSO$_2$R$^4$, C(O)NR$^4$SO$_2$R$^4$, SO$_2$NH$_2$, SO$_2$NHR$^4$, SO$_2$N(R$^4$)$_2$, C(O)H, C(O)OH, OH, (O), CN, NO$_2$, CF$_3$, CF$_2$CF$_3$, OCF$_3$, OCF$_2$CF$_3$, F, Cl, Br and I; wherein each R$^3$ aryl, heteroaryl, heterocyclyl, cycloalkyl, and cycloalkenyl is optionally substituted with one or more substituents independently selected from the group consisting of R$^5$, OR$^5$, SR$^5$, S(O)R$^5$, SO$_2$R$^5$, C(O)R$^5$, CO(O)R$^5$, OC(O)R$^5$, OC(O)OR$^5$, NH$_2$, NHR$^5$, N(R$^5$)$_2$, NHC(O)R$^5$, NR$^5$C(O)R$^5$, NHS(O)$_2$R$^5$, NR$^5$S(O)$_2$R$^5$, NHC(O)OR$^5$, NR$^5$C(O)OR$^5$, NHC(O)NH$_2$, NHC(O)NHR$^5$, NHC(O)N(R$^5$)$_2$, NR$^5$C(O)NHR$^5$, NR$^5$C(O)N(R$^5$)$_2$, C(O)NH$_2$, C(O)NHR$^5$, C(O)N(R$^5$)$_2$, C(O)NHOH, C(O)NHOR$^5$, C(O)NHSO$_2$R$^5$, C(O)NR$^5$SO$_2$R$^5$, SO$_2$NH$_2$, SO$_2$NHR$^5$, SO$_2$N(R$^5$)$_2$, C(O)H, C(O)OH, C(N)NH$_2$, C(N)NHR$^5$, C(N)N(R$^5$)$_2$, CNOH, CNOCH$_3$, OH, (O), CN, NO$_2$, CF$_3$, CF$_2$CF$_3$, OCF$_3$, OCF$_2$CF$_3$, F, Cl, Br and I. In another embodiment of Formula (VI), R$^3$, at each occurrence, is independently C$_1$-C$_6$ alkyl; wherein each R$^3$ C$_1$-C$_6$ alkyl is optionally substituted with one or more substituents independently selected from the group consisting of SO$_2$R$^4$, C(O)R$^4$, NHS(O)$_2$R$^4$, C(O)NH$_2$, C(O)NHR$^4$, C(O)N(R$^4$)$_2$, SO$_2$NH$_2$, and OH. In another embodiment of Formula (VI), R$^3$, at each occurrence, is independently selected from the group consisting of heteroaryl, heterocyclyl, and cycloalkyl; wherein each R$^3$ heteroaryl, heterocyclyl, and cycloalkyl is optionally substituted with one or more substituents independently selected from the group consisting of R$^5$ and CN.

In one embodiment of Formula (VI), R$^4$ is at each occurrence, is independently selected from the group consisting of C$_1$-C$_6$ alkyl, C$_2$-C$_6$ alkenyl, C$_2$-C$_6$ alkynyl, aryl, heteroaryl, heterocyclyl, cycloalkyl, and cycloalkenyl; wherein each R$^4$ C$_1$-C$_6$ alkyl, C$_2$-C$_6$ alkenyl, and C$_2$-C$_6$ alkynyl is optionally substituted with one or more substituents independently selected from the group consisting of NH$_2$, C(O)NH$_2$, SO$_2$NH$_2$, C(O)H, C(O)OH, OH, (O), CN, NO$_2$, CF$_3$, $CF_2CF_3$, $OCF_3$, $OCF_2CF_3$, F, Cl, Br and I; wherein each $R^4$ aryl, heteroaryl, heterocyclyl, cycloalkyl, and cycloalkenyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I. In another embodiment of Formula (VI), $R^4$ at each occurrence, is $C_1$-$C_6$ alkyl. In another embodiment of Formula (VI), $R^4$ at each occurrence, is heterocyclyl; wherein each $R^4$ heterocyclyl is optionally substituted with one or more substituents independently selected from the group consisting of OH, and F.

In one embodiment of Formula (VI), $R^5$ is at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^5$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I; wherein each $R^5$ aryl, heteroaryl, heterocyclyl, cycloalkyl, and cycloalkenyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I. In another embodiment of Formula (VI), $R^5$ is at each occurrence, is independently $C_1$-$C_6$ alkyl.

In one embodiment of Formula (VI), $A^3$ is selected from the group consisting of aryl, heterocyclyl, and heteroaryl, wherein the $A^3$ aryl, heterocyclyl, and heteroaryl are optionally substituted with one or more substituents independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, $C(O)OH$, CN, F, Cl, Br and I;

$R^1$, at each occurrence, is independently selected from the group consisting of $C_1$-$C_6$ alkyl, aryl, heteroaryl, heterocyclyl, and cycloalkyl; wherein each $R^1$ $C_1$-$C_6$ alkyl is optionally substituted with one or more substituents independently selected from the group consisting of $C(O)OH$, OH, F, Cl, Br and I; wherein each $R^1$ aryl, heteroaryl, heterocyclyl, cycloalkyl, and cycloalkenyl is optionally substituted with one or more substituents independently selected from the group consisting of $R^3$, $SO_2R^3$, $C(O)R^3$, $CO(O)R^3$, $C(O)NH_2$, $C(O)NHR^3$, $C(O)N(R^3)_2$, $SO_2N(R^3)_2$, $C(O)C(O)NH_2$, $C(O)C(O)N(R^3)_2$, OH, (O), F, Cl, Br and I;

$R^3$, at each occurrence, is independently selected from the group consisting of $C_1$-$C_6$ alkyl, heteroaryl, heterocyclyl, and cycloalkyl; wherein each $R^3$ $C_1$-$C_6$ alkyl is optionally substituted with one or more substituents independently selected from the group consisting of $SO_2R^4$, $C(O)R^4$, $NHS(O)_2R^4$, $C(O)NH_2$, $C(O)NHR^4$, $C(O)N(R^4)_2$, $SO_2NH_2$, F, Cl, Br and I; wherein each $R^3$ heteroaryl and heterocyclyl is optionally substituted with one or more substituents independently selected from the group consisting of $R^5$, CN, F, Cl, Br and I;

$R^4$ is at each occurrence, is independently selected from the group consisting of $C_1$-$C_6$ alkyl and heterocyclyl; wherein each $R^4$ heterocyclyl is optionally substituted with one or more substituents independently selected from the group consisting of OH, F, Cl, Br and I; and $R^5$ is at each occurrence, is independently $C_1$-$C_6$ alkyl.

Still another embodiment pertains to compounds of Formula (VI), selected from the group consisting of:

(3R,4S)-1-[(1S)-2,3-dihydro-1H-inden-1-yl]-4-[4-(methane sulfonyl)phenyl]-N,N-dimethylpyrrolidin-3-amine;

(3R,4S)-1-[(1S)-7-fluoro-2,3-dihydro-1H-inden-1-yl]-4-[4-(methanesulfonyl)phenyl]-N,N-dimethylpyrrolidin-3-amine;

1-[4-(4-{(3S,4R)-4-(dimethylamino)-1-[(1S)-7-fluoro-2,3-dihydro-1H-inden-1-yl]pyrrolidin-3-yl}phenyl)piperazin-1-yl]ethan-1-one;

(3R,4S)-1-[(1S)-7-fluoro-2,3-dihydro-1H-inden-1-yl]-N,N-dimethyl-4-(1-methyl-1H-indol-3-yl)pyrrolidin-3-amine; and pharmaceutically acceptable salts thereof.

One embodiment pertains to compounds or pharmaceutically acceptable salts thereof, which are useful as inhibitors of EED, the compounds having Formula (VII)

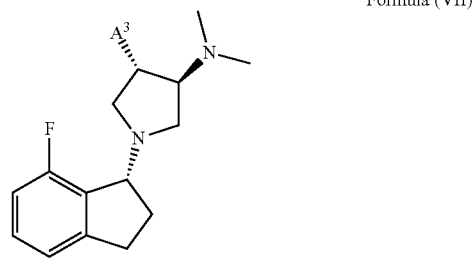

Formula (VII)

wherein $A^3$ is selected from the group consisting of aryl, heterocyclyl, and heteroaryl, wherein the $A^3$ aryl, heterocyclyl, and heteroaryl are optionally substituted with one or more substituents independently selected from the group consisting of $R^1$, $OR^1$, $SR^1$, $S(O)R^1$, $SO_2R^1$, $C(O)R^1$, $CO(O)R^1$, $OC(O)R^1$, $OC(O)OR^1$, $NH_2$, $NHR^1$, $N(R^1)_2$, $NHC(O)R^1$, $NR^1C(O)R^1$, $NHS(O)_2R^1$, $NR^1S(O)_2R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $C(O)NH_2$, $C(O)NHR^1$, $C(O)N(R^1)_2$, $C(O)NHOH$, $C(O)NHOR^1$, $C(O)NHSO_2R^1$, $C(O)NR^1SO_2R^1$, $SO_2NH_2$, $SO_2NHR^1$, $SO_2N(R^1)_2$, $C(O)H$, $C(O)OH$, $C(N)NH_2$, $C(N)NHR^1$, $C(N)N(R^1)_2$, CNOH, $CNOCH_3$, OH, (O), CN, $NO_2$, $CF_3$, $CF_2CF_3$, $OCF_3$, $OCF_2CF_3$, F, Cl, Br and I;

$R^1$, at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^1$ $C_1$-$C_6$ alkyl, $C_2$-$C_6$ alkenyl, and $C_2$-$C_6$ alkynyl is optionally substituted with one or more substituents independently selected from the group consisting of $R^2$, $OR^2$, $SR^2$, $S(O)R^2$, $SO_2R^2$, $C(O)R^2$, $CO(O)R^2$, $OC(O)R^2$, $OC(O)OR^2$, $NH_2$, $NHR^2$, $N(R^2)_2$, $NHC(O)R^2$, $NR^2C(O)R^2$, $NHS(O)_2R^2$, $NR^2S(O)_2R^2$, $NHC(O)OR^2$, $NR^2C(O)OR^2$, $NHC(O)NH_2$, $NHC(O)NHR^2$, $NHC(O)N(R^2)_2$, $NR^2C(O)NHR^2$, $NR^2C(O)N(R^2)_2$, $C(O)NH_2$, $C(O)NHR^2$, $C(O)N(R^2)_2$, $C(O)NHOH$, $C(O)NHOR^2$, $C(O)NHSO_2R^2$, $C(O)NR^2SO_2R^2$, $SO_2NH_2$, $SO_2NHR^2$, $SO_2N(R^2)_2$, $C(O)H$, $C(O)OH$, OH, (O), CN, $NO_2$, $CF_3$, $CF_2CF_3$, $OCF_3$, $OCF_2CF_3$, F, Cl, Br and I; wherein each $R^1$ aryl, heteroaryl, heterocyclyl, cycloalkyl, and cycloalkenyl is optionally substituted with one or more substituents independently selected from the group consisting of $R^3$, $OR^3$, $SR^3$, $S(O)R^3$, $SO_2R^3$, $C(O)R^3$, $CO(O)R^3$, $OC(O)R^3$, $OC(O)OR^3$, $NH_2$, $NHR^3$, $N(R^3)_2$, $NHC(O)R^3$, $NR^3C(O)R^3$, $NHS(O)_2R^3$, $NR^3S(O)_2R^3$, $NHC(O)OR^3$, $NR^3C(O)OR^3$, $NHC(O)NH_2$, $NHC(O)NHR^3$, $NHC(O)N(R^3)_2$, $NR^3C(O)NHR^3$, $NR^3C(O)N(R^3)_2$, $C(O)NH_2$, $C(O)NHR^3$, $C(O)N(R^3)_2$, $C(O)NHOH$, $C(O)NHOR^3$, $C(O)NHSO_2R^3$, $C(O)NR^3SO_2R^3$, $SO_2NH_2$, $SO_2NHR^3$, $SO_2N(R^3)_2$, $C(O)H$, $C(O)OH$, $C(O)C(O)NH_2$, $C(O)C(O)NHR^3$, $C(O)C(O)N(R^3)_2$, $C(N)NH_2$, $C(N)NHR^3$, $C(N)N$ (R³)₂, CNOH, CNOCH₃, OH, (O), CN, NO₂, CF₃, CF₂CF₃, OCF₃, OCF₂CF₃, F, Cl, Br and I;

R², at each occurrence, is independently selected from the group consisting of C₁-C₆ alkyl, C₂-C₆ alkenyl, C₂-C₆ alkynyl, aryl, heteroaryl, heterocyclyl, cycloalkyl, and cycloalkenyl; wherein each R² C₁-C₆ alkyl, C₂-C₆ alkenyl, and C₂-C₆ alkynyl is optionally substituted with one or more substituents independently selected from the group consisting of NH₂, C(O)NH₂, SO₂NH₂, C(O)H, C(O)OH, OH, (O), CN, NO₂, CF₃, CF₂CF₃, OCF₃, OCF₂CF₃, F, Cl, Br and I; wherein each R² aryl, heteroaryl, heterocyclyl, cycloalkyl, and cycloalkenyl is optionally substituted with one or more substituents independently selected from the group consisting of NH₂, C(O)NH₂, SO₂NH₂, C(O)H, C(O)OH, OH, (O), CN, NO₂, CF₃, CF₂CF₃, OCF₃, OCF₂CF₃, F, Cl, Br and I;

R³, at each occurrence, is independently selected from the group consisting of C₁-C₆ alkyl, C₂-C₆ alkenyl, C₂-C₆ alkynyl, aryl, heteroaryl, heterocyclyl, cycloalkyl, and cycloalkenyl; wherein each R³ C₁-C₆ alkyl, C₂-C₆ alkenyl, and C₂-C₆ alkynyl is optionally substituted with one or more substituents independently selected from the group consisting of R⁴, OR⁴, SR⁴, S(O)R⁴, SO₂R⁴, C(O)R⁴, CO(O)R⁴, OC(O)R⁴, OC(O)OR⁴, NH₂, NHR⁴, N(R⁴)₂, NHC(O)R⁴, NR⁴C(O)R⁴, NHS(O)₂R⁴, NR⁴S(O)₂R⁴, NHC(O)OR⁴, NR⁴C(O)OR⁴, NHC(O)NH₂, NHC(O)NHR⁴, NHC(O)N(R⁴)₂, NR⁴C(O)NHR⁴, NR⁴C(O)N(R⁴)₂, C(O)NH₂, C(O)NHR⁴, C(O)N(R⁴)₂, C(O)NHOH, C(O)NHOR⁴, C(O)NHSO₂R⁴, C(O)NR⁴SO₂R⁴, SO₂NH₂, SO₂NHR⁴, SO₂N(R⁴)₂, C(O)H, C(O)OH, OH, (O), CN, NO₂, CF₃, CF₂CF₃, OCF₃, OCF₂CF₃, F, Cl, Br and I; wherein each R³ aryl, heteroaryl, heterocyclyl, cycloalkyl, and cycloalkenyl is optionally substituted with one or more substituents independently selected from the group consisting of R⁵, OR⁵, SR⁵, S(O)R⁵, SO₂R⁵, C(O)R⁵, CO(O)R⁵, OC(O)R⁵, OC(O)OR⁵, NH₂, NHR⁵, N(R⁵)₂, NHC(O)R⁵, NR⁵C(O)R⁵, NHS(O)₂R⁵, NR⁵S(O)₂R⁵, NHC(O)OR⁵, NR⁵C(O)OR⁵, NHC(O)NH₂, NHC(O)NHR⁵, NHC(O)N(R⁵)₂, NR⁵C(O)NHR⁵, NR⁵C(O)N(R⁵)₂, C(O)NH₂, C(O)NHR⁵, C(O)N(R⁵)₂, C(O)NHOH, C(O)NHOR⁵, C(O)NHSO₂R⁵, C(O)NR⁵SO₂R⁵, SO₂NH₂, SO₂NHR⁵, SO₂N(R⁵)₂, C(O)H, C(O)OH, C(N)NH₂, C(N)NHR⁵, C(N)N(R⁵)₂, CNOH, CNOCH₃, OH, (O), CN, NO₂, CF₃, CF₂CF₃, OCF₃, OCF₂CF₃, F, Cl, Br and I;

R⁴ is at each occurrence, is independently selected from the group consisting of C₁-C₆ alkyl, C₂-C₆ alkenyl, C₂-C₆ alkynyl, aryl, heteroaryl, heterocyclyl, cycloalkyl, and cycloalkenyl; wherein each R⁴ C₁-C₆ alkyl, C₂-C₆ alkenyl, and C₂-C₆ alkynyl is optionally substituted with one or more substituents independently selected from the group consisting of NH₂, C(O)NH₂, SO₂NH₂, C(O)H, C(O)OH, OH, (O), CN, NO₂, CF₃, CF₂CF₃, OCF₃, OCF₂CF₃, F, Cl, Br and I; wherein each R⁴ aryl, heteroaryl, heterocyclyl, cycloalkyl, and cycloalkenyl is optionally substituted with one or more substituents independently selected from the group consisting of NH₂, C(O)NH₂, SO₂NH₂, C(O)H, C(O)OH, OH, (O), CN, NO₂, CF₃, CF₂CF₃, OCF₃, OCF₂CF₃, F, Cl, Br and I; and R⁵ is at each occurrence, is independently selected from the group consisting of C₁-C₆ alkyl, C₂-C₆ alkenyl, C₂-C₆ alkynyl, aryl, heteroaryl, heterocyclyl, cycloalkyl, and cycloalkenyl; wherein each R⁵ C₁-C₆ alkyl, C₂-C₆ alkenyl, and C₂-C₆ alkynyl is optionally substituted with one or more substituents independently selected from the group consisting of NH₂, C(O)NH₂, SO₂NH₂, C(O)H, C(O)OH, OH, (O), CN, NO₂, CF₃, CF₂CF₃, OCF₃, OCF₂CF₃, F, Cl, Br and I; wherein each R⁵ aryl, heteroaryl, heterocyclyl, cycloalkyl, and cycloalkenyl is optionally substituted with one or more substituents independently selected from the group consisting of NH₂, C(O)NH₂, SO₂NH₂, C(O)H, C(O)OH, OH, (O), CN, NO₂, CF₃, CF₂CF₃, OCF₃, OCF₂CF₃, F, Cl, Br and I.

In one embodiment of Formula (VII), A³ is selected from the group consisting of aryl, heterocyclyl, and heteroaryl, wherein the A³ aryl, heterocyclyl, and heteroaryl are optionally substituted with one or more substituents independently selected from the group consisting of R¹, OR¹, SR¹, S(O)R¹, SO₂R¹, C(O)R¹, CO(O)R¹, OC(O)R¹, OC(O)OR¹, NH₂, NHR¹, N(R¹)₂, NHC(O)R¹, NR¹C(O)R¹, NHS(O)₂R¹, NR¹S(O)₂R¹, NHC(O)OR¹, NR¹C(O)OR¹, NHC(O)NH₂, NHC(O)NHR¹, NHC(O)N(R¹)₂, NR¹C(O)NHR¹, NR¹C(O)N(R¹)₂, C(O)NH₂, C(O)NHR¹, C(O)N(R¹)₂, C(O)NHOH, C(O)NHOR¹, C(O)NHSO₂R¹, C(O)NR¹SO₂R¹, SO₂NH₂, SO₂NHR¹, SO₂N(R¹)₂, C(O)H, C(O)OH, C(N)NH₂, C(N)NHR¹, C(N)N(R¹)₂, CNOH, CNOCH₃, OH, (O), CN, NO₂, CF₃, CF₂CF₃, OCF₃, OCF₂CF₃, F, Cl, Br and I. In another embodiment of Formula (VII), A³ is selected from the group consisting of aryl, heterocyclyl, and heteroaryl, wherein the A³ aryl, heterocyclyl, and heteroaryl are optionally substituted with one or more substituents independently selected from the group consisting of R¹, OR¹, SO₂R¹, C(O)R¹, CO(O)R¹, C(O)NH₂, C(O)NHR¹, C(O)N(R¹)₂, SO₂NH₂, C(O)OH, CN, F, Cl, Br and I. In another embodiment of Formula (VII), A³ is aryl, wherein the A³ aryl is optionally substituted with one or more substituents independently selected from the group consisting of R¹, OR¹, SO₂R¹, C(O)R¹, CO(O)R¹, C(O)NH₂, C(O)NHR¹, C(O)N(R¹)₂, SO₂NH₂, C(O)OH, CN, F, Cl, Br and I. In another embodiment of Formula (VII), A³ is aryl, wherein the A³ aryl is substituted with one substituent independently selected from the group consisting of R¹, OR¹, SO₂R¹, C(O)R¹, CO(O)R¹, C(O)NH₂, C(O)NHR¹, C(O)N(R¹)₂, SO₂NH₂, C(O)OH, CN, F, Cl, Br and I. In another embodiment of Formula (VII), A³ is aryl, wherein the A³ aryl is substituted with two substituents independently selected from the group consisting of R¹, OR¹, SO₂R¹, C(O)R¹, CO(O)R¹, C(O)NH₂, C(O)NHR¹, C(O)N(R¹)₂, SO₂NH₂, C(O)OH, CN, F, Cl, Br and I. In another embodiment of Formula (VII), A³ is heterocyclyl, wherein the A³ heterocyclyl is optionally substituted with one or more substituents independently selected from the group consisting of R¹, OR¹, SO₂R¹, C(O)R¹, CO(O)R¹, C(O)NH₂, C(O)NHR¹, C(O)N(R¹)₂, SO₂NH₂, C(O)OH, CN, F, Cl, Br and I. In another embodiment of Formula (VII), A³ is heterocyclyl, wherein the A³ heterocyclyl is unsubstituted. In another embodiment of Formula (VII), A³ is heterocyclyl, wherein the A³ heterocyclyl is substituted with one substituent independently selected from the group consisting of R¹, OR¹, SO₂R¹, C(O)R¹, CO(O)R¹, C(O)NH₂, C(O)NHR¹, C(O)N(R¹)₂, SO₂NH₂, C(O)OH, CN, F, Cl, Br and I. In another embodiment of Formula (VII), A³ is heterocyclyl, wherein the A³ heterocyclyl is substituted with two substituents independently selected from the group consisting of R¹, OR¹, SO₂R¹, C(O)R¹, CO(O)R¹, C(O)NH₂, C(O)NHR¹, C(O)N(R¹)₂, SO₂NH₂, C(O)OH, CN, F, Cl, Br and I. In another embodiment of Formula (VII), A³ is heteroaryl, wherein the A³ heteroaryl is optionally substituted with one or more substituents independently selected from the group consisting of R¹, OR¹, SO₂R¹, C(O)R¹, CO(O)R¹, C(O)NH₂, C(O)NHR¹, C(O)N(R¹)₂, SO₂NH₂, C(O)OH, CN, F, Cl, Br and I. In another embodiment of Formula (VII), A³ is heteroaryl, wherein the A³ heteroaryl is unsubstituted. In another embodiment of Formula (VII), A³ is heteroaryl, wherein the A³ heteroaryl is substituted with one substituent independently selected from the group consisting of R¹, OR¹, SO₂R¹, C(O)R¹, CO(O)R¹, C(O)NH₂, C(O)NHR¹, C(O)N(R¹)₂, SO₂NH₂, C(O)OH, CN, F, Cl, Br and I. In another embodiment of Formula (VII), $A^3$ is heteroaryl, wherein the $A^3$ heteroaryl is substituted with two substituents independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, $C(O)OH$, $CN$, F, Cl, Br and I.

In one embodiment of Formula (VII), $R^1$, at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^1$ $C_1$-$C_6$ alkyl, $C_2$-$C_6$ alkenyl, and $C_2$-$C_6$ alkynyl is optionally substituted with one or more substituents independently selected from the group consisting of $R^2$, $OR^2$, $SR^2$, $S(O)R^2$, $SO_2R^2$, $C(O)R^2$, $CO(O)R^2$, $OC(O)R^2$, $OC(O)OR^2$, $NH_2$, $NHR^2$, $N(R^2)_2$, $NHC(O)R^2$, $NR^2C(O)R^2$, $NHS(O)_2R^2$, $NR^2S(O)_2R^2$, $NHC(O)OR^2$, $NR^2C(O)OR^2$, $NHC(O)NH_2$, $NHC(O)NHR^2$, $NHC(O)N(R^2)_2$, $NR^2C(O)NHR^2$, $NR^2C(O)N(R^2)_2$, $C(O)NH_2$, $C(O)NHR^2$, $C(O)N(R^2)_2$, $C(O)NHOH$, $C(O)NHOR^2$, $C(O)NHSO_2R^2$, $C(O)NR^2SO_2R^2$, $SO_2NH_2$, $SO_2NHR^2$, $SO_2N(R^2)_2$, $C(O)H$, $C(O)OH$, OH, (O), CN, $NO_2$, $CF_3$, $CF_2CF_3$, $OCF_3$, $OCF_2CF_3$, F, Cl, Br and I; wherein each $R^1$ aryl, heteroaryl, heterocyclyl, cycloalkyl, and cycloalkenyl is optionally substituted with one or more substituents independently selected from the group consisting of $R^3$, $OR^3$, $SR^3$, $S(O)R^3$, $SO_2R^3$, $C(O)R^3$, $CO(O)R^3$, $OC(O)R^3$, $OC(O)OR^3$, $NH_2$, $NHR^3$, $N(R^3)_2$, $NHC(O)R^3$, $NR^3C(O)R^3$, $NHS(O)_2R^3$, $NR^3S(O)_2R^3$, $NHC(O)OR^3$, $NR^3C(O)OR^3$, $NHC(O)NH_2$, $NHC(O)NHR^3$, $NHC(O)N(R^3)_2$, $NR^3C(O)NHR^3$, $NR^3C(O)N(R^3)_2$, $C(O)NH_2$, $C(O)NHR^3$, $C(O)N(R^3)_2$, $C(O)NHOH$, $C(O)NHOR^3$, $C(O)NHSO_2R^3$, $C(O)NR^3SO_2R^3$, $SO_2NH_2$, $SO_2NHR^3$, $SO_2N(R^3)_2$, $C(O)H$, $C(O)OH$, $C(O)C(O)NH_2$, $C(O)C(O)NHR^3$, $C(O)C(O)N(R^3)_2$, $C(N)NH_2$, $C(N)NHR^3$, $C(N)N(R^3)_2$, CNOH, CNOCH$_3$, OH, (O), CN, $NO_2$, $CF_3$, $CF_2CF_3$, $OCF_3$, $OCF_2CF_3$, F, Cl, Br and I. In another embodiment of Formula (VII), $R^1$, at each occurrence, is $C_1$-$C_6$ alkyl; wherein each $R^1$ $C_1$-$C_6$ alkyl is optionally substituted with one or more substituents independently selected from the group consisting of $C(O)OH$ and OH. In another embodiment of Formula (VII), $R^1$, at each occurrence, is independently selected from the group consisting of aryl, heteroaryl, heterocyclyl, and cycloalkyl; wherein each $R^1$ aryl, heteroaryl, heterocyclyl, and cycloalkyl is optionally substituted with one or more substituents independently selected from the group consisting of $R^3$, $SO_2R^3$, $C(O)R^3$, $CO(O)R^3$, $C(O)NH_2$, $C(O)NHR^3$, $C(O)N(R^3)_2$, $SO_2N(R^3)_2$, $C(O)C(O)NH_2$, $C(O)C(O)N(R^3)_2$, OH, (O), and F.

In one embodiment of Formula (VII), $R^3$, at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^3$ $C_1$-$C_6$ alkyl, $C_2$-$C_6$ alkenyl, and $C_2$-$C_6$ alkynyl is optionally substituted with one or more substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, OH, (O), CN, $NO_2$, $CF_3$, $CF_2CF_3$, $OCF_3$, $OCF_2CF_3$, F, Cl, Br and I; wherein each $R^3$ aryl, heteroaryl, heterocyclyl, cycloalkyl, and cycloalkenyl is optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, $C(N)NH_2$, $C(N)NHR^5$, $C(N)N(R^5)_2$, CNOH, CNOCH$_3$, OH, (O), CN, $NO_2$, $CF_3$, $CF_2CF_3$, $OCF_3$, $OCF_2CF_3$, F, Cl, Br and I. In another embodiment of Formula (VII), $R^3$, at each occurrence, is independently $C_1$-$C_6$ alkyl; wherein each $R^3$ $C_1$-$C_6$ alkyl is optionally substituted with one or more substituents independently selected from the group consisting of $SO_2R^4$, $C(O)R^4$, $NHS(O)_2R^4$, $C(O)NH_2$, $C(O)NHR^4$, $C(O)N(R^4)_2$, $SO_2NH_2$, and OH. In another embodiment of Formula (VII), $R^3$, at each occurrence, is independently selected from the group consisting of heteroaryl, heterocyclyl, and cycloalkyl; wherein each $R^3$ heteroaryl, heterocyclyl, and cycloalkyl is optionally substituted with one or more substituents independently selected from the group consisting of $R^5$ and CN.

In one embodiment of Formula (VII), $R^4$ is at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^4$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I; wherein each $R^4$ aryl, heteroaryl, heterocyclyl, cycloalkyl, and cycloalkenyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I. In another embodiment of Formula (VII), $R^4$ at each occurrence, is $C_1$-$C_6$ alkyl. In another embodiment of Formula (VII), $R^4$ at each occurrence, is heterocyclyl; wherein each $R^4$ heterocyclyl is optionally substituted with one or more substituents independently selected from the group consisting of OH, and F.

In one embodiment of Formula (VII), $R^5$ is at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^5$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I; wherein each $R^5$ aryl, heteroaryl, heterocyclyl, cycloalkyl, and cycloalkenyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I. In another embodiment of Formula (VII), $R^5$ is at each occurrence, is independently $C_1$-$C_6$ alkyl.

In one embodiment of Formula (VII), $A^3$ is selected from the group consisting of aryl, heterocyclyl, and heteroaryl, wherein the $A^3$ aryl, heterocyclyl, and heteroaryl are optionally substituted with one or more substituents independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, $C(O)OH$, CN, F, Cl, Br and I;

$R^1$, at each occurrence, is independently selected from the group consisting of $C_1$-$C_6$ alkyl, aryl, heteroaryl, heterocyclyl, and cycloalkyl; wherein each $R^1$ $C_1$-$C_6$ alkyl is optionally substituted with one or more substituents independently selected from the group consisting of $C(O)OH$, OH, F, Cl, Br and I; wherein each $R^1$ aryl, heteroaryl, heterocyclyl, cycloalkyl, and cycloalkenyl is optionally substituted with one or more substituents independently selected from the group consisting of $R^3$, $SO_2R^3$, $C(O)R^3$, $CO(O)R^3$, $C(O)NH_2$, $C(O)NHR^3$, $C(O)N(R^3)_2$, $SO_2N(R^3)_2$, $C(O)C(O)NH_2$, $C(O)C(O)N(R^3)_2$, OH, (O), F, Cl, Br and I;

$R^3$, at each occurrence, is independently selected from the group consisting of $C_1$-$C_6$ alkyl, heteroaryl, heterocyclyl, and cycloalkyl; wherein each $R^3$ $C_1$-$C_6$ alkyl is optionally substituted with one or more substituents independently selected from the group consisting of $SO_2R^4$, $C(O)R^4$, $NHS(O)_2R^4$, $C(O)NH_2$, $C(O)NHR^4$, $C(O)N(R^4)_2$, $SO_2NH_2$, F, Cl, Br and I; wherein each $R^3$ heteroaryl and heterocyclyl is optionally substituted with one or more substituents independently selected from the group consisting of $R^5$, CN, F, Cl, Br and I;

$R^4$ is at each occurrence, is independently selected from the group consisting of $C_1$-$C_6$ alkyl and heterocyclyl; wherein each $R^4$ heterocyclyl is optionally substituted with one or more substituents independently selected from the group consisting of OH, F, Cl, Br and I; and $R^5$ is at each occurrence, is independently $C_1$-$C_6$ alkyl.

Still another embodiment pertains to compounds of Formula (VII), selected from the group consisting of:
(3R,4S)-1-[(1R)-7-fluoro-2,3-dihydro-1H-inden-1-yl]-4-[4-(methanesulfonyl)phenyl]-N,N-dimethylpyrrolidin-3-amine;
1-[4-(4-{(3S,4R)-4-(dimethylamino)-1-[(1R)-7-fluoro-2,3-dihydro-1H-inden-1-yl]pyrrolidin-3-yl}phenyl)piperazin-1-yl]ethan-1-one;
(3R,4S)-1-[(1R)-7-fluoro-2,3-dihydro-1H-inden-1-yl]-N,N-dimethyl-4-(1-methyl-1H-indol-3-yl)pyrrolidin-3-amine;
and pharmaceutically acceptable salts thereof.

One embodiment pertains to compounds or pharmaceutically acceptable salts thereof, which are useful as inhibitors of EED, the compounds having Formula (VIII)

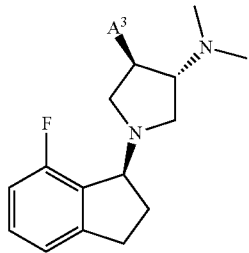

Formula (VIII)

wherein $A^3$ is selected from the group consisting of aryl, heterocyclyl, and heteroaryl, wherein the $A^3$ aryl, heterocyclyl, and heteroaryl are optionally substituted with one or more substituents independently selected from the group consisting of $R^1$, $OR^1$, $SR^1$, $S(O)R^1$, $SO_2R^1$, $C(O)R^1$, $CO(O)R^1$, $OC(O)R^1$, $OC(O)OR^1$, $NH_2$, $NHR^1$, $N(R^1)_2$, $NHC(O)R^1$, $NR^1C(O)R^1$, $NHS(O)_2R^1$, $NR^1S(O)_2R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $C(O)NH_2$, $C(O)NHR^1$, $C(O)N(R^1)_2$, $C(O)NHOH$, $C(O)NHOR^1$, $C(O)NHSO_2R^1$, $C(O)NR^1SO_2R^1$, $SO_2NH_2$, $SO_2NHR^1$, $SO_2N(R^1)_2$, $C(O)H$, $C(O)OH$, $C(N)NH_2$, $C(N)NHR^1$, $C(N)N(R^1)_2$, CNOH, $CNOCH_3$, OH, (O), CN, $NO_2$, $CF_3$, $CF_2CF_3$, $OCF_3$, $OCF_2CF_3$, F, Cl, Br and I;

$R^1$, at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^1$ $C_1$-$C_6$ alkyl, $C_2$-$C_6$ alkenyl, and $C_2$-$C_6$ alkynyl is optionally substituted with one or more substituents independently selected from the group consisting of $R^2$, $OR^2$, $SR^2$, $S(O)R^2$, $SO_2R^2$, $C(O)R^2$, $CO(O)R^2$, $OC(O)R^2$, $OC(O)OR^2$, $NH_2$, $NHR^2$, $N(R^2)_2$, $NHC(O)R^2$, $NR^2C(O)R^2$, $NHS(O)_2R^2$, $NR^2S(O)_2R^2$, $NHC(O)OR^2$, $NR^2C(O)OR^2$, $NHC(O)NH_2$, $NHC(O)NHR^2$, $NHC(O)N(R^2)_2$, $NR^2C(O)NHR^2$, $NR^2C(O)N(R^2)_2$, $C(O)NH_2$, $C(O)NHR^2$, $C(O)N(R^2)_2$, $C(O)NHOH$, $C(O)NHOR^2$, $C(O)NHSO_2R^2$, $C(O)NR^2SO_2R^2$, $SO_2NH_2$, $SO_2NHR^2$, $SO_2N(R^2)_2$, $C(O)H$, $C(O)OH$, OH, (O), CN, $NO_2$, $CF_3$, $CF_2CF_3$, $OCF_3$, $OCF_2CF_3$, F, Cl, Br and I; wherein each $R^1$ aryl, heteroaryl, heterocyclyl, cycloalkyl, and cycloalkenyl is optionally substituted with one or more substituents independently selected from the group consisting of $R^3$, $OR^3$, $SR^3$, $S(O)R^3$, $SO_2R^3$, $C(O)R^3$, $CO(O)R^3$, $OC(O)R^3$, $OC(O)OR^3$, $NH_2$, $NHR^3$, $N(R^3)_2$, $NHC(O)R^3$, $NR^3C(O)R^3$, $NHS(O)_2R^3$, $NR^3S(O)_2R^3$, $NHC(O)OR^3$, $NR^3C(O)OR^3$, $NHC(O)NH_2$, $NHC(O)NHR^3$, $NHC(O)N(R^3)_2$, $NR^3C(O)NHR^3$, $NR^3C(O)N(R^3)_2$, $C(O)NH_2$, $C(O)NHR^3$, $C(O)N(R^3)_2$, $C(O)NHOH$, $C(O)NHOR^3$, $C(O)NHSO_2R^3$, $C(O)NR^3SO_2R^3$, $SO_2NH_2$, $SO_2NHR^3$, $SO_2N(R^3)_2$, $C(O)H$, $C(O)OH$, $C(O)C(O)NH_2$, $C(O)C(O)NHR^3$, $C(O)C(O)N(R^3)_2$, $C(N)NH_2$, $C(N)NHR^3$, $C(N)N(R^3)_2$, CNOH, $CNOCH_3$, OH, (O), CN, $NO_2$, $CF_3$, $CF_2CF_3$, $OCF_3$, $OCF_2CF_3$, F, Cl, Br and I;

$R^2$, at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^2$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I; wherein each $R^2$ aryl, heteroaryl, heterocyclyl, cycloalkyl, and cycloalkenyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I;

$R^3$, at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^3$ $C_1$-$C_6$ alkyl, $C_2$-$C_6$ alkenyl, and $C_2$-$C_6$ alkynyl is optionally substituted with one or more substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, OH, (O), CN, $NO_2$, $CF_3$, $CF_2CF_3$, $OCF_3$, $OCF_2CF_3$, F, Cl, Br and I; wherein each $R^3$ aryl, heteroaryl, heterocyclyl, cycloalkyl, and cycloalkenyl is optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, $C(N)NH_2$, $C(N)NHR^5$, $C(N)N(R^5)_2$, CNOH, $CNOCH_3$, OH, (O), CN, $NO_2$, $CF_3$, $CF_2CF_3$, $OCF_3$, $OCF_2CF_3$, F, Cl, Br and I;

$R^4$ is at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^4$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)NH_2$, $SO_2NH_2$, $C(O)H$, $C(O)OH$, $OH$, $(O)$, $CN$, $NO_2$, $CF_3$, $CF_2CF_3$, $OCF_3$, $OCF_2CF_3$, F, Cl, Br and I; wherein each $R^4$ aryl, heteroaryl, heterocyclyl, cycloalkyl, and cycloalkenyl is optionally substituted with one or more substituents independently selected from the group consisting of $NH_2$, $C(O)NH_2$, $SO_2NH_2$, $C(O)H$, $C(O)OH$, $OH$, $(O)$, $CN$, $NO_2$, $CF_3$, $CF_2CF_3$, $OCF_3$, $OCF_2CF_3$, F, Cl, Br and I; and $R^5$ is at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^5$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)NH_2$, $SO_2NH_2$, $C(O)H$, $C(O)OH$, $OH$, $(O)$, $CN$, $NO_2$, $CF_3$, $CF_2CF_3$, $OCF_3$, $OCF_2CF_3$, F, Cl, Br and I; wherein each $R^5$ aryl, heteroaryl, heterocyclyl, cycloalkyl, and cycloalkenyl is optionally substituted with one or more substituents independently selected from the group consisting of $NH_2$, $C(O)NH_2$, $SO_2NH_2$, $C(O)H$, $C(O)OH$, $OH$, $(O)$, $CN$, $NO_2$, $CF_3$, $CF_2CF_3$, $OCF_3$, $OCF_2CF_3$, F, Cl, Br and I.

In one embodiment of Formula (VIII), $A^3$ is selected from the group consisting of aryl, heterocyclyl, and heteroaryl, wherein the $A^3$ aryl, heterocyclyl, and heteroaryl are optionally substituted with one or more substituents independently selected from the group consisting of $R^1$, $OR^1$, $SR^1$, $S(O)R^1$, $SO_2R^1$, $C(O)R^1$, $CO(O)R^1$, $OC(O)R^1$, $OC(O)OR^1$, $NH_2$, $NHR^1$, $N(R^1)_2$, $NHC(O)R^1$, $NR^1C(O)R^1$, $NHS(O)_2R^1$, $NR^1S(O)_2R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $C(O)NH_2$, $C(O)NHR^1$, $C(O)N(R^1)_2$, $C(O)NHOH$, $C(O)NHOR^1$, $C(O)NHSO_2R^1$, $C(O)NR^1SO_2R^1$, $SO_2NH_2$, $SO_2NHR^1$, $SO_2N(R^1)_2$, $C(O)H$, $C(O)OH$, $C(N)NH_2$, $C(N)NHR^1$, $C(N)N(R^1)_2$, $CNOH$, $CNOCH_3$, $OH$, $(O)$, $CN$, $NO_2$, $CF_3$, $CF_2CF_3$, $OCF_3$, $OCF_2CF_3$, F, Cl, Br and I. In another embodiment of Formula (VIII), $A^3$ is selected from the group consisting of aryl, heterocyclyl, and heteroaryl, wherein the $A^3$ aryl, heterocyclyl, and heteroaryl are optionally substituted with one or more substituents independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, $C(O)OH$, $CN$, F, Cl, Br and I. In another embodiment of Formula (VIII), $A^3$ is aryl, wherein the $A^3$ aryl is optionally substituted with one or more substituents independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, $C(O)OH$, $CN$, F, Cl, Br and I. In another embodiment of Formula (VIII), $A^3$ is aryl, wherein the $A^3$ aryl is substituted with one substituent independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, $C(O)OH$, $CN$, F, Cl, Br and I. In another embodiment of Formula (VIII), $A^3$ is aryl, wherein the $A^3$ aryl is substituted with two substituents independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, $C(O)OH$, $CN$, F, Cl, Br and I. In another embodiment of Formula (VIII), $A^3$ is heterocyclyl, wherein the $A^3$ heterocyclyl is optionally substituted with one or more substituents independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, $C(O)OH$, $CN$, F, Cl, Br and I. In another embodiment of Formula (VIII), $A^3$ is heterocyclyl, wherein the $A^3$ heterocyclyl is unsubstituted. In another embodiment of Formula (VIII), $A^3$ is heterocyclyl, wherein the $A^3$ heterocyclyl is substituted with one substituent independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, $C(O)OH$, $CN$, F, Cl, Br and I. In another embodiment of Formula (VIII), $A^3$ is heterocyclyl, wherein the $A^3$ heterocyclyl is substituted with two substituents independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, $C(O)OH$, $CN$, F, Cl, Br and I. In another embodiment of Formula (VIII), $A^3$ is heteroaryl, wherein the $A^3$ heteroaryl is optionally substituted with one or more substituents independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, $C(O)OH$, $CN$, F, Cl, Br and I. In another embodiment of Formula (VIII), $A^3$ is heteroaryl, wherein the $A^3$ heteroaryl is unsubstituted. In another embodiment of Formula (VIII), $A^3$ is heteroaryl, wherein the $A^3$ heteroaryl is substituted with one substituent independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, $C(O)OH$, $CN$, F, Cl, Br and I. In another embodiment of Formula (VIII), $A^3$ is heteroaryl, wherein the $A^3$ heteroaryl is substituted with two substituents independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, $C(O)OH$, $CN$, F, Cl, Br and I.

In one embodiment of Formula (VIII), $R^1$, at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^1$ $C_1$-$C_6$ alkyl, $C_2$-$C_6$ alkenyl, and $C_2$-$C_6$ alkynyl is optionally substituted with one or more substituents independently selected from the group consisting of $R^2$, $OR^2$, $SR^2$, $S(O)R^2$, $SO_2R^2$, $C(O)R^2$, $CO(O)R^2$, $OC(O)R^2$, $OC(O)OR^2$, $NH_2$, $NHR^2$, $N(R^2)_2$, $NHC(O)R^2$, $NR^2C(O)R^2$, $NHS(O)_2R^2$, $NR^2S(O)_2R^2$, $NHC(O)OR^2$, $NR^2C(O)OR^2$, $NHC(O)NH_2$, $NHC(O)NHR^2$, $NHC(O)N(R^2)_2$, $NR^2C(O)NHR^2$, $NR^2C(O)N(R^2)_2$, $C(O)NH_2$, $C(O)NHR^2$, $C(O)N(R^2)_2$, $C(O)NHOH$, $C(O)NHOR^2$, $C(O)NHSO_2R^2$, $C(O)NR^2SO_2R^2$, $SO_2NH_2$, $SO_2NHR^2$, $SO_2N(R^2)_2$, $C(O)H$, $C(O)OH$, $OH$, $(O)$, $CN$, $NO_2$, $CF_3$, $CF_2CF_3$, $OCF_3$, $OCF_2CF_3$, F, Cl, Br and I; wherein each $R^1$ aryl, heteroaryl, heterocyclyl, cycloalkyl, and cycloalkenyl is optionally substituted with one or more substituents independently selected from the group consisting of $R^3$, $OR^3$, $SR^3$, $S(O)R^3$, $SO_2R^3$, $C(O)R^3$, $CO(O)R^3$, $OC(O)R^3$, $OC(O)OR^3$, $NH_2$, $NHR^3$, $N(R^3)_2$, $NHC(O)R^3$, $NR^3C(O)R^3$, $NHS(O)_2R^3$, $NR^3S(O)_2R^3$, $NHC(O)OR^3$, $NR^3C(O)OR^3$, $NHC(O)NH_2$, $NHC(O)NHR^3$, $NHC(O)N(R^3)_2$, $NR^3C(O)NHR^3$, $NR^3C(O)N(R^3)_2$, $C(O)NH_2$, $C(O)NHR^3$, $C(O)N(R^3)_2$, $C(O)NHOH$, $C(O)NHOR^3$, $C(O)NHSO_2R^3$, $C(O)NR^3SO_2R^3$, $SO_2NH_2$, $SO_2NHR^3$, $SO_2N(R^3)_2$, $C(O)H$, $C(O)OH$, $C(O)C(O)NH_2$, $C(O)C(O)NHR^3$, $C(O)C(O)N(R^3)_2$, $C(N)NH_2$, $C(N)NHR^3$, $C(N)N(R^3)_2$, $CNOH$, $CNOCH_3$, $OH$, $(O)$, $CN$, $NO_2$, $CF_3$, $CF_2CF_3$, $OCF_3$, $OCF_2CF_3$, F, Cl, Br and I. In another embodiment of Formula (VIII), $R^1$, at each occurrence, is $C_1$-$C_6$ alkyl; wherein each $R^1$ $C_1$-$C_6$ alkyl is optionally substituted with one or more substituents independently selected from the group consisting of $C(O)OH$ and $OH$. In another embodiment of Formula (VIII), $R^1$, at each occurrence, is independently selected from the group consisting of aryl, heteroaryl, heterocyclyl, and cycloalkyl; wherein each $R^1$ aryl, heteroaryl, heterocyclyl, and cycloalkyl is optionally substituted with one or more substituents independently selected from the group consisting of $R^3$, $SO_2R^3$, $C(O)R^3$, $CO(O)R^3$, $C(O)NH_2$, $C(O)NHR^3$, $C(O)N(R^3)_2$, $SO_2N(R^3)_2$, $C(O)C(O)NH_2$, $C(O)C(O)N(R^3)_2$, OH, (O), and F.

In one embodiment of Formula (VIII), $R^3$, at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^3$ $C_1$-$C_6$ alkyl, $C_2$-$C_6$ alkenyl, and $C_2$-$C_6$ alkynyl is optionally substituted with one or more substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, OH, (O), CN, $NO_2$, $CF_3$, $CF_2CF_3$, $OCF_3$, $OCF_2CF_3$, F, Cl, Br and I; wherein each $R^3$ aryl, heteroaryl, heterocyclyl, cycloalkyl, and cycloalkenyl is optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, $C(N)NH_2$, $C(N)NHR^5$, $C(N)N(R^5)_2$, CNOH, $CNOCH_3$, OH, (O), CN, $NO_2$, $CF_3$, $CF_2CF_3$, $OCF_3$, $OCF_2CF_3$, F, Cl, Br and I. In another embodiment of Formula (VIII), $R^3$, at each occurrence, is independently $C_1$-$C_6$ alkyl; wherein each $R^3$ $C_1$-$C_6$ alkyl is optionally substituted with one or more substituents independently selected from the group consisting of $SO_2R^4$, $C(O)R^4$, $NHS(O)_2R^4$, $C(O)NH_2$, $C(O)NHR^4$, $C(O)N(R^4)_2$, $SO_2NH_2$, and OH. In another embodiment of Formula (VIII), $R^3$, at each occurrence, is independently selected from the group consisting of heteroaryl, heterocyclyl, and cycloalkyl; wherein each $R^3$ heteroaryl, heterocyclyl, and cycloalkyl is optionally substituted with one or more substituents independently selected from the group consisting of $R^5$ and CN.

In one embodiment of Formula (VIII), $R^4$ is at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^4$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I; wherein each $R^4$ aryl, heteroaryl, heterocyclyl, cycloalkyl, and cycloalkenyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I. In another embodiment of Formula (VIII), $R^4$ at each occurrence, is $C_1$-$C_6$ alkyl. In another embodiment of Formula (VIII), $R^4$ at each occurrence, is heterocyclyl; wherein each $R^4$ heterocyclyl is optionally substituted with one or more substituents independently selected from the group consisting of OH, and F.

In one embodiment of Formula (VIII), $R^5$ is at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^5$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I; wherein each $R^5$ aryl, heteroaryl, heterocyclyl, cycloalkyl, and cycloalkenyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I. In another embodiment of Formula (VIII), $R^5$ is at each occurrence, is independently $C_1$-$C_6$ alkyl.

In one embodiment of Formula (VIII), $A^3$ is selected from the group consisting of aryl, heterocyclyl, and heteroaryl, wherein the $A^3$ aryl, heterocyclyl, and heteroaryl are optionally substituted with one or more substituents independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, $C(O)OH$, CN, F, Cl, Br and I;

$R^1$, at each occurrence, is independently selected from the group consisting of $C_1$-$C_6$ alkyl, aryl, heteroaryl, heterocyclyl, and cycloalkyl; wherein each $R^1$ $C_1$-$C_6$ alkyl is optionally substituted with one or more substituents independently selected from the group consisting of $C(O)OH$, OH, F, Cl, Br and I; wherein each $R^1$ aryl, heteroaryl, heterocyclyl, cycloalkyl, and cycloalkenyl is optionally substituted with one or more substituents independently selected from the group consisting of $R^3$, $SO_2R^3$, $C(O)R^3$, $CO(O)R^3$, $C(O)NH_2$, $C(O)NHR^3$, $C(O)N(R^3)_2$, $SO_2N(R^3)_2$, $C(O)C(O)NH_2$, $C(O)C(O)N(R^3)_2$, OH, (O), F, Cl, Br and I;

$R^3$, at each occurrence, is independently selected from the group consisting of $C_1$-$C_6$ alkyl, heteroaryl, heterocyclyl, and cycloalkyl; wherein each $R^3$ $C_1$-$C_6$ alkyl is optionally substituted with one or more substituents independently selected from the group consisting of $SO_2R^4$, $C(O)R^4$, $NHS(O)_2R^4$, $C(O)NH_2$, $C(O)NHR^4$, $C(O)N(R^4)_2$, $SO_2NH_2$, F, Cl, Br and I; wherein each $R^3$ heteroaryl and heterocyclyl is optionally substituted with one or more substituents independently selected from the group consisting of $R^5$, CN, F, Cl, Br and I;

$R^4$ is at each occurrence, is independently selected from the group consisting of $C_1$-$C_6$ alkyl and heterocyclyl; wherein each $R^4$ heterocyclyl is optionally substituted with one or more substituents independently selected from the group consisting of OH, F, Cl, Br and I; and $R^5$ is at each occurrence, is independently $C_1$-$C_6$ alkyl.

Still another embodiment pertains to compounds of Formula (VIII), selected from the group consisting of:

(3S,4R)-1-[(1S)-7-fluoro-2,3-dihydro-1H-inden-1-yl]-4-{4-[4-(methanesulfonyl)piperazin-1-yl]phenyl}N,N-dimethylpyrrolidin-3-amine;

(3S,4R)-1-[(1S)-2,3-dihydro-1H-inden-1-yl]-4-[4-(methanesulfonyl)phenyl]-N,N-dimethylpyrrolidin-3-amine;

(3S,4R)-1-[(1S)-7-fluoro-2,3-dihydro-1H-inden-1-yl]-4-[4-(methanesulfonyl)phenyl]-N,N-dimethylpyrrolidin-3-amine;

1-[4-(4-{(3R,4S)-4-(dimethylamino)-1-[(1S)-7-fluoro-2,3-dihydro-1H-inden-1-yl]pyrrolidin-3-yl}phenyl)piperazin-1-yl]ethan-1-one; and pharmaceutically acceptable salts thereof.

One embodiment pertains to compounds or pharmaceutically acceptable salts thereof, which are useful as inhibitors of EED, the compounds having Formula (IX)

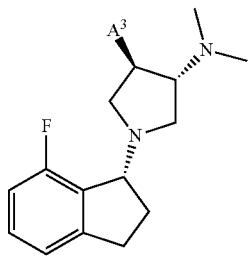

Formula (IX)

wherein

A³ is selected from the group consisting of aryl, heterocyclyl, and heteroaryl, wherein the A³ aryl, heterocyclyl, and heteroaryl are optionally substituted with one or more substituents independently selected from the group consisting of $R^1$, $OR^1$, $SR^1$, $S(O)R^1$, $SO_2R^1$, $C(O)R^1$, $CO(O)R^1$, $OC(O)R^1$, $OC(O)OR^1$, $NH_2$, $NHR^1$, $N(R^1)_2$, $NHC(O)R^1$, $NR^1C(O)R^1$, $NHS(O)_2R^1$, $NR^1S(O)_2R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $C(O)NH_2$, $C(O)NHR^1$, $C(O)N(R^1)_2$, $C(O)NHOH$, $C(O)NHOR^1$, $C(O)NHSO_2R^1$, $C(O)NR^1SO_2R^1$, $SO_2NH_2$, $SO_2NHR^1$, $SO_2N(R^1)_2$, $C(O)H$, $C(O)OH$, $C(N)NH_2$, $C(N)NHR^1$, $C(N)N(R^1)_2$, CNOH, $CNOCH_3$, OH, (O), CN, $NO_2$, $CF_3$, $CF_2CF_3$, $OCF_3$, $OCF_2CF_3$, F, Cl, Br and I;

$R^1$, at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^1$ $C_1$-$C_6$ alkyl, $C_2$-$C_6$ alkenyl, and $C_2$-$C_6$ alkynyl is optionally substituted with one or more substituents independently selected from the group consisting of $R^2$, $OR^2$, $SR^2$, $S(O)R^2$, $SO_2R^2$, $C(O)R^2$, $CO(O)R^2$, $OC(O)R^2$, $OC(O)OR^2$, $NH_2$, $NHR^2$, $N(R^2)_2$, $NHC(O)R^2$, $NR^2C(O)R^2$, $NHS(O)_2R^2$, $NR^2S(O)_2R^2$, $NHC(O)OR^2$, $NR^2C(O)OR^2$, $NHC(O)NH_2$, $NHC(O)NHR^2$, $NHC(O)N(R^2)_2$, $NR^2C(O)NHR^2$, $NR^2C(O)N(R^2)_2$, $C(O)NH_2$, $C(O)NHR^2$, $C(O)N(R^2)_2$, $C(O)NHOH$, $C(O)NHOR^2$, $C(O)NHSO_2R^2$, $C(O)NR^2SO_2R^2$, $SO_2NH_2$, $SO_2NHR^2$, $SO_2N(R^2)_2$, $C(O)H$, $C(O)OH$, OH, (O), CN, $NO_2$, $CF_3$, $CF_2CF_3$, $OCF_3$, $OCF_2CF_3$, F, Cl, Br and I; wherein each $R^1$ aryl, heteroaryl, heterocyclyl, cycloalkyl, and cycloalkenyl is optionally substituted with one or more substituents independently selected from the group consisting of $R^3$, $OR^3$, $SR^3$, $S(O)R^3$, $SO_2R^3$, $C(O)R^3$, $CO(O)R^3$, $OC(O)R^3$, $OC(O)OR^3$, $NH_2$, $NHR^3$, $N(R^3)_2$, $NHC(O)R^3$, $NR^3C(O)R^3$, $NHS(O)_2R^3$, $NR^3S(O)_2R^3$, $NHC(O)OR^3$, $NR^3C(O)OR^3$, $NHC(O)NH_2$, $NHC(O)NHR^3$, $NHC(O)N(R^3)_2$, $NR^3C(O)NHR^3$, $NR^3C(O)N(R^3)_2$, $C(O)NH_2$, $C(O)NHR^3$, $C(O)N(R^3)_2$, $C(O)NHOH$, $C(O)NHOR^3$, $C(O)NHSO_2R^3$, $C(O)NR^3SO_2R^3$, $SO_2NH_2$, $SO_2NHR^3$, $SO_2N(R^3)_2$, $C(O)H$, $C(O)OH$, $C(O)C(O)NH_2$, $C(O)C(O)NHR^3$, $C(O)C(O)N(R^3)_2$, $C(N)NH_2$, $C(N)NHR^3$, $C(N)N(R^3)_2$, CNOH, $CNOCH_3$, OH, (O), CN, $NO_2$, $CF_3$, $CF_2CF_3$, $OCF_3$, $OCF_2CF_3$, F, Cl, Br and I;

$R^2$, at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^2$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I; wherein each $R^2$ aryl, heteroaryl, heterocyclyl, cycloalkyl, and cycloalkenyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I;

$R^3$, at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^3$ $C_1$-$C_6$ alkyl, $C_2$-$C_6$ alkenyl, and $C_2$-$C_6$ alkynyl is optionally substituted with one or more substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, OH, (O), CN, $NO_2$, $CF_3$, $CF_2CF_3$, $OCF_3$, $OCF_2CF_3$, F, Cl, Br and I; wherein each $R^3$ aryl, heteroaryl, heterocyclyl, cycloalkyl, and cycloalkenyl is optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, $C(N)NH_2$, $C(N)NHR^5$, $C(N)N(R^5)_2$, CNOH, $CNOCH_3$, OH, (O), CN, $NO_2$, $CF_3$, $CF_2CF_3$, $OCF_3$, $OCF_2CF_3$, F, Cl, Br and I;

$R^4$ is at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^4$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I; wherein each $R^4$ aryl, heteroaryl, heterocyclyl, cycloalkyl, and cycloalkenyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I; and $R^5$ is at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^5$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I; wherein each $R^5$ aryl, heteroaryl, heterocyclyl, cycloalkyl, and cycloalkenyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I.

In one embodiment of Formula (IX), A³ is selected from the group consisting of aryl, heterocyclyl, and heteroaryl, wherein the A³ aryl, heterocyclyl, and heteroaryl are optionally substituted with one or more substituents independently selected from the group consisting of $R^1$, $OR^1$, $SR^1$, $S(O)R^1$, $SO_2R^1$, $C(O)R^1$, $CO(O)R^1$, $OC(O)R^1$, $OC(O)OR^1$, $NH_2$, $NHR^1$, $N(R^1)_2$, $NHC(O)R^1$, $NR^1C(O)R^1$, $NHS(O)_2R^1$, $NR^1S(O)_2R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $C(O)NH_2$, $C(O)NHR^1$, $C(O)N(R^1)_2$, $C(O)NHOH$, $C(O)NHOR^1$, $C(O)NHSO_2R^1$, $C(O)NR^1SO_2R^1$, $SO_2NH_2$, $SO_2NHR^1$, $SO_2N(R^1)_2$, $C(O)H$, $C(O)OH$, $C(N)NH_2$, $C(N)NHR^1$, $C(N)N(R^1)_2$, $CNOH$, $CNOCH_3$, $OH$, $(O)$, $CN$, $NO_2$, $CF_3$, $CF_2CF_3$, $OCF_3$, $OCF_2CF_3$, F, Cl, Br and I. In another embodiment of Formula (IX), $A^3$ is selected from the group consisting of aryl, heterocyclyl, and heteroaryl, wherein the $A^3$ aryl, heterocyclyl, and heteroaryl are optionally substituted with one or more substituents independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, $C(O)OH$, CN, F, Cl, Br and I. In another embodiment of Formula (IX), $A^3$ is aryl, wherein the $A^3$ aryl is optionally substituted with one or more substituents independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, $C(O)OH$, CN, F, Cl, Br and I. In another embodiment of Formula (IX), $A^3$ is aryl, wherein the $A^3$ aryl is substituted with one substituent independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, $C(O)OH$, CN, F, Cl, Br and I. In another embodiment of Formula (IX), $A^3$ is aryl, wherein the $A^3$ aryl is substituted with two substituents independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, $C(O)OH$, CN, F, Cl, Br and I. In another embodiment of Formula (IX), $A^3$ is heterocyclyl, wherein the $A^3$ heterocyclyl is optionally substituted with one or more substituents independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, $C(O)OH$, CN, F, Cl, Br and I. In another embodiment of Formula (IX), $A^3$ is heterocyclyl, wherein the $A^3$ heterocyclyl is unsubstituted. In another embodiment of Formula (IX), $A^3$ is heterocyclyl, wherein the $A^3$ heterocyclyl is substituted with one substituent independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, $C(O)OH$, CN, F, Cl, Br and I. In another embodiment of Formula (IX), $A^3$ is heterocyclyl, wherein the $A^3$ heterocyclyl is substituted with two substituents independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, $C(O)OH$, CN, F, Cl, Br and I. In another embodiment of Formula (IX), $A^3$ is heteroaryl, wherein the $A^3$ heteroaryl is optionally substituted with one or more substituents independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, $C(O)OH$, CN, F, Cl, Br and I. In another embodiment of Formula (IX), $A^3$ is heteroaryl, wherein the $A^3$ heteroaryl is unsubstituted. In another embodiment of Formula (IX), $A^3$ is heteroaryl, wherein the $A^3$ heteroaryl is substituted with one substituent independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, $C(O)OH$, CN, F, Cl, Br and I. In another embodiment of Formula (IX), $A^3$ is heteroaryl, wherein the $A^3$ heteroaryl is substituted with two substituents independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, $C(O)OH$, CN, F, Cl, Br and I.

In one embodiment of Formula (IX), $R^1$, at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^1$ $C_1$-$C_6$ alkyl, $C_2$-$C_6$ alkenyl, and $C_2$-$C_6$ alkynyl is optionally substituted with one or more substituents independently selected from the group consisting of $R^2$, $OR^2$, $SR^2$, $S(O)R^2$, $SO_2R^2$, $C(O)R^2$, $CO(O)R^2$, $OC(O)R^2$, $OC(O)OR^2$, $NH_2$, $NHR^2$, $N(R^2)_2$, $NHC(O)R^2$, $NR^2C(O)R^2$, $NHS(O)_2R^2$, $NR^2S(O)_2R^2$, $NHC(O)OR^2$, $NR^2C(O)OR^2$, $NHC(O)NH_2$, $NHC(O)NHR^2$, $NHC(O)N(R^2)_2$, $NR^2C(O)NHR^2$, $NR^2C(O)N(R^2)_2$, $C(O)NH_2$, $C(O)NHR^2$, $C(O)N(R^2)_2$, $C(O)NHOH$, $C(O)NHOR^2$, $C(O)NHSO_2R^2$, $C(O)NR^2SO_2R^2$, $SO_2NH_2$, $SO_2NHR^2$, $SO_2N(R^2)_2$, $C(O)H$, $C(O)OH$, OH, (O), CN, $NO_2$, $CF_3$, $CF_2CF_3$, $OCF_3$, $OCF_2CF_3$, F, Cl, Br and I; wherein each $R^1$ aryl, heteroaryl, heterocyclyl, cycloalkyl, and cycloalkenyl is optionally substituted with one or more substituents independently selected from the group consisting of $R^3$, $OR^3$, $SR^3$, $S(O)R^3$, $SO_2R^3$, $C(O)R^3$, $CO(O)R^3$, $OC(O)R^3$, $OC(O)OR^3$, $NH_2$, $NHR^3$, $N(R^3)_2$, $NHC(O)R^3$, $NR^3C(O)R^3$, $NHS(O)_2R^3$, $NR^3S(O)_2R^3$, $NHC(O)OR^3$, $NR^3C(O)OR^3$, $NHC(O)NH_2$, $NHC(O)NHR^3$, $NHC(O)N(R^3)_2$, $NR^3C(O)NHR^3$, $NR^3C(O)N(R^3)_2$, $C(O)NH_2$, $C(O)NHR^3$, $C(O)N(R^3)_2$, $C(O)NHOH$, $C(O)NHOR^3$, $C(O)NHSO_2R^3$, $C(O)NR^3SO_2R^3$, $SO_2NH_2$, $SO_2NHR^3$, $SO_2N(R^3)_2$, $C(O)H$, $C(O)OH$, $C(O)C(O)NH_2$, $C(O)C(O)NHR^3$, $C(O)C(O)N(R^3)_2$, $C(N)NH_2$, $C(N)NHR^3$, $C(N)N(R^3)_2$, $CNOH$, $CNOCH_3$, OH, (O), CN, $NO_2$, $CF_3$, $CF_2CF_3$, $OCF_3$, $OCF_2CF_3$, F, Cl, Br and I. In another embodiment of Formula (IX), $R^1$, at each occurrence, is $C_1$-$C_6$ alkyl; wherein each $R^1$ $C_1$-$C_6$ alkyl is optionally substituted with one or more substituents independently selected from the group consisting of $C(O)OH$ and OH. In another embodiment of Formula (IX), $R^1$, at each occurrence, is independently selected from the group consisting of aryl, heteroaryl, heterocyclyl, and cycloalkyl; wherein each $R^1$ aryl, heteroaryl, heterocyclyl, and cycloalkyl is optionally substituted with one or more substituents independently selected from the group consisting of $R^3$, $SO_2R^3$, $C(O)R^3$, $CO(O)R^3$, $C(O)NH_2$, $C(O)NHR^3$, $C(O)N(R^3)_2$, $SO_2N(R^3)_2$, $C(O)C(O)NH_2$, $C(O)C(O)N(R^3)_2$, OH, (O), and F.

In one embodiment of Formula (IX), $R^3$, at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^3$ $C_1$-$C_6$ alkyl, $C_2$-$C_6$ alkenyl, and $C_2$-$C_6$ alkynyl is optionally substituted with one or more substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, OH, (O), CN, $NO_2$, $CF_3$, $CF_2CF_3$, $OCF_3$, $OCF_2CF_3$, F, Cl, Br and I; wherein each $R^3$ aryl, heteroaryl, heterocyclyl, cycloalkyl, and cycloalkenyl is optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, $C(N)NH_2$, $C(N)NHR^5$, $C(N)N(R^5)_2$, $CNOH$, $CNOCH_3$, OH, (O), CN, $NO_2$, $CF_3$, $CF_2CF_3$, $OCF_3$, $OCF_2CF_3$, F, Cl, Br and I. In another embodiment of Formula (IX), $R^3$, at each occurrence, is independently $C_1$-$C_6$ alkyl; wherein each $R^3$ $C_1$-$C_6$ alkyl is optionally substituted with one or more substituents independently selected from the group consisting of $SO_2R^4$, $C(O)R^4$, $NHS(O)_2R^4$, $C(O)NH_2$, $C(O)NHR^4$, $C(O)N(R^4)_2$, $SO_2NH_2$, and OH. In another embodiment of Formula (IX), $R^3$, at each occurrence, is independently selected from the group consisting of heteroaryl, heterocyclyl, and cycloalkyl; wherein each $R^3$ heteroaryl, heterocyclyl, and cycloalkyl is optionally substituted with one or more substituents independently selected from the group consisting of $R^5$ and CN.

In one embodiment of Formula (IX), $R^4$ is at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^4$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I; wherein each $R^4$ aryl, heteroaryl, heterocyclyl, cycloalkyl, and cycloalkenyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I. In another embodiment of Formula (IX), $R^4$ at each occurrence, is $C_1$-$C_6$ alkyl. In another embodiment of Formula (IX), $R^4$ at each occurrence, is heterocyclyl; wherein each $R^4$ heterocyclyl is optionally substituted with one or more substituents independently selected from the group consisting of OH, and F.

In one embodiment of Formula (IX), $R^5$ is at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^5$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I; wherein each $R^5$ aryl, heteroaryl, heterocyclyl, cycloalkyl, and cycloalkenyl is optionally substituted with one or more substituents independently selected from the group consisting of $NH_2$, $C(O)NH_2$, $SO_2NH_2$, $C(O)H$, $C(O)OH$, OH, (O), CN, $NO_2$, $CF_3$, $CF_2CF_3$, $OCF_3$, $OCF_2CF_3$, F, Cl, Br and I. In another embodiment of Formula (IX), $R^5$ is at each occurrence, is independently $C_1$-$C_6$ alkyl.

In one embodiment of Formula (IX), $A^3$ is selected from the group consisting of aryl, heterocyclyl, and heteroaryl, wherein the $A^3$ aryl, heterocyclyl, and heteroaryl are optionally substituted with one or more substituents independently selected from the group consisting of $R^1$, $OR^1$, $SO_2R^1$, $C(O)R^1$, $CO(O)R^1$, $C(O)NH_2$, $C(O)NHR^1$, $C(O)N(R^1)_2$, $SO_2NH_2$, $C(O)OH$, CN, F, Cl, Br and I;

$R^1$, at each occurrence, is independently selected from the group consisting of $C_1$-$C_6$ alkyl, aryl, heteroaryl, heterocyclyl, and cycloalkyl; wherein each $R^1$ $C_1$-$C_6$ alkyl is optionally substituted with one or more substituents independently selected from the group consisting of C(O)OH, OH, F, Cl, Br and I; wherein each $R^1$ aryl, heteroaryl, heterocyclyl, cycloalkyl, and cycloalkenyl is optionally substituted with one or more substituents independently selected from the group consisting of $R^3$, $SO_2R^3$, $C(O)R^3$, $CO(O)R^3$, $C(O)NH_2$, $C(O)NHR^3$, $C(O)N(R^3)_2$, $SO_2N(R^3)_2$, $C(O)C(O)NH_2$, $C(O)C(O)N(R^3)_2$, OH, (O), F, Cl, Br and I;

$R^3$, at each occurrence, is independently selected from the group consisting of $C_1$-$C_6$ alkyl, heteroaryl, heterocyclyl, and cycloalkyl; wherein each $R^3$ $C_1$-$C_6$ alkyl is optionally substituted with one or more substituents independently selected from the group consisting of $SO_2R^4$, $C(O)R^4$, $NHS(O)_2R^4$, $C(O)NH_2$, $C(O)NHR^4$, $C(O)N(R^4)_2$, $SO_2NH_2$, F, Cl, Br and I; wherein each $R^3$ heteroaryl and heterocyclyl is optionally substituted with one or more substituents independently selected from the group consisting of $R^5$, CN, F, Cl, Br and I;

$R^4$ is at each occurrence, is independently selected from the group consisting of $C_1$-$C_6$ alkyl and heterocyclyl; wherein each $R^4$ heterocyclyl is optionally substituted with one or more substituents independently selected from the group consisting of OH, F, Cl, Br and I; and $R^5$ is at each occurrence, is independently $C_1$-$C_6$ alkyl.

Still another embodiment pertains to compounds of Formula (IX), selected from the group consisting of:

(3S,4R)-1-[(1R)-7-fluoro-2,3-dihydro-1H-inden-1-yl]-4-{4-[4-(methanesulfonyl)piperazin-1-yl]phenyl}-N,N-dimethylpyrrolidin-3-amine;

(3S,4R)-1-[(1R)-7-fluoro-2,3-dihydro-1H-inden-1-yl]-4-[4-(methanesulfonyl)phenyl]-N,N-dimethylpyrrolidin-3-amine;

1-[4-(4-{(3R,4S)-4-(dimethylamino)-1-[(1R)-7-fluoro-2,3-dihydro-1H-inden-1-yl]pyrrolidin-3-yl}phenyl)piperazin-1-yl]ethan-1-one; and pharmaceutically acceptable salts thereof.

Pharmaceutical Compositions, Combination Therapies, Methods of Use, and Administration One embodiment comprises pharmaceutical compositions comprising a compound having Formula (I) and an excipient.

Another embodiment comprises methods of treating cancer in a mammal comprising administering thereto a therapeutically acceptable amount of a compound having Formula (I).

Another embodiment pertains to compositions for treating diseases during which EED is expressed, said compositions comprising an excipient and a therapeutically effective amount of the compound having Formula (I).

Still another embodiment pertains to methods of treating disease in a patient during which EED is expressed, said methods comprising administering to the patient a therapeutically effective amount of a compound having Formula (I).

In another embodiment, the present invention relates to pharmaceutical compositions comprising a pharmaceutically acceptable excipient and a therapeutically effective amount of a compound of Formula (I), or a pharmaceutically acceptable salt thereof.

In another embodiment, the present invention relates to methods of treating cancer in a patient, comprising administering to a patient suffering from a cancer a therapeutically effective amount of a compound of Formula (I), or a pharmaceutically acceptable salt thereof. In certain embodiments, the cancer is selected from the group consisting of acoustic neuroma, acute leukemia, acute lymphoblastic leukemia, acute myelogenous leukemia, acute t-cell leukemia, basal cell carcinoma, bile duct carcinoma, bladder cancer, brain cancer, breast cancer, bronchogenic carcinoma, Burkitt's lymphoma, cervical cancer, chondrosarcoma, chordoma, choriocarcinoma, chronic leukemia, chronic lymphocytic leukemia, chronic myelocytic leukemia, chronic myelogenous leukemia, colon cancer, colorectal cancer, craniopharyngioma, cystadenocarcinoma, dysplasias, metaplasias, embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, gastric carcinoma, germ cell testicular cancer, gestational trophobalstic disease, glioblastoma, head and neck cancer, heavy chain disease, hemangioblastoma, hepatoma, hepatocellular cancer, hormone insensitive prostate cancer, leiomyosarcoma, liposarcoma, lung cancer, lymphangioendothelio-sarcoma, lymphangiosarcoma, lymphoblastic leukemia, lymphoma, malignancies and hyperproliferative disorders of the bladder, breast, colon, lung, ovaries, pancreas, prostate, skin and uterus, lymphoid malignancies of T-cell or B-cell origin, leukemia, medullary carcinoma, medulloblastoma, melanoma, meningioma, mesothelioma, multiple myeloma, myelogenous leukemia, myeloma, myxosarcoma, neuroblastoma, oligodendroglioma, oral cancer, osteogenic sarcoma, ovarian cancer, pancreatic cancer, papillary adenocarcinomas, papillary carcinoma, peripheral T-cell lymphoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors, stomach cancer, squamous cell carcinoma, synovioma, sweat gland carcinoma, testicular cancer, thyroid cancer, Waldenström's macroglobulinemia, testicular tumors, uterine cancer, and Wilms' tumor. In certain embodiments, the methods further comprise administering a therapeutically effective amount of at least one additional therapeutic agent.

Pharmaceutically acceptable salts have been described in S. M. Berge et al. J. Pharmaceutical Sciences, 1977, 66: 1-19.

Compounds of Formula (I) may contain either a basic or an acidic functionality, or both, and can be converted to a pharmaceutically acceptable salt, when desired, by using a suitable acid or base. The salts may be prepared in situ during the final isolation and purification of the compounds of the invention.

Examples of acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts may be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other examples of organic amines useful for the formation of base addition salts include ethylenediamine, ethanolamine, diethanolamine, piperidine, piperazine and the like.

The term "pharmaceutically acceptable prodrug" or "prodrug" as used herein, represents those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use.

The present invention contemplates compounds of Formula (I) formed by synthetic means or formed by in vivo biotransformation of a prodrug.

Compounds described herein can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

The present invention also provides for pharmaceutical compositions comprising a therapeutically effective amount of a compound of Formula (I), or a pharmaceutically acceptable salt thereof together with a pharmaceutically acceptable carrier, diluent, excipient, or mixture thereof. The phrase "pharmaceutical composition" refers to a composition suitable for administration in medical or veterinary use.

The pharmaceutical compositions that comprise a compound of Formula (I), alone or in combination with a second active pharmaceutical agent, may be administered to the subjects orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents, which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally-administered drug form may be accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In certain embodiments, solid dosage forms may contain from 1% to 95% (w/w) of a compound of Formula (I). In certain embodiments, the compound of Formula (I) may be present in the solid dosage form in a range of from 5% to 70% (w/w). In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

The pharmaceutical composition may be a unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampules. Also, the unit dosage form can be a capsule, tablet, cachet, or lozenge itself, or it can be the appropriate number of any of these in packaged form. The quantity of active component in a unit dose preparation may be varied or adjusted from 0.1 mg to 1000 mg, from 1 mg to 100 mg, or from 1% to 95% (w/w) of a unit dose, according to the particular application and the potency of the active component. The composition can, if desired, also contain other compatible therapeutic agents.

The dose to be administered to a subject may be determined by the efficacy of the particular compound employed and the condition of the subject, as well as the body weight or surface area of the subject to be treated. The size of the dose also will be determined by the existence, nature, and extent of any adverse side-effects that accompany the administration of a particular compound in a particular subject. In determining the effective amount of the compound to be administered in the treatment or prophylaxis of the disorder being treated, the physician can evaluate factors such as the circulating plasma levels of the compound, compound toxicities, and/or the progression of the disease, etc. In general, the dose equivalent of a compound is from about 1 µg/kg to 100 mg/kg for a typical subject.

For administration, compounds of the Formula (I) can be administered at a rate determined by factors that can include, but are not limited to, the $LD_{50}$ of the compound, the pharmacokinetic profile of the compound, contraindicated drugs, and the side-effects of the compound at various concentrations, as applied to the mass and overall health of the subject. Administration can be accomplished via single or divided doses.

The compounds utilized in the pharmaceutical method of the invention can be administered at the initial dosage of about 0.001 mg/kg to about 100 mg/kg daily. In certain embodiments, the daily dose range is from about 0.1 mg/kg to about 10 mg/kg. The dosages, however, may be varied depending upon the requirements of the subject, the severity of the condition being treated, and the compound being employed. Determination of the proper dosage for a particular situation is within the skill of the practitioner. Treatment may be initiated with smaller dosages, which are less than the optimum dose of the compound. Thereafter, the dosage is increased by small increments until the optimum effect under circumstances is reached. For convenience, the total daily dosage may be divided and administered in portions during the day, if desired.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of Formula (I) may also be administered in the form of liposomes. Liposomes generally may be derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form may contain, in addition to a compound of Formula (I), stabilizers, preservatives, excipients and the like. Examples of lipids include, but are not limited to, natural and synthetic phospholipids and phosphatidyl cholines (lecithins), used separately or together.

Methods to form liposomes have been described, see example, Prescott, Ed., Methods in Cell Biology, Volume XIV, Academic Press, New York, N.Y. (1976), p. 33 et seq.

Dosage forms for topical administration of a compound described herein include powders, sprays, ointments and inhalants. The active compound may be mixed under sterile conditions with a pharmaceutically acceptable carrier and any needed preservatives, buffers or propellants which may be required. Opthalmic formulations, eye ointments, powders and solutions are also contemplated as being within the scope of this invention.

The compounds of Formula (I), or pharmaceutically acceptable salts thereof, and pharmaceutical compositions comprising a compound of Formula (I), or a pharmaceutically acceptable salt thereof, can be administered to a subject suffering from an EED-mediated disorder or condition. An "EED-mediated disorder or condition" is characterized by the participation of one or more EED in the inception, manifestation of one or more symptoms or disease markers, severity, or progression of a disorder or condition. An example of a EED-mediated disorder or condition is cancer, including cancers such as, not limited to, acoustic neuroma, acute leukemia, acute lymphoblastic leukemia, acute myelogenous leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer (including estrogen-receptor positive breast cancer), bronchogenic carcinoma, Burkitt's lymphoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, gastric carcinoma, germ cell testicular cancer, gestational trophoblastic disease, glioblastoma, head and neck cancer, heavy chain disease, hemangioblastoma, hepatoma, hepatocellular cancer, hormone insensitive prostate cancer, leiomyosarcoma, liposarcoma, lung cancer (including small cell lung cancer and non-small cell lung cancer), lymphangioendothelio-sarcoma, lymphangiosarcoma, lymphoblastic leukemia, lymphoma (lymphoma, including diffuse large B-cell lymphoma, follicular lymphoma, Hodgkin's lymphoma and non-Hodgkin's lymphoma), malignancies and hyperproliferative disorders of the bladder, breast, colon, lung, ovaries, pancreas, prostate, skin and uterus, lymphoid malignancies of T-cell or B-cell origin, leukemia, medullary carcinoma, medulloblastoma, melanoma, meningioma, mesothelioma, multiple myeloma, myelogenous leukemia, myeloma, myxosarcoma, neuroblastoma, oligodendroglioma, oral cancer, osteogenic sarcoma, ovarian cancer, pancreatic cancer, papillary adenocarcinomas, papillary carcinoma, peripheral T-cell lymphoma, pinealoma, polycythemia vera, prostate cancer (including hormone-insensitive (refractory) prostate cancer), rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), stomach cancer, squamous cell carcinoma, synovioma, sweat gland carcinoma, testicular cancer (including germ cell testicular cancer), thyroid cancer, Waldenström's macroglobulinemia, testicular tumors, uterine cancer, Wilms' tumor and the like.

The term "administering" or "administered" refers to the method of contacting a compound with a subject. Thus, the compounds of Formula (I) can be administered by injection, that is, intravenously, intramuscularly, intracutaneously, subcutaneously, intraduodenally, parentally, or intraperitoneally. In certain embodiments, a compound of Formula (I) may be administered orally. Also, the compounds described herein can be administered by inhalation, for example, intranasally. Additionally, the compounds of Formula (I) can be administered transdermally, topically, via implantation, transdermally, topically, and via implantation. In certain embodiments, the compounds of the Formula (I) may be delivered orally. The compounds can also be delivered rectally, bucally, intravaginally, ocularly, andially, or by insufflation. EED-mediated disorders and conditions can be treated prophylactically, acutely, and chronically using compounds of Formula (I), depending on the nature of the disorder or condition. Typically, the host or subject in each of these methods is human, although other mammals can also benefit from the administration of a compound of Formula (I).

The compounds of Formula (I) can be co-administered to a subject. The term "co-administered" means the administration of two or more different pharmaceutical agents or treatments (e.g., radiation treatment) that are administered to a subject by combination in the same pharmaceutical composition or separate pharmaceutical compositions. Thus co-administration involves administration at the same time of a single pharmaceutical composition comprising two or more pharmaceutical agents or administration of two or more different compositions to the same subject at the same or different times.

The compounds of the invention can be co-administered with a therapeutically effective amount of one or more agents to treat a cancer, where examples of the agents include, such as radiation, alkylating agents, angiogenesis inhibitors, antibodies, antimetabolites, antimitotics, antiproliferatives, antivirals, aurora kinase inhibitors, apoptosis promoters (for example, Bcl-xL, Bcl-w and Bfl-1), Bcr-Abl kinase inhibitors, BiTE (Bi-Specific T cell Engager) antibodies, antibody drug conjugates, biologic response modifiers, cyclin-dependent kinase inhibitors, cell cycle inhibitors, cyclooxygenase-2 inhibitors, DVDs (dual variable domain antibodies), leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPs), intercalating antibiotics, kinase inhibitors, kinesin inhibitors, Jak2 inhibitors, mammalian target of rapamycin inhibitors, microRNA's, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, phosphoinositide-3 kinase (bromodomain) inhibitors, proteosome inhibitors, purine analogs, pyrimidine analogs, receptor tyrosine kinase inhibitors, etinoids/deltoids plant alkaloids, small inhibitory ribonucleic acids (siRNAs), topoisomerase inhibitors, ubiquitin ligase inhibitors, and the like, and in combination with one or more of these agents.

BiTE antibodies are bi-specific antibodies that direct T-cells to attack cancer cells by simultaneously binding the two cells. The T-cell then attacks the target cancer cell. Examples of BiTE antibodies include adecatumumab (Micromet MT201), blinatumomab (Micromet MT103) and the like. Without being limited by theory, one of the mechanisms by which T-cells elicit apoptosis of the target cancer cell is by exocytosis of cytolytic granule components, which include perforin and granzyme B.

SiRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxynucleotide, 2'-OCH$_3$-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand.

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy chain DVD polypeptides and two light chain DVD polypeptides are referred to as DVD Ig's. Each half of a DVD Ig comprises a heavy chain DVD polypeptide, a light chain DVD polypeptide, and two antigen binding sites. Each binding site comprises a heavy chain variable domain and a light chain variable domain with a total of 6 CDRs involved in antigen binding per antigen binding site. Multispecific DVDs include DVD binding proteins that bind DLL4 and VEGF, or C-met and EFGR or ErbB3 and EGFR.

Alkylating agents include altretamine, AMD-473, AP-5280, apaziquone, bendamustine, brostallicin, busulfan, carboquone, carmustine (BCNU), chlorambucil, CLORETAZINE® (laromustine, VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, rofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like.

Antimetabolites include ALIMTA® (pemetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-β-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosfate, pelitrexol, pentostatin, raltitrexed, Ribavirin, triapine, trimetrexate, S-1, tiazofurin, tegafur, TS-1, vidarabine, UFT and the like.

Antivirals include ritonavir, hydroxychloroquine and the like.

Aurora kinase inhibitors include ABT-348, AZD-1152, MLN-8054, VX-680, Aurora A-specific kinase inhibitors, Aurora B-specific kinase inhibitors and pan-Aurora kinase inhibitors and the like.

Bcl-2 protein inhibitors include AT-101 ((−)gossypol), GENASENSE® (G3139 or oblimersen (Bcl-2-targeting antisense oligonucleotide)), IPI-194, IPI-565, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl) propyl)amino)-3-nitrobenzenesulfonamide) (ABT-737), N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide (ABT-263), GX-070 (obatoclax), venetoclax (ABT-199), and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX® (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include EGFR antibodies, ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), HERCEPTIN® (trastuzumab), TYKERB® (lapatinib), OMNITARG® (2C4, petuzumab), TAK-165, GW-572016 (ionafamib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecfic antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FC1, PU-3, radicicol, SNX-2112, STA-9090 VER49009 and the like.

Inhibitors of inhibitors of apoptosis proteins include HGS 1029, GDC-0145, GDC-0152, LCL-161, LBW-242 and the like.

Antibody drug conjugates include anti-CD22-MC-MMAF, anti-CD22-MC-MMAE, anti-CD22-MCC-DM1, CR-011-vcMMAE, PSMA-ADC, MEDI-547, SGN-19Am SGN-35, SGN-75 and the like.

Activators of death receptor pathway include TRAIL, antibodies or other agents that target TRAIL or death receptors (e.g., DR4 and DR5) such as Apomab, conatumumab, ETR2-STO1, GDC0145, (lexatumumab), HGS-1029, LBY-135, PRO-1762 and trastuzumab.

Kinesin inhibitors include Eg5 inhibitors such as AZD4877, ARRY-520; CENPE inhibitors such as GSK923295A and the like.

JAK-2 inhibitors include CEP-701 (lesaurtinib), XL019 and INCB018424 and the like.

MEK inhibitors include ARRY-142886, ARRY-438162 PD-325901, PD-98059 and the like.

mTOR inhibitors include AP-23573, CCI-779, everolimus, RAD-001, rapamycin, temsirolimus, ATP-competitive TORC1/TORC2 inhibitors, including PI-103, PP242, PP30, Torin 1 and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam), ibuprofen cream, ALEVE® (naproxen) and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin, picoplatin and the like.

Polo-like kinase inhibitors include BI-2536 and the like.

Phosphoinositide-3 kinase (PI3K) inhibitors include wortmannin, LY294002, XL-147, CAL-120, ONC-21, AEZS-127, ETP-45658, PX-866, GDC-0941, BGT226, BEZ235, XL765 and the like.

Thrombospondin analogs include ABT-510, ABT-567, ABT-898, TSP-1 and the like.

VEGFR inhibitors include AVASTIN® (bevacizumab), ABT-869, AEE-788, ANGIOZYME™ (a ribozyme that inhibits angiogenesis (Ribozyme Pharmaceuticals (Boulder, Colo.) and Chiron, (Emeryville, Calif.)), axitinib (AG-13736), AZD-2171, CP-547,632, IM-862, MACUGEN (pegaptamib), NEXAVAR® (sorafenib, BAY43-9006), pazopanib (GW-786034), vatalanib (PTK-787, ZK-222584), SUTENT® (sunitinib, SU-11248), VEGF trap, ZACTIMA™ (vandetanib, ZD-6474), GA101, ofatumumab, ABT-806 (mAb-806), ErbB3 specific antibodies, BSG2 specific antibodies, DLL4 specific antibodies and C-met specific antibodies, and the like.

Antibiotics include intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirubicin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzimab, CD20 antibodies types I and II and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL® (flutamide), EVISTA® (raloxifene), AFEMA™ (fadrozole), FARESTON® (toremifene), FASLODEX® (fulvestrant), FEMARA® (letrozole), formestane, glucocorticoids, HECTOROL® (doxercalciferol), RENAGEL® (sevelamer carbonate), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT® (buserelin), TRELSTAR® (luteinizing hormone releasing hormone (LHRH)), VANTAS® (Histrelin implant), VETORYL® (trilostane or modrastane), ZOLADEX® (fosrelin, goserelin) and the like.

Deltoids and retinoids include seocalcitol (EB1089, CB1093), lexacalcitrol (KH1060), fenretinide, PANRETIN® (aliretinoin), ATRAGEN® (liposomal tretinoin), TARGRETIN® (bexarotene), LGD-1550 and the like.

PARP inhibitors include ABT-888 (veliparib), olaparib, KU-59436, AZD-2281, AG-014699, BSI-201, BGP-15, INO-1001, ONO-2231 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b) or interferon gamma-n1, combinations thereof and the like. Other agents include ALFAFERONE®, (IFN-α), BAM-002 (oxidized glutathione), BEROMUN® (tasonermin), BEXXAR® (tositumomab), CAMPATH® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010 (anti-CTLA-4), melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (Bacillus Calmette-Guerin), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth or differentiation of tissue cells to direct them to have anti-tumor activity and include krestin, lentinan, sizofiran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like.

Ubiquitin ligase inhibitors include MDM2 inhibitors, such as nutlins, NEDD8 inhibitors such as MLN4924 and the like.

Compounds of this invention can also be used as radiosensitizers that enhance the efficacy of radiotherapy. Examples of radiotherapy include external beam radiotherapy, teletherapy, brachytherapy and sealed, unsealed source radiotherapy and the like.

Additionally, compounds having Formula (I) may be combined with other chemotherapeutic agents such as ABRAXANE™ (ABI-007), ABT-100 (farnesyl transferase inhibitor), ADVEXIN® (Ad5CMV-p53 vaccine), ALTOCOR® or MEVACOR® (lovastatin), AMPLIGEN® (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxydoxorubicin); O: Vincristine (ONCOVIN®); P: prednisone), CYPAT™ (cyproterone acetate), combreastatin A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-895 If (exatecan mesylate), enzastaurin, EPO906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTAT® (AE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECIN™ (rubitecan), OSIDEM® (antibody-based cell drug), OVAREX® MAb (murine monoclonal antibody), paclitaxel, PANDIMEX™ (aglycone saponins from ginseng comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (Streptomyces staurospores), talabostat (PT100), TARGRETIN® (bexarotene), TAXOPREXIN® (DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS® (trabectedin), ZD-6126, ZINECARD® (dexrazoxane), ZOMETA® (zolendronic acid), zorubicin and the like.

Schemes, Data, and Experimentals

The following abbreviations have the meanings indicated. ADDP means 1,1'-(azodicarbonyl)dipiperidine; AD-mix-β means a mixture of $(DHQD)_2PHAL$, $K_3Fe(CN)_6$, $K_2CO_3$, and $K_2SO_4$; 9-BBN means 9-borabicyclo(3.3.1)nonane; Boc means tert-butoxycarbonyl; $(DHQD)_2PHAL$ means hydroquinidine 1,4-phthalazinediyl diethyl ether; DBU means 1,8-diazabicyclo[5.4.0]undec-7-ene; DIBAL means diisobutylaluminum hydride; DIEA means diisopropylethylamine; DMAP means N,N-dimethylaminopyridine; DMF means N,N-dimethylformamide; dmpe means 1,2-bis(dimethylphosphino)ethane; DMSO means dimethylsulfoxide; dppb means 1,4-bis(diphenylphosphino)-butane; dppe means 1,2-bis(diphenylphosphino)ethane; dppf means 1,1'-bis(diphenylphosphino)ferrocene; dppm means 1,1-bis(diphenylphosphino)methane; EDAC-HCl means 1-(3-dimethylaminopropyl)-3-ethylcarbodiimide hydrochloride; Fmoc means fluorenylmethoxycarbonyl; HATU means O-(7-azabenzotriazol-1-yl)-N,N'N'N'-tetramethyluronium hexafluorophosphate; HMPA means hexamethylphosphoramide; IPA means isopropyl alcohol; MP-BH$_3$ means macroporous triethylammonium methylpolystyrene cyanoborohydride; TEA means triethylamine; TFA means trifluoroacetic acid; THF means tetrahydrofuran; NCS means N-chlorosuccinimide; NMM means N-methylmorpholine; NMP means N-methylpyrrolidine; and PPh$_3$ means triphenylphosphine.

Schemes

The following schemes are presented to provide what is believed to be the most useful and readily understood description of procedures and conceptual aspects of this invention. Compounds of this invention may be made by synthetic chemical processes, examples of which are shown herein. It is meant to be understood that the order of the steps in the processes may be varied, that reagents, solvents and reaction conditions may be substituted for those specifically mentioned, and that vulnerable moieties may be protected and deprotected, as necessary.

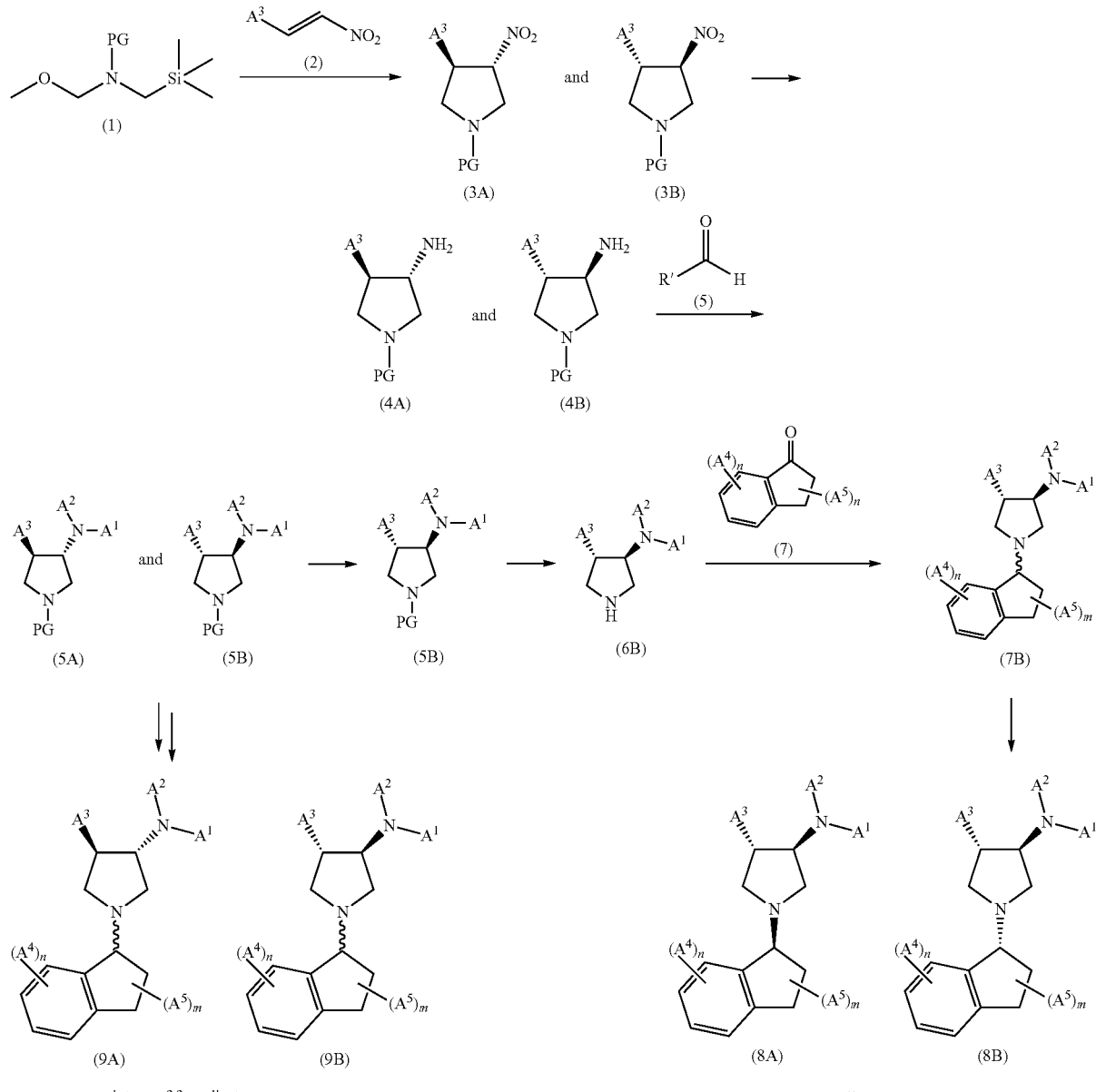

As shown in Scheme 1, compounds of formula (1) wherein PG is a suitable protecting group, can be treated with an acid such as but not limited to trifluoroacetic acid at low temperature in the presence of a compound of formula (2), wherein $A^3$ is as described herein, to provide a mixture of compounds of formula (3A) and (3B). The reaction is typically performed at a low temperature before warming to room temperature, in a solvent such as, but not limited to, dichloromethane, benzene, acetonitrile, or mixtures thereof. Compounds of formula (3A) and (3B) can be treated with hydrogen gas in the presence of a catalyst such as, but not limited to, Raney nickel or platinum(IV) oxide to provide compounds of formula (4A) and (4B). The reaction is typically performed at ambient temperature in a solvent such as, but not limited to, tetrahydrofuran, methanol, or mixtures thereof. Reaction of an aldehyde or ketone of formula (5), wherein R' is hydrogen or methyl, with compounds of formula (4A) and (4B) in the presence of a reducing agent such as but not limited to sodium triacetoxyborohydride or sodium cycanoborohydride, will provide compounds of formula (5A) and (5B), wherein $A^1$ and $A^2$ are as described herein. The reaction is typically performed at ambient temperature in a solvent such as, but not limited to, 1,2-dichloroethane, dichloromethane, methanol, ethanol, tetrahydrofuran, acetonitrile, or mixtures thereof. After separation of compounds of formula (5A) and (5B) using chiral chromatography, the PG protecting group of a compound of formula (5B) can be removed to provide a compound of formula (6B). For example, when PG is a benzyl group, the benzyl group can be removed by hydrogenolysis using palladium hydroxide on carbon in a solvent such as, but not limited to, trifluoroethanol. Reaction of a compound of formula (7), wherein $A^4$, $A^5$, m, and n are as described herein, with compounds of formula (6B) in the presence of a reducing agent such as but not limited to sodium triacetoxyborohydride or sodium cyanoborohydride, will provide compounds of formula (7B). The reaction is typically performed at an elevated temperature in a solvent such as, but not limited to 1,2-dichloroethane, dichloromethane, methanol, ethanol, tetrahydrofuran, acetonitrile, or mixtures thereof. Compounds of formula (7B) can be separated using chromatography to provide compounds of formula (8A) and (8B), which are representative of the compounds of the invention.

Alternatively, a mixture of four diastereomers of formulas (9A) and (9B), which are representative of the compounds of the invention, can be isolated using a similar synthetic pathway, but skipping the chiral separation of the intermediate and final compounds.

Scheme 2

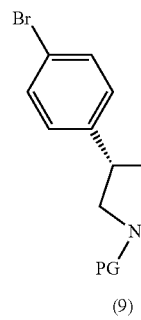

(9)

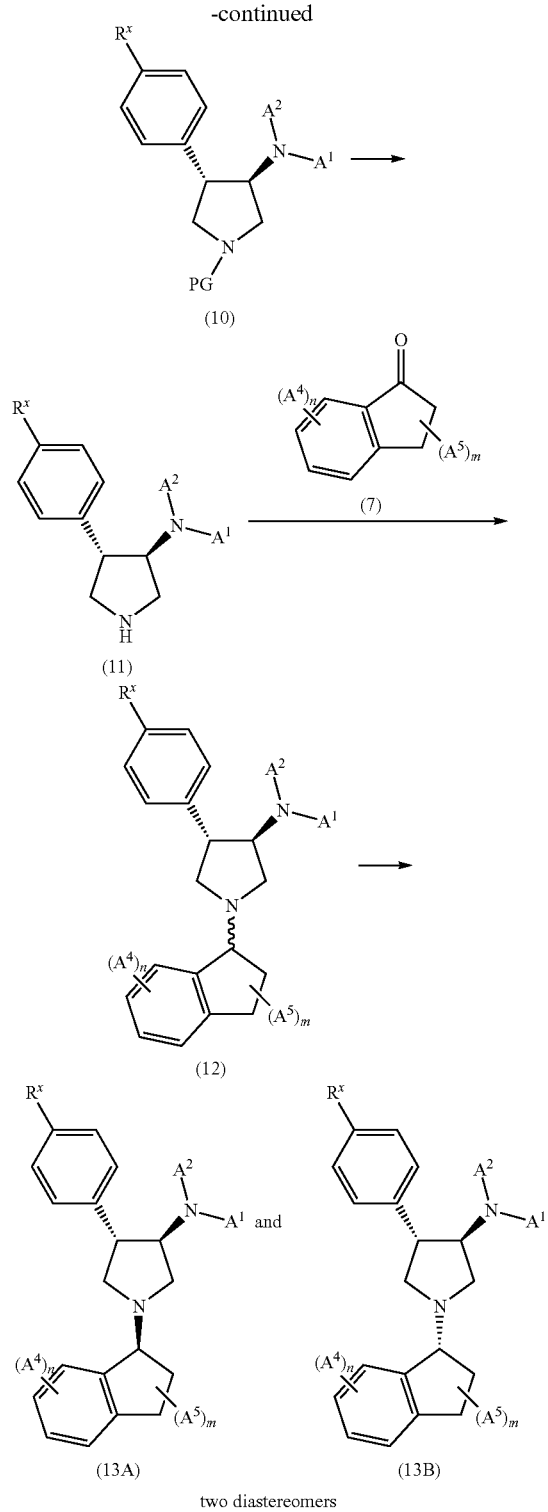

Scheme 2 describes the synthesis of compounds of Formula (I) wherein $A^3$ is a substituted phenyl ring. Compounds of formula (9) can be prepared as described in Scheme 1. Compounds of formula (10), wherein $A^1$ and $A^2$ are as described herein, PG is a suitable protecting group, and $R^x$ is as described for substituents on $A^3$, and can be prepared from compounds of formula (9) using a variety of techniques known to those skilled in the art and readily available in the literature. The nitrogen protecting group (PG) of a compound of formula (10) can be removed to provide a compound of formula (11). For example, when PG is a benzyl group, the benzyl group can be removed by hydrogenolysis as described in Scheme 1. Reaction of a compound of formula (7), wherein $A^4$, $A^5$, m, and n are as described herein, with compounds of formula (11) in the presence of a reducing agent such as but not limited to sodium triacetoxyborohydride or sodium cyanoborohydride, will provide compounds of formula (12). The reaction is typically performed at an elevated temperature in a solvent such as, but not limited to 1,2-dichloroethane, dichloromethane, methanol, ethanol, tetrahydrofuran, acetonitrile, or mixtures thereof. Compounds of formula (12) can be separated using chromatography to provide compounds of formula (13A) and (13B), which are representative of the compounds of the invention.

Testing of Representative Compounds

EED TR-FRET Binding Assay Protocol

Compounds were tested in a modified LanthaScreen competition assay. The in-vitro potency of compounds (IC50/Ki) was measured through the disruption of a TR-FRET donor-acceptor complex of terbium-labeled anti-GST (glutathione-S-transferase) antibody and a custom synthesized Oregon green (499) labeled probe using a potent, pyrrolidine-based EED binder. The fluorescent signal was generated by laser excitation of the terbium labeled anti-GST antibody at 337 nm, which leads to an increase in fluorescence of the acceptor probe, measured as a ratio of the signal at 495 nm/520 nm.

For the assay, compounds were dispensed in assay ready plates using a 3-fold serial dilution from 50 uM to ~8.5 pM using an Echo 550 Acoustic Liquid Handler (Labcyte). The following buffer was used to set up the binding reactions: 20 mM Tris-HCl pH 7.5, 200 mM NaCl, 0.01% Tween-20, 10 uM DTT (dithiothreitol), and 0.05% BSA (bovine serum albumin), with the DTT and BSA added fresh prior to initiating the binding assay. The binding assay was initiated by adding a 10 ul mixture of 1 nM GST-tagged EED binder, 400 nM OG(488) labeled probe, and terbium-labeled antibody to the pre-dispensed compounds. The reactions were then incubated for 1 hour at 25° C. in a humidified chamber prior to detection on the Perkin Elmer Envision plate reader using a Lanthascreen TR-FRET protocol. Results are shown in Table 1.

TABLE 1

| Example | TR-FRET Binding (uM) |
| --- | --- |
| 1 | 0.000313 |
| 2 | 0.000461 |
| 3 | 0.00986 |
| 4 | 0.0132 |
| 5 | 0.011 |
| 6 | 0.00477 |
| 7 | 0.00608 |
| 8 | 0.0107 |
| 9 | 0.0101 |
| 10 | 0.29 |
| 11 | 0.0231 |
| 12 | ND |
| 13 | ND |
| 14 | ND |
| 15 | ND |
| 16 | 0.491 |

TABLE 1-continued

| Example | TR-FRET Binding (uM) |
| --- | --- |
| 17 | ND |
| 18 | 0.0162 |
| 19 | 0.0125 |
| 20 | ND |
| 21 | 0.0707 |
| 22 | 0.00285 |
| 23 | 0.00272 |
| 24 | 0.0205 |
| 25 | 0.0182 |
| 26 | 0.00251 |
| 27 | 0.00184 |
| 28 | 0.489 |
| 29 | 0.0232 |
| 30 | 0.0114 |
| 31 | 0.00819 |
| 32 | 0.00454 |
| 33 | >50 |
| 34 | 0.104 |
| 35 | 0.0068 |
| 36 | 0.0143 |
| 37 | 0.00267 |
| 38 | 0.0687 |
| 39 | 0.00107 |
| 40 | 0.00462 |
| 41 | 0.00199 |
| 42 | >50 |
| 43 | 0.000297 |
| 44 | 0.000652 |
| 45 | 0.000303 |
| 46 | 0.00336 |
| 47 | 0.0423 |
| 48 | 0.018 |
| 49 | 0.000739 |
| 50 | 0.00115 |
| 51 | 0.0124 |
| 52 | 0.0010 |
| 53 | 0.0123 |
| 54 | 0.00106 |
| 55 | 0.0132 |
| 56 | 0.00139 |
| 57 | 0.0123 |
| 58 | 0.00167 |
| 59 | 0.00107 |
| 60 | 0.00662 |
| 61 | 0.00114 |
| 62 | 0.00135 |
| 63 | 0.00147 |
| 64 | 0.000835 |
| 65 | 0.00175 |
| 66 | 0.00268 |
| 67 | 0.00306 |
| 68 | 0.00237 |
| 69 | 0.00389 |
| 70 | 0.000853 |
| 71 | 0.00113 |
| 72 | 0.000923 |
| 73 | 0.000825 |
| 74 | 0.000633 |
| 75 | 0.000906 |
| 76 | ND |
| 77 | 0.00103 |
| 78 | ND |
| 79 | 0.00245 |
| 80 | 0.00944 |
| 81 | 0.0982 |
| 83 | 0.0109 |
| 84 | 0.000296 |
| 85 | 0.000561 |
| 86 | 0.0148 |
| 87 | 0.000481 |
| 88 | 0.0262 |
| 89 | 0.031 |
| 90 | 0.0208 |
| 91 | 0.0307 |
| 92 | 0.066 |
| 93 | 0.00276 |

TABLE 1-continued

| Example | TR-FRET Binding (uM) |
|---|---|
| 94 | 0.0049 |
| 95 | 0.0027 |
| 96 | 0.00426 |
| 97 | 0.0336 |
| 98 | 0.00137 |
| 99 | 0.00191 |
| 100 | 0.0584 |
| 101 | 0.00174 |
| 102 | 0.000335 |
| 103 | 0.00101 |
| 104 | 0.0153 |
| 105 | 0.000347 |
| 106 | 0.000782 |
| 107 | 0.00108 |
| 108 | 0.0015 |
| 109 | 0.0016 |
| 110 | 0.00105 |
| 111 | 0.00259 |
| 112 | 0.0012 |
| 113 | 0.000679 |
| 114 | 0.00558 |
| 115 | 0.00173 |
| 116 | 0.00177 |
| 117 | 0.00126 |
| 118 | 0.00335 |
| 119 | 0.00199 |
| 120 | 0.00346 |
| 121 | 0.00379 |
| 122 | 0.00288 |
| 123 | 0.00353 |
| 124 | 0.00156 |
| 125 | 0.00107 |
| 126 | 0.00214 |
| 127 | 0.00175 |
| 128 | 0.00103 |
| 129 | 0.000739 |
| 130 | 0.00105 |
| 131 | 0.000406 |
| 132 | 0.00144 |
| 133 | 0.00145 |
| 134 | 0.0025 |
| 135 | 0.00145 |
| 136 | 0.00205 |
| 137 | 0.00191 |
| 138 | 0.119 |
| 139 | 0.0835 |
| 140 | 0.0613 |
| 141 | 0.0468 |
| 142 | 0.026 |
| 143 | 0.0194 |
| 144 | 0.0121 |
| 145 | 0.0052 |
| 146 | 0.00458 |
| 147 | 0.00384 |
| 148 | 0.00287 |
| 149 | 0.00258 |
| 150 | 0.0024 |
| 151 | 0.00224 |
| 152 | 0.00204 |
| 153 | 0.00201 |
| 154 | 0.00198 |
| 155 | 0.00175 |
| 156 | 0.00141 |
| 157 | 0.0014 |
| 158 | 0.00137 |
| 159 | 0.00114 |
| 160 | 0.00106 |
| 161 | 0.000669 |
| 162 | 0.000646 |
| 163 | 0.000638 |
| 164 | 0.000494 |
| 165 | 0.00048 |
| 166 | 0.000454 |
| 167 | 0.000399 |

ND = no data

H3K27me3 AlphaLISAR® Assay Protocols

G401 cells (ATCC catalog # CRL-1441) were maintained in McCoy's 5a medium (ATCC) supplemented with 10% heat-inactivated FBS (HyClone) at 37° C. in a humidified $CO_2$ incubator. OCILY19 cells (DSMZ catalog #ACC 528) were maintained in IMDM (Invitrogen) supplemented with 10% human serum (Sigma) at 37° C. in a humidified $CO_2$ incubator. 5,000 cells were plated into each well of 96-well Corning CellBing cell culture plates and incubated overnight at 37° C. in a humidified $CO_2$ incubator. The compounds (1/1,000× final dilution from DMSO stocks into the cell culture medium) were added to the cell culture plates the next day. The cell culture plates were then incubated for 6 more days. H3K27me3 AlphaLISA assay was performed on the cell culture samples by using AlphaLISAR® H3K27me3 Cellular Detection Kit (PerkinElmer) and 96-well white half-area plates (PerkinElmer). Results are shown in Table 2.

TABLE 2

| Example | OCILY-19 IC50 (uM) | G401 IC50 (uM) |
|---|---|---|
| 1 | 0.0621 | 0.0555 |
| 2 | 0.14 | 0.0992 |
| 6 | 1.76 | 0.244 |
| 7 | 3.12 | 3.19 |
| 8 | 0.637 | ND |
| 11 | 0.171 | ND |
| 19 | 0.597 | 0.725 |
| 22 | 0.944 | 0.449 |
| 23 | 0.393 | 0.198 |
| 24 | 0.601 | ND |
| 25 | 1.06 | ND |
| 26 | 1.36 | ND |
| 31 | 3.45 | ND |
| 32 | 2.11 | ND |
| 37 | 0.874 | ND |
| 40 | 1.08 | ND |
| 43 | 0.0504 | 0.0326 |
| 44 | 0.144 | 0.0328 |
| 45 | 0.0433 | 0.0311 |
| 49 | 0.20 | 0.182 |
| 52 | 0.075 | ND |
| 54 | 0.0991 | ND |
| 56 | 0.556 | ND |
| 58 | 0.376 | ND |
| 59 | 0.163 | ND |
| 61 | 0.804 | ND |
| 62 | 0.282 | ND |
| 63 | 0.191 | 0.0556 |
| 64 | 0.334 | ND |
| 65 | 0.306 | 0.576 |
| 70 | 0.248 | 0.129 |
| 71 | 0.155 | 0.0521 |
| 72 | 0.132 | 0.0399 |
| 73 | 0.113 | ND |
| 74 | 0.363 | 0.185 |
| 75 | 3.17 | 2.3 |
| 76 | 1.34 | ND |
| 77 | 0.655 | 0.288 |
| 87 | 0.178 | 0.0626 |
| 88 | 2.44 | ND |
| 89 | 4.35 | ND |
| 101 | 0.368 | ND |
| 102 | 0.101 | 0.0407 |
| 103 | 0.183 | 0.0306 |
| 105 | 0.0271 | 0.0564 |
| 106 | 0.0695 | 0.0344 |
| 107 | 0.497 | 0.084 |
| 110 | 0.379 | 0.225 |
| 112 | 0.446 | 0.0702 |
| 113 | 3.28 | 0.799 |
| 119 | 0.214 | 0.12 |
| 124 | 0.207 | 0.0864 |
| 125 | 0.203 | ND |

TABLE 2-continued

| Example | OCILY-19 IC50 (uM) | G401 IC50 (uM) |
|---|---|---|
| 126 | 0.22 | ND |
| 128 | 0.241 | ND |
| 129 | 0.102 | 0.186 |
| 130 | 0.306 | ND |
| 131 | 0.158 | 0.0573 |
| 132 | 0.162 | 0.0633 |
| 133 | 0.206 | 0.0615 |
| 135 | 0.719 | 0.108 |
| 136 | 0.617 | 0.332 |
| 149 | 1.14 | 0.636 |
| 152 | 1.79 | 0.476 |
| 154 | 0.493 | 0.372 |
| 155 | 3.22 | ND |
| 156 | 0.293 | 0.212 |
| 157 | 0.205 | 0.227 |
| 158 | 0.0872 | 0.127 |
| 159 | 0.237 | 0.158 |
| 160 | 0.152 | 0.19 |
| 161 | 0.571 | 0.151 |
| 162 | 0.492 | 0.291 |
| 163 | 0.583 | ND |
| 164 | 0.461 | 0.291 |
| 165 | 0.272 | 0.0559 |
| 166 | 0.275 | 0.228 |
| 167 | 0.267 | 0.131 |

ND = no data

CTG Assay

Pfeiffer cells (ATCC catalog # CRL-2632) were maintained in IMDM Medium (Invitrogen) supplemented with 10% human serum (Sigma) at 37° C. in a humidified $CO_2$ incubator. 1,000 cells were plated into each well of 96-well Corning CellBing cell culture plates and incubated overnight at 37° C. in a humidified $CO_2$ incubator. The compounds (1/1,000×final dilution from DMSO stocks into the cell culture medium) were added to the cell culture plates the next day. The cell culture plates were then incubated for 10 more days. CTG cell viability assay was performed on the cell culture samples by using CellTiter-Glo® Luminescent Cell Viability Assay Kit (Promega). Results are shown in Table 3.

TABLE 3

| Example | Cell Proliferation IC50 (uM) |
|---|---|
| 1 | 0.0725 |
| 2 | 0.126 |
| 6 | 3.3 |
| 7 | 2.34 |
| 8 | 1.32 |
| 11 | 0.301 |
| 19 | 0.654 |
| 22 | 0.422 |
| 23 | 0.921 |
| 24 | 2.92 |
| 25 | 2.93 |
| 26 | 3.03 |
| 30 | 3.1 |
| 31 | 0.754 |
| 32 | 2.81 |
| 35 | >10 |
| 37 | 2.66 |
| 40 | 0.941 |
| 41 | 0.188 |
| 43 | 0.0334 |
| 44 | 0.0836 |
| 45 | 0.0284 |
| 46 | 1.01 |
| 49 | 0.194 |
| 52 | 0.0894 |
| 54 | 0.114 |
| 56 | 0.145 |
| 58 | 0.314 |
| 59 | 0.127 |
| 60 | 0.302 |
| 61 | 0.204 |
| 62 | 0.429 |
| 63 | 0.0727 |
| 64 | 0.166 |
| 65 | 0.948 |
| 66 | 1.13 |
| 67 | 1.63 |
| 68 | 0.491 |
| 70 | 0.266 |
| 71 | 0.108 |
| 72 | 0.121 |
| 73 | 0.0995 |
| 74 | 0.107 |
| 75 | 1.76 |
| 76 | 1.9 |
| 77 | 1.07 |
| 79 | 1.02 |
| 80 | 1.52 |
| 87 | 0.0941 |
| 88 | 3.55 |
| 89 | 6.37 |
| 95 | 1.72 |
| 98 | 0.126 |
| 99 | 0.303 |
| 102 | 0.0736 |
| 103 | 0.0648 |
| 105 | 0.039 |
| 106 | 0.0749 |
| 107 | 0.284 |
| 108 | 0.152 |
| 109 | 0.141 |
| 110 | 0.111 |
| 111 | 0.171 |
| 112 | 0.133 |
| 113 | 0.399 |
| 114 | 3.13 |
| 115 | 0.224 |
| 116 | 0.0996 |
| 117 | 0.111 |
| 118 | 0.298 |
| 119 | 0.247 |
| 122 | 0.556 |
| 123 | 1.53 |
| 124 | 0.349 |
| 125 | 0.268 |
| 126 | 0.329 |
| 127 | 0.335 |
| 128 | 0.194 |
| 129 | 0.0981 |
| 130 | 0.311 |
| 131 | 0.122 |
| 132 | 0.0943 |
| 133 | 0.133 |
| 134 | 0.833 |
| 135 | 0.115 |
| 136 | 1.52 |
| 137 | 0.299 |
| 146 | 2.9 |
| 147 | 0.535 |
| 148 | >10 |
| 149 | 0.97 |
| 150 | 0.95 |
| 151 | 0.559 |
| 152 | 0.804 |
| 153 | 0.419 |
| 154 | 0.455 |
| 155 | 0.395 |
| 156 | 0.375 |

TABLE 3-continued

| Example | Cell Proliferation IC50 (uM) |
|---|---|
| 157 | 0.354 |
| 158 | 0.385 |
| 159 | 0.246 |
| 160 | 0.301 |
| 161 | 0.293 |
| 162 | 0.216 |
| 163 | 0.271 |
| 164 | 0.148 |
| 165 | 0.286 |
| 166 | 0.129 |
| 167 | 0.143 |

EXPERIMENTALS

The following examples are presented to provide what is believed to be the most useful and readily understood description of procedures and conceptual aspects of this invention. Each exemplified compound and intermediate was named using ACD/Name 2015 release (File Version N20E14, Build 75170, 19 Dec. 2014, Advanced Chemistry Development Inc., Toronto, Ontario), or ChemDraw® Professional Ver. 15.0.0.106 (CambridgeSoft, Cambridge, Mass.).

Example 1

(3R,4S)-1-(7-fluoro-2,3-dihydro-1H-inden-1-yl)-4-{4-[4-(methanesulfonyl)piperazin-1-yl]phenyl}-N,N-dimethylpyrrolidin-3-amine Example 1A rac-(3S,4R)-1-benzyl-3-(4-bromophenyl)-4-nitropyrrolidine To a solution of (E)-1-bromo-4-(2-nitrovinyl)benzene (1 g, 4.39 mmol) and trifluoroacetic acid (three drops) in dichloromethane (9.23 ml) at 0° C. was added a solution of N-benzyl-1-methoxy-N-((trimethylsilyl)methyl)methanamine (1.338 ml, 5.26 mmol) in 9 ml dichloromethane dropwise by syringe. The mixture was stirred at 0° C. for 1 hour, allowed to warm to room temperature, and stirred at room temperature for 1.5 hours. The mixture was added to saturated sodium bicarbonate (25 ml) and the separated organic layer was washed with brine (20 ml), dried with magnesium sulfate, filtered and concentrated. The residue was flash chromatographed (30 mm silica gel column; 5% ethyl acetate/heptanes) to provide the title compound.

Example 1B rac-(3R,4S)-1-benzyl-4-(4-bromophenyl)pyrrolidin-3-amine rac-(3S,4R)-1-Benzyl-3-(4-bromophenyl)-4-nitropyrrolidine (36 g, 100 mmol) and tetrahydrofuran (100 ml) were added to Raney Ni (70 g, 100 mmol) in a 500 mL SS pressure bottle and the mixture was stirred for 2.2 hours at 1 atm hydrogen and 25° C. The suspension was filtered and concentrated to provide the title compound which was used in the next step without purification.

Example 1C (3R,4S)-1-benzyl-4-(4-bromophenyl)-N,N-dimethylpyrrolidin-3-amine

To a solution of (3R,4S)-1-benzyl-4-(4-bromophenyl)pyrrolidin-3-amine (1.193 g, 3.6 mmol) and formaldehyde (aqueous solution, 1.102 ml, 14.40 mmol) in 1,2-dichloroethane (18.00 ml) was added sodium triacetoxyborohydride (3.05 g, 14.40 mmol) in a single portion. The suspension was stirred overnight and was quenched with 30 ml of saturated aqueous sodium bicarbonate. The bilayer was concentrated under vacuum and diluted with ethyl acetate (50 ml). The separated aqueous layer was extracted with ethyl acetate (20 ml) and the combined organic layers were washed with brine (20 ml), dried with magnesium sulfate, filtered and concentrated. The residue was flash chromatographed (Biotage 25 g HP SNAP Cartridge, [3:1 ethyl acetate/ethanol]/heptanes gradient, 5-50%) to afford rac-(3R,4S)-1-benzyl-4-(4-bromophenyl)-N,N-dimethylpyrrolidin-3-amine. The racemic mixture was separated by chiral SFC (ChiralPak AD-H column, 5-50% methanol with 0.1% diethylamine) to provide the title compound.

Example 1D (3R,4S)-1-benzyl-N,N-dimethyl-4-(4-(4-(methylsulfonyl)piperazin-1-yl)phenyl)pyrrolidin-3-amine A suspension of (3R,4S)-1-benzyl-4-(4-bromophenyl)-N,N-dimethylpyrrolidin-3-amine (3.24 g, 9.02 mmol), 1-(methylsulfonyl)piperazine hydrochloride (2.172 g, 10.82 mmol), tris(dibenzylideneacetone)dipalladium (0) (0.826 g, 0.902 mmol), 2-(dicyclohexylphosphine)-2',4',6'-tri-isopropylbiphenyl (0.860 g, 1.803 mmol) and sodium tert-butoxide (2.167 g, 22.54 mmol) in dioxane (32.2 ml) in a 250 ml round bottom flask was taken through three vacuum/nitrogen-purge cycles and heated in a heating block under a condenser at 110° C. for 2 hours. The mixture was diluted with ethyl acetate and filtered through diatomaceous earth with ethyl acetate washes. The filtrate was washed with saturated sodium bicarbonate (20 ml), dried with magnesium sulfate, filtered, and concentrated. The residue was flash chromatographed (50 mm silica gel column; 6.5% methanol/dichloromethane w/0.1% ammonium hydroxide) to afford the title compound.

Example 1E (3R,4S)—N,N-dimethyl-4-(4-(4-(methylsulfonyl)piperazin-1-yl)phenyl)pyrrolidin-3-amine (3R,4S)-1-Benzyl-N,N-dimethyl-4-(4-(4-(methylsulfonyl)piperazin-1-yl)phenyl)pyrrolidin-3-amine (3.65 g, 8.25 mmol) and trifluoroethanol (30 ml) were added to wet 20% palladium hydroxide on carbon (0.2 g, 0.145 mmol) in a 50 ml pressure bottle and the mixture was shaken for 4 hours at 30 psi and room temperature. The mixture was filtered and concentrated to afford the title compound which was used in the next step without purification.

Example 1F (3R,4S)-1-(7-fluoro-2,3-dihydro-1H-inden-1-yl)-4-{4-[4-(methanesulfonyl)piperazin-1-yl]phenyl}-N,N-dimethylpyrrolidin-3-amine To a solution of (3R,4S)—N,N-dimethyl-4-(4-(4-(methylsulfonyl)piperazin-1-yl)phenyl)pyrrolidin-3-amine (2.91 g, 8.26 mmol) and 7-fluoro-2,3-dihydro-1H-inden-1-one (1.364 g, 9.08 mmol) in pH 4 buffered methanol (27.5 ml) was added sodium cyanoborohydride (0.778 g, 12.38 mmol). The resulting cloudy solution was stirred at 50° C. for 2.5 days and was allowed to cool to room temperature. The crude mixture was quenched and made slightly basic with saturated aqueous sodium bicarbonate (30 ml) and solid sodium bicarbonate and was diluted with ethyl acetate (60 ml). The separated aqueous layer was extracted with ethyl acetate (2×30 ml) and the combined organic layers were washed with brine (15 ml), dried with magnesium sulfate, filtered and concentrated. The crude material was flash chromatographed (50 mm silica gel column; 6-7% methanol/dichloromethane w/0.1% ammonium hydroxide) to afford the title compound as well as a mixture of title compound and an impurity. Flash chromatography of the mixture under the same chromatography conditions provided additional title compound. The compound was a 60:40 mixture of epimers as assessed by NMR: $^1$H NMR (501 MHz, DMSO-$d_6$) δ 7.28-7.19 (m, 1H), 7.19-7.12 (m, 2H), 7.08 (d, J=7.4 Hz, 1H), 6.94 (td, J=8.6, 6.1 Hz, 1H), 6.88-6.81 (m, 2H), 4.31 (dd, J=7.4, 1.8 Hz, 0.4H), 4.17 (dd, J=6.9, 1.7 Hz, 0.6H), 3.20 (m, 4H), 3.15 (m, 4H), 3.07-2.95 (m, 2H), 2.89 (s, 3H), 2.87-2.71 (m, 4H), 2.63 (dd, J=9.1, 5.7 Hz, 0.6H), 2.52 (dd, J=9.0, 5.8 Hz, 0.4H), 2.45-2.37 (m, 1H), 2.18 (m, 1H), 2.10-1.92 (m, 1H), 2.03 (s, 3H), 2.02 (s, 3H). MS (ESI(+)) m/e 487 (M+H)$^+$.

Table 4.

The following Examples were prepared using methods similar to those described in Example 1. Some products were purified by silica gel column chromatography while others were purified by reverse-phase HPLC. Accordingly, some Examples were isolated as trifluoroacetic acid salts.

TABLE 5

| Ex | Name | MS |
|---|---|---|
| 2 | rac-(3R,4S)-1-(7-fluoro-2,3-dihydro-1H-inden-1-yl)-4-{4-[4-(methanesulfonyl)piperazin-1-yl]phenyl}-N,N-dimethylpyrrolidin-3-amine | (ESI(+)) m/e 487 (M + H)$^+$ |
| 3 | (3S,4R)-1-(7-fluoro-2,3-dihydro-1H-inden-1-yl)-4-{4-[4-(methanesulfonyl)piperazin-1-yl]phenyl}-N,N-dimethylpyrrolidin-3-amine | (ESI(+)) m/e 487 (M + H)$^+$ |
| 4 | (3S,4R)-1-[(1S)-7-fluoro-2,3-dihydro-1H-inden-1-yl]-4-{4-[4-(methanesulfonyl)piperazin-1-yl]phenyl}-N,N-dimethylpyrrolidin-3-amine | (ESI(+)) m/e 487 (M + H)$^+$ |
| 5 | (3S,4R)-1-[(1R)-7-fluoro-2,3-dihydro-1H-inden-1-yl]-4-{4-[4-(methanesulfonyl)piperazin-1-yl]phenyl}-N,N-dimethylpyrrolidin-3-amine | (ESI(+)) m/e 487 (M + H)$^+$ |
| 6 | rac-(3S,4R)-4-(4-bromophenyl)-1-(7-fluoro-2,3-dihydro-1H-inden-1-yl)-N,N-dimethylpyrrolidin-3-amine | (ESI(+)) m/e 403 (M + H)$^+$ |
| 7 | rac-(3S,4R)-4-(4-chlorophenyl)-1-(7-fluoro-2,3-dihydro-1H-inden-1-yl)-N,N-dimethylpyrrolidin-3-amine | (ESI(+)) m/e 359 (M + H)$^+$ |
| 8 | rac-4-[(3S,4R)-4-(dimethylamino)-1-(7-fluoro-2,3-dihydro-1H-inden-1-yl)pyrrolidin-3-yl]benzene-1-sulfonamide | (ESI(+)) m/e 404 (M + H)$^+$ |
| 9 | (3R,4S)-1-[(1S)-2,3-dihydro-1H-inden-1-yl]-4-[4-(methanesulfonyl)phenyl]-N,N-dimethylpyrrolidin-3-amine | (ESI(+)) m/e 385 (M + H)$^+$ |
| 10 | (3S,4R)-1-[(1S)-2,3-dihydro-1H-inden-1-yl]-4-[4-(methanesulfonyl)phenyl]-N,N-dimethylpyrrolidin-3-amine | (ESI(+)) m/e 385 (M + H)$^+$ |
| 11 | (3R,4S)-1-[(1S)-7-fluoro-2,3-dihydro-1H-inden-1-yl]-4-[4-(methanesulfonyl)phenyl]-N,N-dimethylpyrrolidin-3-amine | (APCI(+)) m/e 403 (M + H)$^+$ |
| 12 | (3R,4S)-1-[(1R)-7-fluoro-2,3-dihydro-1H-inden-1-yl]-4-[4-(methanesulfonyl)phenyl]-N,N-dimethylpyrrolidin-3-amine | (ESI(+)) m/e 403 (M + H)$^+$ |
| 13 | (3S,4R)-1-[(1S)-7-fluoro-2,3-dihydro-1H-inden-1-yl]-4-[4-(methanesulfonyl)phenyl]-N,N-dimethylpyrrolidin-3-amine | (ESI(+)) m/e 403 (M + H)$^+$ |
| 14 | (3S,4R)-1-[(1R)-7-fluoro-2,3-dihydro-1H-inden-1-yl]-4-[4-(methanesulfonyl)phenyl]-N,N-dimethylpyrrolidin-3-amine | (ESI(+)) m/e 403 (M + H)$^+$ |
| 15 | rac-(1S)-1-{(3S,4R)-3-(dimethylamino)-4-[4-(methanesulfonyl)phenyl]pyrrolidin-1-yl}-7-fluoro-2,3-dihydro-1H-inden-5-ol | (ESI(+)) m/e 419 (M + H)$^+$ |
| 16 | rac-(1R,3R)-3-{(3R,4S)-3-(dimethylamino)-4-[4-(methanesulfonyl)phenyl]pyrrolidin-1-yl}-4-fluoro-2,3-dihydro-1H-inden-1-ol | (ESI(+)) m/e 419 (M + H)$^+$ |
| 17 | rac-(1R)-1-{(3S,4R)-3-(dimethylamino)-4-[4-(methanesulfonyl)phenyl]pyrrolidin-1-yl}-7-fluoro-2,3-dihydro-1H-inden-5-ol | (ESI(+)) m/e 419 (M + H)$^+$ |
| 18 | rac-(1S,3S)-3-{(3R,4S)-3-(dimethylamino)-4-[4-(methanesulfonyl)phenyl]pyrrolidin-1-yl}-4-fluoro-2,3-dihydro-1H-inden-1-ol | (ESI(+)) m/e 419 (M + H)$^+$ |
| 19 | rac-4-{(3R,4S)-4-(dimethylamino)-1-[(1R)-7-fluoro-2,3-dihydro-1H-inden-1-yl]pyrrolidin-3-yl}benzonitrile | (ESI(+)) m/e 350 (M + H)$^+$ |

TABLE 5-continued

| Ex | Name | MS |
|---|---|---|
| 20 | rac-methyl 4-[(3R,4S)-1-[(1R)-2,3-dihydro-1H-inden-1-yl]-4-(dimethylamino)pyrrolidin-3-yl]benzoate | (ESI(+)) m/e 365 (M + H)$^+$ |
| 21 | rac-methyl 4-[(3S,4R)-1-(7-chloro-2,3-dihydro-1H-inden-1-yl)-4-(dimethylamino)pyrrolidin-3-yl]benzoate | (ESI(+)) m/e 399 (M + H)$^+$ |
| 22 | rac-methyl 4-[(3R,4S)-4-(dimethylamino)-1-(7-fluoro-2,3-dihydro-1H-inden-1-yl)pyrrolidin-3-yl]benzoate | (ESI(+)) m/e 383 (M + H)$^+$ |
| 23 | rac-(3S,4R)-4-(3,4-dimethoxyphenyl)-1-(7-fluoro-2,3-dihydro-1H-inden-1-yl)-N,N-dimethylpyrrolidin-3-amine | (ESI(+)) m/e 383 (M + H)$^+$ |
| 24 | rac-4-[(3S,4R)-4-(dimethylamino)-1-(7-fluoro-2,3-dihydro-1H-inden-1-yl)pyrrolidin-3-yl]-N-methylbenzamide | (ESI(+)) m/e 382 (M + H)$^+$ |
| 25 | rac-4-[(3S,4R)-1-(7-chloro-2,3-dihydro-1H-inden-1-yl)-4-(dimethylamino)pyrrolidin-3-yl]-N,N-dimethylbenzamide | (ESI(+)) m/e 412 (M + H)$^+$ |
| 26 | rac-4-[(3S,4R)-4-(dimethylamino)-1-(7-fluoro-2,3-dihydro-1H-inden-1-yl)pyrrolidin-3-yl]-N,N-dimethylbenzamide | (ESI(+)) m/e 396 (M + H)$^+$ |
| 27 | rac-(3R,4S)-4-(4-bromo-3-methylphenyl)-1-(7-fluoro-2,3-dihydro-1H-inden-1-yl)-N,N-dimethylpyrrolidin-3-amine | (ESI(+)) m/e 417 (M + H)$^+$ |
| 28 | rac-4-[(3S,4R)-1-(7-chloro-2,3-dihydro-1H-inden-1-yl)-4-(dimethylamino)pyrrolidin-3-yl]benzoic acid | (ESI(+)) m/e 385 (M + H)$^+$ |
| 29 | rac-4-[(3R,4S)-4-(dimethylamino)-1-(7-fluoro-2,3-dihydro-1H-inden-1-yl)pyrrolidin-3-yl]benzoic acid | (ESI(+)) m/e 369 (M + H)$^+$ |
| 30 | rac-(3R,4S)-1-[(3S)-3,7-difluoro-2,3-dihydro-1H-inden-1-yl]-4-[4-(methanesulfonyl)phenyl]-N,N-dimethylpyrrolidin-3-amine | (ESI(+)) m/e 419 (M + H)$^+$ |
| 31 | rac-(3R,4S)-1-[(1R,3S)-3,7-difluoro-2,3-dihydro-1H-inden-1-yl]-4-[4-(methanesulfonyl)phenyl]-N,N-dimethylpyrrolidin-3-amine | (ESI(+)) m/e 419 (M + H)$^+$ |
| 32 | rac-(3R,4S)-1-[(1S,3S)-3,7-difluoro-2,3-dihydro-1H-inden-1-yl]-4-[4-(methanesulfonyl)phenyl]-N,N-dimethylpyrrolidin-3-amine | (ESI(+)) m/e 419 (M + H)$^+$ |
| 33 | (3S)-3-{(3S,4R)-3-(dimethylamino)-4-[4-(methanesulfonyl)phenyl]pyrrolidin-1-yl}-4-fluoro-2,3-dihydro-1H-inden-1-ol | (ESI(+)) m/e 419 (M + H)$^+$ |
| 34 | rac-(1R,3S)-3-{(3R,4S)-3-(dimethylamino)-4-[4-(methanesulfonyl)phenyl]pyrrolidin-1-yl}-4-fluoro-2,3-dihydro-1H-inden-1-ol | (ESI(+)) m/e 419 (M + H)$^+$ |
| 35 | rac-4-[(3R,4S)-4-(dimethylamino)-1-(7-fluoro-2,3-dihydro-1H-inden-1-yl)pyrrolidin-3-yl]benzamide | (ESI(+)) m/e 468 (M + H)$^+$ |
| 36 | rac-4-[(3S,4R)-4-(dimethylamino)-1-(7-fluoro-2,3-dihydro-1H-inden-1-yl)pyrrolidin-3-yl]-2-methylbenzoic acid | (ESI(+)) m/e 383 (M + H)$^+$ |
| 37 | rac-4-[(3S,4R)-4-(dimethylamino)-1-(7-fluoro-2,3-dihydro-1H-inden-1-yl)pyrrolidin-3-yl]-2-methylbenzonitrile | (ESI(+)) m/e 363 (M + H)$^+$ |
| 38 | rac-4-[(3S,4R)-4-(dimethylamino)-1-(2-hydroxy-2,3-dihydro-1H-inden-1-yl)pyrrolidin-3-yl]-2-methylbenzonitrile | (ESI(+)) m/e 362 (M + H)$^+$ |
| 39 | rac-methyl 4-[(3S,4R)-4-(dimethylamino)-1-(7-fluoro-2,3-dihydro-1H-inden-1-yl)pyrrolidin-3-yl]-2-methylbenzoate | (ESI(+)) m/e 397 (M + H)$^+$ |
| 40 | rac-{4-[(3S,4R)-4-(dimethylamino)-1-(7-fluoro-2,3-dihydro-1H-inden-1-yl)pyrrolidin-3-yl]phenyl}[(3S)-3-hydroxypyrrolidin-1-yl]methanone | (ESI(+)) m/e 438 (M + H)$^+$ |
| 41 | rac-(3S,4R)-1-(7-fluoro-2,3-dihydro-1H-inden-1-yl)-N,N-dimethyl-4-[4-(piperazin-1-yl)phenyl]pyrrolidin-3-amine | (ESI(+)) m/e 409 (M + H)$^+$ |
| 42 | 1-(4-{4-[(3S,4R)-1-(2,3-dihydro-1H-inden-1-yl)-4-(dimethylamino)pyrrolidin-3-yl]phenyl}piperazin-1-yl)ethan-1-one | (ESI(+)) m/e 433 (M + H)$^+$ |
| 43 | 1-(4-{4-[(3S,4R)-4-(dimethylamino)-1-(7-fluoro-2,3-dihydro-1H-inden-1-yl)pyrrolidin-3-yl]phenyl}piperazin-1-yl)ethan-1-one | (ESI(+)) m/e 451 (M + H)$^+$ |
| 44 | rac-1-(4-{4-[(3S,4R)-4-(dimethylamino)-1-(7-fluoro-2,3-dihydro-1H-inden-1-yl)pyrrolidin-3-yl]phenyl}piperazin-1-yl)ethan-1-one | (ESI(+)) m/e 451 (M + H)$^+$ |
| 45 | 1-[4-(4-{(3S,4R)-4-(dimethylamino)-1-[(1S)-7-fluoro-2,3-dihydro-1H-inden-1-yl]pyrrolidin-3-yl}phenyl)piperazin-1-yl]ethan-1-one | (ESI(+)) m/e 451 (M + H)$^+$ |

TABLE 5-continued

| Ex | Name | MS |
|---|---|---|
| 46 | 1-[4-(4-{(3S,4R)-4-(dimethylamino)-1-[(1R)-7-fluoro-2,3-dihydro-1H-inden-1-yl]pyrrolidin-3-yl}phenyl)piperazin-1-yl]ethan-1-one | (ESI(+)) m/e 451 (M + H)+ |
| 47 | 1-[4-(4-{(3R,4S)-4-(dimethylamino)-1-[(1S)-7-fluoro-2,3-dihydro-1H-inden-1-yl]pyrrolidin-3-yl}phenyl)piperazin-1-yl]ethan-1-one | (ESI(+)) m/e 451 (M + H)+ |
| 48 | 1-[4-(4-{(3R,4S)-4-(dimethylamino)-1-[(1R)-7-fluoro-2,3-dihydro-1H-inden-1-yl]pyrrolidin-3-yl}phenyl)piperazin-1-yl]ethan-1-one | (ESI(+)) m/e 451 (M + H)+ |
| 49 | rac-(3R,4S)-4-{4-[4-(ethanesulfonyl)piperazin-1-yl]phenyl}-1-(7-fluoro-2,3-dihydro-1H-inden-1-yl)-N,N-dimethylpyrrolidin-3-amine | (ESI(+)) m/e 501 (M + H)+ |
| 50 | tert-butyl 4-{4-[(3R,4S)-4-(dimethylamino)-1-(7-fluoro-2,3-dihydro-1H-inden-1-yl)pyrrolidin-3-yl]phenyl}piperazine-1-carboxylate | (ESI(+)) m/e 509 (M + H)+ |
| 51 | rac-4-{4-[(3S,4R)-4-(dimethylamino)-1-(7-fluoro-2,3-dihydro-1H-inden-1-yl)pyrrolidin-3-yl]benzoyl}-1-methylpiperazin-2-one | (ESI(+)) m/e 465 (M + H)+ |
| 52 | rac-1-(4-{4-[(3R,4S)-4-(dimethylamino)-1-(7-fluoro-2,3-dihydro-1H-inden-1-yl)pyrrolidin-3-yl]phenyl}piperazin-1-yl)-2-hydroxyethan-1-one | (ESI(+)) m/e 467 (M + H)+ |
| 53 | rac-{4-[(3S,4R)-4-(dimethylamino)-1-(7-fluoro-2,3-dihydro-1H-inden-1-yl)pyrrolidin-3-yl]phenyl}[4-(methanesulfonyl)piperazin-1-yl]methanone | (ESI(+)) m/e 515 (M + H)+ |
| 54 | rac-2-(4-{4-[(3R,4S)-4-(dimethylamino)-1-(7-fluoro-2,3-dihydro-1H-inden-1-yl)pyrrolidin-3-yl]phenyl}piperazin-1-yl)-2-oxoacetamide | (ESI(+)) m/e 480 (M + H)+ |
| 55 | rac-1-(4-{4-[(3S,4R)-4-(dimethylamino)-1-(7-fluoro-2,3-dihydro-1H-inden-1-yl)pyrrolidin-3-yl]benzoyl}piperazin-1-yl)ethan-1-one | (ESI(+)) m/e 479 (M + H)+ |
| 56 | rac-4-{4-[(3S,4R)-4-(dimethylamino)-1-(7-fluoro-2,3-dihydro-1H-inden-1-yl)pyrrolidin-3-yl]phenyl}-1-methylpiperazin-2-one | (ESI(+)) m/e 437 (M + H)+ |
| 57 | rac-{4-[(3S,4R)-4-(dimethylamino)-1-(7-fluoro-2,3-dihydro-1H-inden-1-yl)pyrrolidin-3-yl]phenyl}[4-(ethanesulfonyl)piperazin-1-yl]methanone | (ESI(+)) m/e 529 (M + H)+ |
| 58 | rac-4-{4-[(3S,4R)-4-(dimethylamino)-1-(7-fluoro-2,3-dihydro-1H-inden-1-yl)pyrrolidin-3-yl]-2-methylphenyl}-1-methylpiperazin-2-one | (ESI(+)) m/e 451 (M + H)+ |
| 59 | rac-2-(4-{4-[(3R,4S)-4-(dimethylamino)-1-(7-fluoro-2,3-dihydro-1H-inden-1-yl)pyrrolidin-3-yl]phenyl}piperazin-1-yl)-N,N-dimethyl-2-oxoacetamide | (ESI(+)) m/e 508 (M + H)+ |
| 60 | rac-1-(4-{4-[(3S,4R)-4-(dimethylamino)-1-(7-fluoro-2,3-dihydro-1H-inden-1-yl)pyrrolidin-3-yl]-2-methylphenyl}piperazin-1-yl)ethan-1-one | (ESI(+)) m/e 465 (M + H)+ |
| 61 | rac-(3R,4S)-1-(7-fluoro-2,3-dihydro-1H-inden-1-yl)-N,N-dimethyl-4-[4-(4-methylpiperazin-1-yl)phenyl]pyrrolidin-3-amine | (ESI(+)) m/e 423 (M + H)+ |
| 62 | rac-(3R,4S)-4-{4-[4-(ethanesulfonyl)piperazin-1-yl]-3-methylphenyl}-1-(7-fluoro-2,3-dihydro-1H-inden-1-yl)-N,N-dimethylpyrrolidin-3-amine | (ESI(+)) m/e 515 (M + H)+ |
| 63 | rac-4-{4-[(3S,4R)-4-(dimethylamino)-1-(7-fluoro-2,3-dihydro-1H-inden-1-yl)pyrrolidin-3-yl]phenyl}-N,N-dimethylpiperazine-1-carboxamide | (ESI(+)) m/e 480 (M + H)+ |
| 64 | rac-(3R,4S)-4-[4-(4-cyclopropylpiperazin-1-yl)phenyl]-1-(7-fluoro-2,3-dihydro-1H-inden-1-yl)-N,N-dimethylpyrrolidin-3-amine | (ESI(+)) m/e 449 (M + H)+ |
| 65 | rac-(3S,4R)-4-(2H-1,3-benzodioxol-5-yl)-1-(7-fluoro-2,3-dihydro-1H-inden-1-yl)-N,N-dimethylpyrrolidin-3-amine | (ESI(+)) m/e 369 (M + H)+ |
| 66 | rac-(3S,4R)-1-(7-fluoro-2,3-dihydro-1H-inden-1-yl)-N,N-dimethyl-4-[4-(1,3-oxazol-2-yl)phenyl]pyrrolidin-3-amine | (ESI(+)) m/e 392 (M + H)+ |
| 67 | rac-(3R,4S)-1-(7-fluoro-2,3-dihydro-1H-inden-1-yl)-N,N-dimethyl-4-[4-(3-methyl-1,2,4-oxadiazol-5-yl)phenyl]pyrrolidin-3-amine | (ESI(+)) m/e 407 (M + H)+ |
| 68 | rac-(3S,4R)-1-(7-fluoro-2,3-dihydro-1H-inden-1-yl)-N,N-dimethyl-4-[4-(5-methyl-1,3,4-oxadiazol-2-yl)phenyl]pyrrolidin-3-amine | (ESI(+)) m/e 407 (M + H)+ |
| 69 | rac-(3S,4R)-1-(7-fluoro-2,3-dihydro-1H-inden-1-yl)-N,N-dimethyl-4-[4-(4-methyl-1,3-oxazol-2-yl)phenyl]pyrrolidin-3-amine | (ESI(+)) m/e 406 (M + H)+ |
| 70 | rac-(3R,4S)-1-(7-fluoro-2,3-dihydro-1H-inden-1-yl)-N,N-dimethyl-4-[4-(1-methyl-1H-pyrazol-4-yl)phenyl]pyrrolidin-3-amine | (ESI(+)) m/e 405 (M + H)+ |
| 71 | rac-2-(4-{4-[(3S,4R)-4-(dimethylamino)-1-(7-fluoro-2,3-dihydro-1H-inden-1-yl)pyrrolidin-3-yl]phenyl}-1H-pyrazol-1-yl)acetamide | (ESI(+)) m/e 448 (M + H)+ |

TABLE 5-continued

| Ex | Name | MS |
|---|---|---|
| 72 | rac-2-(4-{4-[(3S,4R)-4-(dimethylamino)-1-(7-fluoro-2,3-dihydro-1H-inden-1-yl)pyrrolidin-3-yl]phenyl}-1H-pyrazol-1-yl)-N-methylacetamide | (ESI(+)) m/e 462 (M + H)+ |
| 73 | rac-(3S,4R)-1-(7-fluoro-2,3-dihydro-1H-inden-1-yl)-N,N-dimethyl-4-{4-[4-(1-methyl-1H-imidazole-4-sulfonyl)piperazin-1-yl]phenyl}pyrrolidin-3-amine | (ESI(+)) m/e 553 (M + H)+ |
| 74 | rac-(3S,4R)-1-(7-fluoro-2,3-dihydro-1H-inden-1-yl)-N,N-dimethyl-4-{4-[4-(pyrimidin-4-yl)piperazin-1-yl]phenyl}pyrrolidin-3-amine | (ESI(+)) m/e 487 (M + H)+ |
| 75 | rac-(3S,4R)-1-(7-fluoro-2,3-dihydro-1H-inden-1-yl)-N,N-dimethyl-4-{4-[4-(pyridin-2-yl)piperazin-1-yl]phenyl}pyrrolidin-3-amine | (ESI(+)) m/e 486 (M + H)+ |

The following Examples were prepared using methods similar to those described in Example 1. Some products were purified by silica gel column chromatography while others were purified by reverse-phase HPLC. Accordingly, some Examples were isolated as trifluoroacetic acid salts.

TABLE 6

| Ex | Name | MS |
|---|---|---|
| 76 | (3R,4S)-1-(7-fluoro-2,3-dihydro-1H-inden-1-yl)-N,N-dimethyl-4-(1-methyl-1H-indol-3-yl)pyrrolidin-3-amine | (APCI(+)) m/e 378 (M + H)+ |
| 77 | (3R,4S)-1-[(1S)-7-fluoro-2,3-dihydro-1H-inden-1-yl]-N,N-dimethyl-4-(1-methyl-1H-indol-3-yl)pyrrolidin-3-amine | (ESI(+)) m/e 378 (M + H)+ |
| 78 | (3R,4S)-1-[(1R)-7-fluoro-2,3-dihydro-1H-inden-1-yl]-N,N-dimethyl-4-(1-methyl-1H-indol-3-yl)pyrrolidin-3-amine | (ESI(+)) m/e 378 (M + H)+ |
| 79 | 3-[(3S,4R)-4-(dimethylamino)-1-(7-fluoro-2,3-dihydro-1H-inden-1-yl)pyrrolidin-3-yl]-1-methyl-1H-indole-7-carboxylic acid | (ESI(+)) m/e 422 (M + H)+ |
| 80 | rac-3-[(3S,4R)-4-(dimethylamino)-1-(7-fluoro-2,3-dihydro-1H-inden-1-yl)pyrrolidin-3-yl]-1-methyl-1H-indole-7-carboxylic acid | (ESI(+)) m/e 422 (M + H)+ |
| 81 | 3-[(3R,4S)-4-(dimethylamino)-1-(7-fluoro-2,3-dihydro-1H-inden-1-yl)pyrrolidin-3-yl]-1-methyl-1H-indole-7-carboxylic acid | (ESI(+)) m/e 422 (M + H)+ |
| 83 | rac-methyl 3-[(3R,4S)-4-(dimethylamino)-1-(7-fluoro-2,3-dihydro-1H-inden-1-yl)pyrrolidin-3-yl]-1-methyl-1H-indole-6-carboxylate | (ESI(+)) m/e 436 (M + H)+ |
| 84 | methyl 3-[(3S,4R)-4-(dimethylamino)-1-(7-fluoro-2,3-dihydro-1H-inden-1-yl)pyrrolidin-3-yl]-1-methyl-1H-indole-7-carboxylate | (ESI(+)) m/e 436 (M + H)+ |
| 85 | rac-methyl 3-[(3S,4R)-4-(dimethylamino)-1-(7-fluoro-2,3-dihydro-1H-inden-1-yl)pyrrolidin-3-yl]-1-methyl-1H-indole-7-carboxylate | (ESI(+)) m/e 436 (M + H)+ |
| 86 | methyl 3-[(3R,4S)-4-(dimethylamino)-1-(7-fluoro-2,3-dihydro-1H-inden-1-yl)pyrrolidin-3-yl]-1-methyl-1H-indole-7-carboxylate | (ESI(+)) m/e 436 (M + H)+ |
| 87 | rac-3-[(3S,4R)-4-(dimethylamino)-1-(7-fluoro-2,3-dihydro-1H-inden-1-yl)pyrrolidin-3-yl]-N,N,1-trimethyl-1H-indole-6-carboxamide | (ESI(+)) m/e 449 (M + H)+ |
| 88 | (3R,4S)-1-(2,3-dihydro-1H-inden-1-yl)-N,N-dimethyl-4-(1-methyl-1H-indol-3-yl)pyrrolidin-3-amine | (ESI(+)) m/e 360 (M + H)+ |
| 89 | (3R,4S)-1-(7-chloro-2,3-dihydro-1H-inden-1-yl)-N,N-dimethyl-4-(1-methyl-1H-indol-3-yl)pyrrolidin-3-amine | (ESI(+)) m/e 394 (M + H)+ |
| 90 | rac-(3R,4S)-1-(4-fluoro-2,3-dihydro-1H-inden-1-yl)-N,N-dimethyl-4-(1-methyl-1H-indol-3-yl)pyrrolidin-3-amine | (APCI(+)) m/e 378 (M + H)+ |
| 91 | rac-(3R,4S)-1-(5-fluoro-2,3-dihydro-1H-inden-1-yl)-N,N-dimethyl-4-(1-methyl-1H-indol-3-yl)pyrrolidin-3-amine | (APCI(+)) m/e 378 (M + H)+ |
| 92 | rac-(3R,4S)-1-(6-fluoro-2,3-dihydro-1H-inden-1-yl)-N,N-dimethyl-4-(1-methyl-1H-indol-3-yl)pyrrolidin-3-amine | (APCI(+)) m/e 378 (M + H)+ |
| 93 | rac-(3R,4S)-4-(7-bromo-1-methyl-1H-indol-3-yl)-1-(7-fluoro-2,3-dihydro-1H-inden-1-yl)-N,N-dimethylpyrrolidin-3-amine | (ESI(+)) m/e 456 (M + H)+ |
| 94 | rac-(3R,4S)-4-(6-bromo-1-methyl-1H-indol-3-yl)-1-(7-fluoro-2,3-dihydro-1H-inden-1-yl)-N,N-dimethylpyrrolidin-3-amine | (ESI(+)) m/e 456 (M + H)+ |

TABLE 6-continued

| Ex | Name | MS |
|---|---|---|
| 95 | rac-(3R,4S)-1-(5,7-difluoro-2,3-dihydro-1H-inden-1-yl)-N,N-dimethyl-4-(1-methyl-1H-indol-3-yl)pyrrolidin-3-amine | (ESI(+)) m/e 396 (M + H)+ |
| 96 | (3R,4S)-1-(6,7-difluoro-2,3-dihydro-1H-inden-1-yl)-N,N-dimethyl-4-(1-methyl-1H-indol-3-yl)pyrrolidin-3-amine | (APCI(+)) m/e 396 (M + H)+ |
| 97 | 3-[(3R,4S)-3-(dimethylamino)-4-(1-methyl-1H-indol-3-yl)pyrrolidin-1-yl]-2,3-dihydro-1H-inden-4-ol | (ESI(+)) m/e 376 (M + H)+ |
| 98 | rac-3-[(3S,4R)-4-(dimethylamino)-1-(7-fluoro-2,3-dihydro-1H-inden-1-yl)pyrrolidin-3-yl]-N-(2-hydroxyethyl)-N,1-dimethyl-1H-indole-7-carboxamide | (ESI(+)) m/e 479 (M + H)+ |
| 99 | rac-3-[(3S,4R)-4-(dimethylamino)-1-(7-fluoro-2,3-dihydro-1H-inden-1-yl)pyrrolidin-3-yl]-N,1-dimethyl-1H-indole-7-carboxamide | (ESI(+)) m/e 435 (M + H)+ |
| 100 | (3R,4S)-N,N-dimethyl-1-(7-methyl-2,3-dihydro-1H-inden-1-yl)-4-(1-methyl-1H-indol-3-yl)pyrrolidin-3-amine | (ESI(+)) m/e 374 (M + H)+ |
| 101 | rac-3-[(3S,4R)-4-(dimethylamino)-1-(7-fluoro-2,3-dihydro-1H-inden-1-yl)pyrrolidin-3-yl]-N,N,1-trimethyl-1H-indole-7-carboxamide | (ESI(+)) m/e 449 (M + H)+ |
| 102 | {3-[(3S,4R)-4-(dimethylamino)-1-(7-fluoro-2,3-dihydro-1H-inden-1-yl)pyrrolidin-3-yl]-1-methyl-1H-indol-7-yl}(3-fluoroazetidin-1-yl)methanone | (ESI(+)) m/e 479 (M + H)+ |
| 103 | rac-{3-[(3S,4R)-4-(dimethylamino)-1-(7-fluoro-2,3-dihydro-1H-inden-1-yl)pyrrolidin-3-yl]-1-methyl-1H-indol-7-yl}(3-fluoroazetidin-1-yl)methanone | (ESI(+)) m/e 479 (M + H)+ |
| 104 | {3-[(3R,4S)-4-(dimethylamino)-1-(7-fluoro-2,3-dihydro-1H-inden-1-yl)pyrrolidin-3-yl]-1-methyl-1H-indol-7-yl}(3-fluoroazetidin-1-yl)methanone | (ESI(+)) m/e 479 (M + H)+ |
| 105 | {3-[(3S,4R)-4-(dimethylamino)-1-(7-fluoro-2,3-dihydro-1H-inden-1-yl)pyrrolidin-3-yl]-1-methyl-1H-indol-7-yl}(3-hydroxyazetidin-1-yl)methanone | (ESI(+)) m/e 477 (M + H)+ |
| 106 | rac-{3-[(3S,4R)-4-(dimethylamino)-1-(7-fluoro-2,3-dihydro-1H-inden-1-yl)pyrrolidin-3-yl]-1-methyl-1H-indol-7-yl}(3-hydroxyazetidin-1-yl)methanone | (ESI(+)) m/e 477 (M + H)+ |
| 107 | rac-{3-[(3S,4R)-4-(dimethylamino)-1-(7-fluoro-2,3-dihydro-1H-inden-1-yl)pyrrolidin-3-yl]-1-methyl-1H-indol-6-yl}(3-hydroxyazetidin-1-yl)methanone | (ESI(+)) m/e 477 (M + H)+ |
| 108 | rac-3-[(3S,4R)-4-(dimethylamino)-1-(7-fluoro-2,3-dihydro-1H-inden-1-yl)pyrrolidin-3-yl]-N-(3-hydroxycyclobutyl)-1-methyl-1H-indole-7-carboxamide | (ESI(+)) m/e 491 (M + H)+ |
| 109 | rac-3-[(3S,4R)-4-(dimethylamino)-1-(7-fluoro-2,3-dihydro-1H-inden-1-yl)pyrrolidin-3-yl]-N-(3-hydroxycyclobutyl)-N,1-dimethyl-1H-indole-7-carboxamide | (ESI(+)) m/e 505 (M + H)+ |
| 110 | rac-{3-[(3S,4R)-4-(dimethylamino)-1-(7-fluoro-2,3-dihydro-1H-inden-1-yl)pyrrolidin-3-yl]-1-methyl-1H-indol-7-yl}[3-(methanesulfonyl)azetidin-1-yl]methanone | (ESI(+)) m/e 539 (M + H)+ |
| 111 | rac-{3-[(3S,4R)-4-(dimethylamino)-1-(7-fluoro-2,3-dihydro-1H-inden-1-yl)pyrrolidin-3-yl]-1-methyl-1H-indol-6-yl}[(3S)-3-hydroxypyrrolidin-1-yl]methanone | (ESI(+)) m/e 491 (M + H)+ |
| 112 | rac-{3-[(3S,4R)-4-(dimethylamino)-1-(7-fluoro-2,3-dihydro-1H-inden-1-yl)pyrrolidin-3-yl]-1-methyl-1H-indol-6-yl}[(3R)-3-hydroxypyrrolidin-1-yl]methanone | (ESI(+)) m/e 491 (M + H)+ |
| 113 | rac-[(3S,4S)-3,4-dihydroxypyrrolidin-1-yl]{3-[(3S,4R)-4-(dimethylamino)-1-(7-fluoro-2,3-dihydro-1H-inden-1-yl)pyrrolidin-3-yl]-1-methyl-1H-indol-7-yl}methanone | (ESI(+)) m/e 507 (M + H)+ |
| 114 | rac-[(3S,4S)-3,4-dihydroxypyrrolidin-1-yl]{3-[(3S,4R)-4-(dimethylamino)-1-(7-fluoro-2,3-dihydro-1H-inden-1-yl)pyrrolidin-3-yl]-1-methyl-1H-indol-6-yl}methanone | (ESI(+)) m/e 507 (M + H)+ |
| 115 | rac-3-[(3S,4R)-4-(dimethylamino)-1-(7-fluoro-2,3-dihydro-1H-inden-1-yl)pyrrolidin-3-yl]-N-(1,1-dioxo-1lambda~6~-thiolan-3-yl)-1-methyl-1H-indole-7-carboxamide | (ESI(+)) m/e 539 (M + H)+ |
| 116 | rac-{3-[(3S,4R)-4-(dimethylamino)-1-(7-fluoro-2,3-dihydro-1H-inden-1-yl)pyrrolidin-3-yl]-1-methyl-1H-indol-7-yl}[(2S)-2-(hydroxymethyl)pyrrolidin-1-yl]methanone | (ESI(+)) m/e 539 (M + H)+ |
| 117 | rac-1-{3-[(3S,4R)-4-(dimethylamino)-1-(7-fluoro-2,3-dihydro-1H-inden-1-yl)pyrrolidin-3-yl]-1-methyl-1H-indole-7-carbonyl}-L-prolinamide | (ESI(+)) m/e 518 (M + H)+ |
| 118 | rac-{3-[(3S,4R)-4-(dimethylamino)-1-(7-fluoro-2,3-dihydro-1H-inden-1-yl)pyrrolidin-3-yl]-1-methyl-1H-indol-7-yl}[(3S)-3-hydroxypyrrolidin-1-yl]methanone | (ESI(+)) m/e 491 (M + H)+ |
| 119 | rac-{3-[(3S,4R)-4-(dimethylamino)-1-(7-fluoro-2,3-dihydro-1H-inden-1-yl)pyrrolidin-3-yl]-1-methyl-1H-indol-7-yl}(piperazin-1-yl)methanone | (ESI(+)) m/e 490 (M + H)+ |
| 120 | rac-(3R,4S)-1-(7-fluoro-2,3-dihydro-1H-inden-1-yl)-4-{6-[4-(methanesulfonyl)piperazin-1-yl]-1-methyl-1H-indol-3-yl}-N,N-dimethylpyrrolidin-3-amine | (ESI(+)) m/e 540 (M + H)+ |

TABLE 6-continued

| Ex | Name | MS |
|---|---|---|
| 121 | rac-1-(4-{3-[(3S,4R)-4-(dimethylamino)-1-(7-fluoro-2,3-dihydro-1H-inden-1-yl)pyrrolidin-3-yl]-1-methyl-1H-indol-6-yl}piperazin-1-yl)ethan-1-one | (ESI(+)) m/e 504 $(M + H)^+$ |
| 122 | rac-{3-[(3S,4R)-4-(dimethylamino)-1-(7-fluoro-2,3-dihydro-1H-inden-1-yl)pyrrolidin-3-yl]-1-methyl-1H-indol-6-yl}[4-(methanesulfonyl)piperazin-1-yl]methanone | (ESI(+)) m/e 568 $(M + H)^+$ |
| 123 | rac-1-(4-{3-[(3S,4R)-4-(dimethylamino)-1-(7-fluoro-2,3-dihydro-1H-inden-1-yl)pyrrolidin-3-yl]-1-methyl-1H-indole-6-carbonyl}piperazin-1-yl)ethan-1-one | (ESI(+)) m/e 532 $(M + H)^+$ |
| 124 | rac-4-{3-[(3S,4R)-4-(dimethylamino)-1-(7-fluoro-2,3-dihydro-1H-inden-1-yl)pyrrolidin-3-yl]-1-methyl-1H-indole-7-carbonyl}-N,N-dimethylpiperazine-1-sulfonamide | (ESI(+)) m/e 597 $(M + H)^+$ |
| 125 | rac-4-{3-[(3S,4R)-4-(dimethylamino)-1-(7-fluoro-2,3-dihydro-1H-inden-1-yl)pyrrolidin-3-yl]-1-methyl-1H-indole-7-carbonyl}-1-methylpiperazin-2-one | (ESI(+)) m/e 518 $(M + H)^+$ |
| 126 | rac-{3-[(3S,4R)-4-(dimethylamino)-1-(7-fluoro-2,3-dihydro-1H-inden-1-yl)pyrrolidin-3-yl]-1-methyl-1H-indol-7-yl}[4-(methanesulfonyl)piperazin-1-yl]methanone | (ESI(+)) m/e 568 $(M + H)^+$ |
| 127 | rac-4-{3-[(3S,4R)-4-(dimethylamino)-1-(7-fluoro-2,3-dihydro-1H-inden-1-yl)pyrrolidin-3-yl]-1-methyl-1H-indole-7-carbonyl}-N,N-dimethylpiperazine-1-carboxamide | (ESI(+)) m/e 561 $(M + H)^+$ |
| 128 | rac-1-(4-{3-[(3S,4R)-4-(dimethylamino)-1-(7-fluoro-2,3-dihydro-1H-inden-1-yl)pyrrolidin-3-yl]-1-methyl-1H-indole-7-carbonyl}piperazin-1-yl)ethan-1-one | (ESI(+)) m/e 532 $(M + H)^+$ |
| 129 | rac-4-{3-[(3S,4R)-4-(dimethylamino)-1-(7-fluoro-2,3-dihydro-1H-inden-1-yl)pyrrolidin-3-yl]-1-methyl-1H-indol-7-yl}-1-methylpiperazin-2-one | (ESI(+)) m/e 490 $(M + H)^+$ |
| 130 | rac-{3-[(3S,4R)-4-(dimethylamino)-1-(7-fluoro-2,3-dihydro-1H-inden-1-yl)pyrrolidin-3-yl]-1-methyl-1H-indol-7-yl}[4-(ethanesulfonyl)piperazin-1-yl]methanone | (ESI(+)) m/e 582 $(M + H)^+$ |
| 131 | rac-4-{3-[(3S,4R)-4-(dimethylamino)-1-(7-fluoro-2,3-dihydro-1H-inden-1-yl)pyrrolidin-3-yl]-1-methyl-1H-indol-7-yl}-N,N-dimethylpiperazine-1-carboxamide | (ESI(+)) m/e 533 $(M + H)^+$ |
| 132 | [4-(azetidine-1-sulfonyl)piperazin-1-yl]{3-[(3S,4R)-4-(dimethylamino)-1-(7-fluoro-2,3-dihydro-1H-inden-1-yl)pyrrolidin-3-yl]-1-methyl-1H-indol-7-yl}methanone | (ESI(+)) m/e 609 $(M + H)^+$ |
| 133 | 1-(4-{3-[(3S,4R)-4-(dimethylamino)-1-(7-fluoro-2,3-dihydro-1H-inden-1-yl)pyrrolidin-3-yl]-1-methyl-1H-indole-7-carbonyl}piperazine-1-sulfonyl)azetidine-3-carbonitrile | (ESI(+)) m/e 634 $(M + H)^+$ |
| 134 | rac-8-{3-[(3S,4R)-4-(dimethylamino)-1-(7-fluoro-2,3-dihydro-1H-inden-1-yl)pyrrolidin-3-yl]-1-methyl-1H-indole-7-carbonyl}hexahydro-2H-pyrazino[1,2-a]pyrazin-1(6H)-one | (ESI(+)) m/e 559 $(M + H)^+$ |
| 135 | rac-{3-[(3S,4R)-4-(dimethylamino)-1-(7-fluoro-2,3-dihydro-1H-inden-1-yl)pyrrolidin-3-yl]-1-methyl-1H-indol-7-yl}[4-(1-methyl-1H-imidazole-5-sulfonyl)piperazin-1-yl]methanone | (ESI(+)) m/e 634 $(M + H)^+$ |
| 136 | rac-{3-[(3S,4R)-4-(dimethylamino)-1-(7-fluoro-2,3-dihydro-1H-inden-1-yl)pyrrolidin-3-yl]-1-methyl-1H-indol-7-yl}[4-(3,5-dimethyl-1H-pyrazole-4-sulfonyl)piperazin-1-yl]methanone | (ESI(+)) m/e 648 $(M + H)^+$ |
| 137 | rac-{3-[(3S,4R)-4-(dimethylamino)-1-(7-fluoro-2,3-dihydro-1H-inden-1-yl)pyrrolidin-3-yl]-1-methyl-1H-indol-7-yl}[4-(pyridazin-3-yl)piperazin-1-yl]methanone | (ESI(+)) m/e 568 $(M + H)^+$ |

The following Examples were prepared using methods similar to those described in Example 1. Some products were purified by silica gel column chromatography while others were purified by reverse-phase HPLC. Accordingly, some Examples were isolated as trifluoroacetic acid salts.

| Ex | Name | MS |
|---|---|---|
| 138 | rac-(3R,4S)-1-[(1S)-7-fluoro-2,3-dihydro-1H-inden-1-yl]-N,N-dimethyl-4-(1-methyl-1H-pyrrolo[3,2-b]pyridin-3-yl)pyrrolidin-3-amine | (ESI(+)) m/e 379 $(M + H)^+$ |
| 139 | rac-(3S,4R)-4-(2,3-dihydro-1-benzofuran-3-yl)-1-[(1R)-7-fluoro-2,3-dihydro-1H-inden-1-yl]-N,N-dimethylpyrrolidin-3-amine | (ESI(+)) m/e 367 $(M + H)^+$ |
| 140 | rac-(3S,4R)-1-(7-fluoro-2,3-dihydro-1H-inden-1-yl)-N,N-dimethyl-4-(5,6,7,8-tetrahydroimidazo[1,2-a]pyridin-3-yl)pyrrolidin-3-amine | (ESI(+)) m/e 369 $(M + H)^+$ |
| 141 | rac-(3R,4S)-1-(7-fluoro-2,3-dihydro-1H-inden-1-yl)-N,N-dimethyl-4-(1-methyl-1H-pyrrolo[3,2-c]pyridin-3-yl)pyrrolidin-3-amine | (ESI(+)) m/e 379 $(M + H)^+$ |
| 142 | rac-(3R,4S)-4-(2,3-dihydro-1-benzofuran-3-yl)-1-[(1R)-7-fluoro-2,3-dihydro-1H-inden-1-yl]-N,N-dimethylpyrrolidin-3-amine | (ESI(+)) m/e 367 $(M + H)^+$ |

-continued

| Ex | Name | MS |
|---|---|---|
| 143 | rac-(3R,4S)-1-[(1R)-7-fluoro-2,3-dihydro-1H-inden-1-yl]-N,N-dimethyl-4-(1-methyl-1H-pyrrolo[3,2-b]pyridin-3-yl)pyrrolidin-3-amine | (ESI(+)) m/e 379 (M + H)+ |
| 144 | rac-(3R,4S)-1-(7-fluoro-2,3-dihydro-1H-inden-1-yl)-N,N-dimethyl-4-(oxan-4-yl)pyrrolidin-3-amine | (ESI(+)) m/e 333 (M + H)+ |
| 145 | rac-(3S,4R)-1-(7-fluoro-2,3-dihydro-1H-inden-1-yl)-N,N-dimethyl-4-[6-(piperazin-1-yl)pyridin-3-yl]pyrrolidin-3-amine | (ESI(+)) m/e 410 (M + H)+ |
| 146 | rac-(3R,4S)-1-(7-fluoro-2,3-dihydro-1H-inden-1-yl)-N,N-dimethyl-4-(1-phenylpiperidin-4-yl)pyrrolidin-3-amine | (ESI(+)) m/e 408 (M + H)+ |
| 147 | rac-2-(4-{5-[(3R,4S)-4-(dimethylamino)-1-(7-fluoro-2,3-dihydro-1H-inden-1-yl)pyrrolidin-3-yl]pyridin-2-yl}piperazin-1-yl)-N,N-dimethylacetamide | (ESI(+)) m/e 495 (M + H)+ |
| 148 | rac-(3R,4S)-1-(7-fluoro-2,3-dihydro-1H-inden-1-yl)-N,N-dimethyl-4-(1-methyl-1H-pyrrolo[2,3-d]pyridin-3-yl)pyrrolidin-3-amine | (ESI(+)) m/e 379 (M + H)+ |
| 149 | rac-(3R,4S)-1-(7-fluoro-2,3-dihydro-1H-inden-1-yl)-N,N-dimethyl-4-[1-(pyridin-3-yl)piperidin-4-yl]pyrrolidin-3-amine | (ESI(+)) m/e 409 (M + H)+ |
| 150 | rac-2-(4-{5-[(3R,4S)-4-(dimethylamino)-1-(7-fluoro-2,3-dihydro-1H-inden-1-yl)pyrrolidin-3-yl]pyridin-2-yl}-1H-pyrazol-1-yl)-1-(3-hydroxyazetidin-1-yl)ethan-1-one | (ESI(+)) m/e 505 (M + H)+ |
| 151 | rac-(4-{5-[(3R,4S)-4-(dimethylamino)-1-(7-fluoro-2,3-dihydro-1H-inden-1-yl)pyrrolidin-3-yl]pyridin-2-yl}piperazin-1-yl)(oxetan-3-yl)methanone | (ESI(+)) m/e 492 (M + H)+ |
| 152 | rac-(3R,4S)-1-(7-fluoro-2,3-dihydro-1H-inden-1-yl)-N,N-dimethyl-4-[1-(pyridin-2-yl)piperidin-4-yl]pyrrolidin-3-amine | (ESI(+)) m/e 409 (M + H)+ |
| 153 | rac-2-(4-{5-[(3R,4S)-4-(dimethylamino)-1-(7-fluoro-2,3-dihydro-1H-inden-1-yl)pyrrolidin-3-yl]pyridin-2-yl}-1H-pyrazol-1-yl)-1-(3-fluoroazetidin-1-yl)ethan-1-one | (ESI(+)) m/e 507 (M + H)+ |
| 154 | rac-6-{4-[(3S,4R)-4-(dimethylamino)-1-(7-fluoro-2,3-dihydro-1H-inden-1-yl)pyrrolidin-3-yl]piperidin-1-yl}-N-methylpyridine-3-carboxamide | (ESI(+)) m/e 466 (M + H)+ |
| 155 | rac-N-[2-(4-{5-[(3R,4S)-4-(dimethylamino)-1-(7-fluoro-2,3-dihydro-1H-inden-1-yl)pyrrolidin-3-yl]pyridin-2-yl}piperazin-1-yl)-2-oxoethyl]methanesulfonamide | (ESI(+)) m/e 545 (M + H)+ |
| 156 | rac-(3R,4S)-1-(7-fluoro-2,3-dihydro-1H-inden-1-yl)-N,N-dimethyl-4-(1-methyl-1H-indazol-3-yl)pyrrolidin-3-amine | (ESI(+)) m/e 404 (M + H)+ |
| 157 | rac-1-(4-{5-[(3R,4S)-4-(dimethylamino)-1-(7-fluoro-2,3-dihydro-1H-inden-1-yl)pyrrolidin-3-yl]pyridin-2-yl}piperazin-1-yl)-2-(methanesulfonyl)ethan-1-one | (ESI(+)) m/e 528 (M + H)+ |
| 158 | rac-2-(4-{5-[(3R,4S)-4-(dimethylamino)-1-(7-fluoro-2,3-dihydro-1H-inden-1-yl)pyrrolidin-3-yl]pyridin-2-yl}-1H-pyrazol-1-yl)acetamide | (ESI(+)) m/e 449 (M + H)+ |
| 159 | rac-2-(4-{5-[(3R,4S)-4-(dimethylamino)-1-(7-fluoro-2,3-dihydro-1H-inden-1-yl)pyrrolidin-3-yl]pyridin-2-yl}-1H-pyrazol-1-yl)-N,N-dimethylacetamide | (ESI(+)) m/e 477 (M + H)+ |
| 160 | rac-2-(4-{5-[(3R,4S)-4-(dimethylamino)-1-(7-fluoro-2,3-dihydro-1H-inden-1-yl)pyrrolidin-3-yl]pyridin-2-yl}piperazin-1-yl)-2-oxoethane-1-sulfonamide | (ESI(+)) m/e 531 (M + H)+ |
| 161 | rac-2-(4-{5-[(3R,4S)-4-(dimethylamino)-1-(7-fluoro-2,3-dihydro-1H-inden-1-yl)pyrrolidin-3-yl]pyridin-2-yl}-1H-pyrazol-1-yl)-N-methylacetamide | (ESI(+)) m/e 463 (M + H)+ |
| 162 | rac-2-{4-[(3S,4R)-4-(dimethylamino)-1-(7-fluoro-2,3-dihydro-1H-inden-1-yl)pyrrolidin-3-yl]piperidin-1-yl}-1,3-thiazole-5-carboxamide | (ESI(+)) m/e 458 (M + H)+ |
| 163 | rac-5-{4-[(3S,4R)-4-(dimethylamino)-1-(7-fluoro-2,3-dihydro-1H-inden-1-yl)pyrrolidin-3-yl]piperidin-1-yl}pyrazine-2-carboxamide | (ESI(+)) m/e 453 (M + H)+ |
| 164 | rac-(3R,4S)-1-(7-fluoro-2,3-dihydro-1H-inden-1-yl)-N,N-dimethyl-4-(1-methyl-1H-pyrrolo[2,3-b]pyridin-3-yl)pyrrolidin-3-amine | (ESI(+)) m/e 379 (M + H)+ |
| 165 | rac-6-{4-[(3S,4R)-4-(dimethylamino)-1-(7-fluoro-2,3-dihydro-1H-inden-1-yl)pyrrolidin-3-yl]piperidin-1-yl}pyridazine-3-carboxamide | (ESI(+)) m/e 453 (M + H)+ |
| 166 | rac-4-{4-[(3S,4R)-4-(dimethylamino)-1-(7-fluoro-2,3-dihydro-1H-inden-1-yl)pyrrolidin-3-yl]piperidin-1-yl}benzamide | (ESI(+)) m/e 451 (M + H)+ |
| 167 | rac-6-{4-[(3S,4R)-4-(dimethylamino)-1-(7-fluoro-2,3-dihydro-1H-inden-1-yl)pyrrolidin-3-yl]piperidin-1-yl}pyridine-3-carboxamide | (ESI(+)) m/e 452 (M + H)+ |

We claim:
1. A compound of Formula (I), or a pharmaceutically acceptable salt thereof,

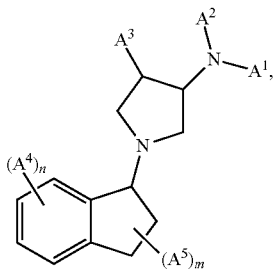

Formula (I)

wherein
$A^1$ and $A^2$ are each independently $C_1$-$C_2$ alkyl;
$A^3$ is selected from the group consisting of aryl, heterocyclyl, and heteroaryl, wherein the $A^3$ aryl, heterocyclyl, and heteroaryl are optionally substituted with one or more substituents independently selected from the group consisting of $R^1$, $OR^1$, $SR^1$, $S(O)R^1$, $SO_2R^1$, $C(O)R^1$, $CO(O)R^1$, $OC(O)R^1$, $OC(O)OR^1$, $NH_2$, $NHR^1$, $N(R^1)_2$, $NHC(O)R^1$, $NR^1C(O)R^1$, $NHS(O)_2R^1$, $NR^1S(O)_2R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $C(O)NH_2$, $C(O)NHR^1$, $C(O)N(R^1)_2$, $C(O)NHOH$, $C(O)NHOR^1$, $C(O)NHSO_2R^1$, $C(O)NR^1SO_2R^1$, $SO_2NH_2$, $SO_2NHR^1$, $SO_2N(R^1)_2$, $C(O)H$, $C(O)OH$, $C(N)NH_2$, $C(N)NHR^1$, $C(N)N(R^1)_2$, $CNOH$, $CNOCH_3$, $OH$, $(O)$, $CN$, $NO_2$, $CF_3$, $CF_2CF_3$, $OCF_3$, $OCF_2CF_3$, F, Cl, Br and I;
$A^4$, at each occurrence, is a substituent on a substitutable position of the benzene ring of the indane independently selected from the group consisting of $C_1$-$C_6$ alkyl, OH, F, Cl, Br and I;
$A^5$ is a substituent on a substitutable position of the cyclopentane ring of the indane independently selected from the group consisting of $C_1$-$C_6$ alkyl, OH, F, Cl, Br and I;
$R^1$, at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^1$ $C_1$-$C_6$ alkyl, $C_2$-$C_6$ alkenyl, and $C_2$-$C_6$ alkynyl is optionally substituted with one or more substituents independently selected from the group consisting of $R^2$, $OR^2$, $SR^2$, $S(O)R^2$, $SO_2R^2$, $C(O)R^2$, $CO(O)R^2$, $OC(O)R^2$, $OC(O)OR^2$, $NH_2$, $NHR^2$, $N(R^2)_2$, $NHC(O)R^2$, $NR^2C(O)R^2$, $NHS(O)_2R^2$, $NR^2S(O)_2R^2$, $NHC(O)OR^2$, $NR^2C(O)OR^2$, $NHC(O)NH_2$, $NHC(O)NHR^2$, $NHC(O)N(R^2)_2$, $NR^2C(O)NHR^2$, $NR^2C(O)N(R^2)_2$, $C(O)NH_2$, $C(O)NHR^2$, $C(O)N(R^2)_2$, $C(O)NHOH$, $C(O)NHOR^2$, $C(O)NHSO_2R^2$, $C(O)NR^2SO_2R^2$, $SO_2NH_2$, $SO_2NHR^2$, $SO_2N(R^2)_2$, $C(O)H$, $C(O)OH$, $(O)$, $CN$, $NO_2$, $CF_3$, $CF_2CF_3$, $OCF_3$, $OCF_2CF_3$, F, Cl, Br and I; wherein each $R^1$ aryl, heteroaryl, heterocyclyl, cycloalkyl, and cycloalkenyl is optionally substituted with one or more substituents independently selected from the group consisting of $R^3$, $OR^3$, $SR^3$, $S(O)R^3$, $SO_2R^3$, $C(O)R^3$, $CO(O)R^3$, $OC(O)R^3$, $OC(O)OR^3$, $NH_2$, $NHR^3$, $N(R^3)_2$, $NHC(O)R^3$, $NR^3C(O)R^3$, $NHS(O)_2R^3$, $NR^3S(O)_2R^3$, $NHC(O)OR^3$, $NR^3C(O)OR^3$, $NHC(O)NH_2$, $NHC(O)NHR^3$, $NHC(O)N(R^3)_2$, $NR^3C(O)NHR^3$, $NR^3C(O)N(R^3)_2$, $C(O)NH_2$, $C(O)NHR^3$, $C(O)N(R^3)_2$, $C(O)NHOH$, $C(O)NHOR^3$, $C(O)NHSO_2R^3$, $C(O)NR^3SO_2R^3$, $SO_2NH_2$, $SO_2NHR^3$, $SO_2N(R^3)_2$, $C(O)H$, $C(O)OH$, $C(O)C(O)NH_2$, $C(O)C(O)NHR^3$, $C(O)C(O)N(R^3)_2$, $C(N)NH_2$, $C(N)NHR^3$, $C(N)N(R^3)_2$, $CNOH$, $CNOCH_3$, $OH$, $(O)$, $CN$, $NO_2$, $CF_3$, $CF_2CF_3$, $OCF_3$, $OCF_2CF_3$, F, Cl, Br and I;
$R^2$, at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^2$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)NH_2$, $SO_2NH_2$, $C(O)H$, $C(O)OH$, $OH$, $(O)$, $CN$, $NO_2$, $CF_3$, $CF_2CF_3$, $OCF_3$, $OCF_2CF_3$, F, Cl, Br and I; wherein each $R^2$ aryl, heteroaryl, heterocyclyl, cycloalkyl, and cycloalkenyl is optionally substituted with one or more substituents independently selected from the group consisting of $NH_2$, $C(O)NH_2$, $SO_2NH_2$, $C(O)H$, $C(O)OH$, $OH$, $(O)$, $CN$, $NO_2$, $CF_3$, $CF_2CF_3$, $OCF_3$, $OCF_2CF_3$, F, Cl, Br and I;
$R^3$, at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^3$ $C_1$-$C_6$ alkyl, $C_2$-$C_6$ alkenyl, and $C_2$-$C_6$ alkynyl is optionally substituted with one or more substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $OH$, $(O)$, $CN$, $NO_2$, $CF_3$, $CF_2CF_3$, $OCF_3$, $OCF_2CF_3$, F, Cl, Br and I; wherein each $R^3$ aryl, heteroaryl, heterocyclyl, cycloalkyl, and cycloalkenyl is optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)R^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, $C(N)NH_2$, $C(N)NHR^5$, $C(N)N(R^5)_2$, $CNOH$, $CNOCH_3$, $OH$, $(O)$, $CN$, $NO_2$, $CF_3$, $CF_2CF_3$, $OCF_3$, $OCF_2CF_3$, F, Cl, Br and I;
$R^4$ is at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each $R^4$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)NH_2$, $SO_2NH_2$, $C(O)H$, $C(O)OH$, $OH$, $(O)$, $CN$, $NO_2$, $CF_3$, $CF_2CF_3$, $OCF_3$, $OCF_2CF_3$, F, Cl, Br and I; wherein each $R^4$ aryl, heteroaryl, heterocyclyl, cycloalkyl, and cycloalkenyl is optionally substituted with one or more substituents independently selected from the group consisting of $NH_2$, $C(O)NH_2$, $SO_2NH_2$, $C(O)H$, $C(O)OH$, $OH$, $(O)$, $CN$, $NO_2$, $CF_3$, $CF_2CF_3$, $OCF_3$, $OCF_2CF_3$, F, Cl, Br and I;

149

R⁵ is at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each R⁵ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)NH_2$, $SO_2NH_2$, C(O)H, C(O)OH, OH, (O), CN, $NO_2$, $CF_3$, $CF_2CF_3$, $OCF_3$, $OCF_2CF_3$, F, Cl, Br and I; wherein each R⁵ aryl, heteroaryl, heterocyclyl, cycloalkyl, and cycloalkenyl is optionally substituted with one or more substituents independently selected from the group consisting of $NH_2$, $C(O)NH_2$, $SO_2NH_2$, C(O)H, C(O)OH, OH, (O), CN, $NO_2$, $CF_3$, $CF_2CF_3$, $OCF_3$, $OCF_2CF_3$, F, Cl, Br and I;

n is 0, 1, or 2; and m is 0 or 1.

2. A compound of Formula (IIIa) or Formula (IIIb), or a pharmaceutically acceptable salt thereof,

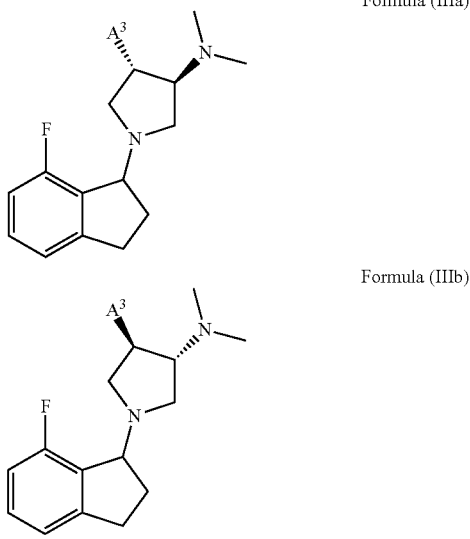

Formula (IIIa)

Formula (IIIb)

wherein

A³ is selected from the group consisting of aryl, heterocyclyl, and heteroaryl, wherein the A³ aryl, heterocyclyl, and heteroaryl are optionally substituted with one or more substituents independently selected from the group consisting of R¹, OR¹, SR¹, S(O)R¹, $SO_2R^1$, C(O)R¹, CO(O)R¹, OC(O)R¹, OC(O)OR¹, $NH_2$, NHR¹, $N(R^1)_2$, NHC(O)R¹, NR¹C(O)R¹, $NHS(O)_2R^1$, $NR^1S(O)_2R^1$, NHC(O)OR¹, NR¹C(O)OR¹, NHC(O)$NH_2$, NHC(O)NHR¹, NHC(O)N(R¹)$_2$, NR¹C(O)NHR¹, NR¹C(O)N(R¹)$_2$, C(O)$NH_2$, C(O)NHR¹, C(O)N(R¹)$_2$, C(O)NHOH, C(O)NHOR¹, C(O)NHSO$_2$R¹, C(O)NR¹SO$_2$R¹, $SO_2NH_2$, $SO_2NHR^1$, $SO_2N(R^1)_2$, C(O)H, C(O)OH, C(N)$NH_2$, C(N)NHR¹, C(N)N(R¹)$_2$, CNOH, CNOCH$_3$, OH, (O), CN, $NO_2$, $CF_3$, $CF_2CF_3$, $OCF_3$, $OCF_2CF_3$, F, Cl, Br and I;

R¹, at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each R¹ $C_1$-$C_6$ alkyl, $C_2$-$C_6$ alkenyl, and $C_2$-$C_6$ alkynyl is optionally substituted with one or more substituents independently selected from the group consisting of R², OR², SR², S(O)R², $SO_2R^2$, C(O)R², CO(O)R², OC(O)R², OC(O)OR², $NH_2$, NHR², $N(R^2)_2$, NHC(O)R², NR²C(O)R², $NHS(O)_2R^2$, $NR^2S(O)_2R^2$, NHC(O)OR², NR²C(O)OR², NHC(O)$NH_2$, NHC(O)NHR², NHC(O)N(R²)$_2$, NR²C(O)NHR², NR²C(O)N(R²)$_2$, C(O)$NH_2$, C(O)NHR², C(O)N(R²)$_2$, C(O)NHOH, C(O)NHOR², C(O)NHSO$_2$R², C(O)NR²SO$_2$R², $SO_2NH_2$, $SO_2NHR^2$, $SO_2N(R^2)_2$, C(O)H, C(O)OH, OH, (O), CN, $NO_2$, $CF_3$, $CF_2CF_3$, $OCF_3$, $OCF_2CF_3$, F, Cl, Br and I; wherein each R¹ aryl, heteroaryl, heterocyclyl, cycloalkyl, and cycloalkenyl is optionally substituted with one or more substituents independently selected from the group consisting of R³, OR³, SR³, S(O)R³, $SO_2R^3$, C(O)R³, CO(O)R³, OC(O)R³, OC(O)OR³, $NH_2$, NHR³, $N(R^3)_2$, NHC(O)R³, NR³C(O)R³, $NHS(O)_2R^3$, $NR^3S(O)_2R^3$, NHC(O)OR³, NR³C(O)OR³, NHC(O)$NH_2$, NHC(O)NHR³, NHC(O)N(R³)$_2$, NR³C(O)NHR³, NR³C(O)N(R³)$_2$, C(O)$NH_2$, C(O)NHR³, C(O)N(R³)$_2$, C(O)NHOH, C(O)NHOR³, C(O)NHSO$_2$R³, C(O)NR³SO$_2$R³, $SO_2NH_2$, $SO_2NHR^3$, $SO_2N(R^3)_2$, C(O)H, C(O)OH, C(O)C(O)$NH_2$, C(O)C(O)NHR³, C(O)C(O)N(R³)$_2$, C(N)$NH_2$, C(N)NHR³, C(N)N(R³)$_2$, CNOH, CNOCH$_3$, OH, (O), CN, $NO_2$, $CF_3$, $CF_2CF_3$, $OCF_3$, $OCF_2CF_3$, F, Cl, Br and I;

R², at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each R² $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)NH_2$, $SO_2NH_2$, C(O)H, C(O)OH, OH, (O), CN, $NO_2$, $CF_3$, $CF_2CF_3$, $OCF_3$, $OCF_2CF_3$, F, Cl, Br and I; wherein each R² aryl, heteroaryl, heterocyclyl, cycloalkyl, and cycloalkenyl is optionally substituted with one or more substituents independently selected from the group consisting of $NH_2$, $C(O)NH_2$, $SO_2NH_2$, C(O)H, C(O)OH, OH, (O), CN, $NO_2$, $CF_3$, $CF_2CF_3$, $OCF_3$, $OCF_2CF_3$, F, Cl, Br and I;

R³, at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each R³ $C_1$-$C_6$ alkyl, $C_2$-$C_6$ alkenyl, and $C_2$-$C_6$ alkynyl is optionally substituted with one or more substituents independently selected from the group consisting of R⁴, OR⁴, SR⁴, S(O)R⁴, $SO_2R^4$, C(O)R⁴, CO(O)R⁴, OC(O)R⁴, OC(O)OR⁴, $NH_2$, NHR⁴, $N(R^4)_2$, NHC(O)R⁴, NR⁴C(O)R⁴, $NHS(O)_2R^4$, $NR^4S(O)_2R^4$, NHC(O)OR⁴, NR⁴C(O)OR⁴, NHC(O)$NH_2$, NHC(O)NHR⁴, NHC(O)N(R⁴)$_2$, NR⁴C(O)NHR⁴, NR⁴C(O)N(R⁴)$_2$, C(O)$NH_2$, C(O)NHR⁴, C(O)N(R⁴)$_2$, C(O)NHOH, C(O)NHOR⁴, C(O)NHSO$_2$R⁴, C(O)NR⁴SO$_2$R⁴, $SO_2NH_2$, $SO_2NHR^4$, $SO_2N(R^4)_2$, C(O)H, C(O)OH, OH, (O), CN, $NO_2$, $CF_3$, $CF_2CF_3$, $OCF_3$, $OCF_2CF_3$, F, Cl, Br and I; wherein each R³ aryl, heteroaryl, heterocyclyl, cycloalkyl, and cycloalkenyl is optionally substituted with one or more substituents independently selected from the group consisting of R⁵, OR⁵, SR⁵, S(O)R⁵, $SO_2R^5$, C(O)R⁵, CO(O)R⁵, OC(O)R⁵, OC(O)OR⁵, $NH_2$, NHR⁵, $N(R^5)_2$, NHC(O)R⁵, NR⁵C(O)R⁵, $NHS(O)_2R^5$, $NR^5S(O)_2R^5$, NHC(O)OR⁵, NR⁵C(O)OR⁵, NHC(O)$NH_2$, NHC(O)NHR⁵, NHC(O)N(R⁵)$_2$, NR⁵C(O)NHR⁵, NR⁵C(O)N(R⁵)$_2$, C(O)$NH_2$, C(O)NHR⁵, C(O)N(R⁵)$_2$, C(O)NHOH, C(O)NHOR⁵, C(O)NHSO$_2$R⁵, C(O)NR⁵SO$_2$R⁵, $SO_2NH_2$, $SO_2NHR^5$, $SO_2N(R^5)_2$, C(O)H, C(O)OH, C(N)$NH_2$, C(N)NHR⁵, C(N)N(R⁵)₂, CNOH, CNOCH₃, OH, (O), CN, NO₂, CF₃, CF₂CF₃, OCF₃, OCF₂CF₃, F, Cl, Br and I;

- R⁴ is at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each R⁴ $C_1$-$C_6$ alkyl, $C_2$-$C_6$ alkenyl, and $C_2$-$C_6$ alkynyl is optionally substituted with one or more substituents independently selected from the group consisting of NH₂, C(O)NH₂, SO₂NH₂, C(O)H, C(O)OH, OH, (O), CN, NO₂, CF₃, CF₂CF₃, OCF₃, OCF₂CF₃, F, Cl, Br and I; wherein each R⁴ aryl, heteroaryl, heterocyclyl, cycloalkyl, and cycloalkenyl is optionally substituted with one or more substituents independently selected from the group consisting of NH₂, C(O)NH₂, SO₂NH₂, C(O)H, C(O)OH, OH, (O), CN, NO₂, CF₃, CF₂CF₃, OCF₃, OCF₂CF₃, F, Cl, Br and I; and
- R⁵ is at each occurrence, is independently selected from the group consisting of $C_1$-$C_6$ alkyl, $C_2$-$C_6$ alkenyl, $C_2$-$C_6$ alkynyl, aryl, heteroaryl, heterocyclyl, cycloalkyl, and cycloalkenyl; wherein each R⁵ $C_1$-$C_6$ alkyl, $C_2$-$C_6$ alkenyl, and $C_2$-$C_6$ alkynyl is optionally substituted with one or more substituents independently selected from the group consisting of NH₂, C(O)NH₂, SO₂NH₂, C(O)H, C(O)OH, OH, (O), CN, NO₂, CF₃, CF₂CF₃, OCF₃, OCF₂CF₃, F, Cl, Br and I; wherein each R⁵ aryl, heteroaryl, heterocyclyl, cycloalkyl, and cycloalkenyl is optionally substituted with one or more substituents independently selected from the group consisting of NH₂, C(O)NH₂, SO₂NH₂, C(O)H, C(O)OH, OH, (O), CN, NO₂, CF₃, CF₂CF₃, OCF₃, OCF₂CF₃, F, Cl, Br and I.

3. The compound of claim 1, or a pharmaceutically acceptable salt thereof, wherein A¹ and A² are each CH₃.

4. The compound of claim 1 or a pharmaceutically acceptable salt thereof, wherein A³ is aryl, wherein the A³ aryl is optionally substituted with one or more substituents independently selected from the group consisting of R¹, OR¹, SO₂R¹, C(O)R¹, CO(O)R¹, C(O)NH₂, C(O)NHR¹, C(O)N(R¹)₂, SO₂NH₂, C(O)OH, CN, F, Cl, Br and I.

5. The compound of claim 1 or a pharmaceutically acceptable salt thereof, wherein A³ is heterocyclyl, wherein the A³ heterocyclyl is optionally substituted with one or more substituents independently selected from the group consisting of R¹, OR¹, SO₂R¹, C(O)R¹, CO(O)R¹, C(O)NH₂, C(O)NHR¹, C(O)N(R¹)₂, SO₂NH₂, C(O)OH, CN, F, Cl, Br and I.

6. The compound of claim 1 or a pharmaceutically acceptable salt thereof, wherein A³ is heteroaryl, wherein the A³ heteroaryl is optionally substituted with one or more substituents independently selected from the group consisting of R¹, OR¹, SO₂R¹, C(O)R¹, CO(O)R¹, C(O)NH₂, C(O)NHR¹, C(O)N(R¹)₂, SO₂NH₂, C(O)OH, CN, F, Cl, Br and I.

7. A compound selected from the group consisting of
- (3R,4S)-1-(7-fluoro-2,3-dihydro-1H-inden-1-yl)-4-{4-[4-(methanesulfonyl)piperazin-1-yl]phenyl}-N,N-dimethylpyrrolidin-3-amine;
- rac-(3R,4S)-1-(7-fluoro-2,3-dihydro-1H-inden-1-yl)-4-{4-[4-(methanesulfonyl)piperazin-1-yl]phenyl}-N,N-dimethylpyrrolidin-3-amine;
- (3S,4R)-1-(7-fluoro-2,3-dihydro-1H-inden-1-yl)-4-{4-[4-(methanesulfonyl)piperazin-1-yl]phenyl}-N,N-dimethylpyrrolidin-3-amine;
- (3S,4R)-1-[(1S)-7-fluoro-2,3-dihydro-1H-inden-1-yl]-4-{4-[4-(methanesulfonyl)piperazin-1-yl]phenyl}-N,N-dimethylpyrrolidin-3-amine;
- (3S,4R)-1-[(1R)-7-fluoro-2,3-dihydro-1H-inden-1-yl]-4-{4-[4-(methanesulfonyl)piperazin-1-yl]phenyl}-N,N-dimethylpyrrolidin-3-amine;
- rac-(3S,4R)-4-(4-bromophenyl)-1-(7-fluoro-2,3-dihydro-1H-inden-1-yl)-N,N-dimethylpyrrolidin-3-amine;
- rac-(3S,4R)-4-(4-chlorophenyl)-1-(7-fluoro-2,3-dihydro-1H-inden-1-yl)-N,N-dimethylpyrrolidin-3-amine;
- rac-4-[(3S,4R)-4-(dimethylamino)-1-(7-fluoro-2,3-dihydro-1H-inden-1-yl)pyrrolidin-3-yl]benzene-1-sulfonamide;
- (3R,4S)-1-[(1S)-2,3-dihydro-1H-inden-1-yl]-4-[4-(methanesulfonyl)phenyl]-N,N-dimethylpyrrolidin-3-amine;
- (3S,4R)-1-[(1S)-2,3-dihydro-1H-inden-1-yl]-4-[4-(methanesulfonyl)phenyl]-N,N-dimethylpyrrolidin-3-amine;
- (3R,4S)-1-[(1S)-7-fluoro-2,3-dihydro-1H-inden-1-yl]-4-[4-(methanesulfonyl)phenyl]-N,N-dimethylpyrrolidin-3-amine;
- (3R,4S)-1-[(1R)-7-fluoro-2,3-dihydro-1H-inden-1-yl]-4-[4-(methane sulfonyl)phenyl]-N,N-dimethylpyrrolidin-3-amine;
- (3S,4R)-1-[(1S)-7-fluoro-2,3-dihydro-1H-inden-1-yl]-4-[4-(methanesulfonyl)phenyl]-N,N-dimethylpyrrolidin-3-amine;
- (3S,4R)-1-[(1R)-7-fluoro-2,3-dihydro-1H-inden-1-yl]-4-[4-(methane sulfonyl)phenyl]-N,N-dimethylpyrrolidin-3-amine;
- rac-(1S)-1-{(3S,4R)-3-(dimethylamino)-4-[4-(methanesulfonyl)phenyl]pyrrolidin-1-yl}-7-fluoro-2,3-dihydro-1H-inden-5-ol;
- rac-(1R,3R)-3-{(3R,4S)-3-(dimethylamino)-4-[4-(methanesulfonyl)phenyl]pyrrolidin-1-yl}-4-fluoro-2,3-dihydro-1H-inden-1-ol;
- rac-(1R)-1-{(3S,4R)-3-(dimethylamino)-4-[4-(methanesulfonyl)phenyl]pyrrolidin-1-yl}-7-fluoro-2,3-dihydro-1H-inden-5-ol;
- rac-(1S,3S)-3-{(3R,4S)-3-(dimethylamino)-4-[4-(methanesulfonyl)phenyl]pyrrolidin-1-yl}-4-fluoro-2,3-dihydro-1H-inden-1-ol;
- rac-4-{(3R,4S)-4-(dimethylamino)-1-[(1R)-7-fluoro-2,3-dihydro-1H-inden-1-yl]pyrrolidin-3-yl}benzonitrile;
- rac-methyl 4-[(3R,4S)-1-[(1R)-2,3-dihydro-1H-inden-1-yl]-4-(dimethylamino)pyrrolidin-3-yl]benzoate;
- rac-methyl 4-[(3S,4R)-1-(7-chloro-2,3-dihydro-1H-inden-1-yl)-4-(dimethylamino)pyrrolidin-3-yl]benzoate;
- rac-methyl 4-[(3S,4R)-4-(dimethylamino)-1-(7-fluoro-2,3-dihydro-1H-inden-1-yl)pyrrolidin-3-yl]benzoate;
- rac-(3S,4R)-4-(3,4-dimethoxyphenyl)-1-(7-fluoro-2,3-dihydro-1H-inden-1-yl)-N,N-dimethylpyrrolidin-3-amine;
- rac-4-[(3S,4R)-4-(dimethylamino)-1-(7-fluoro-2,3-dihydro-1H-inden-1-yl)pyrrolidin-3-yl]-N-methylbenzamide;
- rac-4-[(3S,4R)-1-(7-chloro-2,3-dihydro-1H-inden-1-yl)-4-(dimethylamino)pyrrolidin-3-yl]-N-dimethylbenzamide;
- rac-4-[(3S,4R)-4-(dimethylamino)-1-(7-fluoro-2,3-dihydro-1H-inden-1-yl)pyrrolidin-3-yl]-N,N-dimethylbenzamide;
- rac-(3R,4S)-4-(4-bromo-3-methylphenyl)-1-(7-fluoro-2,3-dihydro-1H-inden-1-yl)-N,N-dimethylpyrrolidin-3-amine;
- rac-4-[(3S,4R)-1-(7-chloro-2,3-dihydro-1H-inden-1-yl)-4-(dimethylamino)pyrrolidin-3-yl]benzoic acid;

rac-4-[(3R,4S)-4-(dimethylamino)-1-(7-fluoro-2,3-di-hydro-1H-inden-1-yl)pyrrolidin-3-yl]benzoic acid;

rac-(3R,4S)-1-[(3S)-3,7-difluoro-2,3-dihydro-1H-inden-1-yl]-4-[4-(methanesulfonyl)phenyl]-N,N-dimethyl-pyrrolidin-3-amine;

rac-(3R,4S)-1-[(1R,3S)-3,7-difluoro-2,3-dihydro-1H-inden-1-yl]-4-[4-(methanesulfonyl)phenyl]-N,N-dimethylpyrrolidin-3-amine;

rac-(3R,4S)-1-[(1S,3S)-3,7-difluoro-2,3-dihydro-1H-inden-1-yl]-4-[4-(methanesulfonyl)phenyl]-N,N-dimethylpyrrolidin-3-amine;

(3S)-3-{(3S,4R)-3-(dimethylamino)-4-[4-(methanesulfonyl)phenyl]pyrrolidin-1-yl}-4-fluoro-2,3-dihydro-1H-inden-1-ol;

rac-(1R,3S)-3-{(3R,4S)-3-(dimethylamino)-4-[4-(methanesulfonyl)phenyl]pyrrolidin-1-yl}-4-fluoro-2,3-dihydro-1H-inden-1-ol;

rac-4-[(3R,4S)-4-(dimethylamino)-1-(7-fluoro-2,3-di-hydro-1H-inden-1-yl)pyrrolidin-3-yl]benzamide;

rac-4-[(3S,4R)-4-(dimethylamino)-1-(7-fluoro-2,3-di-hydro-1H-inden-1-yl)pyrrolidin-3-yl]-2-methylbenzoic acid;

rac-4-[(3S,4R)-4-(dimethylamino)-1-(7-fluoro-2,3-di-hydro-1H-inden-1-yl)pyrrolidin-3-yl]-2-methylbenzonitrile;

rac-4-[(3S,4R)-4-(dimethylamino)-1-(2-hydroxy-2,3-di-hydro-1H-inden-1-yl)pyrrolidin-3-yl]-2-methylbenzonitrile;

rac-methyl 4-[(3S,4R)-4-(dimethylamino)-1-(7-fluoro-2,3-dihydro-1H-inden-1-yl)pyrrolidin-3-yl]-2-methyl-benzoate;

rac-{4-[(3S,4R)-4-(dimethylamino)-1-(7-fluoro-2,3-di-hydro-1H-inden-1-yl)pyrrolidin-3-yl]phenyl}[(3S)-3-hydroxypyrrolidin-1-yl]methanone;

rac-(3S,4R)-1-(7-fluoro-2,3-dihydro-1H-inden-1-yl)-N, N-dimethyl-4-[4-(piperazin-1-yl)phenyl]pyrrolidin-3-amine;

1-(4-{4-[(3S,4R)-1-(2,3-dihydro-1H-inden-1-yl)-4-(dimethylamino)pyrrolidin-3-yl]phenyl}piperazin-1-yl)ethan-1-one;

1-(4-{4-[(3S,4R)-4-(dimethylamino)-1-(7-fluoro-2,3-di-hydro-1H-inden-1-yl)pyrrolidin-3-yl]phenyl}piperazin-1-yl)ethan-1-one;

rac-1-(4-{4-[(3S,4R)-4-(dimethylamino)-1-(7-fluoro-2,3-dihydro-1H-inden-1-yl)pyrrolidin-3-yl]phenyl}piperazin-1-yl)ethan-1-one;

1-[4-(4-{(3S,4R)-4-(dimethylamino)-1-[(1S)-7-fluoro-2,3-dihydro-1H-inden-1-yl]pyrrolidin-3-yl}phenyl)piperazin-1-yl]ethan-1-one;

1-[4-(4-{(3S,4R)-4-(dimethylamino)-1-[(1R)-7-fluoro-2,3-dihydro-1H-inden-1-yl]pyrrolidin-3-yl}phenyl)piperazin-1-yl]ethan-1-one;

1-[4-(4-{(3R,4S)-4-(dimethylamino)-1-[(1S)-7-fluoro-2,3-dihydro-1H-inden-1-yl]pyrrolidin-3-yl}phenyl)piperazin-1-yl]ethan-1-one;

1-[4-(4-{(3R,4S)-4-(dimethylamino)-1-[(1R)-7-fluoro-2,3-dihydro-1H-inden-1-yl]pyrrolidin-3-yl}phenyl)piperazin-1-yl]ethan-1-one;

rac-(3R,4S)-4-{4-[4-(ethanesulfonyl)piperazin-1-yl]phenyl}-1-(7-fluoro-2,3-dihydro-1H-inden-1-yl)-N,N-dimethylpyrrolidin-3-amine;

tert-butyl 4-{4-[(3R,4S)-4-(dimethylamino)-1-(7-fluoro-2,3-dihydro-1H-inden-1-yl)pyrrolidin-3-yl]phenyl}piperazine-1-carboxylate;

rac-4-{4-[(3S,4R)-4-(dimethylamino)-1-(7-fluoro-2,3-di-hydro-1H-inden-1-yl)pyrrolidin-3-yl]benzoyl}-1-methylpiperazin-2-one;

rac-1-(4-{4-[(3R,4S)-4-(dimethylamino)-1-(7-fluoro-2,3-dihydro-1H-inden-1-yl)pyrrolidin-3-yl]phenyl}piperazin-1-yl)-2-hydroxyethan-1-one;

rac-{4-[(3S,4R)-4-(dimethylamino)-1-(7-fluoro-2,3-di-hydro-1H-inden-1-yl)pyrrolidin-3-yl]phenyl}[4-(methanesulfonyl)piperazin-1-yl]methanone;

rac-2-(4-{4-[(3R,4S)-4-(dimethylamino)-1-(7-fluoro-2,3-dihydro-1H-inden-1-yl)pyrrolidin-3-yl]phenyl}piperazin-1-yl)-2-oxoacetamide;

rac-1-(4-{4-[(3S,4R)-4-(dimethylamino)-1-(7-fluoro-2,3-dihydro-1H-inden-1-yl)pyrrolidin-3-yl]benzoyl}piperazin-1-yl)ethan-1-one;

rac-4-{4-[(3S,4R)-4-(dimethylamino)-1-(7-fluoro-2,3-di-hydro-1H-inden-1-yl)pyrrolidin-3-yl]phenyl}-1-methylpiperazin-2-one;

rac-{4-[(3S,4R)-4-(dimethylamino)-1-(7-fluoro-2,3-di-hydro-1H-inden-1-yl)pyrrolidin-3-yl]phenyl}[4-(ethanesulfonyl)piperazin-1-yl]methanone;

rac-4-{4-[(3S,4R)-4-(dimethylamino)-1-(7-fluoro-2,3-di-hydro-1H-inden-1-yl)pyrrolidin-3-yl]-2-methylphenyl}-1-methylpiperazin-2-one;

rac-2-(4-{4-[(3R,4S)-4-(dimethylamino)-1-(7-fluoro-2,3-dihydro-1H-inden-1-yl)pyrrolidin-3-yl]phenyl}piperazin-1-yl)-N,N-dimethyl-2-oxoacetamide;

rac-1-(4-{4-[(3S,4R)-4-(dimethylamino)-1-(7-fluoro-2,3-dihydro-1H-inden-1-yl)pyrrolidin-3-yl]-2-methylphenyl}piperazin-1-yl)ethan-1-one;

rac-(3R,4S)-1-(7-fluoro-2,3-dihydro-1H-inden-1-yl)-N, N-dimethyl-4-[4-(4-methylpiperazin-1-yl)phenyl]pyrrolidin-3-amine;

rac-(3R,4S)-4-{4-[4-(ethanesulfonyl)piperazin-1-yl]-3-methylphenyl}-1-(7-fluoro-2,3-dihydro-1H-inden-1-yl)-N,N-dimethylpyrrolidin-3-amine;

rac-4-{4-[(3S,4R)-4-(dimethylamino)-1-(7-fluoro-2,3-di-hydro-1H-inden-1-yl)pyrrolidin-3-yl]phenyl}-N,N-dimethylpiperazine-1-carboxamide;

rac-(3R,4S)-4-[4-(4-cyclopropylpiperazin-1-yl)phenyl]-1-(7-fluoro-2,3-dihydro-1H-inden-1-yl)-N,N-dimethylpyrrolidin-3-amine;

rac-(3S,4R)-4-(2H-1,3-benzodioxol-5-yl)-1-(7-fluoro-2,3-dihydro-1H-inden-1-yl)-N,N-dimethylpyrrolidin-3-amine;

rac-(3S,4R)-1-(7-fluoro-2,3-dihydro-1H-inden-1-yl)-N, N-dimethyl-4-[4-(1,3-oxazol-2-yl)phenyl]pyrrolidin-3-amine;

rac-(3R,4S)-1-(7-fluoro-2,3-dihydro-1H-inden-1-yl)-N, N-dimethyl-4-[4-(3-methyl-1,2,4-oxadiazol-5-yl)phenyl]pyrrolidin-3-amine;

rac-(3S,4R)-1-(7-fluoro-2,3-dihydro-1H-inden-1-yl)-N, N-dimethyl-4-[4-(5-methyl-1,3,4-oxadiazol-2-yl)phenyl]pyrrolidin-3-amine;

rac-(3S,4R)-1-(7-fluoro-2,3-dihydro-1H-inden-1-yl)-N, N-dimethyl-4-[4-(4-methyl-1,3-oxazol-2-yl)phenyl]pyrrolidin-3-amine;

rac-(3R,4S)-1-(7-fluoro-2,3-dihydro-1H-inden-1-yl)-N, N-dimethyl-4-[4-(1-methyl-1H-pyrazol-4-yl)phenyl]pyrrolidin-3-amine;

rac-2-(4-{4-[(3S,4R)-4-(dimethylamino)-1-(7-fluoro-2,3-dihydro-1H-inden-1-yl)pyrrolidin-3-yl]phenyl}-1H-pyrazol-1-yl)acetamide;

rac-2-(4-{4-[(3S,4R)-4-(dimethylamino)-1-(7-fluoro-2,3-dihydro-1H-inden-1-yl)pyrrolidin-3-yl]phenyl}-1H-pyrazol-1-yl)-N-methylacetamide;

rac-(3S,4R)-1-(7-fluoro-2,3-dihydro-1H-inden-1-yl)-N, N-dimethyl-4-{4-[4-(1-methyl-1H-imidazole-4-sulfonyl)piperazin-1-yl]phenyl}pyrrolidin-3-amine;

rac-(3S,4R)-1-(7-fluoro-2,3-dihydro-1H-inden-1-yl)-N,
N-dimethyl-4-{4-[4-(pyrimidin-4-yl)piperazin-1-yl]
phenyl}pyrrolidin-3-amine;
rac-(3S,4R)-1-(7-fluoro-2,3-dihydro-1H-inden-1-yl)-N,
N-dimethyl-4-{4-[4-(pyridin-2-yl)piperazin-1-yl]
phenyl}pyrrolidin-3-amine;
(3R,4S)-1-(7-fluoro-2,3-dihydro-1H-inden-1-yl)-N,N-dimethyl-4-(1-methyl-1H-indol-3-yl)pyrrolidin-3-amine;
(3R,4S)-1-[(1S)-7-fluoro-2,3-dihydro-1H-inden-1-yl]-N,
N-dimethyl-4-(1-methyl-1H-indol-3-yl)pyrrolidin-3-amine;
(3R,4S)-1-[(1R)-7-fluoro-2,3-dihydro-1H-inden-1-yl]-N,
N-dimethyl-4-(1-methyl-1H-indol-3-yl)pyrrolidin-3-amine;
3-[(3S,4R)-4-(dimethylamino)-1-(7-fluoro-2,3-dihydro-1H-inden-1-yl)pyrrolidin-3-yl]-1-methyl-1H-indole-7-carboxylic acid;
rac-3-[(3S,4R)-4-(dimethylamino)-1-(7-fluoro-2,3-dihydro-1H-inden-1-yl)pyrrolidin-3-yl]-1-methyl-1H-indole-7-carboxylic acid;
3-[(3R,4S)-4-(dimethylamino)-1-(7-fluoro-2,3-dihydro-1H-inden-1-yl)pyrrolidin-3-yl]-1-methyl-1H-indole-7-carboxylic acid;
rac-methyl 3-[(3R,4S)-4-(dimethylamino)-1-(7-fluoro-2,3-dihydro-1H-inden-1-yl)pyrrolidin-3-yl]-1-methyl-1H-indole-6-carboxylate;
methyl 3-[(3S,4R)-4-(dimethylamino)-1-(7-fluoro-2,3-dihydro-1H-inden-1-yl)pyrrolidin-3-yl]-1-methyl-1H-indole-7-carboxylate;
rac-methyl 3-[(3S,4R)-4-(dimethylamino)-1-(7-fluoro-2,3-dihydro-1H-inden-1-yl)pyrrolidin-3-yl]-1-methyl-1H-indole-7-carboxylate;
methyl 3-[(3S,4S)-4-(dimethylamino)-1-(7-fluoro-2,3-dihydro-1H-inden-1-yl)pyrrolidin-3-yl]-1-methyl-1H-indole-7-carboxylate;
rac-3-[(3S,4R)-4-(dimethylamino)-1-(7-fluoro-2,3-dihydro-1H-inden-1-yl)pyrrolidin-3-yl]-N,N,1-trimethyl-1H-indole-6-carboxamide;
(3R,4S)-1-(2,3-dihydro-1H-inden-1-yl)-N,N-dimethyl-4-(1-methyl-1H-indol-3-yl)pyrrolidin-3-amine;
(3R,4S)-1-(7-chloro-2,3-dihydro-1H-inden-1-yl)-N,N-dimethyl-4-(1-methyl-1H-indol-3-yl)pyrrolidin-3-amine;
rac-(3R,4S)-1-(4-fluoro-2,3-dihydro-1H-inden-1-yl)-N,
N-dimethyl-4-(1-methyl-1H-indol-3-yl)pyrrolidin-3-amine;
rac-(3R,4S)-1-(5-fluoro-2,3-dihydro-1H-inden-1-yl)-N,
N-dimethyl-4-(1-methyl-1H-indol-3-yl)pyrrolidin-3-amine;
rac-(3R,4S)-1-(6-fluoro-2,3-dihydro-1H-inden-1-yl)-N,
N-dimethyl-4-(1-methyl-1H-indol-3-yl)pyrrolidin-3-amine;
rac-(3R,4S)-4-(7-bromo-1-methyl-1H-indol-3-yl)-1-(7-fluoro-2,3-dihydro-1H-inden-1-yl)-N,N-dimethylpyrrolidin-3-amine;
rac-(3R,4S)-4-(6-bromo-1-methyl-1H-indol-3-yl)-1-(7-fluoro-2,3-dihydro-1H-inden-1-yl)-N,N-dimethylpyrrolidin-3-amine;
rac-(3R,4S)-1-(5,7-difluoro-2,3-dihydro-1H-inden-1-yl)-N,N-dimethyl-4-(1-methyl-1H-indol-3-yl)pyrrolidin-3-amine;
(3R,4S)-1-(6,7-difluoro-2,3-dihydro-1H-inden-1-yl)-N,
N-dimethyl-4-(1-methyl-1H-indol-3-yl)pyrrolidin-3-amine;
3-[(3R,4S)-3-(dimethylamino)-4-(1-methyl-1H-indol-3-yl)pyrrolidin-1-yl]-2,3-dihydro-1H-inden-4-ol;
rac-3-[(3S,4R)-4-(dimethylamino)-1-(7-fluoro-2,3-dihydro-1H-inden-1-yl)pyrrolidin-3-yl]-N-(2-hydroxyethyl)-N,1-dimethyl-1H-indole-7-carboxamide;
rac-3-[(3S,4R)-4-(dimethylamino)-1-(7-fluoro-2,3-dihydro-1H-inden-1-yl)pyrrolidin-3-yl]-N,1-dimethyl-1H-indole-7-carboxamide;
(3R,4S)—N,N-dimethyl-1-(7-methyl-2,3-dihydro-1H-inden-1-yl)-4-(1-methyl-1H-indol-3-yl)pyrrolidin-3-amine;
rac-3-[(3S,4R)-4-(dimethylamino)-1-(7-fluoro-2,3-dihydro-1H-inden-1-yl)pyrrolidin-3-yl]-N,N,1-trimethyl-1H-indole-7-carboxamide;
{3-[(3S,4R)-4-(dimethylamino)-1-(7-fluoro-2,3-dihydro-1H-inden-1-yl)pyrrolidin-3-yl]-1-methyl-1H-indol-7-yl}(3-fluoroazetidin-1-yl)methanone;
rac-{3-[(3S,4R)-4-(dimethylamino)-1-(7-fluoro-2,3-dihydro-1H-inden-1-yl)pyrrolidin-3-yl]-1-methyl-1H-indol-7-yl}(3-fluoroazetidin-1-yl)methanone;
{3-[(3R,4S)-4-(dimethylamino)-1-(7-fluoro-2,3-dihydro-1H-inden-1-yl)pyrrolidin-3-yl]-1-methyl-1H-indol-7-yl}(3-fluoroazetidin-1-yl)methanone;
{3-[(3S,4R)-4-(dimethylamino)-1-(7-fluoro-2,3-dihydro-1H-inden-1-yl)pyrrolidin-3-yl]-1-methyl-1H-indol-7-yl}(3-hydroxyazetidin-1-yl)methanone;
rac-{3-[(3S,4R)-4-(dimethylamino)-1-(7-fluoro-2,3-dihydro-1H-inden-1-yl)pyrrolidin-3-yl]-1-methyl-1H-indol-7-yl}(3-hydroxyazetidin-1-yl)methanone;
rac-{3-[(3S,4R)-4-(dimethylamino)-1-(7-fluoro-2,3-dihydro-1H-inden-1-yl)pyrrolidin-3-yl]-1-methyl-1H-indol-6-yl}(3-hydroxyazetidin-1-yl)methanone;
rac-3-[(3S,4R)-4-(dimethylamino)-1-(7-fluoro-2,3-dihydro-1H-inden-1-yl)pyrrolidin-3-yl]-N-(3-hydroxycyclobutyl)-1-methyl-1H-indole-7-carboxamide;
rac-3-[(3S,4R)-4-(dimethylamino)-1-(7-fluoro-2,3-dihydro-1H-inden-1-yl)pyrrolidin-3-yl]-N-(3-hydroxycyclobutyl)-N,1-dimethyl-1H-indole-7-carboxamide;
rac-{3-[(3S,4R)-4-(dimethylamino)-1-(7-fluoro-2,3-dihydro-1H-inden-1-yl)pyrrolidin-3-yl]-1-methyl-1H-indol-7-yl}[3-(methanesulfonyl)azetidin-1-yl]methanone;
rac-{3-[(3S,4R)-4-(dimethylamino)-1-(7-fluoro-2,3-dihydro-1H-inden-1-yl)pyrrolidin-3-yl]-1-methyl-1H-indol-6-yl}[(3S)-3-hydroxypyrrolidin-1-yl]methanone;
rac-{3-[(3S,4R)-4-(dimethylamino)-1-(7-fluoro-2,3-dihydro-1H-inden-1-yl)pyrrolidin-3-yl]-1-methyl-1H-indol-6-yl}[(3R)-3-hydroxypyrrolidin-1-yl]methanone;
rac-[(3S,4S)-3,4-dihydroxypyrrolidin-1-yl]{3-[(3S,4R)-4-(dimethylamino)-1-(7-fluoro-2,3-dihydro-1H-inden-1-yl)pyrrolidin-3-yl]-1-methyl-1H-indol-7-yl}methanone;
rac-[(3S,4S)-3,4-dihydroxypyrrolidin-1-yl]{3-[(3S,4R)-4-(dimethylamino)-1-(7-fluoro-2,3-dihydro-1H-inden-1-yl)pyrrolidin-3-yl]-1-methyl-1H-indol-6-yl}methanone;
rac-3-[(3S,4R)-4-(dimethylamino)-1-(7-fluoro-2,3-dihydro-1H-inden-1-yl)pyrrolidin-3-yl]-N-(1,1-dioxo-1lambda~6~-thiolan-3-yl)-1-methyl-1H-indole-7-carboxamide;
rac-{3-[(3S,4R)-4-(dimethylamino)-1-(7-fluoro-2,3-dihydro-1H-inden-1-yl)pyrrolidin-3-yl]-1-methyl-1H-indol-7-yl}[(2S)-2-(hydroxymethyl)pyrrolidin-1-yl]methanone;
rac-1-{3-[(3S,4R)-4-(dimethylamino)-1-(7-fluoro-2,3-dihydro-1H-inden-1-yl)pyrrolidin-3-yl]-1-methyl-1H-indole-7-carbonyl}-L-prolinamide;

rac-{3-[(3S,4R)-4-(dimethylamino)-1-(7-fluoro-2,3-dihydro-1H-inden-1-yl)pyrrolidin-3-yl]-1-methyl-1H-indol-7-yl}[(3S)-3-hydroxypyrrolidin-1-yl]methanone;

rac-{3-[(3S,4R)-4-(dimethylamino)-1-(7-fluoro-2,3-dihydro-1H-inden-1-yl)pyrrolidin-3-yl]-1-methyl-1H-indol-7-yl}(piperazin-1-yl)methanone;

rac-(3R,4S)-1-(7-fluoro-2,3-dihydro-1H-inden-1-yl)-4-{6-[4-(methanesulfonyl)piperazin-1-yl]-1-methyl-1H-indol-3-yl}-N,N-dimethylpyrrolidin-3-amine;

rac-1-(4-{3-[(3S,4R)-4-(dimethylamino)-1-(7-fluoro-2,3-dihydro-1H-inden-1-yl)pyrrolidin-3-yl]-1-methyl-1H-indol-6-yl}piperazin-1-yl)ethan-1-one;

rac-{3-[(3S,4R)-4-(dimethylamino)-1-(7-fluoro-2,3-dihydro-1H-inden-1-yl)pyrrolidin-3-yl]-1-methyl-1H-indol-6-yl}[4-(methanesulfonyl)piperazin-1-yl]methanone;

rac-1-(4-{3-[(3S,4R)-4-(dimethylamino)-1-(7-fluoro-2,3-dihydro-1H-inden-1-yl)pyrrolidin-3-yl]-1-methyl-1H-indole-6-carbonyl}piperazin-1-yl)ethan-1-one;

rac-4-{3-[(3S,4R)-4-(dimethylamino)-1-(7-fluoro-2,3-dihydro-1H-inden-1-yl)pyrrolidin-3-yl]-1-methyl-1H-indole-7-carbonyl}-N,N-dimethylpiperazine-1-sulfonamide;

rac-4-{3-[(3S,4R)-4-(dimethylamino)-1-(7-fluoro-2,3-dihydro-1H-inden-1-yl)pyrrolidin-3-yl]-1-methyl-1H-indole-7-carbonyl}-1-methylpiperazin-2-one;

rac-{3-[(3S,4R)-4-(dimethylamino)-1-(7-fluoro-2,3-dihydro-1H-inden-1-yl)pyrrolidin-3-yl]-1-methyl-1H-indol-7-yl}[4-(methanesulfonyl)piperazin-1-yl]methanone;

rac-4-{3-[(3S,4R)-4-(dimethylamino)-1-(7-fluoro-2,3-dihydro-1H-inden-1-yl)pyrrolidin-3-yl]-1-methyl-1H-indole-7-carbonyl}-N,N-dimethylpiperazine-1-carboxamide;

rac-1-(4-{3-[(3S,4R)-4-(dimethylamino)-1-(7-fluoro-2,3-dihydro-1H-inden-1-yl)pyrrolidin-3-yl]-1-methyl-1H-indole-7-carbonyl}piperazin-1-yl)ethan-1-one;

rac-4-{3-[(3S,4R)-4-(dimethylamino)-1-(7-fluoro-2,3-dihydro-1H-inden-1-yl)pyrrolidin-3-yl]-1-methyl-1H-indol-7-yl}-1-methylpiperazin-2-one;

rac-{3-[(3S,4R)-4-(dimethylamino)-1-(7-fluoro-2,3-dihydro-1H-inden-1-yl)pyrrolidin-3-yl]-1-methyl-1H-indol-7-yl}[4-(ethanesulfonyl)piperazin-1-yl]methanone;

rac-4-{3-[(3S,4R)-4-(dimethylamino)-1-(7-fluoro-2,3-dihydro-1H-inden-1-yl)pyrrolidin-3-yl]-1-methyl-1H-indol-7-yl}-N,N-dimethylpiperazine-1-carboxamide;

[4-(azetidine-1-sulfonyl)piperazin-1-yl]{3-[(3S,4R)-4-(dimethylamino)-1-(7-fluoro-2,3-dihydro-1H-inden-1-yl)pyrrolidin-3-yl]-1-methyl-1H-indol-7-yl}methanone;

1-(4-{3-[(3S,4R)-4-(dimethylamino)-1-(7-fluoro-2,3-dihydro-1H-inden-1-yl)pyrrolidin-3-yl]-1-methyl-1H-indole-7-carbonyl}piperazine-1-sulfonyl)azetidine-3-carbonitrile;

rac-8-{3-[(3S,4R)-4-(dimethylamino)-1-(7-fluoro-2,3-dihydro-1H-inden-1-yl)pyrrolidin-3-yl]-1-methyl-1H-indole-7-carbonyl}hexahydro-2H-pyrazino[1,2-a]pyrazin-1(6H)-one;

rac-{3-[(3S,4R)-4-(dimethylamino)-1-(7-fluoro-2,3-dihydro-1H-inden-1-yl)pyrrolidin-3-yl]-1-methyl-1H-indol-7-yl}[4-(1-methyl-1H-imidazole-5-sulfonyl)piperazin-1-yl]methanone;

rac-{3-[(3S,4R)-4-(dimethylamino)-1-(7-fluoro-2,3-dihydro-1H-inden-1-yl)pyrrolidin-3-yl]-1-methyl-1H-indol-7-yl}[4-(3,5-dimethyl-1H-pyrazole-4-sulfonyl)piperazin-1-yl]methanone;

rac-{3-[(3S,4R)-4-(dimethylamino)-1-(7-fluoro-2,3-dihydro-1H-inden-1-yl)pyrrolidin-3-yl]-1-methyl-1H-indol-7-yl}[4-(pyridazin-3-yl)piperazin-1-yl]methanone;

rac-(3R,4S)-1-[(1S)-7-fluoro-2,3-dihydro-1H-inden-1-yl]-N,N-dimethyl-4-(1-methyl-1H-pyrrolo[3,2-b]pyridin-3-yl)pyrrolidin-3-amine;

rac-(3S,4R)-4-(2,3-dihydro-1-benzofuran-3-yl)-1-[(1R)-7-fluoro-2,3-dihydro-1H-inden-1-yl]-N,N-dimethylpyrrolidin-3-amine;

rac-(3S,4R)-1-(7-fluoro-2,3-dihydro-1H-inden-1-yl)-N,N-dimethyl-4-(5,6,7,8-tetrahydroimidazo[1,2-a]pyridin-3-yl)pyrrolidin-3-amine;

rac-(3R,4S)-1-(7-fluoro-2,3-dihydro-1H-inden-1-yl)-N,N-dimethyl-4-(1-methyl-1H-pyrrolo[3,2-c]pyridin-3-yl)pyrrolidin-3-amine;

rac-(3R,4S)-4-(2,3-dihydro-1-benzofuran-3-yl)-1-[(1R)-7-fluoro-2,3-dihydro-1H-inden-1-yl]-N,N-dimethylpyrrolidin-3-amine;

rac-(3R,4S)-1-[(1R)-7-fluoro-2,3-dihydro-1H-inden-1-yl]-N,N-dimethyl-4-(1-methyl-1H-pyrrolo[3,2-b]pyridin-3-yl)pyrrolidin-3-amine;

rac-(3R,4S)-1-(7-fluoro-2,3-dihydro-1H-inden-1-yl)-N,N-dimethyl-4-(oxan-4-yl)pyrrolidin-3-amine;

rac-(3S,4R)-1-(7-fluoro-2,3-dihydro-1H-inden-1-yl)-N,N-dimethyl-4-[6-(piperazin-1-yl)pyridin-3-yl]pyrrolidin-3-amine;

rac-(3R,4S)-1-(7-fluoro-2,3-dihydro-1H-inden-1-yl)-N,N-dimethyl-4-(1-phenylpiperidin-4-yl)pyrrolidin-3-amine;

rac-2-(4-{5-[(3R,4S)-4-(dimethylamino)-1-(7-fluoro-2,3-dihydro-1H-inden-1-yl)pyrrolidin-3-yl]pyridin-2-yl}piperazin-1-yl)-N,N-dimethylacetamide;

rac-(3R,4S)-1-(7-fluoro-2,3-dihydro-1H-inden-1-yl)-N,N-dimethyl-4-(1-methyl-1H-pyrrolo[2,3-c]pyridin-3-yl)pyrrolidin-3-amine;

rac-(3R,4S)-1-(7-fluoro-2,3-dihydro-1H-inden-1-yl)-N,N-dimethyl-4-[1-(pyridin-3-yl)piperidin-4-yl]pyrrolidin-3-amine;

rac-2-(4-{5-[(3R,4S)-4-(dimethylamino)-1-(7-fluoro-2,3-dihydro-1H-inden-1-yl)pyrrolidin-3-yl]pyridin-2-yl}-1H-pyrazol-1-yl)-1-(3-hydroxyazetidin-1-yl)ethan-1-one;

rac-(4-{5-[(3R,4S)-4-(dimethylamino)-1-(7-fluoro-2,3-dihydro-1H-inden-1-yl)pyrrolidin-3-yl]pyridin-2-yl}piperazin-1-yl)(oxetan-3-yl)methanone;

rac-(3R,4S)-1-(7-fluoro-2,3-dihydro-1H-inden-1-yl)-N,N-dimethyl-4-[1-(pyridin-2-yl)piperidin-4-yl]pyrrolidin-3-amine;

rac-2-(4-{5-[(3R,4S)-4-(dimethylamino)-1-(7-fluoro-2,3-dihydro-1H-inden-1-yl)pyrrolidin-3-yl]pyridin-2-yl}-1H-pyrazol-1-yl)-1-(3-fluoroazetidin-1-yl)ethan-1-one;

rac-6-{4-[(3S,4R)-4-(dimethylamino)-1-(7-fluoro-2,3-dihydro-1H-inden-1-yl)pyrrolidin-3-yl]piperidin-1-yl}-N-methylpyridine-3-carboxamide;

rac-N-[2-(4-{5-[(3R,4S)-4-(dimethylamino)-1-(7-fluoro-2,3-dihydro-1H-inden-1-yl)pyrrolidin-3-yl]pyridin-2-yl}piperazin-1-yl)-2-oxoethyl]methanesulfonamide;

rac-(3R,4S)-1-(7-fluoro-2,3-dihydro-1H-inden-1-yl)-N,N-dimethyl-4-(1-methyl-1H-indazol-3-yl)pyrrolidin-3-amine;

rac-1-(4-{5-[(3R,4S)-4-(dimethylamino)-1-(7-fluoro-2,3-dihydro-1H-inden-1-yl)pyrrolidin-3-yl]pyridin-2-yl}piperazin-1-yl)-2-(methanesulfonyl)ethan-1-one;

rac-2-(4-{5-[(3R,4S)-4-(dimethylamino)-1-(7-fluoro-2,3-dihydro-1H-inden-1-yl)pyrrolidin-3-yl]pyridin-2-yl}-1H-pyrazol-1-yl)acetamide;

rac-2-(4-{5-[(3R,4S)-4-(dimethylamino)-1-(7-fluoro-2,3-dihydro-1H-inden-1-yl)pyrrolidin-3-yl]pyridin-2-yl}-1H-pyrazol-1-yl)-N,N-dimethylacetamide;

rac-2-(4-{5-[(3R,4S)-4-(dimethylamino)-1-(7-fluoro-2,3-dihydro-1H-inden-1-yl)pyrrolidin-3-yl]pyridin-2-yl}piperazin-1-yl)-2-oxoethane-1-sulfonamide;

rac-2-(4-{5-[(3R,4S)-4-(dimethylamino)-1-(7-fluoro-2,3-dihydro-1H-inden-1-yl)pyrrolidin-3-yl]pyridin-2-yl}-1H-pyrazol-1-yl)-N-methylacetamide;

rac-2-{4-[(3S,4R)-4-(dimethylamino)-1-(7-fluoro-2,3-dihydro-1H-inden-1-yl)pyrrolidin-3-yl]piperidin-1-yl}-1,3-thiazole-5-carboxamide;

rac-5-{4-[(3S,4R)-4-(dimethylamino)-1-(7-fluoro-2,3-dihydro-1H-inden-1-yl)pyrrolidin-3-yl]piperidin-1-yl}pyrazine-2-carboxamide;

rac-(3R,4S)-1-(7-fluoro-2,3-dihydro-1H-inden-1-yl)-N,N-dimethyl-4-(1-methyl-1H-pyrrolo[2,3-b]pyridin-3-yl)pyrrolidin-3-amine;

rac-6-{4-[(3S,4R)-4-(dimethylamino)-1-(7-fluoro-2,3-dihydro-1H-inden-1-yl)pyrrolidin-3-yl]piperidin-1-yl}pyridazine-3-carboxamide;

rac-4-{4-[(3S,4R)-4-(dimethylamino)-1-(7-fluoro-2,3-dihydro-1H-inden-1-yl)pyrrolidin-3-yl]piperidin-1-yl}benzamide;

rac-6-{4-[(3S,4R)-4-(dimethylamino)-1-(7-fluoro-2,3-dihydro-1H-inden-1-yl)pyrrolidin-3-yl]piperidin-1-yl}pyridine-3-carboxamide; and pharmaceutically acceptable salts thereof.

8. A pharmaceutical composition comprising a pharmaceutically acceptable excipient and a therapeutically effective amount of a compound of claim 1 or a pharmaceutically acceptable salt thereof.

9. A method of treating an EED-mediated cancer in a patient, comprising administering to a patient suffering from an EED-mediated cancer a therapeutically effective amount of a compound of claim 1, or a pharmaceutically acceptable salt thereof.

* * * * *